United States Patent
Getts et al.

(10) Patent No.: US 12,030,938 B2
(45) Date of Patent: Jul. 9, 2024

(54) ENGINEERED CHIMERIC FUSION PROTEIN COMPOSITIONS AND METHODS OF USE THEREOF

(71) Applicant: Myeloid Therapeutics, Inc., Cambridge, MA (US)

(72) Inventors: Daniel Getts, Stow, MA (US); Yuxiao Wang, Belmont, MA (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 18/157,643

(22) Filed: Jan. 20, 2023

(65) Prior Publication Data

US 2023/0303684 A1 Sep. 28, 2023

Related U.S. Application Data

(63) Continuation of application No. PCT/US2022/020787, filed on Mar. 17, 2022.

(60) Provisional application No. 63/255,540, filed on Oct. 14, 2021, provisional application No. 63/243,947, filed on Sep. 14, 2021, provisional application No. 63/172,922, filed on Apr. 9, 2021, provisional application No. 63/162,352, filed on Mar. 17, 2021.

(51) Int. Cl.
    *C07K 16/28* (2006.01)
    *A61P 35/00* (2006.01)
    *C07K 14/735* (2006.01)

(52) U.S. Cl.
    CPC .............. *C07K 16/28* (2013.01); *A61P 35/00* (2018.01); *C07K 14/70535* (2013.01); *C07K 2317/565* (2013.01); *C07K 2317/622* (2013.01); *C07K 2319/02* (2013.01); *C07K 2319/03* (2013.01)

(58) Field of Classification Search
    CPC .............. C07K 16/28; C07K 14/70535; C07K 2317/565; C07K 2317/622; C07K 2319/02; C07K 2319/03; A61P 35/00
See application file for complete search history.

(56) References Cited

U.S. PATENT DOCUMENTS

| | | |
|---|---|---|
| 5,585,089 A | 12/1996 | Queen et al. |
| 5,633,234 A | 5/1997 | August et al. |
| 5,639,642 A | 6/1997 | Kjeldsen et al. |
| 5,641,870 A | 6/1997 | Rinderknecht et al. |
| 5,693,761 A | 12/1997 | Queen et al. |
| 5,766,903 A | 6/1998 | Sarnow et al. |
| 5,773,244 A | 6/1998 | Ares, Jr. et al. |
| 5,776,910 A | 7/1998 | Schreiber et al. |
| 5,869,046 A | 2/1999 | Presta et al. |
| 6,194,204 B1 | 2/2001 | Crawford et al. |

(Continued)

FOREIGN PATENT DOCUMENTS

| | | |
|---|---|---|
| CA | 2850380 C | 8/2015 |
| EP | 0404097 A2 | 12/1990 |

(Continued)

OTHER PUBLICATIONS

Ali et al.: Induction of neoantigen-reactive T cells from healthy donors. Nature Protocols (2019).

(Continued)

*Primary Examiner* — Ruixiang Li
(74) *Attorney, Agent, or Firm* — Wilson Sonsini Goodrich & Rosati

(57) ABSTRACT

Compositions and methods for making and using engineered cells, such as, engineered myeloid cells that express a chimeric fusion protein that has a binding domain capable to binding surface molecules on target cells such as diseased cells.

30 Claims, 75 Drawing Sheets

Specification includes a Sequence Listing.

(56) References Cited

U.S. PATENT DOCUMENTS

| | | |
|---|---|---|
| 6,210,963 B1 | 4/2001 | Haddada et al. |
| 6,248,516 B1 | 6/2001 | Winter et al. |
| 6,455,299 B1 | 9/2002 | Steinman et al. |
| 6,602,709 B1 | 8/2003 | Albert et al. |
| 6,734,014 B1 | 5/2004 | Hwu et al. |
| 6,936,468 B2 | 8/2005 | Robbins et al. |
| 7,833,789 B2 | 11/2010 | Naldini et al. |
| 7,871,613 B2 | 1/2011 | Kinoshita et al. |
| 7,919,086 B2 | 4/2011 | Nakano et al. |
| 8,198,020 B2 | 6/2012 | Francois et al. |
| 9,045,541 B2 | 6/2015 | Eckelman et al. |
| 9,149,519 B2 | 10/2015 | Landau et al. |
| 9,221,908 B2 | 12/2015 | Frazier et al. |
| 9,428,569 B2 | 8/2016 | Spencer et al. |
| 9,518,116 B2 | 12/2016 | Frazier et al. |
| 9,663,575 B2 | 5/2017 | Eckelman et al. |
| 9,745,368 B2 | 8/2017 | Milone et al. |
| 9,850,312 B2 | 12/2017 | Agatsuma et al. |
| 9,913,920 B2 | 3/2018 | Movahedi et al. |
| 10,034,900 B2 | 7/2018 | Senju |
| 10,081,680 B2 | 9/2018 | Weiskopf et al. |
| 10,155,038 B2 | 12/2018 | Rabinovich et al. |
| 10,259,873 B2 | 4/2019 | Frazier et al. |
| 10,329,329 B2 | 6/2019 | Stone et al. |
| 10,415,017 B2 | 9/2019 | O'Neill |
| 10,428,143 B2 | 10/2019 | Krummel et al. |
| 10,782,300 B2 | 9/2020 | Ohtomo et al. |
| 10,980,836 B1 | 4/2021 | Getts et al. |
| 11,013,764 B2 | 5/2021 | Getts et al. |
| 11,026,973 B2 | 6/2021 | Getts et al. |
| 11,034,749 B2 | 6/2021 | Gill et al. |
| 11,041,023 B2 | 6/2021 | Vale et al. |
| 11,376,326 B2 | 7/2022 | Ohtomo et al. |
| 11,517,589 B2 | 12/2022 | Wagner et al. |
| 11,628,218 B2 | 4/2023 | Getts et al. |
| 11,767,362 B1 | 9/2023 | Endo et al. |
| 2002/0132224 A1 | 9/2002 | Poznansky et al. |
| 2003/0130496 A1 | 7/2003 | Winter et al. |
| 2004/0053873 A1 | 3/2004 | Barman et al. |
| 2006/0018889 A1 | 1/2006 | Li et al. |
| 2008/0003614 A1 | 1/2008 | Chen et al. |
| 2011/0287038 A1 | 11/2011 | Slawin et al. |
| 2011/0293603 A1 | 12/2011 | Saraiva et al. |
| 2012/0045389 A1 | 2/2012 | Gassull Duro et al. |
| 2013/0280285 A1 | 10/2013 | Schonfeld et al. |
| 2014/0134142 A1 | 5/2014 | Smith et al. |
| 2014/0140989 A1 | 5/2014 | Eckelman et al. |
| 2014/0161805 A1 | 6/2014 | Jamieson et al. |
| 2014/0242701 A1 | 8/2014 | Shiku et al. |
| 2015/0057161 A1 | 2/2015 | Schultze et al. |
| 2016/0038541 A1 | 2/2016 | Stripecke et al. |
| 2016/0045551 A1 | 2/2016 | Brentjens et al. |
| 2016/0137733 A1 | 5/2016 | Frazier et al. |
| 2016/0145348 A1 | 5/2016 | Stephan |
| 2016/0250258 A1 | 9/2016 | Delaney et al. |
| 2016/0251435 A1 | 9/2016 | Eckelman et al. |
| 2017/0010270 A1 | 1/2017 | Ohtomo et al. |
| 2017/0087185 A1 | 3/2017 | Crane et al. |
| 2017/0151281 A1 | 6/2017 | Wagner et al. |
| 2017/0151282 A1 | 6/2017 | Discher et al. |
| 2017/0166657 A1 | 6/2017 | O'Neill et al. |
| 2017/0204422 A1 | 7/2017 | Nelson et al. |
| 2017/0226183 A1 | 8/2017 | Schiffer-Mannioui |
| 2017/0246278 A1 | 8/2017 | Vera Valdes et al. |
| 2017/0292118 A1 | 10/2017 | Duchateau et al. |
| 2018/0000899 A1 | 1/2018 | Francois et al. |
| 2018/0030553 A1 | 2/2018 | Tang et al. |
| 2018/0105600 A1 | 4/2018 | Pons et al. |
| 2018/0118803 A1 | 5/2018 | Brentjens et al. |
| 2018/0133252 A9 | 5/2018 | Wilson et al. |
| 2018/0171021 A1 | 6/2018 | Karlsson et al. |
| 2018/0186855 A1 | 7/2018 | Rosenthal |
| 2018/0186878 A1 | 7/2018 | Rosenthal |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2018/0334653 A1 | 11/2018 | O'Neill |
| 2019/0008897 A1 | 1/2019 | Scatena et al. |
| 2019/0010219 A1 | 1/2019 | Short |
| 2019/0023761 A1 | 1/2019 | Pule et al. |
| 2019/0038671 A1 | 2/2019 | Fan et al. |
| 2019/0062450 A1 | 2/2019 | De Palma et al. |
| 2019/0070277 A1 | 3/2019 | O'Neill et al. |
| 2019/0233496 A1 | 8/2019 | Rosenthal |
| 2019/0240343 A1 | 8/2019 | Ahmed et al. |
| 2019/0263928 A1 | 8/2019 | Watanabe et al. |
| 2019/0292257 A1 | 9/2019 | Bedoya et al. |
| 2019/0336615 A1 | 11/2019 | Thompson et al. |
| 2019/0345217 A1 | 11/2019 | Ma et al. |
| 2019/0381158 A1 | 12/2019 | Gunn |
| 2020/0216542 A1 | 7/2020 | Ohtomo et al. |
| 2020/0239592 A1 | 7/2020 | Vale et al. |
| 2020/0247870 A1 | 8/2020 | Gill et al. |
| 2020/0255517 A1 | 8/2020 | Riddell et al. |
| 2020/0345773 A1 | 11/2020 | Getts et al. |
| 2020/0345774 A1 | 11/2020 | Getts et al. |
| 2021/0002377 A1 | 1/2021 | Brogdon et al. |
| 2021/0046110 A1 | 2/2021 | Gill et al. |
| 2021/0095001 A1 | 4/2021 | Gill et al. |
| 2021/0252053 A1 | 8/2021 | Wagner et al. |
| 2021/0277140 A1 | 9/2021 | Vale et al. |
| 2021/0299172 A1 | 9/2021 | Getts et al. |
| 2021/0361703 A1 | 11/2021 | Getts et al. |
| 2022/0000917 A1 | 1/2022 | Klichinsky et al. |
| 2022/0000918 A1 | 1/2022 | Klichinsky et al. |
| 2022/0001021 A1 | 1/2022 | Uhl et al. |
| 2022/0001031 A1 | 1/2022 | Getts et al. |
| 2022/0002375 A1 | 1/2022 | Gill et al. |
| 2022/0002376 A1 | 1/2022 | Gill et al. |
| 2022/0002377 A1 | 1/2022 | Gill et al. |
| 2022/0002675 A1 | 1/2022 | Klichinsky et al. |
| 2022/0033465 A1 | 2/2022 | Gill et al. |
| 2022/0033466 A1 | 2/2022 | Gill et al. |
| 2022/0033467 A1 | 2/2022 | Gill et al. |
| 2022/0033468 A1 | 2/2022 | Gill et al. |
| 2022/0041688 A1 | 2/2022 | Gill et al. |
| 2022/0073639 A1 | 3/2022 | Ruella et al. |
| 2022/0098273 A1 | 3/2022 | Corey |
| 2022/0118010 A1 | 4/2022 | Wagner et al. |
| 2022/0152199 A1 | 5/2022 | Getts et al. |
| 2022/0175830 A1 | 6/2022 | Wagner et al. |
| 2022/0175831 A1 | 6/2022 | Wagner et al. |
| 2022/0202856 A1 | 6/2022 | Wagner et al. |
| 2022/0233586 A1 | 7/2022 | Wagner et al. |
| 2022/0241428 A1 | 8/2022 | Getts et al. |
| 2022/0378824 A1 | 12/2022 | Getts et al. |
| 2023/0046472 A1 | 2/2023 | Getts et al. |
| 2023/0055143 A1 | 2/2023 | Gilbreth et al. |
| 2023/0146706 A1 | 5/2023 | Kwon et al. |
| 2023/0220107 A1 | 7/2023 | Wu et al. |
| 2023/0277659 A1 | 9/2023 | Getts et al. |
| 2024/0033355 A1 | 2/2024 | Lu et al. |

FOREIGN PATENT DOCUMENTS

| | | |
|---|---|---|
| EP | 0338841 B1 | 3/1995 |
| EP | 2626415 A2 | 8/2013 |
| EP | 2953643 A1 | 12/2015 |
| EP | 2242512 B1 | 4/2016 |
| EP | 3197495 A1 | 8/2017 |
| EP | 3328402 A1 | 6/2018 |
| EP | 2956343 B1 | 12/2018 |
| EP | 3504244 A1 | 7/2019 |
| EP | 3519441 A1 | 8/2019 |
| EP | 3574018 A2 | 12/2019 |
| EP | 3574018 A4 | 10/2020 |
| GB | 2572005 A | 9/2019 |
| WO | WO-9201813 A1 | 2/1992 |
| WO | WO-9301161 A1 | 1/1993 |
| WO | WO-9425591 A1 | 11/1994 |
| WO | WO-9505835 A1 | 3/1995 |
| WO | WO-1995005835 A1 | 3/1995 |
| WO | WO-02077029 A2 | 10/2002 |

(56) References Cited

FOREIGN PATENT DOCUMENTS

| | | |
|---|---|---|
| WO | WO-02077029 A3 | 5/2003 |
| WO | WO-2004050855 A2 | 6/2004 |
| WO | WO-2004050855 A3 | 2/2005 |
| WO | WO-2006006693 A1 | 1/2006 |
| WO | WO-2007113572 A1 | 10/2007 |
| WO | WO-2008011599 A2 | 1/2008 |
| WO | WO-2008011599 A3 | 2/2009 |
| WO | WO-2011070109 A1 | 6/2011 |
| WO | WO-2012005763 A1 | 1/2012 |
| WO | WO-2012170930 A1 | 12/2012 |
| WO | WO-2013123088 A1 | 8/2013 |
| WO | WO-2013185552 A1 | 12/2013 |
| WO | WO-2014055668 A1 | 4/2014 |
| WO | WO-2014123580 A1 | 8/2014 |
| WO | WO-2014153114 A1 | 9/2014 |
| WO | WO-2016033331 A1 | 3/2016 |
| WO | WO-2016040441 A1 | 3/2016 |
| WO | WO-2016049641 A1 | 3/2016 |
| WO | WO-2016070136 A1 | 5/2016 |
| WO | WO-2016109410 A2 | 7/2016 |
| WO | WO-2016126213 A1 | 8/2016 |
| WO | WO-2016126608 A1 | 8/2016 |
| WO | WO-2016138491 A1 | 9/2016 |
| WO | WO-2016149254 A1 | 9/2016 |
| WO | WO-2016172606 A1 | 10/2016 |
| WO | WO-2017019848 A1 | 2/2017 |
| WO | WO-2017025944 A2 | 2/2017 |
| WO | WO-2017044487 A1 | 3/2017 |
| WO | WO-2017050884 A1 | 3/2017 |
| WO | WO-2017025944 A3 | 4/2017 |
| WO | WO-2017136633 A1 | 8/2017 |
| WO | WO-2017172981 A2 | 10/2017 |
| WO | WO-2018038684 A1 | 3/2018 |
| WO | WO-2018064076 A1 | 4/2018 |
| WO | WO-2018073394 A1 | 4/2018 |
| WO | WO-2018083126 A1 | 5/2018 |
| WO | WO-2018140831 A3 | 8/2018 |
| WO | WO-2018158350 A1 | 9/2018 |
| WO | WO-2018169948 A1 | 9/2018 |
| WO | WO-2018231871 A1 | 12/2018 |
| WO | WO-2019005641 A1 | 1/2019 |
| WO | WO-2019032624 A1 | 2/2019 |
| WO | WO-2019040135 A1 | 2/2019 |
| WO | WO-2019055946 A1 | 3/2019 |
| WO | WO-2019067328 A1 | 4/2019 |
| WO | WO-2019070704 A1 | 4/2019 |
| WO | WO-2019086512 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO-2019201995 A1 | 10/2019 |
| WO | WO-2020095044 A1 | 5/2020 |
| WO | WO-2020097193 A1 | 5/2020 |
| WO | WO-2020223550 A1 | 11/2020 |
| WO | WO-2020252208 A2 | 12/2020 |
| WO | WO-2020252208 A3 | 1/2021 |
| WO | WO-2021046243 A2 | 3/2021 |
| WO | WO-2021046243 A3 | 6/2021 |
| WO | WO-2021119538 A1 | 6/2021 |
| WO | WO-2021263152 A1 | 12/2021 |
| WO | WO-2022036265 A1 | 2/2022 |
| WO | WO-2022067033 A1 | 3/2022 |
| WO | WO-2022166876 A1 | 8/2022 |
| WO | WO-2022231425 A1 | 11/2022 |
| WO | WO-2022236049 A1 | 11/2022 |
| WO | WO-2023030539 A1 | 3/2023 |
| WO | WO-2023172916 A2 | 9/2023 |

OTHER PUBLICATIONS

Altschul et al.: Basic Local Alignment Search Tool. J Mol Biol 215(3):403-410 (1990).

Alvey el al.: SIRPA-Inhibited, Marrow-Derived macrophages engorge, accumulate, and differentiate in Antibody-Targeted regression of solid tumors. Current Biology 27:2065-2077 (2017).

Alvey et al. Engineering macrophages to eat Cancer: from "marker of self" CD47 and phagocytosis to differentiation. Journal of Leukocyte Biology 102:31-40 (2017).

Ancuta et al.: (BMC Genomics 10:403, pp. 1-19 (2009 )).

Andreesen et al.: Adoptive transfer of tumor cytotoxic macrophages generated in vitro from circulating blood monocytes: a new approach to Cancer immunotherapy. Cancer Research 50:7450-7456 (1990).

Auffray et al.: Blood monocytes: development, heterogeneity, and relationship with dendritic cells, Annual Rev. Immunol. 27:669-92 (2009).

Azad et al. γ-Tilmanocept, a New Radiopharmaceutical Tracer for Cancer Sentinel Lymph Nodes, Binds to the Mannose Receptor (CD206). J. Immunol. 195:2019-2029 (2015). Epub Jul. 22, 2015.

Baeuerle et al. Synthetic TRUC receptors engaging the complete T cell Receptor for potent anti-tumor response. Nat Commun 10:2087 (2019).

Batista et al.: B cells acquire antigen from target cells after synapse formation. Nature 411:489-494 (2001).

Beningo et al.: Fc-receptor-mediated phagocytosis is regulated by mechanical properties of the target. Journal of Cell Science 115:849-856 (2002).

Berger et al.: Efficient Elutriation of monocytes within a closed system (Elutra™). Journal of Immunological Methods 298:61-72 (2005).

Bhatta P, Humphreys DP. Relative Contribution of Framework and CDR Regions in Antibody Variable Domains to Multimerisation of Fv- and scFv-Containing Bispecific Antibodies. Antibodies (Basel). Aug. 31, 2018;7(3):35.

Bhattacharjee et al.: Monocytes isolated by positive and negative magnetic sorting techniques show different molecular characteristics and immunophenotypic behaviour. F100Research p. 1-13 (2018).

Biglari et al.: Human monocytes expressing a CEA-specific chimeric CD64 receptor specifically target CEA-expressing tumour cells in vitro and in vivo. Gene Therapy 13, 602-610 (2006).

Blumenthal et al.: Development and Characterization of Chimeric Antigen Receptor Monocytes (CAR Mono), a Novel Cell Therapy Platform for Solid Tumor Immunotherapy. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-104-Daniel-Blumenthal-Carisma-Therapeutics.pdf.

Blumenthal et al.: Pre-clinical development of CAR Monocytes (CAR Mono) for solid tumor immunotherapy. Poster Presentation. The American Association for Cancer Research (AACR) Annual Meeting, New Orleans, LA, United States (2022) https://secureservercdn.net/45.40.149.113/74d.fcf.myftpupload.com/wp-content/uploads/2022/07/Poster-5000-Daniel-Blumenthal-Carisma-Therapeutics.pdf.

Bournazos et al.: The Role and Function of Fcγ Receptors on Myeloid Cells. Microbiol Spectr 4(6) (2016).

Brooks et al.: Binding of cytoplasmic proteins to the CD19 intracellular domain is high affinity, competitive, and multimeric. The Journal of Immunology 172:7556-7564 (2004).

Bu el al.: Analysis of the interaction of ZAP-70 and syk protein-tyrosine kinases with the T-cell antigen receptor by plasmon resonance. PNAS 92:5106-5110 (1995).

Chen et al.: Functional Interrogation of Primary Human T Cells via CRISPR Genetic Editing. The Journal of Immunology 201:1586-1598 (2018).

Chen IJ, et al. Selective antibody activation through protease-activated pro-antibodies that mask binding sites with inhibitory domains. Sci Rep. Sep. 14, 2017;7(1):11587.

Cieslewicz et al. Targeted delivery of proapoptotic peptides to tumor-associated macrophages improves survival. PNAS USA 110(40):15919-15924 (2013).

Corriden R, Insel PA. New insights regarding the regulation of chemotaxis by nucleotides, adenosine, and their receptors. Purinergic Signal. Sep. 2012;8(3):587-98. Epub Apr. 15, 2012.

Cros et al.: Human CD14dim) Monocytes Patrol and Sense Nucleic Acids and viruses via TLR7 and TLR8 Receptors. Immunity 33:375-386, (2010).

(56) References Cited

OTHER PUBLICATIONS

Da Silva et al.: MICA/B antibody induces macrophage-mediated immunity against acute myeloid leukemia. Blood 139(2):205-216 doi: 10.1182/blood.2021011619 (2022).
Daeron et al.: Fc Receptors. Current Topics in Microbiology and Immunology, vol. 382 (2014).
De Kleer et al.: Ontogeny of myeloid cells. frontiers in Immunology 5(423):1-11 (2014).
De Kleer I, et al. Ontogeny of myeloid cells. Front Immunol. Sep. 3, 2014;5:423.
De Oliveria et al.: Modification of Hematopoietic Stem/Progenitor Cells with CD19-Specific Chimeric Antigen Receptros as a Novel Approach for Cancer Immunotherapy. Human Gene Therapy 24:824-839 (2013).
Devereux et al., "A Comprehensive Set of Sequence Analysis Programs for the VAX," Nucleic Acids Research 11:12(1 Pt 1):387-395 (Jan. 1984).
Dotti et al. Design and Development of Therapies using Chimeric Antigen Receptor-Expressing T cells. Immunol Rev. 257(1):35 pgs (2014).
Egan TJ, et al. Novel multispecific heterodimeric antibody format allowing modular assembly of variable domain fragments. MAbs. Jan. 2017;9(1):68-84. Epub Oct. 27, 2016.
Engel et al.: Abnormal B lymphocyte development, activation, and differentiation in mice that lack or overexpress the CD19 signal transduction molecule. Immunity 3:39-50 (1995).
Fesnak et al.: Engineered T cells: the promise and challenges of cancer immunotherapy. Nature Reviews Cancer 16:566-581 (2016).
Final Office Action issued in corresponding U.S. Appl. No. 15/048,922 dated Jul. 13, 2018.
Final Office Action issued in corresponding U.S. Appl. No. 17/227,193 dated Mar. 8, 2022.
Final Office Action issued in corresponding U.S. Appl. No. 17/715,710 dated Apr. 6, 2023.
Fix., Oral controlled release technology for peptides: status and future prospects. Pharm Res., 13(12):1760-1764 (1996).
Flynn et al.: Mammalian Y RNAs are modified at discrete guanosine residues with N-glycans. BioRxiv 787614 (2019).
Flynn RA, et al. Small RNAs are modified with N-glycans and displayed on the surface of living cells. Cell. Jun. 10, 2021;184(12):3109-3124.e22. Epub May 17, 2021.
Fong et al.: High expression of TROP2 correlates with poor prognosis in pancreatic cancer. Br J Cancer 99(8):1290-5. doi: 10.1038/sj.bjc.6604677 (2008).
Fraser et al.: Development, functional characterization and validation of methodology for GMP-compliant manufacture of phagocytic macrophages: A novel cellular therapeutic for liver cirrhosis. Cyotherapy ISSN 1465-3249 (2017).
Freeman et al.: Integrins Form an Expanding Diffusional Barrier that Coordinates Phagocytosis. Cell 164:128-140 (2016).
Freeman et al.: Phagocytosis: receptors, signal integration, and the cytoskeleton. Immunological Reviews 262:193-215 (2014).
Gabitova et al.: Anti-HER2 CAR monocytes demonstrate targeted anti-tumor activity and enable a single day cell manufacturing process. Poster Presentation. The American Association for Cancer Research (AACR) Annual Meeting, Philadelphia, PA, United States (2021). https://secureservercdn.net/45.40.149.113/74d.fcf.myftpupload.com/wp-content/uploads/2021/09/Anti-HER2-CAR-monocytes_AACR2021.pdf.
Gardai et al.: Cell-surface calreticulin initiates clearance of viable or apoptotic cells through trans-activation of LRP on the phagocyte. Cell 123:321-334 (2005).
Geissmann et al.: Blood Monocytes Consist of Two Principal Subsets with Distinct Migratory Properties. Immunity (19):71-82 (2003).
Getts et al.: Harnessing nanoparticles for immune modulation. Trends Immunol 36(7):419-427 (2015).
Getts et al.: Microparticles bearing encephalitogenic peptides induce T-cell tolerance and ameliorate experimental autoimmune encephalomyelitis. Nat Biotechnol 30(12):1217-1224 (2012).
Gordon: Phagocytosis: An Immunobiologic Process. Immunity 44 (2016).
Ham JS, et al. Elevated serum interleukin-10 level and M2 macrophage infiltration are associated with poor survival in angioimmunoblastic T-cell lymphoma. Oncotarget. Jul. 17, 2017;8(44):76231-76240.
Harland et al.: Stability of RNA in developing Xenopus embryos and identification of a destabilizing sequence in TFIIIA messenger RNA. Development 102(4):837-852 (1988).
Harshyne et al.: A Role for Class a Scavenger Receptor in Dendritic Cell Nibbling from Live Cells. The Journal of Immunology 170:2302-2309 (2003).
Harshyne et al.: Dendritic cells acquire antigens from live cells for Cross-Presentation to CTL. The Journal of Immunology 166:3717-3723 (2001).
Haso et al.: Anti-CD22-chimeric antigen receptors targeting B-cell precursor acute lymphoblastic leukemia. Blood 121:1165-1174 (2013).
Holtz, Kathleen M. et al.: Modifications of cysteine residues in the transmembrane and cytoplasmic domains of a recombinant hemagglutinin protein prevent cross-linked multimer formation and potency loss. BMC Biotechnology 14(111):1-20 (2014). DOI: 10.1186/s12896-014-0111-y.
Hou X, et al. Lipid nanoparticles for mRNA delivery. Nat Rev Mater. 2021;6(12):1078-1094. Epub Aug. 10, 2021.
Huang et al.: Antigen-loaded monocyte administration induces potent therapeutic antitumor T cell responses, The Journal of Clinical Investigation, p. 1-15 (2020).
Hudson et al.: Engineered antibodies. Nature Medicine 9(1):129-134 (2003).
Hui et al.: T cell constimulatory receptor CD28 is a primary target for PD-1-mediated inhibition. Science 355(6332):1428-1433 (2017).
Ingersoll et al.: Brief Report: Pilot Randomized Controlled Trial of Reciprocal Imitation Training for Teaching Elicited and Spontaneous Imitation to Children with Autism, J Autism Dev Disord 40(9):1154-1160 (2010).
International Search Report and Written Opinion for PCT/US2020/030837 issued Oct. 1, 2020.
Italiani et al.: From Monocytes to M1/M2 Macrophages: Phenotypical vs. Functional Differentiation. Front Immunol 17(5):514 (2014).
Jadus et al.: Macrophages can recognize and kill tumor cells bearing the membrane isoform of macrophage colony-stimulating factor. Blood 87:5232-5241 (1996).
Jaiswal et al.: CD47 is upregulated on circulating hematopoietic stem cells and leukemia cells to avoid phagocytosis. Cell 138:271-285 (2009).
James et al.: Biophysical mechanism of T-cell receptor triggering in a reconstituted system. Nature 487:64-69 (2012).
Jarrosson-Wuilleme et al.: Transduction of nondividing human macrophages with gammaretrovirus-derived vectors. J Virol. 80(3):1152-1159 doi:10.1128/JVI.80.3.1152-1159.2006 (2006).
Joly et al.: What is trogocytosis and what is its purpose? Nature Immunology 4:815 (2003).
Kearney, Stacy et al.: Differential effects of type I and II interferons on myeloid cells and resistance to intracellular bacterial infections. Immunol Res. 55(0):187-200 (2013). doi: 10.1007/s12026-012-8362-y.
Kim et al.: Monocyte Enrichment from Leukapheresis products by using the Elutra cell separator. Transfusion 47:2290-2296 (2007).
Kimmel et al.: [54] Identification and characterization of specific clones: Strategy for confirming the validity of presumptive clones. Methods in enzymology 152:507-511 (1987).
Kimmel et al.: Preparation of cDNA and the generation of cDNA libraries: overview. Methods Enzymol 152:307-316 (1987).
Klichinsky et al.: Human chimeric antigen receptor macrophages for cancer immunotherapy. Nat Biotechnol. 38(8):947-953 (2020); Epub (2020).
Klichinsky M. et al., "CAR-Macrophage for Cancer Immunotherapy: Latest Findings from the CT-0508 Clinical Trial" YouTube, https://youtu.be/2Ag7SVM-fPg, published Jun. 27, 2022, https://carismatx.com/programs/ct-0508/.
Kloepper J, et al. Ang-2/VEGF bispecific antibody reprograms macrophages and resident microglia to anti-tumor phenotype and

(56) References Cited

OTHER PUBLICATIONS prolongs glioblastoma survival. Proc Natl Acad Sci U S A. Apr. 19, 2016;113(16):4476-81. Epub Apr. 4, 2016.
Kochenderfer et al.: Construction and preclinical evaluation of an anti-CD19 chimeric antigen receptor. Journal of Immunotherapy 32:689-702 (2009).
Kowalski et al.: Delivering the Messenger: Advances in Technologies for Therapeutic mRNA Delivery. Mol. Ther 27(4):710-728 (2019).
Kwon B. CD137-CD137 Ligand Interactions in Inflammation. Immune Netw. Jun. 2009;9(3):84-9. Epub Jun. 30, 2009.
Lacerna et al.: Adoptive cancer immunotherapy utilizing lymphokine activated killer cells and gamma interferon activated killer monocytes. Pharmacology & Therapeutics 38:453-465 (1988).
Laird et al.: (J. Leukocyte Biology 85: 966-977 (2009)).
Lee et al.: Macrophage-based cell therapies: the long and winding road. Journal of Controlled Release 240:527-540 (2016).
Levine et al.: Global Manufacturing of CAR T Cell Therapy. Mol Ther Methods Clin Dev. 4:92-101 (2016).
Li B, et al. CD89-mediated recruitment of macrophages via a bispecific antibody enhances anti-tumor efficacy. Oncoimmunology. Oct. 12, 2017;7(1):e1380142.
Lim, et al., "Antisense oligonucleotide modulation of non-productive alternative splicing upregulates gene expression" (2020) Nature Communication.
Lim et al.: The Principles of Engineering Immune Cells to Treat Cancer. Cell 168:724-740 (2017).
Liu et al.: Overexpression of TROP2 predicts poor prognosis of patients with cervical cancer and promotes the proliferation and invasion of cervical cancer cells by regulating ERK signaling pathway. PLoS One 8(9):e75864, pp. 1-14 doi:10.1371/journal.pone.0075864 (2013).
Liu et al.: Phosphorylation of innate immune adaptor proteins MAVS, STING, and TRIF induces IRF3 activation. Science 347(6227):1217 (2015). DOI: 10.1126/science.aaa2630.
Lloyd et al., "Modelling the Human Immune Response: Performance of a 10" Human Antibody Repertoire Against a Broad Panel of Therapeutically Relevant Antigens," Protein Engineering Design & Selection 22(3):159-168 (2009) (Published online Oct. 29, 2008).
Majeti et al.: CD47 is an adverse prognostic factor and therapeutic antibody target on human acute myeloid leukemia stem cells. Cell 138:286-299 (2009).
Matsuyoshi et al.: Enchanced Priming of Antigen-Specific CTL's In Vivo by Embryonic Stem Cell-Derived Dendritic Cells Expressing Chemokine Along with Antigenic Protein: Application to Antitumor Vaccination. The Journal of Immunology 172:776-786 (2004).
Mayordomo et al.: Bone marrow-derived dendritic cells pulsed with synthetic tumour peptides elicit protective and therapeutic antitumour immunity. Nature Medicine 1:1297-1302 (1995).
McCaffrey et al.: RNA Interference in Adult Mice. Nature 418:38-39 (2002).
McEver et al.: Selectins: initiators of leucocyte adhesion and signalling at the vascular wall. Cardovascular Research 107:331-339 (2015).
Medzihradszky, K.F.: Lessons in de novo peptide sequencing by tandem mass spectrometry. Mass Spectrom Rev 34(1):43-63 (2015).
Mildner et al.: Distinct and Non-Redundant Roles of Microglia and Myeloid Subsets in Mouse Models of Alzheimer's Disease. Neurobiology of Disease, J. Neurosci. 31(31):11159-11171 (2011).
Mo F, et al. Engineered off-the-shelf therapeutic T cells resist host immune rejection. Nat Biotechnol. Jan. 2021;39(1):56-63. Epub Jul. 13, 2020.
Morrissey et al.: Chimeric antigen receptors that trigger phagocytosis. eLife p. 1-21 (2018).
Mukherjee et al.: Non-Classical monocytes display inflammatory features: Validation in Sepsis and Systemic Lupus Erythematous. Scientific Reports p. 1-14 (2015).

Nakamizo et al.: Single-cell analysis of human skin identifies CD14+ type 3 dendritic cells co-producing IL1B and IL23A in psoriasis. J Exp Med 218(9):e20202345 (2021). https://doi.org/10.1084/jem.20202345.
Nakayama M. Macrophage Recognition of Crystals and Nanoparticles. Front Immunol. Jan. 29, 2018;9:103.
Ning et al.: TROP2 correlates with microvessel density and poor prognosis in hilar cholangiocarcinoma. J Gastrointest Surg 17(2):360-368 doi:10.1007/s11605-012-2105-1 (2013).
Oates et al.: Characterizing the polarization continuum of macrophage subtypes M1, M2a and M2c. bioRxiv (2022). doi: https://doi.org/10.1101/2022.06.13.495868.
Office Action issued in corresponding U.S. Appl. No. 15/048,922 dated Sep. 21, 2017.
Office Action issued in corresponding U.S. Appl. No. 17/227,193 dated Nov. 12, 2021.
Office Action issued in corresponding U.S. Appl. No. 17/715,710 dated Nov. 30, 2022.
Office Action issued in U.S. Appl. No. 17/227,193 dated Jun. 22, 2022.
Olingy et al.: Monocyte heterogeneity and functions in cancer. J Leukoc Biol. 106(2):309-322 (2019). doi: 10.1002/JLB.4RI0818-311R. Epub (2019).
Orecchioni et al.: Macrophage Polarization: Different Gene Signatures in M1(LPS+) vs. Classically and M2(LPS-) vs. Alternatively Activated Macrophages. Front Immunol. (2019); 10:1084. Erratum in: Front Immunol. 25;11:234 (2020).
Oshi et al.: M1 Macrophage and M1/M2 ratio defined by transcriptomic signatures resemble only part of their conventional clinical characteristics in breast cancer. Sci Rep. 10(1):16554 (2020).
Oviedo-Boyso et al.: The Phosphoinositide-3-Kinase-Akt Signaling Pathway Is Important for *Staphylococcus aureus* Internalization by Endothelial Cells Infection and Immunity 79(11):4569-4577 (2011).
Passlick et al.: Identification and Characterization of a Novel Monocyte Subpopulation in Human Peripheral Blood. Article in Blood 74:2527-2534 (1989).
Patel et al.: The fate and lifespan of human monocyte subsets in steady state and systemic inflammation. J. Exp. Med. 214(7):1913-1923 (2017).
PCT/US2019/060052 International Search Report and Written Opinion dated Apr. 30, 2020.
PCT/US2020/030837 International Search Report and Written Opinion dated Sep. 1, 2020.
PCT/US2020/037312 International Search Report dated Nov. 30, 2020.
PCT/US2020/049240 International Search Report dated Mar. 26, 2021.
PCT/US2020/064686 International Preliminary Report on Patentability mailed Jun. 23, 2022.
PCT/US2020/064686 International Search Report and Written Opinion dated Apr. 6, 2021.
PCT/US2021/058104 International Search Report and Written Opinion dated Apr. 28, 2022.
PCT/US2022/020787 International Search Report and Written Opinion dated Sep. 28, 2022.
Penberthy et al.: Apoptotic cell recognition receptors and scavenger receptors. Immunological Reviews 269:44-59 (2016).
Pierini et al.: Chimeric antigen receptor macrophages (CAR-M) elicit a systemic anti-tumor immune response and synergize with PD-1 blockade in immunocompetent mouse models of HER2+ solid tumors. Poster Presentation. Society for Immunotherapy of Cancer (SITC) Meeting, Virtual (2020). https://secureservercdn.net/45.40.149.113/74d.fcf.myftpupload.com/wp-content/uploads/2021/09/CAR-M-syngeneic-model_SITC2020.pdf.
Pierini et al.: Chimeric antigen receptor macrophages (CAR-M) sensitize solid tumors to anti-PD1 immunotherapy. Poster Presentation. The American Association for Cancer Research (AACR) Annual Meeting, New Orleans, LA, United States (2022). https://secureservercdn.net/45.40.149.113/74d.fcf.myftpupload.com/wp-content/uploads/2022/07/AACR2022_CARMaPD11.pdf.
Pluckthun et al.: The Pharmacology of Monoclonal Antibodies. Springer-Verlag 11:69-315 (1994).

(56) References Cited

OTHER PUBLICATIONS

Putnam. Antisense strategies and therapeutic applications. Am. J. Health Syst. Pharm. 53:151-160 (1996), erratum at Am. J. Health Syst. Pharm. 53:325 (1996).
Qi J, et al. Potent and Selective Antitumor Activity of a T-Cell Engaging Bispecific Antibody Targeting a Membrane-Proximal Epitope of ROR1. bioRxiv 219402. Preprint at https://doi.org/10.1101/219402 (2017). Now published in Proceedings of the National Academy of Sciences doi: 10.1073/pnas.1719905115.
Ralston et al.: Trogocytosis by Entamoeba histolytica contributes to cell killing and tissue invasion. Nature 508:526-530 (2014).
Ravin. Chapter 76: Preformulation. Remington's Pharmaceutical Sciences, 17th ed., Mack Publishing Company, Easton, Pa. (pp. 1409-1423) (1985).
Rayamajhi, Manira et al.: Antagonistic crosstalk between type I and II interferons and increased host susceptibility to bacterial infections. Virulence 1(5):481-422 (2010).
Reiss et al.: A Phase 1, First-In-Human (FIH) Study of the Anti-HER2 CAR Macrophage CT-0508 in Participants with HER2 Overexpressing Solid Tumors. Poster Presentation. American Society of Clinical Oncology (ASCO) Annual Meeting, New Chicago, IL, United States (2022). https://secureservercdn.net/45.40.149.113/74d.fcf.myftpupload.com/wp-content/uploads/2022/07/ASCO-Data-In-Person-2022.final_.pdf.
Reiss et al.: LBA (951): A Phase 1 first in human study of adenovirally transduced anti-HER2 CAR Macrophages in subjects with HER2 overexpressing solid tumors: preliminary safety, pharmacokinetics, and TME reprogramming data. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/Poster-LBA951-CT-0508-Study-101-SITC-FINAL.pdf.
Roberts et al.: Antigen-Specific Cytolysis by Neutrophils and NK Cells Expressing Chimeric Immune Receptros Bearing xx Signaling Domains. J Immunol 161:375-384 (1998).
Roberts et al.: Critical Role for CD103(+)/CD141(+) Dendritic Cells Bearing CCR7 for Tumor Antigen Trafficking and Priming of T Cell Immunity in Melanoma. Cancer Cell 30:324-336 (2016).
Rosales et al: Phagocytosis: A Fundamental Process in Immunity. BioMed Research International, Article ID 9042851 (2017).
Rossjohn, J., 2015, Annu Rev Immunol. 2015;33:169-200. {doi: 10.1146/annurev-immunol-032414-112334. Epub Dec. 10, 2014}.
Ruiz-Aguilar et al.: Human CD16+ and CD16+ monocyte subsets display unique effector properties in inflammatory conditions in vivo. Journal of Leukocyte Biology 90:1119-1131 (2011).
Sadler, AJ et al.: Interferon-inducible antiviral effectors. Nature Reviews Immunology 8:559-568 (2008).
Salmon H, et al. Expansion and Activation of CD103(+) Dendritic Cell Progenitors at the Tumor Site Enhances Tumor Responses to Therapeutic PD-L1 and BRAF Inhibition. Immunity. Apr. 19, 2016;44(4):924-38.
Samanen et al. Chemical approaches to improve the oral bioavailability of peptidergic molecules. J. Pharm. Pharmacol. 48:119-135 (1996).
Scherberich et al.: CD14++ monocytes, CD14+/CD16+ subset and soluble CD14 as biological markers of inflammatory systemic diseases and monitoring immunosuppressive therapy. Clin Chem Lab Med. 37(3):209-13 (1999).
Schlam et al.: Phosphoinositide 3-kinase enables phagocytosis of large particles by terminating actin assembly through Rac/Cdc42 GRPase-activating proteins. Nature Communications (2015).
Schroers R, et al. Transduction of human PBMC-derived dendritic cells and macrophages by an HIV-1-based lentiviral vector system. Mol Ther. Feb. 2000;1(2):171-9.
Senju et al.: Generation and genetic modification of dendritic cells derived from mouse embryonic stem cells derived from mouse embryonics stem cells. Blood 101(9):3501-3508 (2003).
Senju et al.: Generation of dendritic cells and macrophages from human induced pluripotent stem cells aiming at cell therapy. Gene Therapy 18:874-883 (2011).
Shanmugam A, et al. Synthetic Toll like receptor-4 (TLR-4) agonist peptides as a novel class of adjuvants. PLoS One. 2012;7(2):e30839. Epub Feb. 20, 2012.
Silverstein RL., Mechanisms of Cell Signaling by the Scavenger Receptor CD36: Implications in Atherosclerosis and Thrombosis, Transactions of the American Clinical and Climatological Association, vol. 121, 2010.
Singh P, et al. Anti-claudin 18.2 antibody as new targeted therapy for advanced gastric cancer. J Hematol Oncol. May 12, 2017;10(1):105.
Sloas et al.: SIRPα-Deficient CAR-Macrophages Exhibit Enhanced Anti-Tumor Function and Bypass the CD47 Immune Checkpoint. Poster Presentation. Society for Immunotherapy of Cancer (SITC) Meeting, Washington, DC, United States (2021). https://secureservercdn.net/45.40.149.113/74d.fcf.myftpupload.com/wp-content/uploads/2021/11/CRISPR_CAR-M_Poster_101721_share-Read-Only.pdf.
Soderberg et al. (J. Virology 67(6): 3166-3175 (1993)).
Strauss et al.: The immunophenotype of antigen presenting cells of the mononuclear phagocyte system in a normal human liver—A systematic review. Journal of Hepatology 62:458-468 (2015).
Supplementary European Search Report dated Dec. 16, 2022 issued in European Patent Application No. 20798060.
Tippet et al.: (J. Leukocyte Biology 93:913-920 (2013)).
Tseng et al.: Anti-CD47 antibody-mediated phagocytosis of cancer by macrophages primes an effective antitumor T-cell response. PNAS 110:11103-11108 (2013).
Tuveson et al.: CD19 of B cells as a surrogate kinase insert region to bindphosphatidylinositol 3-kinase. Science 260:986-989 (1993).
Villanueva MT. Macrophages get a CAR. Nat Rev Drug Discov. 19(5):308 (2020).
Wang et al.: Innate Immune Cells: A Potential and Promising Cell Population for Treating Osteosarcoma. Front Immunol. 10(1114):1-14 doi:10.3389/fimmu.2019.01114 (2019).
Weischenfeldt et al.: Bone Marrow-Derived Macrophages (BMM): Isolation and Applications. Cold Spring Harbor Protocols 2008:pdb.prot5080.
Wilkinson et al. (Med. Microbio. Immunol. 204:273-284 (2015)).
Wong et al.: The three human monocyte subsets: implications for health and disease. Immunol Res. 2012; 53(1-3):41-57. Epub (2012).
Xia et al.: siRNA-mediated gene silencing in vitro and in vivo. Nat Biotechnol. 20:1006-1010 (2002).
Xiao et al.: Electrophysiological Characteristics of Primary Afferent Fibers After Systemic Administration of Anti-GC2 Ganglioside Antibody, Pain69: 145-151 (1997).
Xiao et al.: Identification and characterization of fully human anti-CD22 monoclonal antibodies. mAbs 1:297-303 (2009).
Yang M, et al. Stromal Infiltration of Tumor-Associated Macrophages Conferring Poor Prognosis of Patients with Basal-Like Breast Carcinoma. J Cancer. Jun. 6, 2018;9(13):2308-2316.
Yong et al: A role for multiple chimeric antigen receptor-expressing leukocytes in antigen-specific responses to cancer. Oncotarget 7(23):34582-34598 (2016).
Yong et al.: Using electroporation to determine function of a chimeric antigen receptor in T cell and macrophage cell lines. The Open Gene Therapy Journal 23:5(1) (2013).
Zhao et al.: Trop2 is overexpressed in gastric cancer and predicts poor prognosis. Oncotarget 7(5):6136-6145 doi:10.18632/oncotarget.6733 (2016).

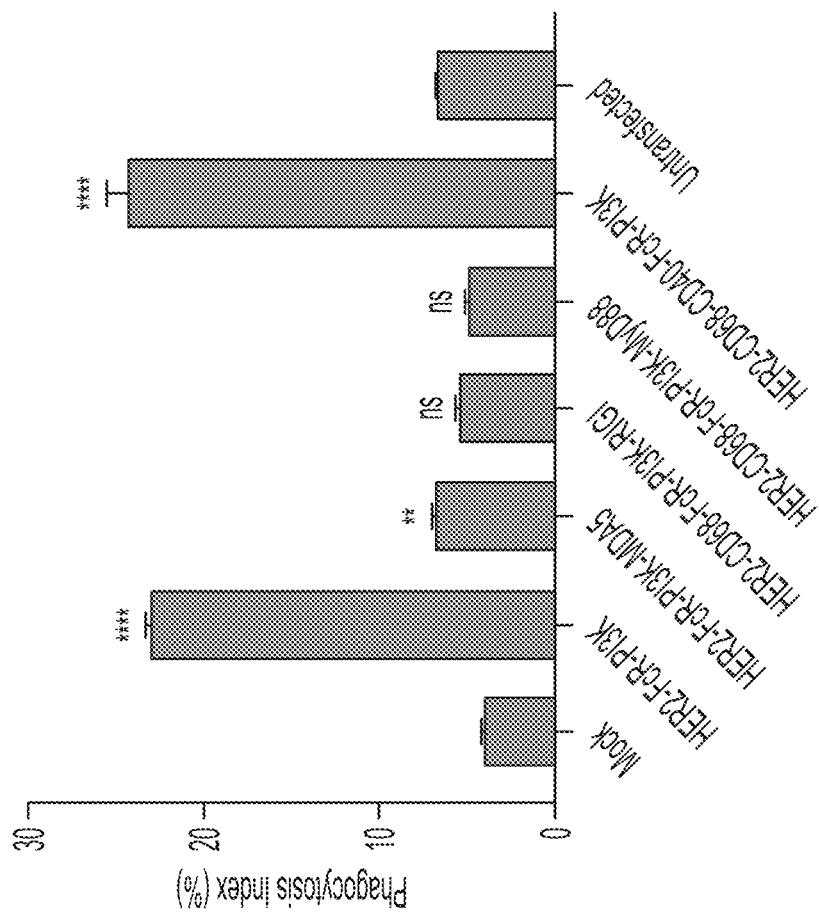

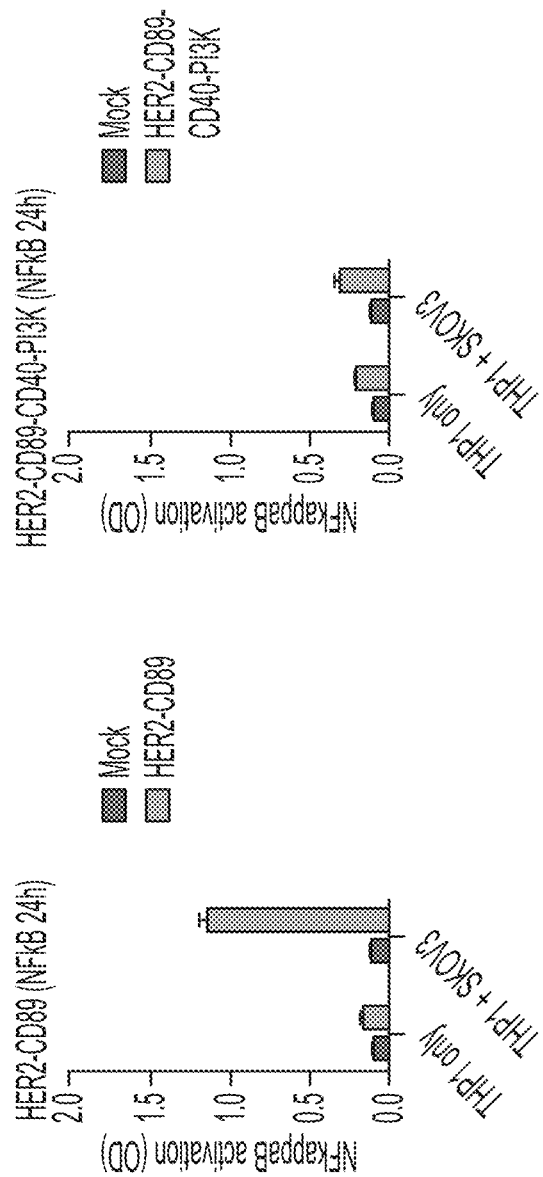
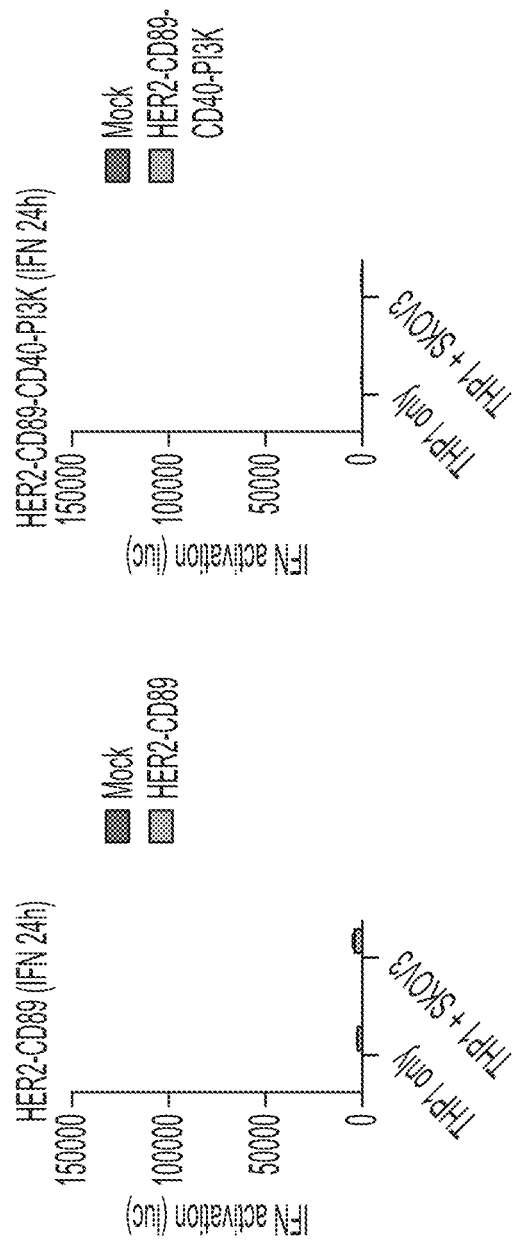
FIG. 5E
FIG. 5F

SEQUENCE LISTING

```
Sequence total quantity: 287
SEQ ID NO: 1              moltype = AA   length = 432
FEATURE                   Location/Qualifiers
REGION                    1..432
                          note = Description of Artificial Sequence: Synthetic
                          polypeptide
source                    1..432
                          mol_type = protein
                          organism = synthetic construct
SEQUENCE: 1
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RRLKIQVRKA  360
AITSYEKSDG VYTGLSTRNQ ETYETLKHEK PPQGSGSYED MRGILYAAPQ LRSIRGQPGP  420
NHEEDADSYE NM                                                     432

SEQ ID NO: 2              moltype = AA   length = 436
FEATURE                   Location/Qualifiers
REGION                    1..436
                          note = Description of Artificial Sequence: Synthetic
                          polypeptide
source                    1..436
                          mol_type = protein
                          organism = synthetic construct
SEQUENCE: 2
MWLQSLLLLG TVACSISDIQ MTQSPSSLSA SVGDRVTITC RASQDVNTAV AWYQQKPGKA   60
PKLLIYSASF LYSGVPSRFS GSRSGTDFTL TISSLQPEDF ATYYCQQHYT TPPTFGQGTK  120
VEIKRTGSTS GSGKPGSGEG SEVQLVESGG GLVQPGGSLR LSCAASGFNI KDTYIHWVRQ  180
APGKGLEWVA RIYPTNGYTR YADSVKGRFT ISADTSKNTA YLQMNSLRAE DTAVYYCSRW  240
GGDGFYAMDV WGQGTLVTVS SGGGGSGAL SNSIMYFSHF VPVFLPAKPT TTPAPRPPTP  300
APTIASQPLS LRPEACRPAA GGAVHTRGLD IYIWAPLAGT CGVLLLSLVI TLYCRRLKIQ  360
VRKAAITSYE KSDGVYTGLS TRNQETYETL KHEKPPQGSG SYEDMRGILY AAPQLRSIRG  420
QPGPNHEEDA DSYENM                                                 436

SEQ ID NO: 3              moltype = AA   length = 454
FEATURE                   Location/Qualifiers
REGION                    1..454
                          note = Description of Artificial Sequence: Synthetic
                          polypeptide
source                    1..454
                          mol_type = protein
                          organism = synthetic construct
SEQUENCE: 3
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQKKVAKKPT NKAPHPKQEP QEINFPDDLP  420
GSNTAAPVQE TLHGCQPVTQ EDGKESRISV QERQ                             454

SEQ ID NO: 4              moltype = AA   length = 607
FEATURE                   Location/Qualifiers
REGION                    1..607
                          note = Description of Artificial Sequence: Synthetic
                          polypeptide
source                    1..607
                          mol_type = protein
                          organism = synthetic construct
SEQUENCE: 4
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSMSNG YSTDENFRYL ISCFRARVKM  420
YIQVEPVLDY LTFPLPAEVKE QIQRTVATSG NMQAVELLLS TLEKGVWHLG WTREFVEALR  480
RTGSPLAARY MNPELTDLPS PSFENAHDEY LQLLNLLQPT LVDKLLVRDV LDKCMEEELL  540
TIEDRNRIAA AENNGNESGV RELLKRIVQK ENWFSAFLNV LRQTGNNELV QELTGSDCSE  600
SNAEIEN                                                           607

SEQ ID NO: 5              moltype = AA   length = 615
FEATURE                   Location/Qualifiers
```

```
REGION                    1..615
                          note = Description of Artificial Sequence: Synthetic
                            polypeptide
source                    1..615
                          mol_type = protein
                          organism = synthetic construct
SEQUENCE: 5
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YPCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSQRWK SKLYSIVCGK STPEKEGELE  420
GTTTKPLAPN PSFSPTPGFT PTLGFSPVPS STFTSSSTYT PGDCPNFAAP RREVAPPYQG  480
ADPILATALA SDPIPNPLQK WEDSAHKPQS LDTDDPATLY AVVENVPPLR WKEFVRRLGL  540
SDHEIDRLEL QNGRCLREAQ YSMLATWRRR TPRREATLEL LGRVLRDMDL LGCLEDIEEA  600
LCGPAALPPA PSLLR                                                  615

SEQ ID NO: 6              moltype = AA  length = 567
FEATURE                   Location/Qualifiers
REGION                    1..567
                          note = Description of Artificial Sequence: Synthetic
                            polypeptide
source                    1..567
                          mol_type = protein
                          organism = synthetic construct
SEQUENCE: 6
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YPCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSPLCL QREAKVPHLP ADKARGTQGP  420
EQQHLLITAP SSSSSSLESS ASALDRRAPT RNQPQAPGVE ASGAGEARAS TGSSDSSPGG  480
HGTQVNVTCI VNVCSSSDHS SQCSSQASST MGDTDSSPSE SPKDEQVPFS KEECAFRSQL  540
ETPETLLGST EEKPLPLGVP DAGMKPS                                     567

SEQ ID NO: 7              moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 7
MWLQSLLLLG TVACSIS                                                  17

SEQ ID NO: 8              moltype = AA  length = 116
FEATURE                   Location/Qualifiers
REGION                    1..116
                          note = Description of Artificial Sequence: Synthetic
                            polypeptide
source                    1..116
                          mol_type = protein
                          organism = synthetic construct
SEQUENCE: 8
EIQLVQSGGG LVKPGGSVRI SCAASGYTFT NYGMNWVRQA PGKGLEWMGW INTHTGEPTY   60
ADSFKGRFTF SLDDSKNTAY LQINSLRAED TAVYFCTRRG YDWYFDVWGQ GTTVTV      116

SEQ ID NO: 9              moltype = AA  length = 107
FEATURE                   Location/Qualifiers
REGION                    1..107
                          note = Description of Artificial Sequence: Synthetic
                            polypeptide
source                    1..107
                          mol_type = protein
                          organism = synthetic construct
SEQUENCE: 9
DIQMTQSPSS LSASVGDRVT ITCRASQDIN SYLSWFQQKP GKAPKTLIYR ANRLESGVPS   60
RFSGSGSGTD YTLTISSLQY EDFGIYYCQQ YDESPWTFGG GTKLEIK                107

SEQ ID NO: 10             moltype = AA  length = 240
FEATURE                   Location/Qualifiers
REGION                    1..240
                          note = Description of Artificial Sequence: Synthetic
                            polypeptide
source                    1..240
```

```
                        mol_type = protein
                        organism = synthetic construct
SEQUENCE: 10
EIQLVQSGGG LVKPGGSVRI SCAASGYTFT NYGMNWVRQA PGKGLEWMGW INTHTGEPTY    60
ADSFKGRFTF SLDDSKNTAY LQINSLRAED TAVYFCTRRG YDWYFDVWGQ GTTVTVSSGG   120
GGSGGGGSGG GGSDIQMTQS PSSLSASVGD RVTITCRASQ DINSYLSWFQ QKPGKAPKTL   180
IYRANRLESG VPSRFSGSGS GTDYTLTISS LQYEDFGIYY CQQYDESPWT FGGGTKLEIK   240

SEQ ID NO: 11           moltype = AA  length = 257
FEATURE                 Location/Qualifiers
REGION                  1..257
                        note = Description of Artificial Sequence: Synthetic
                         polypeptide
source                  1..257
                        mol_type = protein
                        organism = synthetic construct
SEQUENCE: 11
MWLQSLLLLG TVACSISEIQ LVQSGGGLVK PGGSVRISCA ASGYTFTNYG MNWVRQAPGK    60
GLEWMGWINT HTGEPTYADS FKGRFTFSLD DSKNTAYLQI NSLRAEDTAV YFCTRRGYDW   120
YFDVWGQGTT VTVSSGGGGS GGGGSGGGGS DIQMTQSPSS LSASVGDRVT ITCRASQDIN   180
SYLSWFQQKP GKAPKTLIYR ANRLESGVPS RFSGSGSGTD YTLTISSLQY EDFGIYYCQQ   240
YDESPWTFGG GTKLEIK                                                 257

SEQ ID NO: 12           moltype = AA  length = 130
FEATURE                 Location/Qualifiers
REGION                  1..130
                        note = Description of Artificial Sequence: Synthetic
                         polypeptide
source                  1..130
                        mol_type = protein
                        organism = synthetic construct
SEQUENCE: 12
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTG STSGSGKPGS   120
GEGSEVQLVE                                                         130

SEQ ID NO: 13           moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 13
LVQPGGSLRL SCAASGFNIK DTYIHWVRQA PGKGLEWVAR IYPTNGYTRY ADSVKGRFTI    60
SADTSKNTAY LQMNSLRAED TAVYYCSRWG GDGFYAMDVW GQGTLVTV                108

SEQ ID NO: 14           moltype = AA  length = 255
FEATURE                 Location/Qualifiers
REGION                  1..255
                        note = Description of Artificial Sequence: Synthetic
                         polypeptide
source                  1..255
                        mol_type = protein
                        organism = synthetic construct
SEQUENCE: 14
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTG STSGSGKPGS   120
GEGSEVQLVE SSGGGGSGGG GSGGGGSLVQ PGGSLRLSCA ASGFNIKDTY IHWVRQAPGK   180
GLEWVARIYP TNGYTRYADS VKGRFTISAD TSKNTAYLQM NSLRAEDTAV YYCSRWGGDG   240
FYAMDVWGQG TLVTV                                                   255

SEQ ID NO: 15           moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 15
IYIWAPLAGT CGVLLLSLVI T                                             21

SEQ ID NO: 16           moltype = AA  length = 24
FEATURE                 Location/Qualifiers
REGION                  1..24
                        note = Description of Artificial Sequence: Synthetic peptide
source                  1..24
                        mol_type = protein
```

```
                                organism = synthetic construct
SEQUENCE: 16
IYIWAPLAGT CGVLLLSLVI TLYC                                            24

SEQ ID NO: 17           moltype = AA   length = 26
FEATURE                 Location/Qualifiers
REGION                  1..26
                        note = Description of Artificial Sequence: Synthetic peptide
source                  1..26
                        mol_type = protein
                        organism = synthetic construct
SEQUENCE: 17
IYLIIGICGG GSLLMVFVAL LVFYIT                                          26

SEQ ID NO: 18           moltype = AA   length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 18
FWVLVVVGGV LACYSLLVTV AFIIFWV                                         27

SEQ ID NO: 19           moltype = AA   length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 19
ILLPLIIGLI LLGLLALVLI AFCII                                           25

SEQ ID NO: 20           moltype = AA   length = 86
FEATURE                 Location/Qualifiers
REGION                  1..86
                        note = Description of Artificial Sequence: Synthetic
                         polypeptide
source                  1..86
                        mol_type = protein
                        organism = synthetic construct
SEQUENCE: 20
ALSNSIMYFS HFVPVFLPAK PTTTPAPRPP TPAPTIASQP LSLRPEACRP AAGGAVHTRG     60
LDIYIWAPLA GTCGVLLLSL VITLYC                                          86

SEQ ID NO: 21           moltype = AA   length = 83
FEATURE                 Location/Qualifiers
REGION                  1..83
                        note = Description of Artificial Sequence: Synthetic
                         polypeptide
source                  1..83
                        mol_type = protein
                        organism = synthetic construct
SEQUENCE: 21
ALSNSIMYFS HFVPVFLPAK PTTTPAPRPP TPAPTIASQP LSLRPEACRP AAGGAVHTRG     60
LDIYIWAPLA GTCGVLLLSL VIT                                             83

SEQ ID NO: 22           moltype = AA   length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 22
LYCRRLKIQV RKAAITSYEK SDGVYTGLST RNQETYETLK HEKPPQ                    46

SEQ ID NO: 23           moltype = AA   length = 45
FEATURE                 Location/Qualifiers
REGION                  1..45
                        note = Description of Artificial Sequence: Synthetic
                         polypeptide
source                  1..45
                        mol_type = protein
                        organism = synthetic construct
SEQUENCE: 23
LYCRLKIQVR KAAITSYEKS DGVYTGLSTR NQETYETLKH EKPPQ                     45
```

```
SEQ ID NO: 24          moltype = AA   length = 42
FEATURE                Location/Qualifiers
REGION                 1..42
                       note = Description of Artificial Sequence: Synthetic
                        polypeptide
source                 1..42
                       mol_type = protein
                       organism = synthetic construct
SEQUENCE: 24
RLKIQVRKAA ITSYEKSDGV YTGLSTRNQE TYETLKHEKP PQ                             42

SEQ ID NO: 25          moltype = AA   length = 43
FEATURE                Location/Qualifiers
REGION                 1..43
                       note = Description of Artificial Sequence: Synthetic
                        polypeptide
source                 1..43
                       mol_type = protein
                       organism = synthetic construct
SEQUENCE: 25
RRLKIQVRKA AITSYEKSDG VYTGLSTRNQ ETYETLKHEK PPQ                            43

SEQ ID NO: 26          moltype = AA   length = 35
FEATURE                Location/Qualifiers
REGION                 1..35
                       note = Description of Artificial Sequence: Synthetic
                        polypeptide
source                 1..35
                       mol_type = protein
                       organism = synthetic construct
SEQUENCE: 26
YEDMRGILYA APQLRSIRGQ PGPNHEEDAD SYENM                                     35

SEQ ID NO: 27          moltype = AA   length = 62
FEATURE                Location/Qualifiers
REGION                 1..62
                       note = Description of Artificial Sequence: Synthetic
                        polypeptide
source                 1..62
                       mol_type = protein
                       organism = synthetic construct
SEQUENCE: 27
KKVAKKPTNK APHPKQEPQE INFPDDLPGS NTAAPVQETL HGCQPVTQED GKESRISVQE          60
RQ                                                                        62

SEQ ID NO: 28          moltype = AA   length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 28
QRWKSKLYSI VCGKSTPEKE GELEGTTTKP LAPNPSFSPT PGFTPTLGFS PVPSSTFTSS          60
STYTPGDCPN FAAPRREVAP PYQGADPILA TALASDPIPN PLQKWEDSAH KPQSLDTDDP         120
ATLYAVVENV PPLRWKEFVR RLGLSDHEID RLELQNGRCL REAQYSMLAT WRRRTPRREA         180
TLELLGRVLR DMDLLGCLED IEEALCGPAA LPPAPSLLR                                219

SEQ ID NO: 29          moltype = AA   length = 171
FEATURE                Location/Qualifiers
REGION                 1..171
                       note = Description of Artificial Sequence: Synthetic
                        polypeptide
source                 1..171
                       mol_type = protein
                       organism = synthetic construct
SEQUENCE: 29
PLCLQREAKV PHLPADKARG TQGPEQQHLL ITAPSSSSSS LESSASALDR RAPTRNQPQA          60
PGVEASGAGE ARASTGSSDS SPGGHGTQVN VTCIVNVCSS SDHSSQCSSQ ASSTMGDTDS         120
SPSESPKDEQ VPFSKEECAF RSQLETPETL LGSTEEKPLP LGVPDAGMKP S                  171

SEQ ID NO: 30          moltype = AA   length = 211
FEATURE                Location/Qualifiers
REGION                 1..211
                       note = Description of Artificial Sequence: Synthetic
                        polypeptide
source                 1..211
```

```
                              mol_type = protein
                              organism = synthetic construct
SEQUENCE: 30
MSNGYSTDEN FRYLISCFRA RVKMYIQVEP VLDYLTFLPA EVKEQIQRTV ATSGNMQAVE      60
LLLSTLEKGV WHLGWTREFV EALRRTGSPL AARYMNPELT DLPSPSFENA HDEYLQLLNL     120
LQPTLVDKLL VRDVLDKCME EELLTIEDRN RIAAAENNGN ESGVRELLKR IVQKENWFSA     180
FLNVLRQTGN NELVQELTGS DCSESNAEIE N                                    211

SEQ ID NO: 31                 moltype = AA   length = 191
FEATURE                       Location/Qualifiers
REGION                        1..191
                              note = Description of Artificial Sequence: Synthetic
                               polypeptide
source                        1..191
                              mol_type = protein
                              organism = synthetic construct
SEQUENCE: 31
MEFGLSWLFL VAILKGVQCG LLDLRQGMFA QLVAQNVLLI DGPLSWYSDP GLAGVSLTGG      60
LSYKEDTKEL VVAKAGVYYV FFQLELRRVV AGEGSGSVSL ALHLQPLRSA AGAAALALTV     120
DLPPASSEAR NSAFGFQGRL LHLSAGQRLG VHLHTEARAR HAWQLTQGAT VLGLFRVTPE     180
IPAGLPSPRS E                                                          191

SEQ ID NO: 32                 moltype = AA   length = 247
FEATURE                       Location/Qualifiers
REGION                        1..247
                              note = Description of Artificial Sequence: Synthetic
                               polypeptide
source                        1..247
                              mol_type = protein
                              organism = synthetic construct
SEQUENCE: 32
QVQLVQSGAE VKKPGASVKV SCKASGYTFT NYGMNWVRQA PGQGLEWMGW INTYTGEPTY      60
ADAFKGRVTM TTDTSTSTAY MELRSLRSDD TAVYYCARDY GDYGMDYWGQ GTTVTVSSGS     120
TSGSGKPGSS EGSTKGDIVM TQSPDSLAVS LGERATINCR ASKSVSTSGY SPMHWYQQKP     180
GQPPKLLIYL ASNLESGVPD RFSGSGSGTD FTLTISSLQA EDVAVYYCQH SREVPWTFGQ     240
GTKVEIK                                                               247

SEQ ID NO: 33                 moltype = AA   length = 247
FEATURE                       Location/Qualifiers
REGION                        1..247
                              note = Description of Artificial Sequence: Synthetic
                               polypeptide
source                        1..247
                              mol_type = protein
                              organism = synthetic construct
SEQUENCE: 33
QVQLQESGPG LVKPSQTLSL TCTVSGGSIS SGYNWHWIRQ PPGKGLEWIG YIHYTGSTNY      60
NPALRSRVTI SVDTSKNQFS LKLSSVTAAD TAVYYCARIY NGNSFPYWGQ GTTVTVSSGG     120
GGSGGGGSGG GGSDIVMTQS PDSLAYSLGE RATINCKSSQ SLFNSGNQKN YLTWYQQKPG     180
QPPKLLIYWA STRESGVPDR FSGSGSGTDI FITISSLQAE DVAVYYCQNA YSFPYTFGGG     240
TKLEIKR                                                               247

SEQ ID NO: 34                 moltype = AA   length = 244
FEATURE                       Location/Qualifiers
REGION                        1..244
                              note = Description of Artificial Sequence: Synthetic
                               polypeptide
source                        1..244
                              mol_type = protein
                              organism = synthetic construct
SEQUENCE: 34
DIQLTQSPSS LSASVGDRVS ITCKASQDVS IAVAWYQQKP GKAPKLLIYS ASYRYTGVPD      60
RFSGSGSGTD FTLTISSLQP EDFAVYYCQQ HYITPLTFGA GTKVEIKRGG GGSGGGGSGG     120
GGSQVQLQQS GSELKKPGAS VKVSCKASGY TFTNYGMNWV KQAPGQGLKW MGWINTYTGE     180
PTYTDDFKGR FAFSLDTSVS TAYLQISSLK ADDTAVYFCA RGGFGSSYWY FDVWGQGSLV     240
TVSS                                                                  244

SEQ ID NO: 35                 moltype = AA   length = 244
FEATURE                       Location/Qualifiers
REGION                        1..244
                              note = Description of Artificial Sequence: Synthetic
                               polypeptide
source                        1..244
                              mol_type = protein
                              organism = synthetic construct
SEQUENCE: 35
QVQLQQSGSE LKKPGASVKV SCKASGYTFT NYGMNWVKQA PGQGLKWMGW INTYTGEPTY      60
TDDFKGRFAF SLDTSVSTAY LQISSLKADD TAVYFCARGG FGSSYWYFDV WGQGSLVTVS     120
SGGGGSGGGG SGGGGSDIQL TQSPSSLSAS VGDRVSITCK ASQDVSIAVA WYQQKPGKAP     180
```

```
KLLIYSASYR YTGVPDRFSG SGSGTDFTLT ISSLQPEDFA VYYCQQHYIT PLTFGAGTKV  240
EIKR                                                              244

SEQ ID NO: 36            moltype = AA  length = 186
FEATURE                  Location/Qualifiers
REGION                   1..186
                         note = Description of Artificial Sequence: Synthetic
                         polypeptide
source                   1..186
                         mol_type = protein
                         organism = synthetic construct
SEQUENCE: 36
MTTEQRRSLQ AFQDYIRKTL DPTYILSYMA PWFREEEVQY IQAEKNNKGP MEAATLFLKF  60
LLELQEEGWF RGFLDALDHA GYSGLYEAIE SWDFKKIEKL EEYRLLLKRL QPEFKTRIIP  120
TDIISDLSEC LINQECEEIL QICSTKGMMA GAEKLVECLL RSDKENWPKT LKLALEKERN  180
KFSELW                                                            186

SEQ ID NO: 37            moltype = AA  length = 296
FEATURE                  Location/Qualifiers
REGION                   1..296
                         note = Description of Artificial Sequence: Synthetic
                         polypeptide
source                   1..296
                         mol_type = protein
                         organism = synthetic construct
SEQUENCE: 37
MAAGGPGAGS AAPVSSTSSL PLAALNMRVR RRLSLFLNVR TQVAADWTAL AEEMDFEYLE  60
IRQLETQADP TGRLLDAWQG RPGASVGRLL ELLTKLGRDD VLLELGPSIE EDCQKYILKQ  120
QQEEAEKPLQ VAAVDSSVPR TAELAGITTL DDPLGHMPER FDAFICYCPS DIQFVQEMIR  180
QLEQTNYRLK LCVSDRDVLP GTCVWSIASE LIEKRCRRMV VVVSDDYLQS KECDFQTKFA  240
LSLSPGAHQK RLIPIKYKAM KKEFPSILRF ITVCDYTNPC TKSWFWTRLA KALSLP     296

SEQ ID NO: 38            moltype = AA  length = 39
FEATURE                  Location/Qualifiers
REGION                   1..39
                         note = Description of Artificial Sequence: Synthetic
                         polypeptide
source                   1..39
                         mol_type = protein
                         organism = synthetic construct
SEQUENCE: 38
VTVGSLKTSA VPSTSTMSQE PELLISGMEK PLPLRTDFS                         39

SEQ ID NO: 39            moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 39
PSYPMPVQET QAPES                                                   15

SEQ ID NO: 40            moltype = AA  length = 50
FEATURE                  Location/Qualifiers
REGION                   1..50
                         note = Description of Artificial Sequence: Synthetic
                         polypeptide
source                   1..50
                         mol_type = protein
                         organism = synthetic construct
SEQUENCE: 40
SSAWLDSSSE NRGLGSELSK PGVLASQVDS PFSGCFEDLA ISASTSLGMG             50

SEQ ID NO: 41            moltype = AA  length = 255
FEATURE                  Location/Qualifiers
REGION                   1..255
                         note = Description of Artificial Sequence: Synthetic
                         polypeptide
source                   1..255
                         mol_type = protein
                         organism = synthetic construct
SEQUENCE: 41
MACTGPSLPS AFDILGAAGQ DKLLYLKHKL KTPRPGCQGQ DLLHAMVLLK LGQETEARIS  60
LEALKADAVA RLVARQWAGV DSTEDPEEPP DVSWAVARLY HLLAEEKLCP ASLRDVAYQE  120
AVRTLSSRDD HRLGELQDEA RNRCGWDIAG DPGSIRTLQS NLGCLPPSSA LPSGTRSLPR  180
PIDGVSDWSQ GCSLRSTGSP ASLASNLEIS QSPTMPFLSL HRSPHGPSKL CDDPQASLVP  240
EPVPGGCQEP EEMSW                                                  255
```

```
SEQ ID NO: 42            moltype = AA   length = 23
FEATURE                  Location/Qualifiers
REGION                   1..23
                         note = Description of Artificial Sequence: Synthetic peptide
source                   1..23
                         mol_type = protein
                         organism = synthetic construct
SEQUENCE: 42
MSTEITEIST PSLHISQYSN VNP                                            23

SEQ ID NO: 43            moltype = AA   length = 235
FEATURE                  Location/Qualifiers
REGION                   1..235
                         note = Description of Artificial Sequence: Synthetic
                          polypeptide
source                   1..235
                         mol_type = protein
                         organism = synthetic construct
SEQUENCE: 43
GSIRTLQSNL GCLPPSSALP SGTRSLPRPI DGVSDWSQGC SLRSTGSPAS LASNLEISQS     60
PTMPFLSLHR SPHGPSKLCD DPQASLVPEP VPGGCQEPEE MSWPPSGEIA SPPELPSSPP    120
PGLPEVAPDA TSTGLPDTPA APETSTNYPV ECTEGSAGPQ SLPLPILEPV KNPCSVKDQT    180
PLQLSVEDTT SPNTKPCPPT PTTPETSPPP PPPPPSSTPC SAHLTPSSLF PSSLE         235

SEQ ID NO: 44            moltype = AA   length = 393
FEATURE                  Location/Qualifiers
REGION                   1..393
                         note = Description of Artificial Sequence: Synthetic
                          polypeptide
source                   1..393
                         mol_type = protein
                         organism = synthetic construct
SEQUENCE: 44
GSIRTLQSNL GCLPPSSALP SGTRSLPRPI DGVSDWSQGC SLRSTGSPAS LASNLEISQS     60
PTMPFLSLHR SPHGPSKLCD DPQASLVPEP VPGGCQEPEE MSWPPSGEIA SPPELPSSPP    120
PGLPEVAPDA TSTGLPDTPA APETSTNYPV ECTEGSAGPQ SLPLPILEPV KNPCSVKDQT    180
PLQLSVEDTT SPNTKPCPPT PTTPETSPPP PPPPPSSTPC SAHLTPSSLF PSSLESSSEQ    240
KFYNFVILHA RADEHIALRV REKLEALGVP DGATFCEDFQ VPGRGELSCL QDAIDHSAFI    300
ILLLTSNFDC RLSLHQVNQA MMSNLTRQGS PDCVIPFLPL ESSPAQLSSD TASLLSGLVR    360
LDEHSQIFAR KVANTFKPHR LQARKAMWRK EQD                                 393

SEQ ID NO: 45            moltype = AA   length = 69
FEATURE                  Location/Qualifiers
REGION                   1..69
                         note = Description of Artificial Sequence: Synthetic
                          polypeptide
source                   1..69
                         mol_type = protein
                         organism = synthetic construct
SEQUENCE: 45
PSYPMPVQET QAPESGGGSS SAWLDSSSEN RGLGSELSKP GVLASQVDSP FSGCFEDLAI     60
SASTSLGMG                                                             69

SEQ ID NO: 46            moltype = AA   length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 46
ILLPLIIGLI LLGLLALVLI AFAII                                           25

SEQ ID NO: 47            moltype = AA   length = 607
FEATURE                  Location/Qualifiers
REGION                   1..607
                         note = Description of Artificial Sequence: Synthetic
                          polypeptide
source                   1..607
                         mol_type = protein
                         organism = synthetic construct
SEQUENCE: 47
MWLQSLLLLG TVACSISEIQ LVQSGGGLVK PGGSVRISCA ASGYTFTNYG MNWVRQAPGK     60
GLEWMGWINT HTGEPTYADS FKGRFTFSLD DSKNTAYLQI NSLRAEDTAV YFCTRRGYDW    120
YFDVWGQGTT VTVSSGGGGS GGGGSGGGGS DIQMTQSPSS LSASVGDRVT ITCRASQDIN    180
SYLSWFQQKP GKAPKTLIYR ANRLESGVPS RFSGSGSGTD YTLTISSLQY EDFGIYYCQQ    240
YDESPWTFGG GTKLEIKSGG GGSGALSNSI MYFSHFVPVF LPAKPTTTPA PRPPTPAPTI    300
ASQPLSLRPE ACRPAAGGAV HTRGLDIYIW APLAGTCGVL LLSLVITLYC RLKIQVRKAA    360
ITSYEKSDGV YTGLSTRNQE TYETLKHEKP PQGSGSMSNG YSTDENFRYL ISCFRARVKM    420
```

```
YIQVEPVLDY LTFLPAEVKE QIQRTVATSG NMQAVELLLS TLEKGVWHLG WTREFVEALR    480
RTGSPLAARY MNPELTDLPS PSFENAHDEY LQLLNLLQPT LVDKLLVRDV LDKCMEEELL    540
TIEDRNRIAA AENNGNESGV RELLKRIVQK ENWFSAFLNV LRQTGNNELV QELTGSDCSE    600
SNAEIEN                                                              607

SEQ ID NO: 48           moltype = DNA   length = 1821
FEATURE                 Location/Qualifiers
misc_feature            1..1821
                        note = Description of Artificial Sequence: Synthetic
                         polynucleotide
source                  1..1821
                        mol_type = other DNA
                        organism = synthetic construct
SEQUENCE: 48
atgtggctgc agagcctgct gctgctgggc accgtggcgt gcagcattag cgaaattcag    60
ctggtgcaga gcggcggcgg cctggtgaaa ccgggcggca gcgtgcgcat tagctgcgcg    120
gcgagcggct atacctttac caactatggc atgaactggg tgcgccaggc gccgggcaaa    180
ggcctggaat ggatgggctg gattaacacc cataccggcg aaccgaccta tgcggatagc    240
tttaaaggcc gctttacctt tagcctggat gatagcaaaa acaccgcgta tctgcagatt    300
aacagcctgc gcgcggaaga taccgcggtg tattttgtgc ccgccgcggg ctatgattgg    360
tattttgatg tgtggggcca gggcaccacc gtgaccgtga gcgcggcggc ggcggcagcg    420
gccggcggcg gcagcggcgg cggcggcagc gatattcaga tgacccagag cccgagcagc    480
ctgagcgcga gcgtgggcga tcgcgtgacc attcctgcc gcgcgagcca ggatattaac    540
agctatctga gctggtttca gcagaaaccg ggcaaagcgc gaaaaccct gatttatcgc    600
gcgaaccgcc tggaaagcgg cgtgccgagc cgctttagcg gcagcggcag cggcaccgat    660
tatacctga ccattagcag cctgcagtat gaagattttg cattattat tgccagcag    720
tatgatgaaa gcccgtggac ctttggcggc ggcaccaaac tggaaattaa agcggcggc    780
ggcggcagcg gcgcgctgag caacagcatt atgtatttta gccattttgt gccggtgttt    840
ctgccggcga aaccgaccac caccccggcg ccgcgcccgc cgaccccggc cgaccatt    900
gcgagccagc cgctgagcct gcgccccgaa gcgtgccgcc cggcgcggg ccgcgcgtg    960
catacccgcg gcctggatat ttatatttgg gcgccgctgg cgggcacctg cggcgtgctg    1020
ctgctgagcc tggtgattac cctgtattgc cgcctgaaaa ttcaggtgcg caaagcggcg    1080
attaccagct atgaaaaaag cgatggcgtg tataccggcc tgagcacccg caaccaggaa    1140
acctatgaaa ccctgaaaca tgaaaaaccg ccgcagggca gcggcagcat gagcaacggc    1200
tatagcaccg atgaaaactt tcgctatctg attagctgct ttcgcgcgcg cgtgaaaatg    1260
tatattcagg tggaaccggt gctggattat ctgaccttc tgccggcgga agtgaaagaa    1320
cagattcagc gcaccgtggc gaccagcggc aacatgcagg cggtggaact gctgctgagc    1380
acccctggaaa aaggcgtgtg gcatctgggc tggacccgcg aatttgtgga agcgctgcgc    1440
cgcaccggca gcccgctggc ggcgcgctat atgaaccgca aactgaccga tctgccgagc    1500
ccgagctttg aaaacgcgca tgatgaatat ctgcagctgc tgaacctgct gcagccgacc    1560
ctggtgata aactgctggt gcgcgatgtg ctggataaat gcatggaaga gaactgctg    1620
accattgaag atcgcaaccg cattgcgcg cggaaaaca acggcaacga aagcggcgtg    1680
cgcgaactgc tgaaacgcat tgtgcagaaa gaaaactggt ttagcgcgtt tctgaacgtg    1740
ctgcgccaga ccggcaacaa cgaactggtg caggaactga ccggcagcga ttgcagcgaa    1800
agcaacgcgg aaattgaaaa c                                              1821

SEQ ID NO: 49           moltype = DNA   length = 1821
FEATURE                 Location/Qualifiers
misc_feature            1..1821
                        note = Description of Artificial Sequence: Synthetic
                         polynucleotide
source                  1..1821
                        mol_type = other DNA
                        organism = synthetic construct
SEQUENCE: 49
atgtggctgc agagcctgct gctgctgggc accgtggcgt gcagcattag cgaaattcag    60
ctggtgcaga gcggcggcgg cctggtgaaa ccgggcggca gcgtgcgcat tagctgcgcg    120
gcgagcggct atacctttac caactatggc atgaactggg tgcgccaggc gccgggcaaa    180
ggcctggaat ggatgggctg gattaacacc cataccggcg aaccgaccta tgcggatagc    240
tttaaaggcc gctttacctt tagcctggat gatagcaaaa acaccgcgta tctgcagatt    300
aacagcctgc gcgcggaaga taccgcggtg tattttgtgc ccgccgcggg ctatgattgg    360
tattttgatg tgtggggcca gggcaccacc gtgaccgtga gcgcggcggc ggcggcagcg    420
gccggcggcg gcagcggcgg cggcggcagc gatattcaga tgacccagag cccgagcagc    480
ctgagcgcga gcgtgggcga tcgcgtgacc attcctgcc gcgcgagcca ggatattaac    540
agctatctga gctggtttca gcagaaaccg ggcaaagcgc gaaaaccct gatttatcgc    600
gcgaaccgcc tggaaagcgg cgtgccgagc cgctttagcg gcagcggcag cggcaccgat    660
tatcctga ccattagcag cctgcagtat gaagattttg cattattat tgccagcag    720
tatgatgaaa gcccgtggac ctttggcggc ggcaccaaac tggaaattaa agcggcggc    780
ggcggcagcg gcgcgctgag caacagcatt atgtatttta gccattttgt gccggtgttt    840
ctgccggcga aaccgaccac caccccggcg ccgcgcccgc cgaccccggc cgaccatt    900
gcgagccagc cgctgagcct gcgccccgaa gcgtgccgcc cggcgcggg ccgcgcgtg    960
catacccgcg gcctggatat ttatatttgg gcgccgctgg cgggcacctg cggcgtgctg    1020
ctgctgagcc tggtgattac cctgtattgc cgcctgaaaa ttcaggtgcg caaagcggcg    1080
attaccagct atgaaaaaag cgatggcgtg tataccggcc tgagcacccg caaccaggaa    1140
acctatgaaa ccctgaaaca tgaaaaaccg ccgcagggca gcggcagcat gagcaacggc    1200
tatagcaccg atgaaaactt tcgctatctg attagctgct ttcgcgcgcg cgtgaaaatg    1260
tatattcagg tggaaccggt gctggattat ctgaccttc tgccggcgga agtgaaagaa    1320
cagattcagc gcaccgtggc gaccagcggc aacatgcagg cggtggaact gctgctgagc    1380
acccctggaaa aaggcgtgtg gcatctgggc tggacccgcg aatttgtgga agcgctgcgc    1440
```

```
cgcaccggca gcccgctggc ggcgcgctat atgaacccgg aactgaccga tctgccgagc 1500
ccgagctttg aaaacgcgca tgatgaatat ctgcagctgc tgaacctgct gcagccgacc 1560
ctggtggata aactgctggt gcgcgatgtg ctggataaat gcatggaaga agaactgctg 1620
accattgaag atcgcaaccg cattgcggcg gcggaaaaca acggcaacga aagcggcgtg 1680
cgcgaactgc tgaaacgcat tgtgcagaaa gaaaactggt ttagcgcgtt tctgaacgtg 1740
ctgcgccaga ccggcaacaa cgaactggtg caggaactga ccggcagcga ttgcagcgaa 1800
agcaacgcgg aaattgaaaa c                                         1821

SEQ ID NO: 50           moltype = AA  length = 615
FEATURE                 Location/Qualifiers
REGION                  1..615
                        note = Description of Artificial Sequence: Synthetic
                        polypeptide
source                  1..615
                        mol_type = protein
                        organism = synthetic construct
SEQUENCE: 50
MWLQSLLLLG TVACSISEIQ LVQSGGGLVK PGGSVRISCA ASGYTFTNYG MNWVRQAPGK   60
GLEWMGWINT HTGEPTYADS FKGRFTFSLD DSKNTAYLQI NSLRAEDTAV YFCTRRGYDW  120
YFDVWGQGTT VTVSSGGGGS GGGGSGGGGS DIQMTQSPSS LSASVGDRVT ITCRASQDIN  180
SYLSWFQQKP GKAPKTLIYR ANRLESGVPS RFSGSGSGTD YTLTISSLQY EDFGIYYCQQ  240
YDESPWTFGG GTKLEIKSGG GGSGALSNSI MYFSHFVPVF LPAKPTTTPA PRPPTPAPTI  300
ASQPLSLRPE ACRPAAGGAV HTRGLDIYIW APLAGTCGVL LLSLVITLYC RLKIQVRKAA  360
ITSYEKSDGV YTGLSTRNQE TYETLKHEKP PQGSGSQRWK SKLYSIVCGK STPEKEGELE  420
GTTTKPLAPN PSFSPTPGFT PTLGFSPVPS STFTSSSTYT PGDCPNFAAP RREVAPPYQG  480
ADPILATALA SDPIPNPLQK WEDSAHKPQS LDTDDPATLY AVVENVPPLR WKEFVRRLGL  540
SDHEIDRLEL QNGRCLREAQ YSMLATWRRR TPRREATLEL LGRVLRDMDL LGCLEDIEEA  600
LCGPAALPPA PSLLR                                                  615

SEQ ID NO: 51           moltype = DNA  length = 1845
FEATURE                 Location/Qualifiers
misc_feature            1..1845
                        note = Description of Artificial Sequence: Synthetic
                        polynucleotide
source                  1..1845
                        mol_type = other DNA
                        organism = synthetic construct
SEQUENCE: 51
atgtggctgc agagcctgct gctgctgggc accgtggcgt gcagcattag cgaaattcag   60
ctggtgcaga gcggcggcgg cctggtgaaa ccgggcggca gcgtgcgcat tagctgcgcg  120
gcgagcggct atacctttac caactatggc atgaactggg tgcgccaggc gccgggcaaa  180
ggcctggaat ggatgggctg gattaacacc cataccggcg aaccgaccta tgcggatagc  240
tttaaaggcc gctttacctt tagcctggat gatagcaaaa acaccgcgta tctgcagatt  300
aacagcctgc gcgcggaaga taccgcggtg tattttgca  cccgccgcgg ctatgattgg  360
tattttgatg tgtggggcca gggcaccacc gtgaccgtga gcagcggcgg cggcggcagc  420
ggcggcggcg gcagcggcgg cggcggcagc gatattcaga tgacccagag cccgagcagc  480
ctgagcgcga gcgtgggcga tcgcgtgacc attacctgcc gcgcgagcca ggatattaac  540
agctatctga gctggtttca gcagaaaccg ggcaaagcgc cgaaaaccct gatttatcgc  600
gcgaacccgc tggaaagcgg cgtgccgagc cgctttagcg gcagcggcag cggcaccgat  660
tatacccgc ccattagcag cctgcagtat gaagattttg gcatttatta ttgccagcag  720
tatgatgaaa gcccgtggac ctttggcggc ggcaccaaac tggaaattaa aagcggcggc  780
ggcggcagcg gcgcgctgag caacagcatt atgtatttta gccattttgt gccggtgttt  840
ctgccggcga aaccgaccac caccccggcg ccgcgcccgc cgaccccggc gccgaccatt  900
gcgagccagc cgctgagcct gcgcccggaa gcgtgccgcc cggcggcggg cggcgcggtg  960
cataccggcg gcctggatat ttatatttgg gcgccgctgg cgggcacctg cggcgtgctg 1020
ctgctgagcc tggtgattac cctgtattgc cgcctgaaaa ttcaggtgcg caaagcggcg 1080
attaccagct atgaaaaaag cgatggcgtg tataccggcc tgagcacccg caaccaggaa 1140
acctatgaaa ccctgaaaca tgaaaaaccg cagggcgcgg cagcca gcgctggaaa 1200
agcaaactgt atagcattgt gtgcggcaaa agcaccccgg aaaaagaagg cgaactggaa 1260
ggcaccacca ccaaaccgct ggcgccgaac ccgagcttta gcccgacccg gggctttacc 1320
ccgaccctgg gctttagccc ggtgccgagc agcaccttta ccagcagcag cacctatacc 1380
ccgggcgatt gcccgaactt tgcggcgccg cgccgcgaag tggcgccgcc gtatcagggc 1440
gcggatccga ttctggcgac cgcgctggcg agcgatccga ttccgaaccc gctgcagaaa 1500
tgggaagata gcgcgcataa accgcagagc ctggataccg atgatccggc gacc ctgtat 1560
gcggtggtgg aaaacgtgcc gccgctgcgc tggaaagaat tgtgcgccg cctgggcctg 1620
agcgatcatg aaattgatcg cctggaactg cagaacggcc gctgcctgcg cgaagcgcag 1680
tatagcatgc tggcgacctg gcgccgccgc accccgcgcc gcgaagcgac cctggaactg 1740
ctgggccgcg tgctgcgcga tatggatctg ctgggctgcc tggaagatat tgaagaagcg 1800
ctgtgcggcc cggcggcgct gccgccgccg ccgagcctgc tgcgc            1845

SEQ ID NO: 52           moltype = AA  length = 436
FEATURE                 Location/Qualifiers
REGION                  1..436
                        note = Description of Artificial Sequence: Synthetic
                        polypeptide
source                  1..436
                        mol_type = protein
                        organism = synthetic construct
SEQUENCE: 52
```

```
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SSGGGGSGAL SNSIMYFSHF VPVFLPAKPT TTPAPRPPTP   300
APTIASQPLS LRPEACRPAA GGAVHTRGLD IYIWAPLAGT CGVLLLSLVI TLYCRRLKIQ   360
VRKAAITSYE KSDGVYTGLS TRNQETYETL KHEKPPQGSG SYEDMRGILY AAPQLRSIRG   420
QPGPNHEEDA DSYENM                                                  436

SEQ ID NO: 53           moltype = AA  length = 450
FEATURE                 Location/Qualifiers
REGION                  1..450
                        note = Description of Artificial Sequence: Synthetic
                          polypeptide
source                  1..450
                        mol_type = protein
                        organism = synthetic construct
SEQUENCE: 53
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAADYKDDD DKSGGGGSGA LSNSIMYFSH FVPVFLPAKP   300
TTTPAPRPPT PAPTIASQPL SLRPEACRPA AGGAVHTRGL DIYIWAPLAG TCGVLLLSLV   360
ITLYCRRLKI QVRKAAITSY EKSDGVYTGL STRNQETYET LKHEKPPQGS GSKKLLYIFK   420
QPFMRPVQTT QEEDGCSCRF PEEEEGGCEL                                   450

SEQ ID NO: 54           moltype = AA  length = 452
FEATURE                 Location/Qualifiers
REGION                  1..452
                        note = Description of Artificial Sequence: Synthetic
                          polypeptide
source                  1..452
                        mol_type = protein
                        organism = synthetic construct
SEQUENCE: 54
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAADYKDDD DKSGGGGSGA LSNSIMYFSH FVPVFLPAKP   300
TTTPAPRPPT PAPTIASQPL SLRPEACRPA AGGAVHTRGL DIYIWAPLAG TCGVLLLSLV   360
ITLYCKRGRK KLLYIFKQPF MRPVQTTQEE DGCSCRFPEE EEGGCELGSG SLKIQVRKAA   420
ITSYEKSDGV YTGLSTRNQE TYETLKHEKP PQ                                452

SEQ ID NO: 55           moltype = AA  length = 395
FEATURE                 Location/Qualifiers
REGION                  1..395
                        note = Description of Artificial Sequence: Synthetic
                          polypeptide
source                  1..395
                        mol_type = protein
                        organism = synthetic construct
SEQUENCE: 55
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAAILLPLI IGLILLGLLA LVLIAFAIIK KVAKKPTNKA   300
PHPKQEPQEI NFPDDLPGSN TAAPVQETLH GCQPVTQEDG KESRISVQER QGSRLKIQVR   360
KAAITSYEKS DGVYTGLSTR NQETYETLKH EKPPQ                              395

SEQ ID NO: 56           moltype = AA  length = 549
FEATURE                 Location/Qualifiers
REGION                  1..549
                        note = Description of Artificial Sequence: Synthetic
                          polypeptide
source                  1..549
                        mol_type = protein
                        organism = synthetic construct
SEQUENCE: 56
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAAILLPLI IGLILLGLLA LVLIAFAIIR RLKIQVRKAA   300
ITSYEKSDGV YTGLSTRNQE TYETLKHEKP PQGSGSGSMS NGYSTDENFR YLISCFRARV   360
KMYIQVEPVL DYLTFLPAEV KEQIQRTVAT SGNMQAVELL LSTLEKGVWH LGWTREFVEA   420
LRRTGSPLAA RYMNPELTDL PSPSFENAHD EYLQLLNLLQ PTLVDKLLVR DVLDKCMEEE   480
```

```
LLTIEDRNRI AAAENNGNES GVRELLKRIV QKENWFSAFL NVLRQTGNNE LVQELTGSDC    540
SESNAEIEN                                                           549

SEQ ID NO: 57           moltype = AA  length = 357
FEATURE                 Location/Qualifiers
REGION                  1..357
                        note = Description of Artificial Sequence: Synthetic
                         polypeptide
source                  1..357
                        mol_type = protein
                        organism = synthetic construct
SEQUENCE: 57
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAAGSQLPT PVWFHVLFYL AVGIMFLVNT VLWVTIRKEL   300
KRKKKWDLEI SLDSGHEKKV ISSLQEDRHL EEELKCQEQK EEQLQEGVHR KEPQGAT      357

SEQ ID NO: 58           moltype = AA  length = 337
FEATURE                 Location/Qualifiers
REGION                  1..337
                        note = Description of Artificial Sequence: Synthetic
                         polypeptide
source                  1..337
                        mol_type = protein
                        organism = synthetic construct
SEQUENCE: 58
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SAAAGSDSIH QDYTTQNLIR MAVAGLVLVA LLAILVENWH   300
SHTALNKEAS ADVAEPSWSQ QMCQPGLTFA RTPSVCK                            337

SEQ ID NO: 59           moltype = AA  length = 444
FEATURE                 Location/Qualifiers
REGION                  1..444
                        note = Description of Artificial Sequence: Synthetic
                         polypeptide
source                  1..444
                        mol_type = protein
                        organism = synthetic construct
SEQUENCE: 59
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SSGGGGSAAA GSDSIHQDYT TQNLIRMAVA GLVLVALLAI   300
LVENWHSHTA LNKEASADVA EPSWSQQMCQ PGLTFARTPS VCKGTKKVAK KPTNKAPHPK   360
QEPQEINFPD DLPGSNTAAP VQETLHGCQP VTQEDGKESR ISVQERQGSY EDMRGILYAA   420
PQLRSIRGQP GPNHEEDADS YENM                                         444

SEQ ID NO: 60           moltype = AA  length = 590
FEATURE                 Location/Qualifiers
REGION                  1..590
                        note = Description of Artificial Sequence: Synthetic
                         polypeptide
source                  1..590
                        mol_type = protein
                        organism = synthetic construct
SEQUENCE: 60
MWLQSLLLLG TVACSISDIQ MTQSPSSLSA SVGDRVTITC RASQDVNTAV AWYQQKPGKA    60
PKLLIYSASF LYSGVPSRFS GSRSGTDFTL TISSLQPEDF ATYYCQQHYT TPPTFGQGTK   120
VEIKRTGSTS GSGKPGSGEG SEVQLVESGG GLVQPGGSLR LSCAASGFNI KDTYIHWVRQ   180
APGKGLEWVA RIYPTNGYTR YADSVKGRFT ISADTSKNTA YLQMNSLRAE DTAVYYCSRW   240
GGDGFYAMDV WGQGTLVTVS SSGGGGSAAA ILLPLIIGLI LLGLLALVLI AFAIIRRLKI   300
QVRKAAITSY EKSDGVYTGL STRNQETYET LKHEKPPQGS GSYEDMRGIL YAAPQLRSIR   360
GQPGPNHEED ADSYENMGSM SNGYSTDENF RYLISCFRAR VKMYIQVEPV LDYLTFLPAE   420
VKEQIQRTVA TSGNMQAVEL LLSTLEKGVW HLGWTREFVE ALRRTGSPLA ARYMNPELTD   480
LPSPSFENAH DEYLQLLNLL QPTLVDKLLV RDVLDKCMEE ELLTIEDRNR IAAAENNGNE   540
SGVRELLKRI VQKENWFSAF LNVLRQTGNN ELVQELTGSD CSESNAEIEN              590

SEQ ID NO: 61           moltype = AA  length = 565
FEATURE                 Location/Qualifiers
REGION                  1..565
                        note = Description of Artificial Sequence: Synthetic
                         polypeptide
source                  1..565
```

```
                            mol_type = protein
                            organism = synthetic construct
SEQUENCE: 61
MWLQSLLLLG  TVACSISDIQ  MTQSPSSLSA  SVGDRVTITC  RASQDVNTAV  AWYQQKPGKA   60
PKLLIYSASF  LYSGVPSRFS  GSRSGTDFTL  TISSLQPEDF  ATYYCQQHYT  TPPTFGQGTK   120
VEIKRTGSTS  GSGKPGSGEG  SEVQLVESGG  GLVQPGGSLR  LSCAASGFNI  KDTYIHWVRQ   180
APGKGLEWVA  RIYPTNGYTR  YADSVKGRFT  ISADTSKNTA  YLQMNSLRAE  DTAVYYCSRW   240
GGDGFYAMDV  WGQGTLVTVS  SSGGGGSAAA  ILLPLIIGLI  LLGLLALVLI  AFAIIRRLKI   300
QVRKAAITSY  EKSDGVYTGL  STRNQETYET  LKHEKPPQGS  GSYEDMRGIL  YAAPQLRSIR   360
GQPGPNHEED  ADSYENMGSM  TTEQRRSLQA  FQDYIRKTLD  PTYILSYMAP  WFREEEVQYI   420
QAEKNNKGPM  EAATLFLKFL  LELQEEGWFR  GFLDALDHAG  YSGLYEAIES  WDFKKIEKLE   480
EYRLLLKRLQ  PEFKTRIIPT  DIISDLSECL  INQECEEILQ  ICSTKGMMAG  AEKLVECLLR   540
SDKENWPKTL  KLALEKERNK  FSELW                                           565

SEQ ID NO: 62           moltype = AA  length = 533
FEATURE                 Location/Qualifiers
REGION                  1..533
                        note = Description of Artificial Sequence: Synthetic
                        polypeptide
source                  1..533
                        mol_type = protein
                        organism = synthetic construct
SEQUENCE: 62
MWLQSLLLLG  TVACSISDIQ  MTQSPSSLSA  SVGDRVTITC  RASQDVNTAV  AWYQQKPGKA   60
PKLLIYSASF  LYSGVPSRFS  GSRSGTDFTL  TISSLQPEDF  ATYYCQQHYT  TPPTFGQGTK   120
VEIKRTGSTS  GSGKPGSGEG  SEVQLVESGG  GLVQPGGSLR  LSCAASGFNI  KDTYIHWVRQ   180
APGKGLEWVA  RIYPTNGYTR  YADSVKGRFT  ISADTSKNTA  YLQMNSLRAE  DTAVYYCSRW   240
GGDGFYAMDV  WGQGTLVTVS  SSGGGGSAAA  ILLPLIIGLI  LLGLLALVLI  AFAIIRRLKI   300
QVRKAAITSY  EKSDGVYTGL  STRNQETYET  LKHEKPPQGS  GSYEDMRGIL  YAAPQLRSIR   360
GQPGPNHEED  ADSYENMGSA  AGGPGAGSAA  PVSSTSSLPL  AALNMRVRRR  LSLFLNVRTQ   420
VAADWTALAE  EMDFEYLEIR  QLETQADPTG  RLLDAWQGRP  GASVGRLLEL  LTKLGRDDVL   480
LELGPSIEED  CQKYILKQQQ  EEAEKPLQVA  AVDSSVPRTA  ELAGITTLDD  PLG          533

SEQ ID NO: 63           moltype = AA  length = 418
FEATURE                 Location/Qualifiers
REGION                  1..418
                        note = Description of Artificial Sequence: Synthetic
                        polypeptide
source                  1..418
                        mol_type = protein
                        organism = synthetic construct
SEQUENCE: 63
MWLQSLLLLG  TVACSISDIQ  MTQSPSSLSA  SVGDRVTITC  RASQDVNTAV  AWYQQKPGKA   60
PKLLIYSASF  LYSGVPSRFS  GSRSGTDFTL  TISSLQPEDF  ATYYCQQHYT  TPPTFGQGTK   120
VEIKRTGSTS  GSGKPGSGEG  SEVQLVESGG  GLVQPGGSLR  LSCAASGFNI  KDTYIHWVRQ   180
APGKGLEWVA  RIYPTNGYTR  YADSVKGRFT  ISADTSKNTA  YLQMNSLRAE  DTAVYYCSRW   240
GGDGFYAMDV  WGQGTLVTVS  SSGGGGSAAA  ILLPLIIGLI  LLGLLALVLI  AFAIIRRLKI   300
QVRKAAITSY  EKSDGVYTGL  STRNQETYET  LKHEKPPQGS  GSYEDMRGIL  YAAPQLRSIR   360
GQPGPNHEED  ADSYENMGSV  TVGSLKTSAV  PSTSTMSQEP  ELLISGMEKP  LPLRTDFS     418

SEQ ID NO: 64           moltype = AA  length = 448
FEATURE                 Location/Qualifiers
REGION                  1..448
                        note = Description of Artificial Sequence: Synthetic
                        polypeptide
source                  1..448
                        mol_type = protein
                        organism = synthetic construct
SEQUENCE: 64
MWLQSLLLLG  TVACSISDIQ  MTQSPSSLSA  SVGDRVTITC  RASQDVNTAV  AWYQQKPGKA   60
PKLLIYSASF  LYSGVPSRFS  GSRSGTDFTL  TISSLQPEDF  ATYYCQQHYT  TPPTFGQGTK   120
VEIKRTGSTS  GSGKPGSGEG  SEVQLVESGG  GLVQPGGSLR  LSCAASGFNI  KDTYIHWVRQ   180
APGKGLEWVA  RIYPTNGYTR  YADSVKGRFT  ISADTSKNTA  YLQMNSLRAE  DTAVYYCSRW   240
GGDGFYAMDV  WGQGTLVTVS  SSGGGGSAAA  ILLPLIIGLI  LLGLLALVLI  AFAIIRRLKI   300
QVRKAAITSY  EKSDGVYTGL  STRNQETYET  LKHEKPPQGS  GSYEDMRGIL  YAAPQLRSIR   360
GQPGPNHEED  ADSYENMGSP  SYPMPVQETQ  APESGGGSSS  AWLDSSSENR  GLGSELSKPG   420
VLASQVDSPF  SGCFEDLAIS  ASTSLGMG                                         448

SEQ ID NO: 65           moltype = AA  length = 772
FEATURE                 Location/Qualifiers
REGION                  1..772
                        note = Description of Artificial Sequence: Synthetic
                        polypeptide
source                  1..772
                        mol_type = protein
                        organism = synthetic construct
SEQUENCE: 65
MWLQSLLLLG  TVACSISDIQ  MTQSPSSLSA  SVGDRVTITC  RASQDVNTAV  AWYQQKPGKA   60
PKLLIYSASF  LYSGVPSRFS  GSRSGTDFTL  TISSLQPEDF  ATYYCQQHYT  TPPTFGQGTK   120
```

```
VEIKRTGSTS GSGKPGSGEG SEVQLVESGG GLVQPGGSLR LSCAASGFNI KDTYIHWVRQ    180
APGKGLEWVA RIYPTNGYTR YADSVKGRFT ISADTSKNTA YLQMNSLRAE DTAVYYCSRW    240
GGDGFYAMDV WGQGTLVTVS SSGGGGSAAA ILLPLIIGLI LLGLLALVLI AFAIIRRLKI    300
QVRKAAITSY EKSDGVYTGL STRNQETYET LKHEKPPQGS GSYEDMRGIL YAAPQLRSIR    360
GQPGPNHEED ADSYENMGSG SIRTLQSNLG CLPPSSALPS GTRSLPRPID GVSDWSQGCS    420
LRSTGSPASL ASNLEISQSP TMPFLSLHRS PHGPSKLCDD PQASLVPEPV PGGCQEPEEM    480
SWPPSGEIAS PPELPSSPPP GLPEVAPDAT STGLPDTPAA PETSTNYPVE CTEGSAGPQS    540
LPLPILEPVK NPCSVKDQTP LQLSVEDTTS PNTKPCPPTP TTPETSPPPP PPPPSSTPCS    600
AHLTPSSLFP SSLESSSEQK FYNFVILHAR ADEHIALRVR EKLEALGVPD GATFCEDFQV    660
PGRGELSCLQ DAIDHSAFII LLLTSNFDCR LSLHQVNQAM MSNLTRQGSP DCVIPFLPLE    720
SSPAQLSSDT ASLLSGLVRL DEHSQIFARK VANTFKPHRL QARKAMWRKE QD            772

SEQ ID NO: 66           moltype = AA   length = 614
FEATURE                 Location/Qualifiers
REGION                  1..614
                        note = Description of Artificial Sequence: Synthetic
                        polypeptide
source                  1..614
                        mol_type = protein
                        organism = synthetic construct
SEQUENCE: 66
MWLQSLLLLG TVACSISDIQ MTQSPSSLSA SVGDRVTITC RASQDVNTAV AWYQQKPGKA     60
PKLLIYSASF LYSGVPSRFS GSRSGTDFTL TISSLQPEDF ATYYCQQHYT TPPTFGQGTK    120
VEIKRTGSTS GSGKPGSGEG SEVQLVESGG GLVQPGGSLR LSCAASGFNI KDTYIHWVRQ    180
APGKGLEWVA RIYPTNGYTR YADSVKGRFT ISADTSKNTA YLQMNSLRAE DTAVYYCSRW    240
GGDGFYAMDV WGQGTLVTVS SSGGGGSAAA ILLPLIIGLI LLGLLALVLI AFAIIRRLKI    300
QVRKAAITSY EKSDGVYTGL STRNQETYET LKHEKPPQGS GSYEDMRGIL YAAPQLRSIR    360
GQPGPNHEED ADSYENMGSG SIRTLQSNLG CLPPSSALPS GTRSLPRPID GVSDWSQGCS    420
LRSTGSPASL ASNLEISQSP TMPFLSLHRS PHGPSKLCDD PQASLVPEPV PGGCQEPEEM    480
SWPPSGEIAS PPELPSSPPP GLPEVAPDAT STGLPDTPAA PETSTNYPVE CTEGSAGPQS    540
LPLPILEPVK NPCSVKDQTP LQLSVEDTTS PNTKPCPPTP TTPETSPPPP PPPPSSTPCS    600
AHLTPSSLFP SSLE                                                      614

SEQ ID NO: 67           moltype = AA   length = 402
FEATURE                 Location/Qualifiers
REGION                  1..402
                        note = Description of Artificial Sequence: Synthetic
                        polypeptide
source                  1..402
                        mol_type = protein
                        organism = synthetic construct
SEQUENCE: 67
MWLQSLLLLG TVACSISDIQ MTQSPSSLSA SVGDRVTITC RASQDVNTAV AWYQQKPGKA     60
PKLLIYSASF LYSGVPSRFS GSRSGTDFTL TISSLQPEDF ATYYCQQHYT TPPTFGQGTK    120
VEIKRTGSTS GSGKPGSGEG SEVQLVESGG GLVQPGGSLR LSCAASGFNI KDTYIHWVRQ    180
APGKGLEWVA RIYPTNGYTR YADSVKGRFT ISADTSKNTA YLQMNSLRAE DTAVYYCSRW    240
GGDGFYAMDV WGQGTLVTVS SSGGGGSAAA ILLPLIIGLI LLGLLALVLI AFAIIRRLKI    300
QVRKAAITSY EKSDGVYTGL STRNQETYET LKHEKPPQGS GSYEDMRGIL YAAPQLRSIR    360
GQPGPNHEED ADSYENMGSM STEITEISTP SLHISQYSNV NP                       402

SEQ ID NO: 68           moltype = DNA   length = 1824
FEATURE                 Location/Qualifiers
misc_feature            1..1824
                        note = Description of Artificial Sequence: Synthetic
                        polynucleotide
source                  1..1824
                        mol_type = other DNA
                        organism = synthetic construct
SEQUENCE: 68
atgtggctgc agtctctgct gctgctggga acagtggcct gcagcatcag cgacatccag     60
atgacacaga gccctagcag cctgtctgcc tctgtgggcg atagagtgac catcacctgt    120
agagccagcc aggatgtgaa taccgccgtg gcctggtatc agcagaagcc tggaaaagcc    180
cctaagctgc tgatctacag cgccagcttt ctgtacagcg gcgtgccaag cagattcagc    240
ggcagcagat ctggcaccga cttcaccctg accatctcta gcctgcagcc tgaggacttc    300
gccacctact actgccagca gcactacacc acacctccaa cctttggcca gggcaccaag    360
gtggaaatca gagaacagg cagcaccagc ggctctggaa agcctggatc tggcgaagga    420
tctgaggtgc agctggttga atctggcgga ggacttgttc agcctggcgg ctctctgaga    480
ctgtcttgtg ccgccagcgg cttcaacatc aaggacacct acatccactg gtccgacag    540
gcccctggaa agggacttga atgggtcgc agaatctacc ccaccaacgg ctacaccaga    600
tacgccgata gcgtgaaggg cagattcacc atcagcgccg acaccagcaa gaacaccgcc    660
tacctgcaga tgaacagcct gagagccgag gacaccgccg tgtactactg ttctagatgg    720
ggaggcgacg gcttctacgc catggatgtt tggggacagg gcaccctggt cacagttctc    780
tctagcggag gcggaggaag cggagccctg agcaatagca tcatgtactt cagccacttc    840
gtgccctgt ttctgcccgc caagcctaca acaacacccg ctcctagacc actacacca    900
gctcctacaa tcgccagcca gcctctgtct ctcagacctg aagctgtag acctgcagct    960
ggcggagctg tgcataccag aggcctggat atctacattt ggccccctct ggctggcaca   1020
tgtgcggttc tgctgctctc tctggtcatc accctgtact gcagacggct gaagatccaa   1080
gtgcggaagg ccgccatcac cagctacgag aaatctgatg gcgtgtacac cggcctgagc   1140
accggaatc aagaaccta cgagacactg aagcacgaga gcctccaca aatgagtaac       1200
```

```
ggttacagca cggacgagaa cttccgctat ctgattagct gtttccgggc tcgcgtaaag   1260
atgtatatcc aggtagagcc agtgctggat tacctgacgt tcctccctgc cgaggtgaag   1320
gaacagattc agcgaacagt agcgacatca ggaaatatgc aagcggtgga gttgctgctc   1380
tctaccctcg aaaaaggtgt ttggcacctg ggatggacac gggaattcgt cgaagctctc   1440
aggcgaactg gatctcctct tgccgctagg tacatgaacg cggaactcac tgatttgccg   1500
tcaccgtctt tcgagaacgc ccatgatgag tatctccagc ttctgaattt gcttcagcct   1560
accttggtcg acaaactgtt ggttcgggac gttttggaca agtgtatgga ggaggagctg   1620
ctgaccatcg aggacagaaa ccggatagct gcggcagaga caatggcaa cgagtcagga    1680
gttcgggagt tgttgaagag gatagtgcaa aaggagaatt ggttcagcgc tttccttaac   1740
gtactccgac agacaggcaa caatgaactc gtacaagagt tgacagggtc agattgcagt   1800
gaatccaacg ccgaaattga aaat                                          1824

SEQ ID NO: 69           moltype = DNA   length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 69
atgtggctgc agtctctgct gctgctggga acagtggcct gcagcatcag c             51

SEQ ID NO: 70           moltype = DNA   length = 732
FEATURE                 Location/Qualifiers
misc_feature            1..732
                        note = Description of Artificial Sequence: Synthetic
                        polynucleotide
source                  1..732
                        mol_type = other DNA
                        organism = synthetic construct
SEQUENCE: 70
gacatccaga tgacacagag ccctagcagc ctgtctgcct ctgtgggcga tagagtgacc     60
atcacctgta gagccagcca ggatgtgaat accgccgtgg ctggtatca gcagaagcct    120
ggaaaagccc ctaagctgct gatctacagc gccagctttc tgtacagcgg cgtgccaagc   180
agattcagcg gcagcagatc tggcaccgac ttcaccctga ccatctctag cctgcagcct   240
gaggacttcg ccacctacta ctgccagcag cactacacca cacctccaac ctttggccag   300
ggcaccaagg tggaaatcaa gagaacaggc agcaccagcg gctctggaaa gcctggatct   360
ggcgaaggat ctgaggtgca gctggttgaa tctggcggag gacttgttca gcctggccgc   420
tctctgagac tgtcttgtgc cgccagcggc ttcaacatca aggacaccta catccactgg   480
gtccgacagg cccctggaaa gggacttgaa tgggtcgcca gaatctaccc caccaacggc   540
tacaccgat acgccgatag cgtgaagggc agattcacca tcagcgccga caccagcaag   600
aacaccgcct acctgcagat gaacagcctg agagccgagg acaccgccgt gtactactgt   660
tctagatggg gaggcgacgg cttctacgcc atggatgttt ggggacaggg caccctggtc   720
acagtttctt ct                                                       732

SEQ ID NO: 71           moltype = DNA   length = 21
FEATURE                 Location/Qualifiers
misc_feature            1..21
                        note = Description of Artificial Sequence: Synthetic
                        oligonucleotide
source                  1..21
                        mol_type = other DNA
                        organism = synthetic construct
SEQUENCE: 71
agcggaggcg gaggaagcgg a                                              21

SEQ ID NO: 72           moltype = DNA   length = 258
FEATURE                 Location/Qualifiers
misc_feature            1..258
                        note = Description of Artificial Sequence: Synthetic
                        polynucleotide
source                  1..258
                        mol_type = other DNA
                        organism = synthetic construct
SEQUENCE: 72
gccctgagca atagcatcat gtacttcagc cacttcgtgc ccgtgtttct gcccgccaag    60
cctacaacaa cacccgctcc tagaccacct acaccagctc ctacaatcgc cagccagcct   120
ctgtctctca gacctgaagc ctgtagacct gcagctgcg gagctgtgca taccagaggc   180
ctggatatct acatttgggc ccctctggct ggcacatgtg gcgttctgct gctctctctg   240
gtcatcaccc tgtactgc                                                 258

SEQ ID NO: 73           moltype = DNA   length = 129
FEATURE                 Location/Qualifiers
misc_feature            1..129
                        note = Description of Artificial Sequence: Synthetic
                        polynucleotide
source                  1..129
                        mol_type = other DNA
```

```
                    organism = synthetic construct
SEQUENCE: 73
agacggctga agatccaagt gcggaaggcc gccatcacca gctacgagaa atctgatggc    60
gtgtacaccg gcctgagcac ccggaatcaa gaaacctacg agacactgaa gcacgagaag   120
cctccacaa                                                           129

SEQ ID NO: 74           moltype = DNA   length = 633
FEATURE                 Location/Qualifiers
misc_feature            1..633
                        note = Description of Artificial Sequence: Synthetic
                         polynucleotide
source                  1..633
                        mol_type = other DNA
                        organism = synthetic construct
SEQUENCE: 74
atgagtaacg gttacagcac ggacgagaac ttccgctatc tgattagctg tttccgggct    60
cgcgtaaaga tgtatatcca ggtagagcca gtgctggatt acctgacgtt cctccctgcc   120
gaggtgaagg aacagattca gcgaacagta gcgacatcag aaaatatgca agcggtggag   180
ttgctgctct ctaccctcga aaaaggtgtt tggcacctgg gatggacacg ggaattcgtc   240
gaagctctca ggcgaactgg atctcctctt gccgctaggt acatgaaccc ggaactcact   300
gatttgccgt caccgtcttt cgagaacgcc catgatgagt atctccagct tctgaatttg   360
cttcagccta ccttggtcga caactgttg gttcgggacg ttttggacaa gtgtatggag   420
gaggagctgc tgaccatcga ggacagaaac cggatagctg cggcagaaa caatggcaac    480
gagtcaggag ttcggagtt gttgaagagg atagtgcaaa aggagaattg gttcagcgct    540
ttccttaacg tactccgaca gacaggcaac aatgaactcg tacaagagtt gacagggtca   600
gattgcagtg aatccaacgc cgaaattgaa aat                                633

SEQ ID NO: 75           moltype = DNA   length = 1812
FEATURE                 Location/Qualifiers
misc_feature            1..1812
                        note = Description of Artificial Sequence: Synthetic
                         polynucleotide
source                  1..1812
                        mol_type = other DNA
                        organism = synthetic construct
SEQUENCE: 75
atgtggctgc agtctctgct gctgctggga acagtggcct gcagcatcag cgagatccag    60
ctggttcagt ctggcggcgg acttgtgaaa cctggcggat ctgtcagaat cagctgtgcc   120
gccagcggct acaccttcac caactacggc atgaactggt ccgacaggc cctggaaaa    180
ggccttgagt ggatgggctg gatcaatacc cacaccggcg agccaaccta cgccgatagc   240
tttaagggca gattcacctt cagcctggac gacagcaaga acaccgccta cctgcagatc   300
aacagcctga gagccgagga taccgccgtg tacttctgca ccagaagagg ctacgactgg   360
tacttcgatg tgtggggcca gggcaccaca gtgacagttt ctagcggacg cggaggatca   420
ggtggcggtg atctggcgg tggtggctct gatatccaga tgacacagag ccctagcagc   480
ctgtctgcct ctgtgggcga tagagtgacc atcacctgta gagccagcca ggacatcaac   540
agctacctga gctggttcca gcagaagcct ggcaaggccc taagacact gatctaccgg   600
gccaacagac tggaaagcgg cgtgccaagc agattttctg gcagcggctc tggcaccgac   660
tacacctga caatcagcag cctgcagtac gaggacttcg gcatctacta ctgccagcag   720
tacgacgaga gcccttggac atttggcgga ggcaccaagc tggaaatcaa agcggaggc   780
ggaggaagcg gagccctgag caatagcatc atgtacttca gccacttcgt gcccgtgttt   840
ctgcccgcca agcctacaac aacacccgct cctagaccac ctaccaccag tcctacaacc   900
gccagccagc ctctgtctct cagacctgaa gcctgtagac ctgcagctgg cggagctgtg   960
cataccagag gcctggatat ctacatttgg gcccctctgg ctggcacatg tggcgttctg  1020
ctgctctctc tggtcatcac cctgtactgc agacggctga agatccaagt gcggaaggcc  1080
gccatcacca gctacgagaa atctgatggc gtgtacaccg gcctgagcac ccggaatcaa  1140
gaaacctacg agacactgaa gcacgagaag cctccacaaa tgagtaacgg ttacagcacg  1200
gacgagaact tccgctatct gattagctgt ttccgggctc gcgtaaagat gtatatccag  1260
gtagagccag tgctggatta cctgacgttc ctccctgccg aggtgaagga acagattcag  1320
cgaacagtag cgacatcagg aaatatgcaa gcggtggagt tgctgctctc taccctcgaa  1380
aaaggtgttt ggcacctggg atggacacgg gaattcgtcg aagctctcag gcgaactgga  1440
tctcctcttg ccgctaggta catgaacccg gaactcactg atttgccgtc accgtctttc  1500
gagaacgccc atgatgagta tctccagctt ctgaatttgc ttcagcctac cttggtcgac  1560
aaactgttgg ttcgggacgt tttggacaag tgtatggagg aggagctgct gaccatcgag  1620
gacagaaacc ggatagctgc ggcagagaac aatggcaacg agtcaggagt tcggagttca  1680
ttgaagagga tagtgcaaaa ggagaattgg ttcagcgctt tccttaacgt actccgacag  1740
acaggcaaca atgaactcgt acaagagttg acagggtcag attgcagtga atccaacgcc  1800
gaaattgaaa at                                                      1812

SEQ ID NO: 76           moltype = DNA   length = 51
FEATURE                 Location/Qualifiers
misc_feature            1..51
                        note = Description of Artificial Sequence: Synthetic
                         oligonucleotide
source                  1..51
                        mol_type = other DNA
                        organism = synthetic construct
SEQUENCE: 76
atgtggctgc agtctctgct gctgctggga acagtggcct gcagcatcag c             51
```

| SEQ ID NO: 77 | moltype = DNA   length = 720 |
| --- | --- |
| FEATURE | Location/Qualifiers |
| misc_feature | 1..720 |
| | note = Description of Artificial Sequence: Synthetic polynucleotide |
| source | 1..720 |
| | mol_type = other DNA |
| | organism = synthetic construct |

SEQUENCE: 77

```
gagatccagc tggttcagtc tggcggcgga cttgtgaaac ctggcggatc tgtcagaatc    60
agctgtgccg ccagcggcta caccttcacc aactacggca tgaactgggt ccgacaggcc   120
cctggaaaag gccttgagtg gatgggctgg atcaataccc acaccggcga gccaacctac   180
gccgatagct ttaagggcag attcaccttc agcctggacg acagcaagaa caccgcctac   240
ctgcagatca acagcctgag agccgaggat accgccgtgt acttctgcac cagaagagcc   300
tacgactggt acttcgatgt gtggggccag ggcaccacag tgacagtttc tagcggaggc   360
ggaggatcag gtggcggtgg atctggcggt ggtggctctg atatccagat gacacagagc   420
cctagcagcc tgtctgcctc tgtgggcgat agagtgacca tcacctgtag agccagccag   480
gacatcaaca gctacctgag ctggttccag cagaagcctg gcaaggcccc taagacactg   540
atctaccggg ccaacagact ggaaagcggc gtgccaagca gattttctgg cagcggctct   600
ggcaccgact cacccctgac aatcagcagc ctgcagtacg aggacttcgg catctactac   660
tgccagcagt acgacgagag cccttggaca tttggcggag caccaagct ggaaatcaaa    720
```

| SEQ ID NO: 78 | moltype = DNA   length = 21 |
| --- | --- |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |

SEQUENCE: 78

```
agcggaggcg gaggaagcgg a                                               21
```

| SEQ ID NO: 79 | moltype = DNA   length = 258 |
| --- | --- |
| FEATURE | Location/Qualifiers |
| misc_feature | 1..258 |
| | note = Description of Artificial Sequence: Synthetic polynucleotide |
| source | 1..258 |
| | mol_type = other DNA |
| | organism = synthetic construct |

SEQUENCE: 79

```
gccctgagca atagcatcat gtacttcagc cacttcgtgc ccgtgtttct gcccgccaag    60
cctacaacaa cacccgctcc tagaccacct acaccagctc ctacaatcgc cagccagcct   120
ctgtctctca gacctgaagc ctgtagacct gcagctggcg gagctgtgca taccagaggc   180
ctggatatct catttgggc ccctctggct ggcacatgtg gcgttctgct gctctctctg    240
gtcatcaccc ctgtactgc                                                 258
```

| SEQ ID NO: 80 | moltype = DNA   length = 129 |
| --- | --- |
| FEATURE | Location/Qualifiers |
| misc_feature | 1..129 |
| | note = Description of Artificial Sequence: Synthetic polynucleotide |
| source | 1..129 |
| | mol_type = other DNA |
| | organism = synthetic construct |

SEQUENCE: 80

```
agacggctga agatccaagt gcggaaggcc gccatcacca gctacgagaa atctgatggc    60
gtgtacaccg gcctgagcac ccggaatcaa gaaacctacg agacactgaa gcacgagaag   120
cctccacaa                                                            129
```

| SEQ ID NO: 81 | moltype = DNA   length = 633 |
| --- | --- |
| FEATURE | Location/Qualifiers |
| misc_feature | 1..633 |
| | note = Description of Artificial Sequence: Synthetic polynucleotide |
| source | 1..633 |
| | mol_type = other DNA |
| | organism = synthetic construct |

SEQUENCE: 81

```
atgagtaacg gttacagcac ggacgagaac ttccgctatc tgattagctg tttccgggct    60
cgcgtaaaga tgtatatcca ggtagagcca gtgctggatt acctgacgtt cctccctgcc   120
gaggtgaagg aacagattca gcgaacagta gcgacatcag gaaatatgca agcggtggag   180
ttgctgctct ctaccctcga aaaaggtgtt tggcacctgg gatggacacg ggaattcgtc   240
gaagctctca ggcgaactgg atctcctctt gccgctaggt acatgaaccc ggaactcact   300
gatttgccgt caccgtcttt cgagaacgcc catgatgagt atctccagct tctgaatttg   360
cttcagccta ccttggtcga caaactgttg gttcgggacg ttttgacaa gtgtatggag   420
gaggagctgc tgaccatcga ggacagaaac cggatagctc cggcagagaa caatggcaac   480
gagtcaggag ttcgggagtt gttgaagagg atagtgcaaa aggagaattg gttcagcgct   540
```

```
ttccttaacg tactccgaca gacaggcaac aatgaactcg tacaagagtt gacagggtca    600
gattgcagtg aatccaacgc cgaaattgaa aat                                 633

SEQ ID NO: 82           moltype = DNA  length = 1848
FEATURE                 Location/Qualifiers
misc_feature            1..1848
                        note = Description of Artificial Sequence: Synthetic
                        polynucleotide
source                  1..1848
                        mol_type = other DNA
                        organism = synthetic construct
SEQUENCE: 82
atgtggctgc agtctctgct gctgctggga acagtggcct gcagcatcag cgagatccag    60
ctggttcagt ctggcggcgg acttgtgaaa cctggcggat ctgtcagaat cagctgtgcc    120
gccagcggct acaccttcac caactacggc atgaactggg tccgacaggc ccctggaaaa    180
ggccttgagt ggatgggctg gatcaatacc cacaccggcg agccaaccta cgccgatagc    240
tttaagggca gattcacctt cagcctggac acagcaaga acaccgccta cctgcagatc    300
aacagcctga gagccgagga taccgccgtg tacttctgca ccagaagagg ctacgactgg    360
tacttcgatg tgtggggcca gggcaccaca gtgacagttt ctagcggagg cggaggatca    420
ggtggcggtg gatctggcgg tggtggctct gatatccaga tgacacagag ccctagcagc    480
ctgtctgcct ctgtgggcga tagagtgacc atcacctgta gagccagcca ggacatcaac    540
agctacctga gctggttcca gcagaagcct ggcaaggccc ctaagacact gatctaccgg    600
gccaacagac tggaaagcgg cgtgccaagc agatttctg gcagcggctc tggcaccgac    660
tacaccctga caatcagcag cctgcagtac gaggacttcg gcatctacta ctgccagcag    720
tacgacgaga gcccttggac atttggcgga ggcaccaagc tggaaatcaa agcggaggc    780
ggaggaagcg gagccctgag caatagcatc atgtacttca gccactttgt gcccgtgttt    840
ctgcccgcca agcctacaac aacacccgct cctagaccac ctacaccagc tcctacaatc    900
gccagccagc ctctgtctct cagacctgaa gcctgtagac ctgcagctgg cggagctgtg    960
cataccagag gcctggatat ctacattttgg gcccctctgg ctggcacatg tggcgttctg    1020
ctgctctctc tggtcatcac cctgtactgc agacggctga agatccaagt gcggaaggcc    1080
gccatcacca gctacgagaa atctgatggc gtgtacaccg gcctgagcac ccggaatcaa    1140
gaaacctacg agacactgaa gcacgagaag cctccacaag gcagcggcag ccaaagatgg    1200
aagagcaagc tgtatagcat cgtgtgcggc aagtccaccc tgagaagga aggagagctg    1260
gaaggcacca caacaaagcc tctggccct aaccctcat tcagccctac ccccggcttc    1320
acccccaccc tgggatttag ccccgtgccc agcagcacct tcaccagctc tagcacctac    1380
acccctggcg actgccccaa cttcgccgcc cctagacgcg aggtggcccc tccttaccag    1440
ggcgccgacc ctatcctggc cacagccctg gcttctgatc cgattcctaa tcctctgcag    1500
aagtggggag acagcgccca caagcccag agcctggaca ccgacgaccc cgccaccctg    1560
tacgccgtgg tggaaaacgt gcctccactg cggtggaaga agtcgtgcg gcggctgggc    1620
ctgagcgacc acgagatcga cagactggaa ctgcagaacg gccgttgcct gagagaggcc    1680
cagtacagca tgctggcaac atggcggaga agaaacccca aagagaggc caccctggaa    1740
ctgctgggca gagtgctgag agatatggac ctgctgggtt gtctgaaga tatcgaggaa    1800
gccctgtgcg gtcctgccgc tctgcctcct gctccatctc tgctgaga              1848

SEQ ID NO: 83           moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 83
atgtggctgc agtctctgct gctgctggga acagtggcct gcagcatcag c              51

SEQ ID NO: 84           moltype = DNA  length = 720
FEATURE                 Location/Qualifiers
misc_feature            1..720
                        note = Description of Artificial Sequence: Synthetic
                        polynucleotide
source                  1..720
                        mol_type = other DNA
                        organism = synthetic construct
SEQUENCE: 84
gagatccagc tggttcagtc tggcggcgga cttgtgaaac ctggcggatc tgtcagaatc    60
agctgtgccg ccagcggcta caccttcacc aactacggca tgaactgggt ccgacaggcc    120
cctggaaaag gccttgagtg gatgggctgg atcaataccc acaccggcga gccaacctac    180
gccgatagct ttaagggcag attcaccttc agcctggaca cagcaagaa caccgcctac    240
ctgcagatca acagcctgag agccgaggat accgccgtgt acttctgcac cagaagaggc    300
tacgactggt acttcgatgt gtggggccag ggcaccacag tgacagtttc tagcggaggc    360
ggaggatcag gtggcggtgg atctggcggt ggtggctctg atatccagat gacacagagc    420
cctagcagcc tgtctgcctc tgtgggcgat agagtgacca tcacctgtag agccagccag    480
gacatcaaca gctacctgag ctggttccag cagaagcctg gcaaggcccc taagacactg    540
atctaccggg ccaacagact ggaaagcggc gtgccaagca gatttctgg cagcggctct    600
ggcaccgact acaccctgac aatcagcagc ctgcagtacg aggacttcgg catctactac    660
tgccagcagt acgacgagag cccttggaca tttggcggag gcaccaagct ggaaatcaaa    720

SEQ ID NO: 85           moltype = DNA  length = 21
FEATURE                 Location/Qualifiers
```

```
misc_feature            1..21
                        note = Description of Artificial Sequence: Synthetic
                         oligonucleotide
source                  1..21
                        mol_type = other DNA
                        organism = synthetic construct
SEQUENCE: 85
agcggaggcg gaggaagcgg a                                                   21

SEQ ID NO: 86           moltype = DNA  length = 258
FEATURE                 Location/Qualifiers
misc_feature            1..258
                        note = Description of Artificial Sequence: Synthetic
                         polynucleotide
source                  1..258
                        mol_type = other DNA
                        organism = synthetic construct
SEQUENCE: 86
gccctgagca atagcatcat gtacttcagc cacttcgtgc ccgtgtttct gcccgccaag   60
cctacaacaa cacccgctcc tagaccacct acaccagctc ctacaatcgc cagccagcct  120
ctgtctctca gacctgaagc ctgtagacct gcagctggcg gagctgtgca taccagaggc  180
ctggatatct acatttgggc ccctctggct ggcacatgtg gcgttctgct gctctctctg  240
gtcatcaccc tgtactgc                                                258

SEQ ID NO: 87           moltype = DNA  length = 129
FEATURE                 Location/Qualifiers
misc_feature            1..129
                        note = Description of Artificial Sequence: Synthetic
                         polynucleotide
source                  1..129
                        mol_type = other DNA
                        organism = synthetic construct
SEQUENCE: 87
agacggctga agatccaagt gcggaaggcc gccatcacca gctacgagaa atctgatggc   60
gtgtacaccg gcctgagcac ccggaatcaa gaaacctacg agacactgaa gcacgagaag  120
cctccacaa                                                          129

SEQ ID NO: 88           moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 88
ggcagcggca gc                                                       12

SEQ ID NO: 89           moltype = DNA  length = 657
FEATURE                 Location/Qualifiers
misc_feature            1..657
                        note = Description of Artificial Sequence: Synthetic
                         polynucleotide
source                  1..657
                        mol_type = other DNA
                        organism = synthetic construct
SEQUENCE: 89
caaagatgga agagcaagct gtatagcatc gtgtgcggca agtccacccc tgagaaggaa   60
ggagagctgg aaggcaccac aacaaagcct ctggccccta acccctcatt cagccctacc  120
cccggcttca cccccacccct gggatttagc cccgtgccca gcagcacctt caccagctct  180
agcacctaca cccctggcga ctgccccaac ttcgccgccc ctagacgcga ggtgccccct  240
ccttaccagg gcgccgaccc tatcctggcc acagccctgg cttctgatcc gattcctaat  300
cctctgcaga gtgggagga cagcgccac aagcccaga gcctggacac cgacgacccc  360
gccaccctgt acgccgtggt ggaaaacgtg cctccactgc ggtgaaaga gttcgtgcgg  420
cggctgggcc tgagcgacca cgagatcgac agactggaac tgcagaacgg ccgttgcctg  480
agagaggccc agtacagcat gctggcaaca tggcggagaa gaacacccag aagagaggcc  540
accctggaac tgctgggcag agtgctgaga gatatgggacc tgctgggttg tctgaaagat  600
atcgaggaag ccctgtgcgg tcctgccgct ctgcctcctg ctccatctct gctgaga     657

SEQ ID NO: 90           moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 90
MHEEEIYTSL QWDSPAPDTY QKCLSSNKCS GACCL                              35
```

```
SEQ ID NO: 91            moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 91
EIQLVQSGGG LVKPGGSVRI SCAASGYTFT NYGMNWVRQA PGKGLEWMGW INTHTGEPTY    60
ADSFKGRFTF SLDDSKNTAY LQINSLRAED TAVYFCTRRG YDWYFDVWGQ GTTVTVSS     118

SEQ ID NO: 92            moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 92
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIK               107

SEQ ID NO: 93            moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 93
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDVW GQGTLVTVSS  120

SEQ ID NO: 94            moltype = AA  length = 244
FEATURE                  Location/Qualifiers
REGION                   1..244
                         note = Description of Artificial Sequence: Synthetic
                          polypeptide
source                   1..244
                         mol_type = protein
                         organism = synthetic construct
SEQUENCE: 94
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTG STSGSGKPGS  120
GEGSEVQLVE SGGGLVQPGG SLRLSCAASG FNIKDTYIHW VRQAPGKGLE WVARIYPTNG  180
YTRYADSVKG RFTISADTSK NTAYLQMNSL RAEDTAVYYC SRWGGDGFYA MDVWGQGTLV  240
TVSS                                                              244

SEQ ID NO: 95            moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 95
QVQLQQSGSE LKKPGASVKV SCKASGYTFT NYGMNWVKQA PGQGLKWMGW INTYTGEPTY    60
TDDFKGRFAF SLDTSVSTAY LQISSLKADD TAVYFCARGG FGSSYWYFDV WGQGSLVTVS  120
S                                                                 121

SEQ ID NO: 96            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 96
DIQLTQSPSS LSASVGDRVS ITCKASQDVS IAVAWYQQKP GKAPKLLIYS ASYRYTGVPD    60
RFSGSGSGTD FTLTISSLQP EDFAVYYCQQ HYITPLTFGA GTKVEIKR              108

SEQ ID NO: 97            moltype = AA  length = 115
FEATURE                  Location/Qualifiers
```

```
REGION              1..115
                    note = Description of Artificial Sequence: Synthetic
                     polypeptide
source              1..115
                    mol_type = protein
                    organism = synthetic construct
SEQUENCE: 97
QVQLVQSGAE VKKPGASVKV SCKASGYTFT DYEMHWVRQA PGQGLEWMGA LDPKTGDTAY  60
SQKFKGKATL TADKSTSTAY MELSSLTSED TAVYYCTRFY SYTYWGQGTL VTVSS      115

SEQ ID NO: 98       moltype = AA  length = 112
FEATURE             Location/Qualifiers
REGION              1..112
                    note = Description of Artificial Sequence: Synthetic
                     polypeptide
source              1..112
                    mol_type = protein
                    organism = synthetic construct
SEQUENCE: 98
DVVMTQSPLS LPVTPGEPAS ISCRSSQSLV HSNRNTYLHW YLQKPGQSPQ LLIYKVSNRF  60
SGVPDRFSGS GSGTDFTLKI SRVEAEDVGV YYCSQNTHVP PTFGQGTKLE IK         112

SEQ ID NO: 99       moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 99
RGYDWYFDV                                                          9

SEQ ID NO: 100      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 100
QQYDESPWT                                                          9

SEQ ID NO: 101      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 101
WGGDGFYAMD V                                                       11

SEQ ID NO: 102      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 102
QQHYTTPPT                                                          9

SEQ ID NO: 103      moltype = AA  length = 12
FEATURE             Location/Qualifiers
REGION              1..12
                    note = Description of Artificial Sequence: Synthetic peptide
source              1..12
                    mol_type = protein
                    organism = synthetic construct
SEQUENCE: 103
GGFGSSYWYF DV                                                      12

SEQ ID NO: 104      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
```

```
SEQUENCE: 104
QQHYITPLT                                                                    9

SEQ ID NO: 105          moltype = AA  length = 244
FEATURE                 Location/Qualifiers
REGION                  1..244
                        note = Description of Artificial Sequence: Synthetic
                         polypeptide
source                  1..244
                        mol_type = protein
                        organism = synthetic construct
SEQUENCE: 105
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTG STSGSGKPGS   120
GEGSEVQLVE SGGGLVQPGG SLRLSCAASG FNIKDTYIHW VRQAPGKGLE WVARIYPTNG   180
YTRYADSVKG RFTISADTSK NTAYLQMNSL RAEDTAVYYC SRWGGDGFYA MDVWGQGTLV   240
TVSS                                                                244

SEQ ID NO: 106          moltype = AA  length = 242
FEATURE                 Location/Qualifiers
REGION                  1..242
                        note = Description of Artificial Sequence: Synthetic
                         polypeptide
source                  1..242
                        mol_type = protein
                        organism = synthetic construct
SEQUENCE: 106
QVQLVQSGAE VKKPGASVKV SCKASGYTFT DYEMHWVRQA PGQGLEWMGA LDPKTGDTAY    60
SQKFKGKATL TADKSTSTAY MELSSLTSED TAVYYCTRFY SYTYWGQGTL VTVSSGGGGS   120
GGGGSGGGGS DVVMTQSPLS LPVTPGEPAS ISCRSSQSLV HSNRNTYLHW YLQKPGQSPQ   180
LLIYKVSNRF SGVPDRFSGS GSGTDFTLKI SRVEAEDVGV YYCSQNTHVP PTFGQGTKLE   240
IK                                                                  242

SEQ ID NO: 107          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 107
EVQLVESGGG LVQAGGSLRL SCAASGITFS INTMGWYRQA PGKQRELVAL ISSIGDTYYA    60
DSVKGRFTIS RDNAKNTVYL QMNSLKPEDT AVYYCKRFRT AAQGTDYWGQ GTQVTVSS     118

SEQ ID NO: 108          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 108
SLHIS                                                                5

SEQ ID NO: 109          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 109
NLEIS                                                                5

SEQ ID NO: 110          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 110
DLAIS                                                                5

SEQ ID NO: 111          moltype = AA  length = 5
FEATURE                 Location/Qualifiers
REGION                  1..5
                        note = Description of Artificial Sequence: Synthetic peptide
```

```
source                   1..5
                         mol_type = protein
                         organism = synthetic construct
SEQUENCE: 111
ELLIS                                                                       5

SEQ ID NO: 112           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 112
QVQLQESGGG LVQAGGSLRL SCAAPRSIFS INAMGWYRQA PGKQRELVAA ITSGGSPTYA           60
DSVKGRFTIS RDNAKNTVYL QMNSLKAEDT AVYYCATGPY GLDNALDAWG QGTQVTVSS           119

SEQ ID NO: 113           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 113
QVQLQESGGG LVQTGGSLRL ACTASGFTFD DYAIAWFRQA PGKEREFVAA ISWSGGTTHY           60
ADSVKGRFTI SRDNAKNTLY LQMSSLKPED TAVYFCAKSL RSSPSSRWFG SRGQGTQVTV          120
SS                                                                        122

SEQ ID NO: 114           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 114
ATACADTTQY AYDY                                                             14

SEQ ID NO: 115           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 115
ATACADTTLY EYDY                                                             14

SEQ ID NO: 116           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 116
ATACVDTTQY EYDY                                                             14

SEQ ID NO: 117           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 117
ATACADATQH EYDY                                                             14

SEQ ID NO: 118           moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 118
```

```
ATACADTTQY DYDY                                                        14

SEQ ID NO: 119          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 119
ATACADTTQY EYDY                                                        14

SEQ ID NO: 120          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 120
ATACADTTHY EYDY                                                        14

SEQ ID NO: 121          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 121
ATACVITTLY EYDY                                                        14

SEQ ID NO: 122          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 122
ATACAETTLY EYDY                                                        14

SEQ ID NO: 123          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 123
ATACADTTQH EYDY                                                        14

SEQ ID NO: 124          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 124
ATACVDTTHY EYDY                                                        14

SEQ ID NO: 125          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 125
ATACASTTLY EYDY                                                        14

SEQ ID NO: 126          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
```

```
SEQUENCE: 126
ATACVVTTLY EYDY                                                                 14

SEQ ID NO: 127           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 127
ATACGGATGP YDY                                                                  13

SEQ ID NO: 128           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 128
ATACAGAIGP YDY                                                                  13

SEQ ID NO: 129           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 129
ATACVVVGDQ NDY                                                                  13

SEQ ID NO: 130           moltype = AA   length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 130
ATACVVVGDR NDY                                                                  13

SEQ ID NO: 131           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 131
ATDCAGGTST PYDY                                                                 14

SEQ ID NO: 132           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 132
ATDCAGGTAT PYDY                                                                 14

SEQ ID NO: 133           moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 133
ATACVVADRN EYDY                                                                 14

SEQ ID NO: 134           moltype = AA   length = 14
FEATURE                  Location/Qualifiers
REGION                   1..14
                         note = Description of Artificial Sequence: Synthetic peptide
source                   1..14
                         mol_type = protein
```

```
                        -continued organism = synthetic construct
SEQUENCE: 134
ATSCVVVTKN EYDY                                                         14

SEQ ID NO: 135          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 135
ATACSGLTHE YDY                                                          13

SEQ ID NO: 136          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 136
ATTCSGLTHE YDY                                                          13

SEQ ID NO: 137          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 137
ATACANWSSL GPYDY                                                        15

SEQ ID NO: 138          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 138
ATACANWSTL GPYDY                                                        15

SEQ ID NO: 139          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 139
ATACSDPRVY EYDY                                                         14

SEQ ID NO: 140          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 140
ATTCASPEKY EYDY                                                         14

SEQ ID NO: 141          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 141
ATHCGGTSWG TSYDY                                                        15

SEQ ID NO: 142          moltype = AA  length = 15
FEATURE                 Location/Qualifiers
REGION                  1..15
                        note = Description of Artificial Sequence: Synthetic peptide
source                  1..15
```

```
                        mol_type = protein
                        organism = synthetic construct
SEQUENCE: 142
ATHCGGSSWS NEYDY                                                    15

SEQ ID NO: 143          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 143
YARYSGRTY                                                            9

SEQ ID NO: 144          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 144
ASSAWPAGPK HQVEYDY                                                  17

SEQ ID NO: 145          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 145
ATACGSLVGM YDY                                                      13

SEQ ID NO: 146          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 146
ATACGSAVHE YDY                                                      13

SEQ ID NO: 147          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 147
ATDCVGFGSN WFDY                                                     14

SEQ ID NO: 148          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 148
ATACASPVIY EYDY                                                     14

SEQ ID NO: 149          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 149
ATDCAGGVGH EYDY                                                     14

SEQ ID NO: 150          moltype = AA  length = 15
FEATURE                 Location/Qualifiers
REGION                  1..15
                        note = Description of Artificial Sequence: Synthetic peptide
```

```
source                      1..15
                            mol_type = protein
                            organism = synthetic construct
SEQUENCE: 150
ATDCSLHGSD YPYDY                                                          15

SEQ ID NO: 151              moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 151
AVRIYSGSFD NTLAYDY                                                        17

SEQ ID NO: 152              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 152
GFPLAYYA                                                                   8

SEQ ID NO: 153              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 153
GFSLDYYA                                                                   8

SEQ ID NO: 154              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 154
GFPLDYYA                                                                   8

SEQ ID NO: 155              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 155
GFTLDYYA                                                                   8

SEQ ID NO: 156              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 156
GFSLNYYA                                                                   8

SEQ ID NO: 157              moltype = AA  length = 8
FEATURE                     Location/Qualifiers
REGION                      1..8
                            note = Description of Artificial Sequence: Synthetic peptide
source                      1..8
                            mol_type = protein
                            organism = synthetic construct
SEQUENCE: 157
GFTLAYYA                                                                   8

SEQ ID NO: 158              moltype = AA  length = 8
FEATURE                     Location/Qualifiers
REGION                      1..8
```

```
                        -continued source                  1..8
                        mol_type = protein
                        organism = synthetic construct
SEQUENCE: 158
GFTLGYYA                                                                8

SEQ ID NO: 159          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 159
GFPLNYYA                                                                8

SEQ ID NO: 160          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 160
GFPLHYYA                                                                8

SEQ ID NO: 161          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 161
GFSLGYYA                                                                8

SEQ ID NO: 162          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 162
GFPLGYYA                                                                8

SEQ ID NO: 163          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 163
GFPLEYYA                                                                8

SEQ ID NO: 164          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 164
GSDFRADA                                                                8

SEQ ID NO: 165          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 165
GRTFSSYG                                                                8

SEQ ID NO: 166          moltype = AA   length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 166
GFSLAYYA                                                                        8

SEQ ID NO: 167          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 167
GLTFRSVG                                                                        8

SEQ ID NO: 168          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 168
ISNSDGST                                                                        8

SEQ ID NO: 169          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 169
ISASDGST                                                                        8

SEQ ID NO: 170          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 170
ISSSDGST                                                                        8

SEQ ID NO: 171          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 171
ISSSDGNT                                                                        8

SEQ ID NO: 172          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 172
ISSADGST                                                                        8

SEQ ID NO: 173          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 173
ISSSGGST                                                                        8

SEQ ID NO: 174          moltype = AA  length = 8
```

```
FEATURE              Location/Qualifiers
REGION               1..8
                     note = Description of Artificial Sequence: Synthetic peptide
source               1..8
                     mol_type = protein
                     organism = synthetic construct
SEQUENCE: 174
ISSGDGST                                                                      8

SEQ ID NO: 175       moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 175
ISAGDGNT                                                                      8

SEQ ID NO: 176       moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 176
ISSSDDST                                                                      8

SEQ ID NO: 177       moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 177
ISSNDGST                                                                      8

SEQ ID NO: 178       moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 178
ISSPDGST                                                                      8

SEQ ID NO: 179       moltype = AA   length = 8
FEATURE              Location/Qualifiers
REGION               1..8
                     note = Description of Artificial Sequence: Synthetic peptide
source               1..8
                     mol_type = protein
                     organism = synthetic construct
SEQUENCE: 179
ISSRTGGT                                                                      8

SEQ ID NO: 180       moltype = AA   length = 9
FEATURE              Location/Qualifiers
REGION               1..9
                     note = Description of Artificial Sequence: Synthetic peptide
source               1..9
                     mol_type = protein
                     organism = synthetic construct
SEQUENCE: 180
ISAGDGSST                                                                     9

SEQ ID NO: 181       moltype = AA   length = 13
FEATURE              Location/Qualifiers
REGION               1..13
                     note = Description of Artificial Sequence: Synthetic peptide
source               1..13
                     mol_type = protein
                     organism = synthetic construct
SEQUENCE: 181
ISSSDGSSSD GNT                                                               13
```

| | | |
|---|---|---|
| SEQ ID NO: 182<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 182<br>ISSGDGNT | | 8 |
| SEQ ID NO: 183<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 183<br>ISSGDGKT | | 8 |
| SEQ ID NO: 184<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 184<br>ISSSDGGT | | 8 |
| SEQ ID NO: 185<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 185<br>ISSRTGST | | 8 |
| SEQ ID NO: 186<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 186<br>ISSRTGNT | | 8 |
| SEQ ID NO: 187<br>FEATURE<br>REGION<br><br>source | moltype = AA  length = 10<br>Location/Qualifiers<br>1..10<br>note = Description of Artificial Sequence: Synthetic peptide<br>1..10<br>mol_type = protein<br>organism = synthetic construct | |
| SEQUENCE: 187<br>ISSSDGHSST | | 10 |
| SEQ ID NO: 188<br>FEATURE<br>REGION<br><br>source | moltype = AA  length = 9<br>Location/Qualifiers<br>1..9<br>note = Description of Artificial Sequence: Synthetic peptide<br>1..9<br>mol_type = protein<br>organism = synthetic construct | |
| SEQUENCE: 188<br>ISSSSDGNT | | 9 |
| SEQ ID NO: 189<br>FEATURE<br>REGION<br><br>source | moltype = AA  length = 8<br>Location/Qualifiers<br>1..8<br>note = Description of Artificial Sequence: Synthetic peptide<br>1..8<br>mol_type = protein<br>organism = synthetic construct | |
| SEQUENCE: 189<br>ISASNGNT | | 8 |

| | | |
|---|---|---|
| SEQ ID NO: 190 | moltype = AA length = 9 | |
| FEATURE | Location/Qualifiers | |
| REGION | 1..9 | |
| | note = Description of Artificial Sequence: Synthetic peptide | |
| source | 1..9 | |
| | mol_type = protein | |
| | organism = synthetic construct | |
| SEQUENCE: 190 | | |
| ISSGSDGNT | | 9 |
| | | |
| SEQ ID NO: 191 | moltype = AA length = 8 | |
| FEATURE | Location/Qualifiers | |
| REGION | 1..8 | |
| | note = Description of Artificial Sequence: Synthetic peptide | |
| source | 1..8 | |
| | mol_type = protein | |
| | organism = synthetic construct | |
| SEQUENCE: 191 | | |
| ISASDGNT | | 8 |
| | | |
| SEQ ID NO: 192 | moltype = AA length = 7 | |
| FEATURE | Location/Qualifiers | |
| REGION | 1..7 | |
| | note = Description of Artificial Sequence: Synthetic peptide | |
| source | 1..7 | |
| | mol_type = protein | |
| | organism = synthetic construct | |
| SEQUENCE: 192 | | |
| IDSITSI | | 7 |
| | | |
| SEQ ID NO: 193 | moltype = AA length = 16 | |
| FEATURE | Location/Qualifiers | |
| REGION | 1..16 | |
| | note = Description of Artificial Sequence: Synthetic peptide | |
| source | 1..16 | |
| | mol_type = protein | |
| | organism = synthetic construct | |
| SEQUENCE: 193 | | |
| ISWSGGSTIA ASVGST | | 16 |
| | | |
| SEQ ID NO: 194 | moltype = AA length = 11 | |
| FEATURE | Location/Qualifiers | |
| REGION | 1..11 | |
| | note = Description of Artificial Sequence: Synthetic peptide | |
| source | 1..11 | |
| | mol_type = protein | |
| | organism = synthetic construct | |
| SEQUENCE: 194 | | |
| ISSSDGSDGN T | | 11 |
| | | |
| SEQ ID NO: 195 | moltype = AA length = 8 | |
| FEATURE | Location/Qualifiers | |
| REGION | 1..8 | |
| | note = Description of Artificial Sequence: Synthetic peptide | |
| source | 1..8 | |
| | mol_type = protein | |
| | organism = synthetic construct | |
| SEQUENCE: 195 | | |
| ASPSGVIT | | 8 |
| | | |
| SEQ ID NO: 196 | moltype = AA length = 121 | |
| FEATURE | Location/Qualifiers | |
| REGION | 1..121 | |
| | note = Description of Artificial Sequence: Synthetic polypeptide | |
| source | 1..121 | |
| | mol_type = protein | |
| | organism = synthetic construct | |
| SEQUENCE: 196 | | |
| QVQLQESGGG LVHSGGSLRL SCAASGFPLA YYAIGWFRQA PGKEREGVSC ISSSDGNTYY | | 60 |
| ADAVKGRFTI SRDNAKNTVY LQMNSLKPED TAVYYCATAC ADTTQHEYDY WGQGTQVTVS | | 120 |
| S | | 121 |
| | | |
| SEQ ID NO: 197 | moltype = AA length = 121 | |
| FEATURE | Location/Qualifiers | |
| REGION | 1..121 | |
| | note = Description of Artificial Sequence: Synthetic polypeptide | |

```
source                  1..121
                        mol_type = protein
                        organism = synthetic construct
SEQUENCE: 197
QVQLQESGGG LVHSGGSLRL SCAASGFPLD YYAIGWFRQA PGKEREGVSC ISSADGSTYY    60
ADSVKGRFTI SRDNAKNTVY LQMNSLGPED TAVYYCATAC ADTTQYDYDY WGQGTQVTVS   120
S                                                                  121

SEQ ID NO: 198          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 198
QVQLQESGGG LVHSGGSLRL SCAASGFTLD YYAIGWFRRA PGKEREGVSC ISSGDGKTYY    60
ADSVKGRFTI SRDNAKNTVY LQMNSLKPED TAVYYCATAC AGAIGPYDYW GQGTQVTVSS   120

SEQ ID NO: 199          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 199
QVQLQESGGG LVPPGGSLRL SCAASGFPLD YYAIGWFRQA PGKEREGVSC ISSADGSTYY    60
ADSVKGRFTI SRDNAKNTVY LQMNSLGPED TAVYYCATAC ADTTQYDYDY WGQGTQVTVS   120
S                                                                  121

SEQ ID NO: 200          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 200
QVQLQESGGG LVQAGGSLRL SCAASGFSLG YYAIGWFRQA PGKEREGVSC ISSSDGHSST    60
YYADSVKGRF TISRDNAKNT VYLQMNNLKP EDTAVYYCAT DCAGGTATPY DYWGQGTQVT   120
VSS                                                                123

SEQ ID NO: 201          moltype = AA  length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 201
QVQLQESGGG LVQAGGSLRL SCAASGRTFS SYGMGWFRQA PGKEREFVAA ISWSGGSTYY    60
ADSVKGRFTI SRDNAKNTVY LQMNSLKPED TAVYYCASSA WPAGPKHQVE YDYWGQGTQV   120
TVSS                                                               124

SEQ ID NO: 202          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 202
QVQLQESGGG LVQAGGSLRL SCTASGFSLD YYAIGWFRQA PGKEREGVAC ISSRTGSTYY    60
ADSVKGRFTI SRDNAKNTVA LQMNSLKPED TAVYYCATAC VVVGDQNDYW GQGTQVTVSS   120

SEQ ID NO: 203          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
```

```
SEQUENCE: 203
QVQLQESGGG LVQDGGSLRL SCAASGFPLA YYAIGWFRQA PGKEREGVSC ISASDGSTYY    60
ADSVKGRFTI SRDNAKNTVY LQMNSLKPED TAVYYCATAC AETTLYEYDY WGQGTQVTVS   120
S                                                                  121

SEQ ID NO: 204          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 204
QVQLQESGGG LVQPGESLRL SCAASGFPLA YYAIGWFRQA PGKEREGVSC ISSSDGSTYY    60
ADSVKGRFTI SRDNAKNTVY LQMNSLKPED TAVYYCATAC ANWSTLGPYD YWGQGTQVTV   120
SS                                                                 122

SEQ ID NO: 205          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 205
QVQLQESGGG LVQPGESLRL SCAASGFTLA YYAIGWFRQA PGKEREGVSC ISSSDGNTYY    60
ADSVKGRFTI SRDNAKNTVY LQMNRLKPED TAVYYCATAC ADTTQYEYDY WGQGTQVTVS   120
S                                                                  121

SEQ ID NO: 206          moltype = AA   length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 206
QVQLQESGGG LVQPGGSLKL SCAASGSDFR ADAMGWYRQA PGKEREPVAI DSITSIYYVD    60
SVEGRFTISR DNTKNTVYLQ MTSLKPEDTA VYYCYARYSG RTYWGRGTQV TVSS         114

SEQ ID NO: 207          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 207
QVQLQESGGG LVQPGGSLRL SCAASGFPLA YYAIGWFRQA PGKEREGVSC ISASDGSTYY    60
ADSVKGRFTI SRDNAKNTVY LQMNSLRPED TAVYYCATAC ADTTLYEYDY WGQGTQVTVS   120
S                                                                  121

SEQ ID NO: 208          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 208
QVQLQESGGG LVQPGGSLRL SCAASGFPLA YYAIGWFRQA PGKEREGVSC ISSSDGNTYY    60
ADAVKGRFAI SRDNAKNTVY LQMNSLKPED TAVYYCATAC SDPRVYEYDY WGQGTQVTVS   120
S                                                                  121

SEQ ID NO: 209          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 209
QVQLQESGGG LVQPGGSLRL SCAASGFPLA YYAIGWFRQA PGKEREGVSC ISSSDGNTYY    60
```

```
ADAVKGRFTI SRDNAKNTVY LQMNSLKPED TAVYYCATAC ADTTQHEYDY WGQGTQVTVS   120
S                                                                  121

SEQ ID NO: 210          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 210
QVQLQESGGG LVQPGGSLRL SCAASGFPLA YYAIGWFRQA PGKEREGVSC ISSSDGNTYY   60
ADAVKGRFTI SRDNAKNTVY LQMNSLKPED TAVYYCATAC VDTTHYEYDY WGQGTQVTVS   120
S                                                                  121

SEQ ID NO: 211          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 211
QVQLQESGGG LVQPGGSLRL SCAASGFPLA YYAIGWFRQA PGKEREGVSC ISSSDGNTYY   60
ADSVKGRFTI SRDNAKNTVY LQMNSLKPED TAVYYCATAC ADATQHEYDY WGQGTQVTVS   120
S                                                                  121

SEQ ID NO: 212          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 212
QVQLQESGGG LVQPGGSLRL SCAASGFPLA YYAIGWFRQA PGKEREGVSC ISSSDGSTYY   60
ADSVKGRFTI SRDNAKNTVY LQMNSLGPED TAVYYCATAC ADTTQYDYDY WGQGTQVTVS   120
S                                                                  121

SEQ ID NO: 213          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 213
QVQLQESGGG LVQPGGSLRL SCAASGFPLA YYAIGWFRQA PGKEREGVSC ISSSDGSTYY   60
ADSVKGRFTI SRDNAKNTVY LQMNSLKPED TAVYYCATAC ADTTQYEYDY WGQGTQVTVS   120
S                                                                  121

SEQ ID NO: 214          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 214
QVQLQESGGG LVQPGGSLRL SCAASGFPLA YYAIGWFRQA PGKEREGVSC ISSSDGSTYY   60
ADSVKGRFTI SRDNAKNTVY LQMNSLKPED TAVYYCATAC GGATGPYDYW GQGTQVTVSS   120

SEQ ID NO: 215          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 215
QVQLQESGGG LVQPGGSLRL SCAASGFPLA YYAIGWFRRA PGKEREGVSC ISSSDGNTYY   60
ADAVKGRFTI SRDNAKNTVY LQMNSLKPED TAVYYCATAC ADTTQHEYDY WGQGTQVTVS   120
S                                                                  121
```

```
SEQ ID NO: 216          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 216
QVQLQESGGG LVQPGGSLRL SCAASGFPLD YYAIGWFRQA PGKEREGVSC ISAGDGSSTY    60
YADSVKGRFT ISRDNAKNTV YLQMNSLKPE DTAVYYCATA CASTTLYEYD YWGQGTQVTV   120
SS                                                                 122

SEQ ID NO: 217          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 217
QVQLQESGGG LVQPGGSLRL SCAASGFPLD YYAIGWFRQA PGKEREGVSC ISSADGSTYY    60
ADSVKGRFTI SRDNAKNAVY LQMNSLGPED TAVYYCATAC ADTTQYDYDY WGQGTQVTVS   120
S                                                                  121

SEQ ID NO: 218          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 218
QVQLQESGGG LVQPGGSLRL SCAASGFPLD YYAIGWFRQA PGKEREGVSC ISSADGSTYY    60
ADSVKGRFTI SRDNAKNTVY LQMNSLGPED TAVYYCATAC ADTTQYDYDY WGQGTQVTVS   120
S                                                                  121

SEQ ID NO: 219          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 219
QVQLQESGGG LVQPGGSLRL SCAASGFPLD YYAIGWFRQA PGKEREGVSC ISSADGSTYY    60
ADSVKGRFTI SRDNAKNTVY LQMNSLKPED TAVYYCATAC VDTTQYEYDY WGQGTQVTVS   120
S                                                                  121

SEQ ID NO: 220          moltype = AA   length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 220
QVQLQESGGG LVQPGGSLRL SCAASGFPLD YYAIGWFRQA PGKEREGVSC ISSPDGSTYY    60
ADSVKGRFTI SRDNAKNTVY LQMNSLKPED TAVYYCATAC VDTTQYEYDY WGQGTQVTVS   120
S                                                                  121

SEQ ID NO: 221          moltype = AA   length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 221
QVQLQESGGG LVQPGGSLRL SCAASGFPLD YYAIGWFRQA PGKEREGVSC ISSSDGSDGN    60
TYYADSVKGR FTISRDNAKN TVYLQMNSLK PEDTAVYYCA TDCSLHGSDY PYDYWGQGTQ   120
VTVSS                                                              125
```

-continued

```
SEQ ID NO: 222            moltype = AA   length = 121
FEATURE                   Location/Qualifiers
REGION                    1..121
                          note = Description of Artificial Sequence: Synthetic
                          polypeptide
source                    1..121
                          mol_type = protein
                          organism = synthetic construct
SEQUENCE: 222
QVQLQESGGG LVQPGGSLRL SCAASGFPLD YYAIGWFRQA PGKEREGVSC ISSSDGSTYY    60
ADSVKGRFTI SRDNAKNTVY LQMNSLKPED TAVYYCATAC ADTTQYEYDY WGQGTQVTVS   120
S                                                                  121

SEQ ID NO: 223            moltype = AA   length = 121
FEATURE                   Location/Qualifiers
REGION                    1..121
                          note = Description of Artificial Sequence: Synthetic
                          polypeptide
source                    1..121
                          mol_type = protein
                          organism = synthetic construct
SEQUENCE: 223
QVQLQESGGG LVQPGGSLRL SCAASGFPLE YYAIGWFRQA PGKEREGVSC ISSSDGSTYY    60
ADSVKGRFTI SRDNAKNTVY LQMNSLKPED TAVYYCATAC SDPRVYEYDY WGQGTQVTVS   120
S                                                                  121

SEQ ID NO: 224            moltype = AA   length = 121
FEATURE                   Location/Qualifiers
REGION                    1..121
                          note = Description of Artificial Sequence: Synthetic
                          polypeptide
source                    1..121
                          mol_type = protein
                          organism = synthetic construct
SEQUENCE: 224
QVQLQESGGG LVQPGGSLRL SCAASGFPLG YYAIGWFRQA PGKEREGVSC ISSSDDSTYY    60
ADSVKGRFTI SRDNDKNTVY LQMNSLKPED TAVYYCATDC AGGTSTPYDY WGQGTQVTVS   120
S                                                                  121

SEQ ID NO: 225            moltype = AA   length = 121
FEATURE                   Location/Qualifiers
REGION                    1..121
                          note = Description of Artificial Sequence: Synthetic
                          polypeptide
source                    1..121
                          mol_type = protein
                          organism = synthetic construct
SEQUENCE: 225
QVQLQESGGG LVQPGGSLRL SCAASGFPLH YYAIGWFRQA PGKEREGVSC ISSGDGSTYY    60
ADSVKGRFTI SRDNAKNTVY LQMNSLKPED TAVYYCATSC VVVTKNEYDY WGQGTQVTVS   120
S                                                                  121

SEQ ID NO: 226            moltype = AA   length = 120
FEATURE                   Location/Qualifiers
REGION                    1..120
                          note = Description of Artificial Sequence: Synthetic
                          polypeptide
source                    1..120
                          mol_type = protein
                          organism = synthetic construct
SEQUENCE: 226
QVQLQESGGG LVQPGGSLRL SCAASGFPLH YYAIGWFRQA PGKEREGVSC ISSSDGSTYY    60
ADSVKGRFTI SRDNAKNTVY LQMNSLKPED TAVYYCATAC GGATGPYDYW GQGTQVTVSS  120

SEQ ID NO: 227            moltype = AA   length = 121
FEATURE                   Location/Qualifiers
REGION                    1..121
                          note = Description of Artificial Sequence: Synthetic
                          polypeptide
source                    1..121
                          mol_type = protein
                          organism = synthetic construct
SEQUENCE: 227
QVQLQESGGG LVQPGGSLRL SCAASGFPLH YYAIGWFRQA PGKEREGVSC ISSSDGSTYY    60
ADSVKGRFTI SRDNAKNTVY LQMNSLKPED TAVYYCATAC VVADRNEYDY WGQGTQVTVS   120
S                                                                  121

SEQ ID NO: 228            moltype = AA   length = 121
FEATURE                   Location/Qualifiers
```

```
REGION                  1..121
                        note = Description of Artificial Sequence: Synthetic
                          polypeptide
source                  1..121
                        mol_type = protein
                        organism = synthetic construct
SEQUENCE: 228
QVQLQESGGG LVQPGGSLRL SCAASGFPLH YYAIGWFRQA PGKEREGVSC ISSSDGSTYY    60
ADSVKGRFTI SRDNAKNTVY LQMNSLRPED TAVYYCATAC VVADRNEYDY WGQGTQVTVS   120
S                                                                   121

SEQ ID NO: 229          moltype = AA  length = 121
FEATURE                 Location/Qualifiers
REGION                  1..121
                        note = Description of Artificial Sequence: Synthetic
                          polypeptide
source                  1..121
                        mol_type = protein
                        organism = synthetic construct
SEQUENCE: 229
QVQLQESGGG LVQPGGSLRL SCAASGFPLN YYAIGWFRQA PGKEREGVSC ISASDGNTYY    60
ADSVKGRFTI SRDNAKNTVY LQMNSLKPED TAVYYCATTC ASPEKYEYDY WGQGTQVTVS   120
S                                                                   121

SEQ ID NO: 230          moltype = AA  length = 120
FEATURE                 Location/Qualifiers
REGION                  1..120
                        note = Description of Artificial Sequence: Synthetic
                          polypeptide
source                  1..120
                        mol_type = protein
                        organism = synthetic construct
SEQUENCE: 230
QVQLQESGGG LVQPGGSLRL SCAASGFPLN YYAIGWFRQA PGKEREGVSC ISSSDGSTYY    60
ADSVKGRFII SRDNAKNTVY LQMNSLKPED TAVYYCATAC GGATGPYDYW GQGTQVTVSS   120

SEQ ID NO: 231          moltype = AA  length = 120
FEATURE                 Location/Qualifiers
REGION                  1..120
                        note = Description of Artificial Sequence: Synthetic
                          polypeptide
source                  1..120
                        mol_type = protein
                        organism = synthetic construct
SEQUENCE: 231
QVQLQESGGG LVQPGGSLRL SCAASGFPLN YYAIGWFRQA PGKEREGVSC ISSSDGSTYY    60
ADSVKGRFTI SRDNAKNTVY LQMNSLKPED TAVYYCATAC GSAVHEYDYW GQGTQVTVSS   120

SEQ ID NO: 232          moltype = AA  length = 121
FEATURE                 Location/Qualifiers
REGION                  1..121
                        note = Description of Artificial Sequence: Synthetic
                          polypeptide
source                  1..121
                        mol_type = protein
                        organism = synthetic construct
SEQUENCE: 232
QVQLQESGGG LVQPGGSLRL SCAASGFSLA YYAIGWFRQA PGKEREGVSC IAASVGSTYY    60
ADSVKGRFTI SRDDAKNTVY LQMNSLKPED TAVYYCATDC AGGVGHEYDY WGQGTQVTVS   120
S                                                                   121

SEQ ID NO: 233          moltype = AA  length = 120
FEATURE                 Location/Qualifiers
REGION                  1..120
                        note = Description of Artificial Sequence: Synthetic
                          polypeptide
source                  1..120
                        mol_type = protein
                        organism = synthetic construct
SEQUENCE: 233
QVQLQESGGG LVQPGGSLRL SCAASGFSLD YYAIGWFRQA PGKEREGVSC ISSSDGSTYY    60
ADSVKGRFTI SRDNAKNAVY LQMNSLKPED TAVYYCATAC GGATGPYDYW GQGTQVTVSS   120

SEQ ID NO: 234          moltype = AA  length = 121
FEATURE                 Location/Qualifiers
REGION                  1..121
                        note = Description of Artificial Sequence: Synthetic
                          polypeptide
source                  1..121
```

```
                         mol_type = protein
                         organism = synthetic construct
SEQUENCE: 234
QVQLQESGGG LVQPGGSLRL SCAASGFSLD YYAIGWFRQA PGKEREGVSC ISSSDGSTYY    60
ADSVKGRFTI SRDNAKNAVY LQMNSLKPED TAVYYCATAC VDTTQYEYDY WGQGTQVTVS   120
S                                                                  121

SEQ ID NO: 235           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 235
QVQLQESGGG LVQPGGSLRL SCAASGFSLD YYAIGWFRQA PGKEREGVSC ISSSDGSTYY    60
ADSVKGRFTI SRDNAKNTVY LQMNSLKPED TAVYYCATDC AGGTSTPYDY WGQGTQVTVS   120
S                                                                  121

SEQ ID NO: 236           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 236
QVQLQESGGG LVQPGGSLRL SCAASGFSLN YYAIGWFRQA PGKEREGVSC ISAGDGNTYY    60
ADSVKGRFTI SRDNAANTVS LQMDSLKPED TAVYYCATAC VITTLYEYDY WGQGTQVTVS   120
S                                                                  121

SEQ ID NO: 237           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 237
QVQLQESGGG LVQPGGSLRL SCAASGFTLA YYAIGWFRQA PGKEREGVSC ISSSDGSTYY    60
ADSVKGRFTI SRDNAKNTVY LQMNSLKPED TAVYYCATAC ADTTQHEYDY WGQGTQVTVS   120
S                                                                  121

SEQ ID NO: 238           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 238
QVQLQESGGG LVQPGGSLRL SCAASGFTLA YYAIGWFRQA PGKEREGVSC ISSSDGSTYY    60
ADSVKGRFTI SRDNAKNTVY LQMNSLKPED TAVYYCATAC ADTTQYEYDY WGQGTQVTVS   120
S                                                                  121

SEQ ID NO: 239           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 239
QVQLQESGGG LVQPGGSLRL SCAASGFTLD YYAIGWFRQA PGKEREGVAC ISSSDGSTYY    60
ADSVKGRFTI SRDNAKNTVY LQMNSLKPED TAVYYCATAC GGATGPYDYW GQGTQVTVSS   120

SEQ ID NO: 240           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
```

```
SEQUENCE: 240
QVQLQESGGG LVQPGGSLRL SCAASGFTLD YYAIGWFRQA PGKEREGVAC ISSSDGSTYY    60
ADSVKGRFTI SRDNAKNTVY LQMNSLKPQD TAVYYCATAC GSLVGMYDYW GQGTQVTVSP   120

SEQ ID NO: 241          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 241
QVQLQESGGG LVQPGGSLRL SCAASGFTLD YYAIGWFRQA PGKEREGVSC ISASDGNTYY    60
ADSVKGRFTI SRDNAKNTVY LQMNSLKPED TAVYYCATTC ASPEKYEYDY WGQGTQVTVS   120
S                                                                  121

SEQ ID NO: 242          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 242
QVQLQESGGG LVQPGGSLRL SCAASGFTLD YYAIGWFRQA PGKEREGVSC ISASNGNTYY    60
ADSVKGRFTI SRDSAKNTVY LQMNSLKPED TAVYYCATTC SGLTHEYDYW GQGTQVTVSS   120

SEQ ID NO: 243          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 243
QVQLQESGGG LVQPGGSLRL SCAASGFTLD YYAIGWFRQA PGKEREGVSC ISSGDGNTYY    60
ADSVKGRFTI SRDNAKNTVY LQMNSLKPED TAVYYCATAC GGATGPYDYW GQGTQVTVSS   120

SEQ ID NO: 244          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 244
QVQLQESGGG LVQPGGSLRL SCAASGFTLD YYAIGWFRQA PGKEREGVSC ISSGDGSTYY    60
ADSVKGRFTI SRDNAKNTVY LQMNSLKPED TAVYYCATHC GGSSWSNEYD YWGQGTQVTV   120
SS                                                                 122

SEQ ID NO: 245          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 245
QVQLQESGGG LVQPGGSLRL SCAASGFTLD YYAIGWFRQA PGKEREGVSC ISSNDGSTYY    60
ADSVKGRFTI SRDNAKNTVY LQMNSLKPED TAVYYCATAC ADTTQHEYDY WGQGTQVTVS   120
S                                                                  121

SEQ ID NO: 246          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 246
QVQLQESGGG LVQPGGSLRL SCAASGFTLD YYAIGWFRQA PGKEREGVSC ISSSDGGTYY    60
ADSVKGRFTI SRDNAKNTVY LQMNSLKPED TAVYYCATAC GGATGPYDYW GQGTQVTVSS   120
```

```
SEQ ID NO: 247          moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 247
QVQLQESGGG LVQPGGSLRL SCAASGFTLD YYAIGWFRQA PGKEREGVSC ISSSDGSSSD   60
GNTYYADSVK GRFTISRDNA KNTVYLQMNN LKPEDTAVYY CATACVVTTL YEYDYWGQGT  120
QVTVSS                                                             126

SEQ ID NO: 248          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 248
QVQLQESGGG LVQPGGSLRL SCAASGFTLD YYAIGWFRQA PGKEREGVSC ISSSDGSTYY   60
ADSVKGRFTI SRDNAKNTVY LQMNSLKPED TAVYYCATAC ADTTQYEYDY WGQGTQVTVS  120
P                                                                  121

SEQ ID NO: 249          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 249
QVQLQESGGG LVQPGGSLRL SCAASGFTLD YYAIGWFRQA PGKEREGVSC ISSSDGSTYY   60
ADSVKGRFTI SRDNAKNTVY LQMNSLKPED TAVYYCATAC GGATGPYDYW GQGTQVTVSS  120

SEQ ID NO: 250          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 250
QVQLQESGGG LVQPGGSLRL SCAASGFTLD YYAIGWFRQA PGKEREGVSC ISSSGGSTYY   60
ADSVKGRFTI SRDNAKNTVY LQMNMLKPED TAVYYCATAC ADTTQYEYDY WGQGTQVTVS  120
S                                                                  121

SEQ ID NO: 251          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 251
QVQLQESGGG LVQPGGSLRL SCAASGFTLD YYAIGWFRQA PGKEREGVSC ISSSGGSTYY   60
ADSVKGRFTI SRDNAKNTVY LQMNSLKPED TAVYYCATAC ASPVIYEYDY WGQGTQVTVS  120
S                                                                  121

SEQ ID NO: 252          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 252
QVQLQESGGG LVQPGGSLRL SCAASGFTLD YYAIGWFRQA PGKEREGVSC ISSSGGSTYY   60
ADSVKGRFTI SRDNAKNTVY LQMNSLKPED TAVYYCATDC AGGTSTPYDY WGQGTQVTVS  120
S                                                                  121

SEQ ID NO: 253          moltype = AA  length = 121
FEATURE                 Location/Qualifiers
```

```
REGION                    1..121
                          note = Description of Artificial Sequence: Synthetic
                              polypeptide
source                    1..121
                          mol_type = protein
                          organism = synthetic construct
SEQUENCE: 253
QVQLQESGGG LVQPGGSLRL SCAASGFTLG YYAIGWFRQA PGKEREGVSC ISSSDGSTYY    60
ADSVKGRFTI SRDNAKNTVY LQMNSLKPED TAVYYCATAC ADTTQYEYDY WGQGTQVTVS   120
S                                                                   121

SEQ ID NO: 254            moltype = AA  length = 122
FEATURE                   Location/Qualifiers
REGION                    1..122
                          note = Description of Artificial Sequence: Synthetic
                              polypeptide
source                    1..122
                          mol_type = protein
                          organism = synthetic construct
SEQUENCE: 254
QVQLQESGGG LVQPGGSLRL SCAASGFTLG YYAIGWFRQA PGKEREGVSC ISSSDGSTYY    60
ADSVKGRFTI SRDNAKNTVY LQMNSLKPED TAVYYCATAC ANWSSLGPYD YWGQGTQVTV   120
SS                                                                  122

SEQ ID NO: 255            moltype = AA  length = 120
FEATURE                   Location/Qualifiers
REGION                    1..120
                          note = Description of Artificial Sequence: Synthetic
                              polypeptide
source                    1..120
                          mol_type = protein
                          organism = synthetic construct
SEQUENCE: 255
QVQLQESGGG LVQPGGSLRL SCAASGFTLG YYAIGWFRQA PGKEREGVSC ISSSDGSTYY    60
ADSVKGRFTI SRDNAKNTVY LQMNSLKPED TGVYYCATAC GGATGPYDYW GQGTQVTVSS   120

SEQ ID NO: 256            moltype = AA  length = 121
FEATURE                   Location/Qualifiers
REGION                    1..121
                          note = Description of Artificial Sequence: Synthetic
                              polypeptide
source                    1..121
                          mol_type = protein
                          organism = synthetic construct
SEQUENCE: 256
QVQLQESGGG LVQPGGSLRL SCEGSGFSLD YYAIGWFRQA PGKEREGVSC ISSGDGNTYY    60
ADSVKGRFTI SRDNAKNTVY LQMNSLKPED TAVYYCATDC VGFGSNWFDY WGQGTQVTVS   120
S                                                                   121

SEQ ID NO: 257            moltype = AA  length = 120
FEATURE                   Location/Qualifiers
REGION                    1..120
                          note = Description of Artificial Sequence: Synthetic
                              polypeptide
source                    1..120
                          mol_type = protein
                          organism = synthetic construct
SEQUENCE: 257
QVQLQESGGG LVQPGGSLRL SCTASGFSLD YYAIGWFRQA PGKEREGVAC ISSRTGSTYY    60
ADSVKGRFTI SRDNAKNTVA LQMNSLKPED TAVYYCATAC VVVGDQNDYW GQGTQVTVSS   120

SEQ ID NO: 258            moltype = AA  length = 120
FEATURE                   Location/Qualifiers
REGION                    1..120
                          note = Description of Artificial Sequence: Synthetic
                              polypeptide
source                    1..120
                          mol_type = protein
                          organism = synthetic construct
SEQUENCE: 258
QVQLQESGGG LVQPGGSLRL SCTASGFSLD YYAIGWFRQA PGKEREGVSC ISSRTGGTYY    60
ADSVKGRFTI SRDDAKNTVY LQMNSLKPED TAVYYCATAC VVVGDRNDYW GQGTQVTVSS   120

SEQ ID NO: 259            moltype = AA  length = 121
FEATURE                   Location/Qualifiers
REGION                    1..121
                          note = Description of Artificial Sequence: Synthetic
                              polypeptide
source                    1..121
```

```
                        mol_type = protein
                        organism = synthetic construct
SEQUENCE: 259
QVQLQESGGG LVQPGGSLRL SCTASGFSLD YYAIGWFRQA PGKEREGVSC ISSRTGGTYY    60
ADSVKGRFTI SRDNAKNTVY LQMNSLKPED TAVYYCATAC VDTTQYEYDY WGQGTQVTVS   120
S                                                                   121

SEQ ID NO: 260          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 260
QVQLQESGGG LVQPGGSLRL SCTASGFSLD YYAIGWFRQA PGKEREGVSC ISSRTGGTYY    60
ADSVKGRFTI SRDNAKNTVY LQMNSLKPED TAVYYCATAC VVVGDQNDYW GQGTQVTVSS   120

SEQ ID NO: 261          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 261
QVQLQESGGG LVQPGGSLRL SCTASGFSLD YYAIGWFRQA PGKEREGVSC ISSRTGNTYY    60
ADSVKGRFTI SRDDAKNMVY LQMNSLKPED TAVYYCATAC VVVGDQNDYW GQGTQVTVSS   120

SEQ ID NO: 262          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 262
QVQLQESGGG LVQPGGSLRL SCTASGFSLD YYAIGWFRQA PGKEREGVSC ISSRTGSTYY    60
ADSVKGRFTI SRDDAKNTVY LQMNSLKPED TAVYYCATAC VVVGDQNDYW GQGTQVTVSS   120

SEQ ID NO: 263          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 263
QVQLQESGGG LVQPGGSLRL SCTASGFSLG YYAIGWFRQA LGKEREGVSC ISSRTGSTYY    60
ADSVKGRFTV SRDDAKNTVY LQMNSLKPED TAVYYCATAC VVVGDQNDYW GQGTQVTVSS   120

SEQ ID NO: 264          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 264
QVQLQESGGG LVQPGGSLRL SCTASGFSLG YYAIGWFRQA PGKEREGVSC ISSRTGSTYY    60
ADSVKGRFAI SRDDAKNTVY LQMNSLKPED TAVYYCATAC VVVGDQNDYW GQGTQVTVSS   120

SEQ ID NO: 265          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 265
QVQLQESGGG LVQPGGSLRL SCTASGFSLG YYAIGWFRQA PGKEREGVSC ISSRTGSTYY    60
ADSVKGRFTI SRDDAKNTVY LQMNSLKPED TAVYYCATAC VVVGDQNDYW GQGTQVTVSS   120
```

```
SEQ ID NO: 266          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 266
QVQLQESGGG LVQPGGSLRL SCTASGFSLG YYAIGWFRQA PGKEREGVSC ISSRTGSTYY   60
ADSVKGRFTV SRDDAKNTVY LQMNSLKPED TAVYYCATAC VVVGDQNDYW GQGTQVTVSS  120

SEQ ID NO: 267          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 267
QVQLQESGGG LVQPGGSLRL SCVASGFPLD YYAIGWFRQA PGKEREGVSC ISSSDGSTYY   60
ADSVKGRFTI SRDNAKNTVY LQMNSLKPED TAVYYCATAC GGATGPYDYW GQGTQVTVSS  120

SEQ ID NO: 268          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 268
QVQLQESGGG LVQPGGSLRL SCVASGFSLD YYAIGWFRQA PGKEREGVSC ISNSDGSTYY   60
ADSVKGRFTI SRDNAKNTVY LQMNSLKPED TAVYYCATAC ADTTQYAYDY WGQGTQVTVS  120
S                                                                 121

SEQ ID NO: 269          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 269
QVQLQESGGG LVQPGGSLRL SCVASGFTLD YYAIGWFRQA PGKEREGVSC ISSGSDGNTY   60
YADSVKGRFT ISRDNAKNTV YLQMNSLKPE DTAVYYCATA CSGLTHEYDY WGQGTQVTVS  120
S                                                                 121

SEQ ID NO: 270          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 270
QVQLQESGGG LVQPGGSLRL SCVASGFTLD YYAIGWFRQA PGKEREGVSC ISSSDDSTYY   60
ADSVKGRFTI SRDNAKNTVY LQMNSLKPED TAVYYCATAC ADTTQYEYDY WGQGTQVTVS  120
S                                                                 121

SEQ ID NO: 271          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 271
QVQLQESGGG LVQPGGSLRL SCVASGFTLD YYAIGWFRQA PGKEREGVSC ISSSSDGNTY   60
YADSVKGRFT ISRDNAKNTV YLQMNSLKPE DTAVYYCATT CSGLTHEYDY WGQGTQVTVS  120
S                                                                 121

SEQ ID NO: 272          moltype = AA  length = 121
FEATURE                 Location/Qualifiers
REGION                  1..121
```

```
                        note = Description of Artificial Sequence: Synthetic
                         polypeptide
source                  1..121
                        mol_type = protein
                        organism = synthetic construct
SEQUENCE: 272
QVQLQESGGG LVQPGGSLRL SCVASGFTLG YYAIGWFRQA PGKEREGVSC ISSSDGSTYY    60
ADSVKGRFTI SRDNAKNTVY LQMNSLKPED TAVYYCATAC ADTTQYDYDY WGQGTQVTVS   120
S                                                                  121

SEQ ID NO: 273          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 273
QVQLQESGGG LVQPGGSLRL SCVGSGFTLD YYAIGWFRQA PGKEREGVSC ISSNDGSTYY    60
ADSVKGRFTI SRDNAKNTVY LQMNSLKPED TAVYYCATAC GGATGPYDYW GQGTQVTVSS   120

SEQ ID NO: 274          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 274
QVQLQESGGG LVQSGGSLRL SCAASGFPLA YYAIGWFRQA PGKEREGVSC ISASDGSTYY    60
ADSVKGRFTI SRDNAKNTVY LQMNSLKPED TAVYYCATAC AETTLYEYDY WGQGTQVTVS   120
S                                                                  121

SEQ ID NO: 275          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 275
QVQLQESGGG LVQTGGSLRL SCAASGFTLD YYAIGWFRQA PGKEREGVSC ISSSDGSTYY    60
ADSVKGRFTI SRDNAKNTVY LQMNSLKPED TAVYYCATAC GGATGPYDYW GQGTQVTVSS   120

SEQ ID NO: 276          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 276
QVQLQESGGG MVQAGESLRL SCAASGFPLA YYAIGWFRQA PGKEREGVSC ISSSDGNTYY    60
ADSVKGRFTI SRDNAKNTVY LQMNSLKPED TAVYYCATAC ADATQHEYDY WGQGTQVTVS   120
S                                                                  121

SEQ ID NO: 277          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 277
QVQLQESGGG SVQPGESLRL SCAASGFPLD YYAIGWFRQA PGKEREGVSC ISASDGSTYY    60
ADSVKGRFTI SRDNAKNTVY LQMNSLKPED TAVYYCATAC ADTTLYEYDY WGQGTQVTVS   120
S                                                                  121

SEQ ID NO: 278          moltype = AA  length = 121
FEATURE                 Location/Qualifiers
REGION                  1..121
                        note = Description of Artificial Sequence: Synthetic
                         polypeptide
source                  1..121
```

```
                                mol_type = protein
                                organism = synthetic construct
SEQUENCE: 278
QVQLQESGGG SVQPGGSLRL SCAASGFTLD YYAIGWFRQA PGKEREGVSC ISSGDGSTYY       60
ADSVKGRFTI SRDNAKNTVY LQMNSLKPED TAVYYCATAC ADTTHYEYDY WGQGTQVTVS      120
S                                                                      121

SEQ ID NO: 279                  moltype = AA   length = 120
FEATURE                         Location/Qualifiers
REGION                          1..120
                                note = Description of Artificial Sequence: Synthetic
                                  polypeptide
source                          1..120
                                mol_type = protein
                                organism = synthetic construct
SEQUENCE: 279
QVQLQESGGG SVQSGGSLRL SCTASGFSLG YYAIGWFRQA PGKEREGVSC ISSRTGSTYY       60
ADSVKGRFTV SRDDAKNTVY LQMNSLKPED TAVYYCATAC VVVGDQNDYW GQGTQVTVSS      120

SEQ ID NO: 280                  moltype = AA   length = 121
FEATURE                         Location/Qualifiers
REGION                          1..121
                                note = Description of Artificial Sequence: Synthetic
                                  polypeptide
source                          1..121
                                mol_type = protein
                                organism = synthetic construct
SEQUENCE: 280
QVQLQESGGG SVRPGGSLRL SCAASGFPLA YYAIGWFRQA PGKEREGVSC ISSSDGNTYY       60
ADAVKGRFTI SRDNAKNAVY LQMNSLKPED TAVYYCATAC ADTTQHEYDY WGQGTQVTVS      120
S                                                                      121

SEQ ID NO: 281                  moltype = AA   length = 121
FEATURE                         Location/Qualifiers
REGION                          1..121
                                note = Description of Artificial Sequence: Synthetic
                                  polypeptide
source                          1..121
                                mol_type = protein
                                organism = synthetic construct
SEQUENCE: 281
QVQLQESGGG VAQPGGSLRL SCAASGFPLD YYAIGWFRQA PGKEREGVSC ISASDGSTYY       60
ADSVKGRFTI SRDNAKNTVY LQMNSLKPED TAVYYCATAC ADTTLYEYDY WGQGTQVTVS      120
S                                                                      121

SEQ ID NO: 282                  moltype = AA   length = 114
FEATURE                         Location/Qualifiers
REGION                          1..114
                                note = Description of Artificial Sequence: Synthetic
                                  polypeptide
source                          1..114
                                mol_type = protein
                                organism = synthetic construct
SEQUENCE: 282
QVQLQESGGG VVQAGGSLKL SCAASGSDFR ADAMGWYRQA PGKEREPVAI DSITSIYYVD       60
SVEGRFTISR DNTKNTVYLQ MTSLKPEDTA VYYCYARYSG RTYWGRGTQV TVSS            114

SEQ ID NO: 283                  moltype = AA   length = 122
FEATURE                         Location/Qualifiers
REGION                          1..122
                                note = Description of Artificial Sequence: Synthetic
                                  polypeptide
source                          1..122
                                mol_type = protein
                                organism = synthetic construct
SEQUENCE: 283
QVQLQESGGG VVQPGGSLRL SCAASGFSLD YYAIGWFRQA PGKEREGVSC ISSGDGSTYY       60
ADSVKGRFTI SRDNAKNTVY LQMNSLKPED TAVYYCATHC GGTSWGTSYD YWGQGTQVTV     120
SS                                                                    122

SEQ ID NO: 284                  moltype = AA   length = 124
FEATURE                         Location/Qualifiers
REGION                          1..124
                                note = Description of Artificial Sequence: Synthetic
                                  polypeptide
source                          1..124
                                mol_type = protein
                                organism = synthetic construct
SEQUENCE: 284
```

```
                       -continued
QVQLQESGGG VVQPGGSLRL SCAASGLTFR SVGMGWFRRA PGKEREFVAT ASPSGVITYY    60
ADSVKGRFTI SRDNAKNTVY LEMNSLKPED TAVYYCAVRI YSGSFDNTLA YDYWGQGTQV   120
TVSS                                                                124

SEQ ID NO: 285          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 285
QVQLQESGGG VVQPGGSLRL SCTASGFSLG YYAIGWFRQA PGKEREGVSC ISSRTGSTYY    60
ADSVKGRFTV SRDDAKNTVY LQMNSLKPED TAVYYCATAC VVVGDQNDYW GQGTQVTVSS   120

SEQ ID NO: 286          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 286
QVQLQESGGG VVQSGGSLRL SCTASGFSLD YYAIGWFRQA PGKEREGVSC ISSRTGSTYY    60
ADSVKGRFTI SRDDAKNTVY LQMNSLKPED TAVYYCATAC VVVGDQNDYW GQGTQVTVSS   120

SEQ ID NO: 287          moltype = RNA  length = 13
FEATURE                 Location/Qualifiers
misc_feature            1..13
                        note = Description of Artificial Sequence: Synthetic
                         oligonucleotide
source                  1..13
                        mol_type = other RNA
                        organism = synthetic construct
SEQUENCE: 287
wwwtatttat ttw                                                      13
```

ENGINEERED CHIMERIC FUSION PROTEIN COMPOSITIONS AND METHODS OF USE THEREOF

CROSS REFERENCE

This application is a continuation of international application PCT/US2022/020787, filed on Mar. 17, 2022, which claims the benefit of U.S. Provisional Application No. 63/162,352 filed on Mar. 17, 2021, U.S. Provisional Application No. 63/172,922, filed on Apr. 9, 2021, U.S. Provisional Application No. 63/243,947, filed on Sep. 14, 2021, and U.S. Provisional Application No. 63/255,540, filed on Oct. 14, 2021, each of which is incorporated herein by reference in its entirety.

SEQUENCE LISTING

The instant application contains a Sequence Listing which has been submitted electronically in XML format, is named 56371-715_301_SL.xml, and is 414,722 bytes in size. This sequence listing file is incorporated in its entirety. A text file containing the same sequence listing was originally submitted electronically in the parent case in ASCII format created on May 2, 2022, is named 56371-715_601_SL.txt and is 332,110 bytes in size. Said ASCII copy is also hereby incorporated by reference in its entirety.

BACKGROUND

Cellular immunotherapy is a promising new technology for fighting difficult to treat diseases, such as cancer, and persistent infections and also certain diseases that are refractory to other forms of treatment. A major breakthrough has come across with the discovery of CAR-T cell and their potential use in immunotherapy. CAR-T cells are T lymphocytes expressing a chimeric antigen receptor which helps target the T cell to specific diseased cells such as cancer cells, and can induce cytotoxic responses intended to kill the target cancer cell or immunosuppression and/or tolerance depending on the intracellular domain employed and co-expressed immunosuppressive cytokines. Although CAR T cells continue to remain prospective tools for cancer therapy, several limitations along the way has slowed the progress on CAR-T cells and dampened its promise in clinical trials.

Understanding the limitations of CAR-T cells is the key to leveraging the technology and continue innovations towards better immunotherapy models. Specifically, in T cell malignancies, CAR-T cells appear to have faced a major problem. CAR-T cells and malignant T cells share surface antigen in most T cell lymphomas (TCL), therefore, CAR-T cells are subject to cytotoxicity in the same way as cancer cells. In some instances, the CAR-T products may be contaminated by malignant T cells. Additionally, T cell aplasia is a potential problem due to prolonged persistence of the CAR-T cells. Other limitations include the poor ability for CAR-T cells to penetrate into solid tumors and the potent tumor microenvironment which acts to downregulate their anti-tumor potential. CAR-T cell function is also negatively influenced by the immunosuppressive tumor microenvironment (TME) that leads to endogenous T cell inactivation and exhaustion.

Myeloid cells, including macrophages, are cells derived from the myeloid lineage and belong to the innate immune system. They are derived from bone marrow stem cells which egress into the blood and can migrate into tissues. Some of their main functions include phagocytosis, the activation of T cell responses, and clearance of cellular debris and extracellular matrices. They also play an important role in maintaining homeostasis, and initiating and resolving inflammation. Moreover, myeloid cells can differentiate into numerous downstream cells, including macrophages, which can display different responses ranging from pro-inflammatory to anti-inflammatory depending on the type of stimuli they receive from the surrounding microenvironment. Furthermore, tissue macrophages have been shown to play a broad regulatory and activating role on other immune cell types including CD8+ and CD4+ T effector cells, NK cells and T regulatory cells. Macrophages have been shown to be a main immune infiltrate in malignant tumors and have been shown to have a broad immunosuppressive influence on effector immune infiltration and function.

SUMMARY

The diverse functionality of myeloid cells makes them an ideal cell therapy candidate that can be engineered to have numerous therapeutic effects. The present disclosure is related to immunotherapy using myeloid cells (e.g., CD14+ cells) of the immune system, particularly phagocytic cells. A number of therapeutic indications could be contemplated using myeloid cells. For example, myeloid cell immunotherapy could be exceedingly important in treating cancer, autoimmunity, fibrotic diseases and infections. The present disclosure is related to immunotherapy using myeloid cells, including phagocytic cells of the immune system, particularly monocytes. It is an object of the invention disclosed herein to harness one or more of these functions of myeloid cells for therapeutic uses. For example, it is an object of the invention disclosed herein to harness the phagocytic activity of myeloid cells, including engineered myeloid cells, for therapeutic uses. For example, it is an object of the invention disclosed herein to harness the ability of myeloid cells, including engineered myeloid cells, to promote T cell activation. For example, it is an object of the invention disclosed herein to harness the ability of myeloid cells, including engineered myeloid cells, to promote secretion of tumoricidal molecules. For example, it is an object of the invention disclosed herein to harness the ability of myeloid cells, including engineered myeloid cells, to promote recruitment and trafficking of immune cells and molecules. In one aspect the disclosure provides new and useful chimeric constructs that, when expressed in a myeloid cell, the myeloid cell can drive targeted attack and phagocytosis of the molecule, molecular assembly, object or a cell that comprises the target, e.g., a target antigen on its surface. One of the many facets of the present disclosure is to (i) enhance the phagocytic ability of the myeloid cells (e.g., the engineered myeloid cells expressing the new and improved chimeric constructs); help initiate a coordinated and sustained immune response against the target (e.g., target antigen). The present disclosure provides innovative methods and compositions that can successfully transfect or transduce a myeloid cell, or otherwise induce a genetic modification in a myeloid cell, with the purpose of augmenting a functional aspect of a myeloid cell, additionally, without compromising the cell's differentiation capability, maturation potential, and/or its plasticity. The resultant cells may be termed therapeutically effective engineered myeloid cells, or effector myeloid cells. One strategy for improvement described herein is to induce an inflammatory phenotype of the myeloid cells to develop effector myeloid cells. One strategy is to generate effector myeloid cells capable of mounting an inflammatory phenotype upon engagement with the target. In one aspect, the effector myeloid cell is capable of inducing or activating an interferon type I response within the myeloid cells upon engagement to its target. Another strategy is to potentiate the interferon type I response in the myeloid cells to develop these cells into effector myeloid cells. One strategy for inducing an inflammatory phenotype is to induce or activate an NF-kB response in the effector myeloid cell upon engagement to its target. One strategy to develop myeloid cells isolated from a biological sample into effector myeloid cells for immunotherapy described herein is to induce and/or potentiate interferon type I response or NF-kappa B response or both in the myeloid cells.

The present disclosure involves making and using engineered myeloid cells (e.g., CD14+ cells, such as macrophages or other phagocytic cells, which can attack and kill (ATAK) diseased cells directly and/or indirectly, such as cancer cells and infected cells. Engineered myeloid cells, such as macrophages and other phagocytic cells, can be prepared by incorporating nucleic acid sequences (e.g., mRNA, DNA, plasmids, viral constructs) encoding a chimeric fusion protein (CFP), that has an extracellular binding domain specific to disease associated antigens (e.g., cancer antigens), into the cells using, for example, recombinant nucleic acid technology, synthetic nucleic acids, gene editing techniques (e.g., CRISPR), transduction (e.g., using viral constructs), electroporation, or nucleofection. It has been found that myeloid cells can be engineered to have a broad and diverse range of activities. For example, it has been found that myeloid cells can be engineered to express a chimeric fusion protein (CFP) containing an antigen binding domain to have a broad and diverse range of activities. For example, it has been found that myeloid cells can be engineered to have enhanced phagocytic activity such that upon binding of the CFP to an antigen on a target cell, the cell exhibits increased phagocytosis of the target cell. It has also been found that myeloid cells can be engineered to promote T cell activation such that upon binding of the CFP to an antigen on a target cell, the cell promotes activation of T cells, such as T cells in the tumor microenvironment. The engineered myeloid cells can be engineered to promote secretion of tumoricidal molecules such that upon binding of the CFP to an antigen on a target cell, the cell promotes secretion of tumoricidal molecules from nearby cells. The engineered myeloid cells can be engineered to promote recruitment and trafficking of immune cells and molecules such that upon binding of the CFP to an antigen on a target cell, the cell promotes recruitment and trafficking of immune cells and molecules to the target cell or a tumor microenvironment.

The present disclosure is based on the important finding that engineered myeloid cells overcome at least some of the limitations of CAR-T cells, including being readily recruited to solid tumors; having an engineerable duration of survival, therefore lowering the risk of prolonged persistence resulting in aplasia and immunodeficiency; myeloid cells cannot be contaminated with T cells; myeloid cells can avoid fratricide, for example, because they do not express the same antigens as malignant T cells; and myeloid cells have a plethora of anti-tumor functions that can be deployed. In some respects, engineered myeloid derived cells can be safer immunotherapy tools to target and destroy diseased cells.

Moreover, myeloid cells, such as macrophages, have been ubiquitously found in the tumor environment (TME) and are notably the most abundant cells in some tumor types. As part of their role in the immune system, myeloid cells, such as macrophages, are naturally engaged in clearing diseased cells. The present invention relates too harnessing myeloid cell function and specifically for targeting, killing and directly and/or indirectly clearing diseased cells as well as the delivery payloads such as antigens and cytokines.

Engineered myeloid cells can also be short-lived in vivo, phenotypically diverse, sensitive, plastic, and are often found to be difficult to manipulate in vitro. For example, exogenous gene expression in monocytes has been difficult compared to exogenous gene expression in non-hematopoietic cells. There are significant technical difficulties associated with transfecting myeloid cells (e.g., monocytes/macrophages). As professional phagocytes, myeloid cells, such as monocytes/macrophages, comprise many potent degradative enzymes that can disrupt nucleic acid integrity and make gene transfer into these cells an inefficient process. This is especially true of activated macrophages which undergo a dramatic change in their physiology following exposure to immune or inflammatory stimuli. Viral transduction of these cells are not ideal because macrophages are end-stage cells that generally do not divide; therefore, some of the vectors that depend on integration into a replicative genome have met with limited success. Furthermore, macrophages are quite responsive to "danger signals," and therefore several of the original viral vectors that were used for gene transfer induced potent anti-viral responses in these cells making these vectors inappropriate for gene delivery. Additionally, myeloid cells have potential to differentiate into phenotypic variants that have distinct functionality, and under certain circumstances may be ineffective for the purpose intended for in vivo use. For example, a myeloid cell necessary for active migration to tumor and effective tumoricidal activity may be required to be delivered in vivo in a cellular stage that retains its plasticity, based on identification of certain cell surface markers. Myeloid cell plasticity can be affected by the nature of isolation, handling, mode of introduction of nucleic acid material into the cell ex vivo in order to engineer the cell, and so forth. While myeloid cells of various cellular stages (e.g., myeloid cells at high, or low plasticity stages, or myeloid cells with phenotypes conferring to inflammatory or else immunomodulatory function) are each of particular value for the purpose intended for in vivo use, and that all of which are within the purview of the instant disclosure, at least in one aspect, the methods discussed herein focus on generation of a therapeutic myeloid cell population with the retention of a high degree myeloid cell plasticity prior to in vivo administration. In one aspect, the present disclosure provides innovative methods and compositions that can successfully transfect or transduce a myeloid cell, or otherwise induce a genetic modification in a myeloid cell, with the purpose of augmenting a functional aspect of a myeloid cell, additionally, without compromising the cell's differentiation capability, maturation potential, and/or its plasticity.

In one aspect, provided herein, are therapeutic agents that bind to an antigen expressed on a target cell, such as a diseased cell, for example, a cancer cell. Binding of the therapeutic agents to a target antigen on a target cell can initiate the process of destruction of the target cell. In some embodiments, the therapeutic agent is a recombinant nucleic acid that can be expressed in a cell of a subject, such as a mammalian cell, a human cell, a myeloid cell or a monocyte. In some embodiments, the therapeutic agent is a recombinant protein that can bind to a target antigen on a target cell. In some embodiments, the therapeutic agent is a cell, for example, a mammalian cell, a human cell, a myeloid cell or a monocyte, wherein the cell comprises a recombinant nucleic acid, and/or expresses a recombinant protein, such that the myeloid cell can be targeted to a diseased cell, expressing the target antigen on the surface of the cell; and the myeloid cell lyses or phagocytizes the diseased cell.

In one aspect, provided herein is a recombinant nucleic acid encoding a chimeric fusion protein comprising (a) a transmembrane domain and (b) an intracellular domain operably linked to the transmembrane domain, wherein the chimeric fusion protein responds to an extracellular cue, wherein the intracellular domain influences the intracellular mechanism of action and activation of the myeloid cell upon receiving the extracellular cue. In one embodiment, the chimeric fusion protein is a chimeric receptor, having an extracellular antigen binding domain in addition to (a) a transmembrane domain and (b) an intracellular domain operably linked to the transmembrane domain, and engagement of the extracellular antigen binding domain of the chimeric fusion protein to the target antigen that the extracellular binding domain binds to provides the extracellular cue to the receptor and for the receptor mediated activation of the myeloid cell.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain with a Xaa1-Leu-Xaa3-Iso-Ser motif, wherein Xaa1 is a hydrophilic amino acid, and Xaa3 is any amino acid. In some embodiments, the Ser of Xaa1-Leu-Xaa3-Iso-Ser is a phosphorylation site.

In some embodiments, Xaa1 is serine, threonine, tyrosine, histidine, asparagine, aspartic acid, glutamine, glutamic acid, lysine or arginine. In some embodiments, Xaa1 is serine. In some embodiments, Xaa1 is threonine. In some embodiments, Xaa1 is tyrosine. In some embodiments, Xaa1 is histidine. In some embodiments, Xaa1 is asparagine, aspartic acid, glutamine, glutamic acid, lysine or arginine. In some embodiments, Xaa1 is asparagine. In some embodiments, Xaa1 is aspartic acid. In some embodiments, Xaa1 is glutamine. In some embodiments, Xaa1 is glutamic acid. In some embodiments, Xaa1 is lysine. In some embodiments, Xaa1 is arginine.

In some embodiments, Xaa1 is histidine, asparagine, aspartic acid, glutamine, glutamic acid, lysine or arginine. In some embodiments, Xaa1 is histidine. In some embodiments, Xaa1 is asparagine, aspartic acid, glutamine, glutamic acid, lysine or arginine. In some embodiments, Xaa1 is asparagine. In some embodiments, Xaa1 is aspartic acid. In some embodiments, Xaa1 is glutamine. In some embodiments, Xaa1 is glutamic acid. In some embodiments, Xaa1 is lysine. In some embodiments, Xaa1 is arginine. In some embodiments, Xaa1 is not serine. In some embodiments, Xaa1 is not threonine. In some embodiments, Xaa1 is not tyrosine.

In some embodiments, Xaa1 is serine, asparagine, aspartic acid, glutamine, glutamic acid, lysine or arginine. In some embodiments, Xaa1 is serine. In some embodiments, Xaa1 is asparagine. In some embodiments, Xaa1 is aspartic acid. In some embodiments, Xaa1 is glutamine. In some embodiments, Xaa1 is glutamic acid. In some embodiments, Xaa1 is lysine. In some embodiments, Xaa1 is arginine. In some embodiments, Xaa1 is not histidine. In some embodiments, Xaa1 is not threonine. In some embodiments, Xaa1 is not tyrosine.

In some embodiments, Xaa1 is asparagine, aspartic acid, glutamine, glutamic acid, lysine or arginine. In some embodiments, Xaa1 is asparagine. In some embodiments, Xaa1 is aspartic acid. In some embodiments, Xaa1 is glutamine. In some embodiments, Xaa1 is glutamic acid. In some embodiments, Xaa1 is lysine. In some embodiments, Xaa1 is arginine. In some embodiments, Xaa1 is not serine. In some embodiments, Xaa1 is not threonine. In some embodiments, Xaa1 is not tyrosine. In some embodiments, Xaa1 is not histidine.

In some embodiments, Xaa1-Leu-Xaa3-Iso-Ser is SLHIS (SEQ ID NO: 108).

In some embodiments, Xaa1-Leu-Xaa3-Iso-Ser is NLEIS (SEQ ID NO: 109).

In some embodiments, Xaa1-Leu-Xaa3-Iso-Ser is DLAIS (SEQ ID NO: 110).

In some embodiments, Xaa1-Leu-Xaa3-Iso-Ser is ELLIS (SEQ ID NO: 111).

In some aspects, the chimeric fusion protein further comprises an extracellular domain comprising an antigen binding domain, wherein the transmembrane domain is operably linked with the extracellular domain. In some embodiments, the intracellular domain comprises at least one additional intracellular signaling domain. In some embodiments, the at least one additional intracellular signaling domain is derived form an intracellular PI3-kinase recruitment domain, a phagocytosis receptor intracellular domain, a pattern recognition receptor intracellular domain, a CD40 intracellular domain, an FcR intracellular domain, or a cytokine or chemokine receptor intracellular domain. In some embodiments, intracellular signaling domain comprises an amino acid sequence derived from a cytosolic adaptor protein, a mitochondrial membrane protein or an endoplasmic reticulum membrane protein. In one aspect, the intracellular signaling domain of the chimeric fusion protein comprises an amino acid sequence derived from a TRIF protein. In some embodiments, intracellular signaling domain comprises a truncated TRIF intracellular domain. In some embodiments, the sequence of the truncated TRIF intracellular domain is about 150 to 300 amino acids in length, about 150 to 270 amino acids in length, or about 150-250 amino acids in length. In some embodiments, intracellular signaling domain comprises an amino acid sequence having at least 80% sequence identity to SEQ ID NO: 36. In some embodiments, intracellular signaling domain comprises an amino acid sequence having at least 80% sequence identity to SEQ ID NO: 37. In some embodiments, intracellular signaling domain comprises an amino acid sequence having at least 80% sequence identity to SEQ ID NO: 38. In some embodiments, wherein intracellular signaling domain comprises an amino acid sequence having at least 80% sequence identity to SEQ ID NO: 41.

In one aspect, provided herein is a recombinant nucleic acid encoding a chimeric fusion protein comprising (a) a transmembrane domain and (b) an intracellular domain operably linked to the transmembrane domain, wherein the intracellular domain comprises a signaling domain from G protein-coupled receptor 84 (GPR84), G protein subunit beta 2 (GNB2) or Phosphatidylinositol-3,4,5-Trisphosphate Dependent Rac Exchange Factor 1 (PREX1). The intracellular signaling domains of GPR84, GNB2 or PREX1 can have pro-phagocytic activity. In some embodiments, the chimeric fusion protein further comprises an extracellular domain comprising an antigen binding domain, wherein the transmembrane domain is operably linked with the extracellular domain. In some embodiments, the signaling domain from GPR84, GNB2 or PREX1 is an intracellular signaling domain from GPR84, GNB2 or PREX1.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 39.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 40.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 42.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 43.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 45.

In one aspect, provided herein is a recombinant nucleic acid encoding a chimeric fusion protein comprising (a) a transmembrane domain and (b) an extracellular domain comprising an antigen binding domain, wherein the transmembrane domain is operably linked with the extracellular domain, wherein the transmembrane domain is derived from CD68 and comprises a mutation that inhibits or prevents homodimerization.

In some embodiments, the chimeric fusion protein further comprises an intracellular domain operably linked to the transmembrane domain. In some embodiments, the transmembrane domain comprises SEQ ID NO: 47.

In one aspect, provided herein is a recombinant nucleic acid encoding a chimeric fusion protein comprising (a) a transmembrane domain and (b) an extracellular domain comprising an antigen binding domain, wherein the transmembrane domain is operably linked with the extracellular domain, wherein the transmembrane domain is derived from CD64 or CD89; and wherein the chimeric fusion protein lacks an intracellular signaling domain. In some embodiments, the extracellular domain, wherein the transmembrane domain is derived from CD16 protein, e.g., CD16a protein. In some embodiments, the chimeric fusion protein forms a complex with an FcRγ chain when expressed in a cell.

In one aspect, provided herein is a recombinant nucleic acid encoding a chimeric fusion protein comprising (a) a transmembrane domain and (b) an intracellular domain operably linked to the transmembrane domain, wherein the intracellular domain comprises an intracellular signaling domain comprising a sequence having at least 80% amino acid sequence identity to SEQ ID NO: 48.

In some embodiments, the chimeric fusion protein further comprises a second intracellular signaling domain that comprises a PI3 kinase recruitment domain. In some embodiments, the CFP further comprising an intracellular signaling domain comprising fused amino acid sequence comprising SEQ ID NO: 39 and the sequence of an IRF activation enhancing motif. In some embodiments, the CFP further comprising an intracellular signaling domain comprising fused amino acid sequence comprising SEQ ID NO: 40 and the sequence of an IRF activation enhancing motif.

In one embodiment, the CFP further comprising an intracellular signaling domain comprising fused amino acid sequence comprising SEQ ID NO: 39 and SEQ ID NO: 40.

In some embodiments, the intracellular domain binds to an IRF protein. In some embodiments, the intracellular domain comprises a TRAF protein binding domain. In some embodiments, the intracellular domain comprises a TBK1 phosphorylation site. In some embodiments, the CFP further comprises a second, third, or fourth intracellular signaling domain. In some embodiments, the CFP further comprises an extracellular domain comprising an antigen binding domain, wherein the transmembrane domain is operably linked with the extracellular domain.

In some embodiments, the antigen binding domain comprises a domain having an affinity for a tumor antigen. In some embodiments, the extracellular domain comprises a T lymphocyte antigen binding domain. In some embodiments, the extracellular domain comprises a B lymphocyte antigen binding domain. In some embodiments, the antigen to which the antigen binding domain binds is selected from the group consisting of an antigen from CD2, CD3, CD4, CD5, CD7, CCR4, CD8, CD30, CD45, CD56, Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD70, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin, an integrin receptor, Claudin 3.0, Claudin 18.2, Trop-2, PRSS21, VEGFR2, PDGFRβ, SSEA-4, EGFR, NCAM, prostase, PAP, ELF2M, GM3, TEM7R, CLDN6, TSHR, GPRC5D, ALK, Dsg1, Dsg3, and IGLL1. In some embodiments, the antigen binding domain binds to CD5. In some embodiments, the antigen binding domain binds to HER2. In some embodiments, the antigen binding domain binds to CD137, CD70, Claudin 3.0, Claudin 18.2 or Trop-2. In some embodiments, the extracellular domain comprises a first target antigen binding domain, and a second target antigen binding domain that is non-identical to the first target binding domain. In some embodiments, the second target antigen binding domain binds to CD47. In some embodiments, the antigen binding domain comprises a domain having an affinity for a microbial antigen. In some embodiments, the antigen binding domain comprises a domain having an affinity for a viral antigen. In some embodiments, the domain comprises an antibody or a fragment thereof. In some embodiments, the domain comprises an scFv. In some embodiments, the transmembrane domain is derived from the transmembrane domain of CD8a, CD28, CD68, CD2, FcRγ, FcRα, FcRβ, FGRε, syntaxin 3, syntaxin 4, or syntaxin 5. In some embodiments, the extracellular domain comprises a hinge domain connecting the antigen binding domain and the transmembrane domain. In some embodiments, when expressed in a cell, the chimeric fusion protein upon binding to its target antigen activates the intracellular domain to induce IRF activation. In some embodiments, the recombinant nucleic acid is an RNA. In some embodiments, the recombinant nucleic acid is an mRNA. In some embodiments, the recombinant nucleic acid is associated with one or more lipids. In some embodiments, the recombinant nucleic acid is encapsulated in a liposome. In some embodiments, the liposome is a lipid nanoparticle.

In one aspect, provided herein is a recombinant nucleic acid encoding a sequence that is at least 80% identical to SEQ ID NO: 52. In one aspect, provided herein is a recombinant mRNA construct, encoding a sequence that is at least 80% identical to SEQ ID NO: 52. Provided herein is a recombinant mRNA construct, encoding a sequence that is at least 90% identical to SEQ ID NO: 52. Provided herein is a recombinant mRNA construct, encoding a sequence that is identical to SEQ ID NO: 52. In some embodiments, provided herein is a cell comprising a recombinant nucleic acid encoding a sequence of SEQ ID NO: 52 or a sequence having at least 80% sequence identity to SEQ ID NO: 52.

In one aspect, provided herein is a recombinant nucleic acid encoding a sequence that is at least 80% identical to SEQ ID NO: 53. In one aspect, provided herein is a recombinant mRNA construct, encoding a sequence that is at least 80% identical to SEQ ID NO: 53. Provided herein is a recombinant mRNA construct, encoding a sequence that is at least 90% identical to SEQ ID NO: 53. Provided herein is a recombinant mRNA construct, encoding a sequence that is identical to SEQ ID NO: 53. In some embodiments, provided herein is a cell comprising a recombinant nucleic acid encoding a sequence of SEQ ID NO: 53, or a sequence having at least 80% sequence identity to SEQ ID NO: 53.

In one aspect, provided herein is a recombinant nucleic acid encoding a sequence that is at least 80% identical to SEQ ID NO: 54. In one aspect, provided herein is a recombinant mRNA construct, encoding a sequence that is at least 80% identical to SEQ ID NO: 54. Provided herein is a recombinant mRNA construct, encoding a sequence that is at least 90% identical to SEQ ID NO: 54. Provided herein is a recombinant mRNA construct, encoding a sequence that is identical to SEQ ID NO: 54. In some embodiments, provided herein is a cell comprising a recombinant nucleic acid encoding a sequence of SEQ ID NO: 54, or a sequence having at least 80% sequence identity to SEQ ID NO: 54.

In one aspect, provided herein is a recombinant nucleic acid encoding a sequence that is at least 80% identical to SEQ ID NO: 55. In one aspect, provided herein is a recombinant mRNA construct, encoding a sequence that is at least 80% identical to SEQ ID NO: 55. Provided herein is a recombinant mRNA construct, encoding a sequence that is at least 90% identical to SEQ ID NO: 55. Provided herein is a recombinant mRNA construct, encoding a sequence that is identical to SEQ ID NO: 55. In some embodiments, provided herein is a cell comprising a recombinant nucleic acid encoding a sequence of SEQ ID NO: 55, or a sequence having at least 80% sequence identity to SEQ ID NO: 55.

In one aspect, provided herein is a recombinant nucleic acid encoding a sequence that is at least 80% identical to SEQ ID NO: 56. In one aspect, provided herein is a recombinant mRNA construct, encoding a sequence that is at least 80% identical to SEQ ID NO: 56. Provided herein is a recombinant mRNA construct, encoding a sequence that is at least 90% identical to SEQ ID NO: 56. Provided herein is a recombinant mRNA construct, encoding a sequence that is identical to SEQ ID NO: 56. In some embodiments, provided herein is a cell comprising a recombinant nucleic acid encoding a sequence of SEQ ID NO: 56, or a sequence having at least 80% sequence identity to SEQ ID NO: 56.

In one aspect, provided herein is a recombinant nucleic acid encoding a sequence that is at least 80% identical to SEQ ID NO: 57. In one aspect, provided herein is a recombinant mRNA construct, encoding a sequence that is at least 80% identical to SEQ ID NO: 57. Provided herein is a recombinant mRNA construct, encoding a sequence that is at least 90% identical to SEQ ID NO: 57. Provided herein is a recombinant mRNA construct, encoding a sequence that is identical to SEQ ID NO: 57. In some embodiments, provided herein is a cell comprising a recombinant nucleic acid encoding a sequence of SEQ ID NO: 57, or a sequence having at least 80% sequence identity to SEQ ID NO: 57.

In one aspect, provided herein is a recombinant nucleic acid encoding a sequence that is at least 80% identical to SEQ ID NO: 58. In one aspect, provided herein is a recombinant mRNA construct, encoding a sequence that is at least 80% identical to SEQ ID NO: 58. Provided herein is a recombinant mRNA construct, encoding a sequence that is at least 90% identical to SEQ ID NO: 58. Provided herein is a recombinant mRNA construct, encoding a sequence that is identical to SEQ ID NO: 58. In some embodiments, provided herein is a cell comprising a recombinant nucleic acid encoding a sequence of SEQ ID NO: 58, or a sequence having at least 80% sequence identity to SEQ ID NO: 58.

In one aspect, provided herein is a recombinant nucleic acid encoding a sequence that is at least 80% identical to SEQ ID NO: 59. In one aspect, provided herein is a recombinant mRNA construct, encoding a sequence that is at least 80% identical to SEQ ID NO: 59. Provided herein is a recombinant mRNA construct, encoding a sequence that is at least 90% identical to SEQ ID NO: 59. Provided herein is a recombinant mRNA construct, encoding a sequence that is identical to SEQ ID NO: 59. In some embodiments, provided herein is a cell comprising a recombinant nucleic acid encoding a sequence of SEQ ID NO: 59, or a sequence having at least 80% sequence identity to SEQ ID NO: 59.

In one aspect, provided herein is a recombinant nucleic acid encoding a sequence that is at least 80% identical to SEQ ID NO: 60. In one aspect, provided herein is a recombinant mRNA construct, encoding a sequence that is at least 80% identical to SEQ ID NO: 60. Provided herein is a recombinant mRNA construct, encoding a sequence that is at least 90% identical to SEQ ID NO: 60. Provided herein is a recombinant mRNA construct, encoding a sequence that is identical to SEQ ID NO: 60. In some embodiments, provided herein is a cell comprising a recombinant nucleic acid encoding a sequence of SEQ ID NO: 60, or a sequence having at least 80% sequence identity to SEQ ID NO: 60.

In one aspect, provided herein is a recombinant nucleic acid encoding a sequence that is at least 80% identical to SEQ ID NO: 61. In one aspect, provided herein is a recombinant mRNA construct, encoding a sequence that is at least 80% identical to SEQ ID NO: 61. Provided herein is a recombinant mRNA construct, encoding a sequence that is at least 90% identical to SEQ ID NO: 61. Provided herein is a recombinant mRNA construct, encoding a sequence that is identical to SEQ ID NO: 61. In some embodiments, provided herein is a cell comprising a recombinant nucleic acid encoding a sequence of SEQ ID NO: 61, or a sequence having at least 80% sequence identity to SEQ ID NO: 61.

In one aspect, provided herein is a recombinant nucleic acid encoding a sequence that is at least 80% identical to SEQ ID NO: 62. In one aspect, provided herein is a recombinant mRNA construct, encoding a sequence that is at least 80% identical to SEQ ID NO: 62. Provided herein is a recombinant mRNA construct, encoding a sequence that is at least 90% identical to SEQ ID NO: 62. Provided herein is a recombinant mRNA construct, encoding a sequence that is identical to SEQ ID NO: 62. In some embodiments, provided herein is a cell comprising a recombinant nucleic acid encoding a sequence of SEQ ID NO: 62, or a sequence having at least 80% sequence identity to SEQ ID NO: 62.

In one aspect, provided herein is a recombinant nucleic acid encoding a sequence that is at least 80% identical to SEQ ID NO: 63. In one aspect, provided herein is a recombinant mRNA construct, encoding a sequence that is at least 80% identical to SEQ ID NO: 63. Provided herein is a recombinant mRNA construct, encoding a sequence that is at least 90% identical to SEQ ID NO: 63. Provided herein is a recombinant mRNA construct, encoding a sequence that is identical to SEQ ID NO: 63. In some embodiments, provided herein is a cell comprising a recombinant nucleic acid encoding a sequence of SEQ ID NO: 63, or a sequence having at least 80% sequence identity to SEQ ID NO: 63.

In one aspect, provided herein is a recombinant nucleic acid encoding a sequence that is at least 80% identical to SEQ ID NO: 64. In one aspect, provided herein is a recombinant mRNA construct, encoding a sequence that is at least 80% identical to SEQ ID NO: 64. Provided herein is a recombinant mRNA construct, encoding a sequence that is at least 90% identical to SEQ ID NO: 64. Provided herein is a recombinant mRNA construct, encoding a sequence that is identical to SEQ ID NO: 64. In some embodiments, provided herein is a cell comprising a recombinant nucleic acid encoding a sequence of SEQ ID NO: 64, or a sequence having at least 80% sequence identity to SEQ ID NO: 64.

In one aspect, provided herein is a recombinant nucleic acid encoding a sequence that is at least 80% identical to SEQ ID NO: 65. In one aspect, provided herein is a recombinant mRNA construct, encoding a sequence that is at least 80% identical to SEQ ID NO: 65. Provided herein is a recombinant mRNA construct, encoding a sequence that is at least 90% identical to SEQ ID NO: 65. Provided herein is a recombinant mRNA construct, encoding a sequence that is identical to SEQ ID NO: 65. In some embodiments, provided herein is a cell comprising a recombinant nucleic acid encoding a sequence of SEQ ID NO: 65, or a sequence having at least 80% sequence identity to SEQ ID NO: 65.

In one aspect, provided herein is a recombinant nucleic acid encoding a sequence that is at least 80% identical to SEQ ID NO: 66. In one aspect, provided herein is a recombinant mRNA construct, encoding a sequence that is at least 80% identical to SEQ ID NO: 66. Provided herein is a recombinant mRNA construct, encoding a sequence that is at least 90% identical to SEQ ID NO: 66. Provided herein is a recombinant mRNA construct, encoding a sequence that is identical to SEQ ID NO: 66. In some embodiments, provided herein is a cell comprising a recombinant nucleic acid encoding a sequence of SEQ ID NO: 66, or a sequence having at least 80% sequence identity to SEQ ID NO: 66.

In one aspect, provided herein is a recombinant nucleic acid encoding a sequence that is at least 80% identical to SEQ ID NO: 67. In one aspect, provided herein is a recombinant mRNA construct, encoding a sequence that is at least 80% identical to SEQ ID NO: 67. Provided herein is a recombinant mRNA construct, encoding a sequence that is at least 90% identical to SEQ ID NO: 67. Provided herein is a recombinant mRNA construct, encoding a sequence that is identical to SEQ ID NO: 67. In some embodiments, provided herein is a cell comprising a recombinant nucleic acid encoding a sequence of SEQ ID NO: 67, or a sequence having at least 80% sequence identity to SEQ ID NO: 67.

In some embodiments, the recombinant nucleic acid is a plasmid or a vector.

In one aspect, provided herein is a cell comprising the recombinant nucleic acid of any one of the embodiments described above. In some embodiments, the cell is an immune cell. In some embodiments, the cell is a myeloid cell, a lymphoid cell, a precursor cell, a stem cell or an induced pluripotent cell. In some embodiments, the cell is CD14+/CD16−.

In one aspect, provided herein is an engineered cell comprising a recombinant nucleic acid encoding a chimeric fusion protein (CFP), the CFP comprising: (a) an extracellular domain comprising an antigen binding domain; (b) a transmembrane domain operably linked to the extracellular domain, and (c) an intracellular domain operably linked to the transmembrane domain, wherein the intracellular signaling domain comprises an intracellular signaling domain that binds to an IFN transcription factor when activated.

In one aspect, provided herein is an engineered cell comprising a recombinant nucleic acid encoding a chimeric fusion protein (CFP), the CFP comprising: (a) an extracellular domain comprising an antigen binding domain; (b) a transmembrane domain operably linked to the extracellular domain, and (c) an intracellular domain operably linked to the transmembrane domain, wherein the intracellular signaling domain comprises an intracellular signaling domain derived from a mitochondrial receptor.

In some embodiments, the intracellular domain comprises an amino acid sequence having at least 80% sequence identity to SEQ ID NO. 39. In some embodiments, the intracellular domain comprises an amino acid sequence having at least 80% sequence identity to SEQ ID NO. 40.

In some embodiments, the intracellular domain comprises an intracellular signaling domain derived from TLR3, TLR4, TLR7, TLR 9, TRIF, RIG-1, MYD88, MAL, IRAK1, MDA-5, an IFN-receptor, STING, MAVS, TRIF, TASL, NLRP1, NLRP2, NLRP3, NLRP4, NLRP5, NLRP6, NLRP7, NLRP89, NLRP9, NLRP10, NLRP11, NLRP12, NLRP13, NLRP1-14, NOD1, NOD2, Pyrin, AIM2, NLRC4, FCGR3A, FCERIG, CD40, Tank1-binding kinase (TBK), TNFR1, a chemokine, MHC Class II transactivator (CIITA), IPAF, BIRC1, a RIG-I-like receptor (RLR) protein, macrophage galactose-type lectin (MGL), DC-SIGN (CLEC4L), Langerin (CLEC4K), Myeloid DAP12 associating lectin (MDL)-1 (CLEC5A), a DC associated C type lectin 1 (Dectin1) subfamily protein, dectin 1/CLEC7A, DNGR1/CLEC9A, Myeloid C type lectin like receptor (MICL) (CLEC12A), CLEC2 (CLEC1B), CLEC12B, a DC immunoreceptor (DCIR) subfamily protein, DCIR/CLEC4A, Dectin 2/CLEC6A, Blood DC antigen 2 (BDCA2) (CLEC4C), and Mincle (macrophage inducible C type lectin) (CLEC4E).

In some embodiments, the intracellular domain comprises an amino acid sequence having at least 80% sequence identity to SEQ ID NO. 42.

In some embodiments, the intracellular domain comprises an amino acid sequence having at least 80% sequence identity to SEQ ID NO. 43.

In some embodiments, the intracellular domain comprises an amino acid sequence having at least 80% sequence identity to SEQ ID NO. 45.

In some embodiments, the intracellular signaling domain comprises an intracellular signaling domain that binds to a IFN transcription factor when activated.

In some embodiments, the IFN transcription factor is any one of the proteins IRF1-IRF9.

In some embodiments, the intracellular domain comprises a TRAF recruitment domain.

In some embodiments, the intracellular domain that induces an IKK phosphorylation.

In some embodiments, the intracellular domain induces a TBK phosphorylation.

In some embodiments, the antigen binding domain binds to a tumor antigen or a microbial antigen.

In some embodiments, the antigen binding domain binds to one or more of CD2, CD3, CD4, CD5, CD7, CCR4, CD8, CD30, CD45, CD56, Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD70, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin, an integrin receptor, Claudin 3.0, Claudin 18.2, Trop-2, PRSS21, VEGFR2, PDGFRβ, SSEA-4, EGFR, NCAM, prostase, PAP, ELF2M, GM3, TEM7R, CLDN6, TSHR, GPRC5D, ALK, Dsg1, Dsg3, and IGLL1.

In some embodiments, the antigen binding domain binds to a viral antigen.

In some embodiments, the transmembrane domain is derived from the transmembrane domain of CD8a, CD28, CD68, CD2, FcRγ, FcRα, FcRβ, FGRε, syntaxin 3, syntaxin 4, or syntaxin 5.

In some embodiments, the intracellular domain further comprises an intracellular signaling domain derived from an FcRγ, FcRα, or FcRε. In some embodiments, the intracellular domain further comprises PI3-kinase recruitment domain.

In some embodiments, the intracellular signaling domain binds to an IRF transcription factor and activates it upon binding of the antigen binding domain to its cognate antigen.

In some embodiments, the cell induces pro-inflammatory cytokines upon binding of the antigen binding domain to its cognate antigen.

In some embodiments, the pro-inflammatory cytokines comprise one or more of IL-1, IL-6, IL-12, IL-23, TNF, CXCL9, CXCL10, CXCL11, IL-18, IL-23, IL-27 and interferons.

In some embodiments, the cell is a myeloid cell, a lymphocyte or a stem cell.

In some embodiments, the cell is a myeloid cell.

Also provided herein, in one aspect of the disclosure is a pharmaceutical composition comprising the recombinant nucleic acid of any one of the embodiments described herein, the cell of any one of the embodiments described, or the engineered cell of any one of the embodiments described; and a pharmaceutically acceptable excipient In some embodiments, the engineered cell is CD14+/CD16−.

The pharmaceutical composition of the embodiments described above, comprising a population of cells wherein at least 50% of the cells are CD14+/CD16−, and less than 10% cells are dendritic cells. In some embodiments, the cells exhibit high expression of CCR2. In some embodiments, the cells do not exhibit tonal signaling and activation de novo, and exhibit M0, M1 or M2 differentiation upon activation.

In some aspects, provided herein is a method of treating a cancer or a viral infection in a subject comprising: administering to the subject the pharmaceutical composition of any one of the embodiments above.

In some aspects, provided herein is an engineered CD14+/CD16− cell comprising a recombinant nucleic acid encoding a chimeric fusion protein (CFP), the CFP comprising: (a) an extracellular domain comprising an antigen binding domain; (b) a transmembrane domain operably linked to the extracellular domain, and (c) an intracellular domain operably linked to the transmembrane domain, wherein the intracellular signaling domain comprises a domain derived from TRIF.

In some embodiments, the intracellular domain comprising a domain derived from TRIF is a truncated TRIF domain.

In some embodiments, the intracellular domain comprising a domain derived from TRIF comprises less than 300 amino acids.

In some embodiments, the intracellular domain comprising a domain derived from TRIF comprises less than 250 amino acids.

In some embodiments, the intracellular domain comprising a domain derived from TRIF exhibits IFN response upon engagement of the extracellular binding domain with the target.

In one aspect, provided herein is a method of treating a cancer in a subject, comprising administering to the subject a pharmaceutical composition of any one of the embodiments described above.

In one aspect, provided herein is a method of treating a cancer in a subject, comprising administering to the subject the pharmaceutical composition of any one of the embodiments described above.

In some embodiments, the cancer is selected from a group consisting of gastric cancer, ovarian cancer, renal cancer, breast cancer, prostate cancer, liver cancer, brain cancer, lymphoma, leukemia, skin cancer, pancreatic cancer, colorectal cancer, glioblastoma and lung cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 2A lower panel show flow cytometry data demonstrating expression of the respective constructs on the upper panel in a THP-1 cell.

FIG. 2B lower panel show flow cytometry data demonstrating expression of the respective constructs shown in the upper panel in a THP-1 cell.

FIG. 2C lower panel show flow cytometry data demonstrating expression of the respective constructs shown in the upper panel in a THP-1 cell.

FIG. 2D lower panel show flow cytometry data demonstrating expression of the respective constructs shown in the upper panel in a THP-1 cell.

FIG. 4D depicts representative data showing phagocytosis index of myeloid cells expressing each construct as indicated.

FIG. 5E shows data demonstrating NF-kappa B activation in THP-1 cells that were either mock electroporated or electroporated with the indicated CFP construct and assayed after 24 hours of transfection, in presence or absence of target SKOV3 cells. Each of the constructs has a CD89 intracellular signaling domain. CD89 intracellular domain alone is capable of activating NF-kappa B, however additional intracellular domains did not induce NF-kappa B activation.

FIG. 5F shows data demonstrating IFN activation in THP-1 cells 24 hours after transfection with the CFP construct as in FIG. 5E or mock transfected.

Figure 13A:
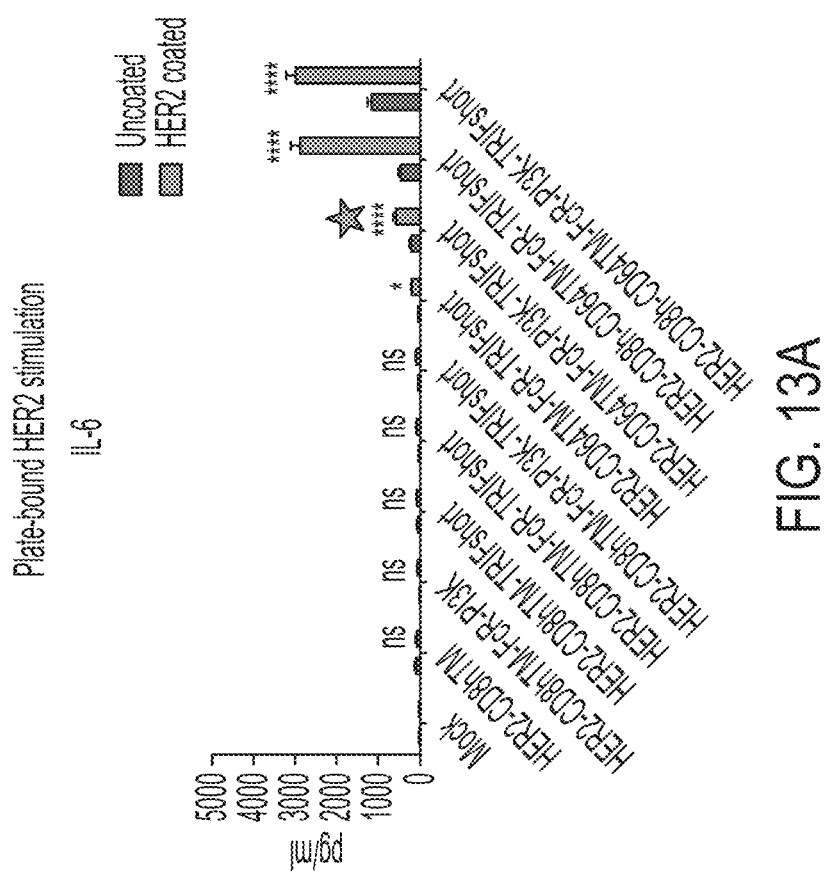
FIG. 13A shows graphs of pro-inflammatory cytokine IL-6 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). For antigen stimulated HER2-CFP primary monocyte samples, a 96-well plate coated with 2.5 μg/mL of HER2-his protein and 100,000 primary human monocytes electroporated with the indicated HER2-CFP constructs were added per well. Supernatant was collected after 48 hours of stimulation and secreted cytokine was analyzed by Luminex. For tumor cell stimulated HER2-CFP primary monocyte samples, 100,000 primary human monocytes electroporated with the indicated HER2-CFP constructs were co-cultured with 20,000 tumor cells (SKOV3-GFP-Luciferase cells or SKBR3-Luciferase cells). Supernatant was collected after 48 hours of stimulation and secreted cytokine was analyzed by Luminex Statistical significance was determined between HER2-CFP electroporated primary monocyte samples co-cultured with tumor cells and mock electroporated primary monocyte samples co-cultured with tumor cells.
Figure 13A:
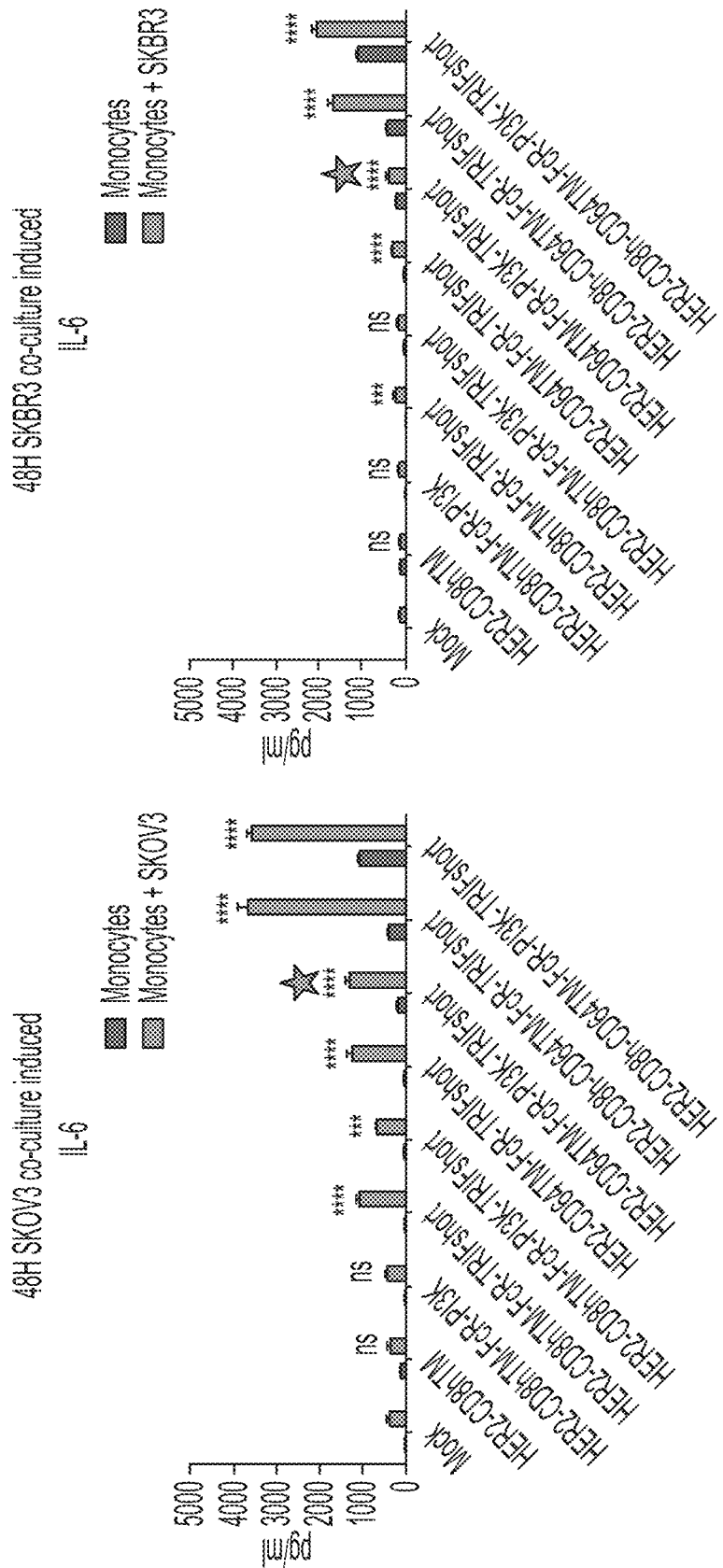
Figure 13B:
FIG. 13B shows graphs of pro-inflammatory cytokine IL-1β induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 13A.
Figure 13B:
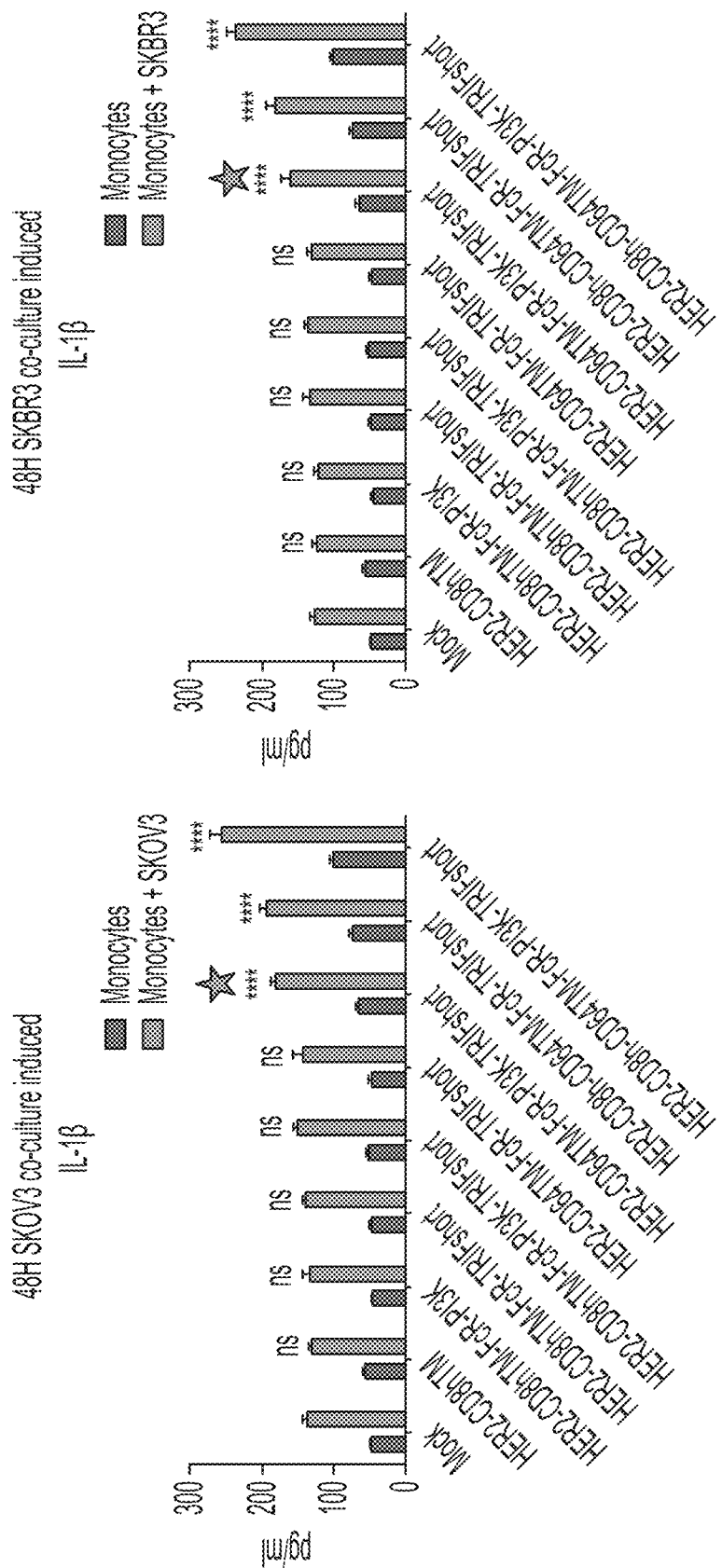
Figure 13C:
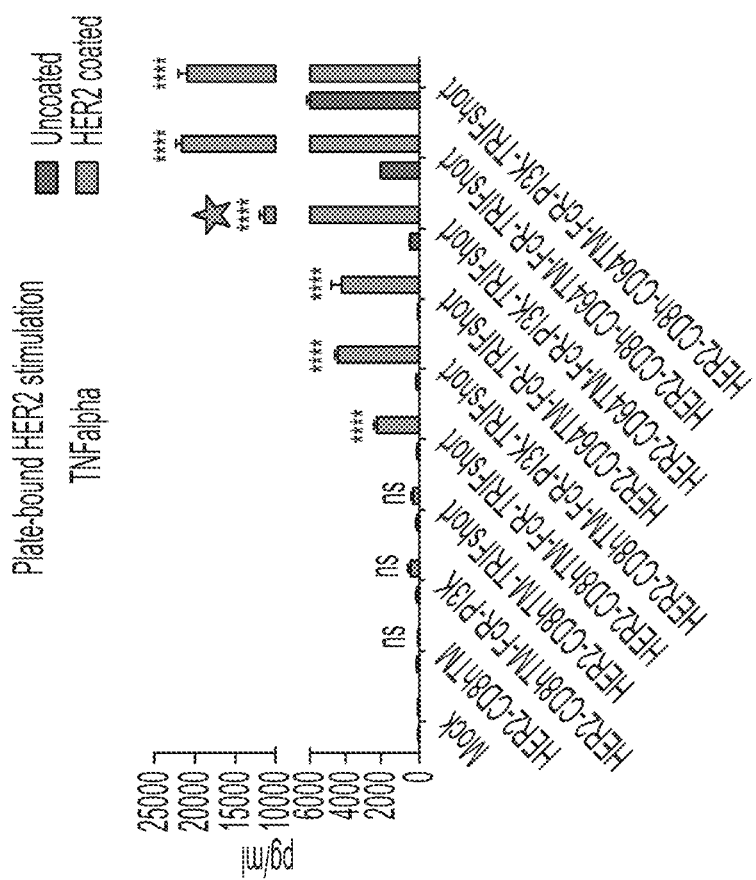
FIG. 13C shows graphs of TNF-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 13A.
Figure 13C:
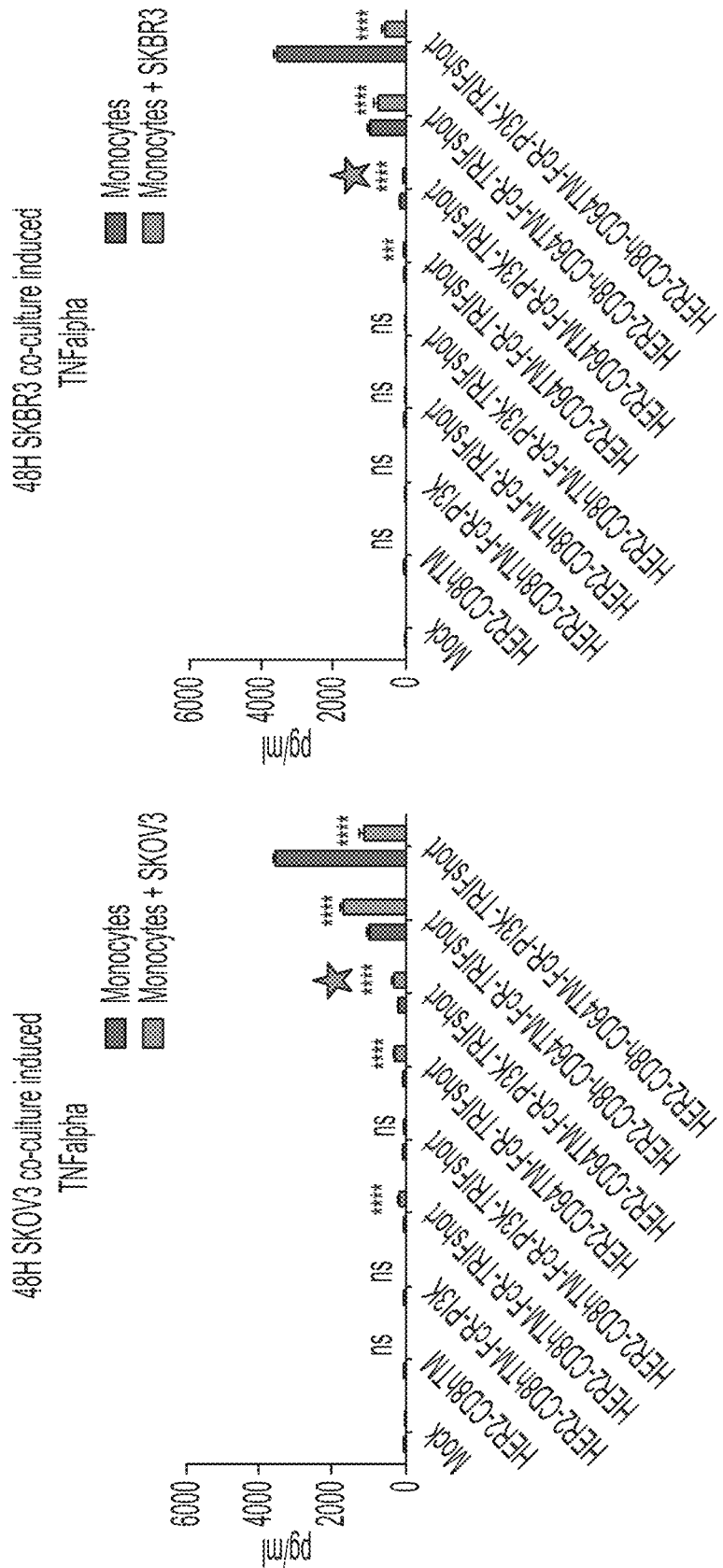
Figure 13D:
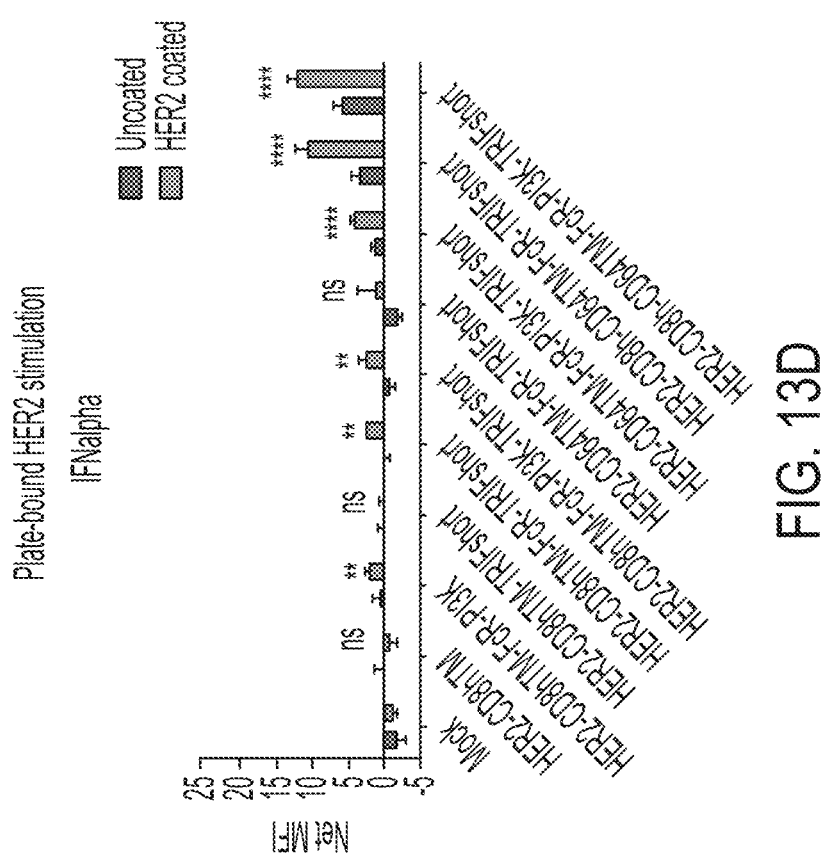
FIG. 13D shows graphs of IFN-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 13A.
Figure 13D:
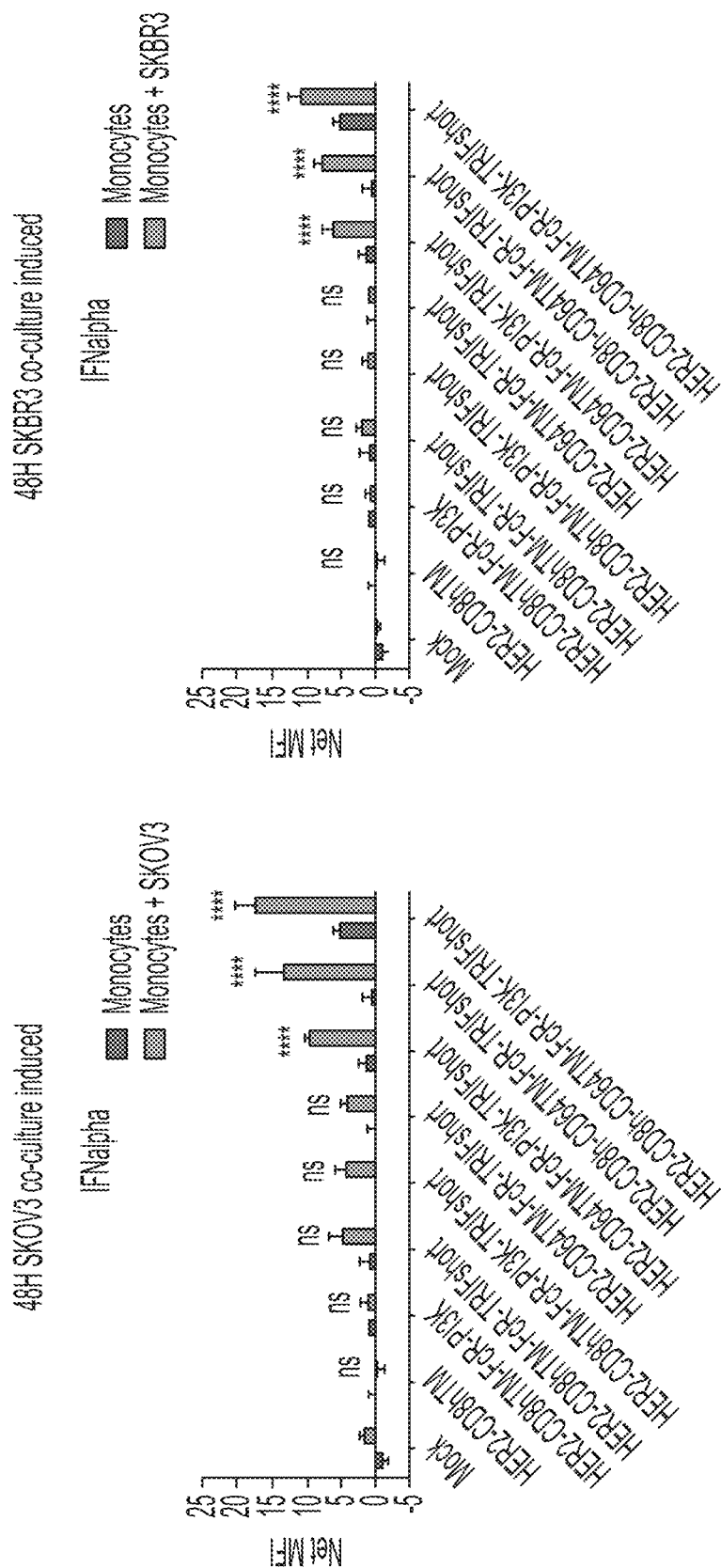
Figure 13E:
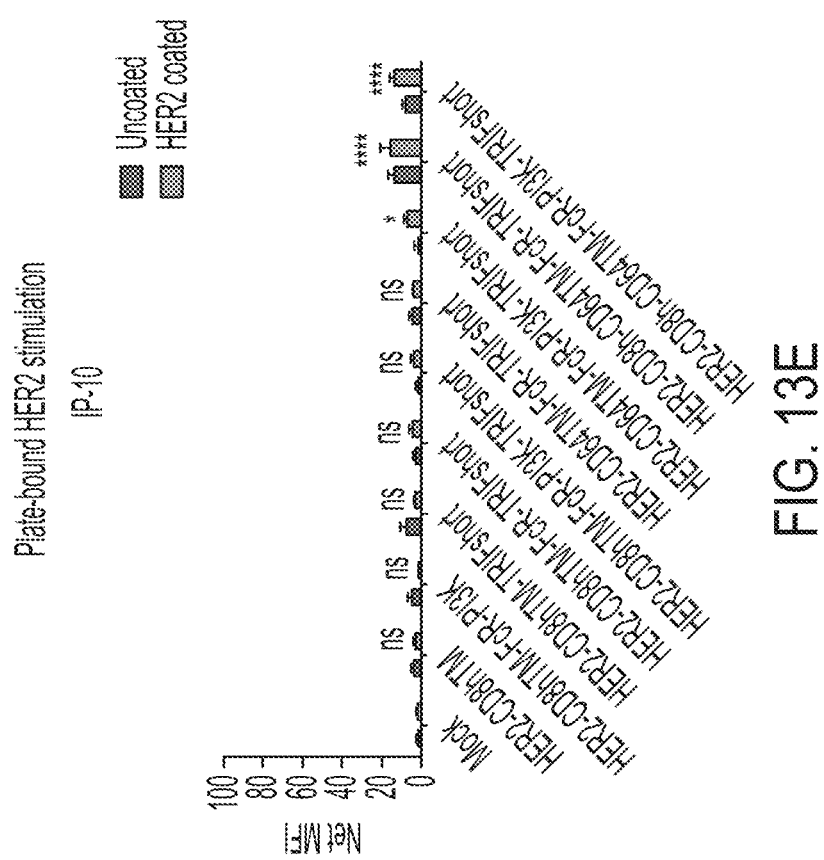
Figure 13E:
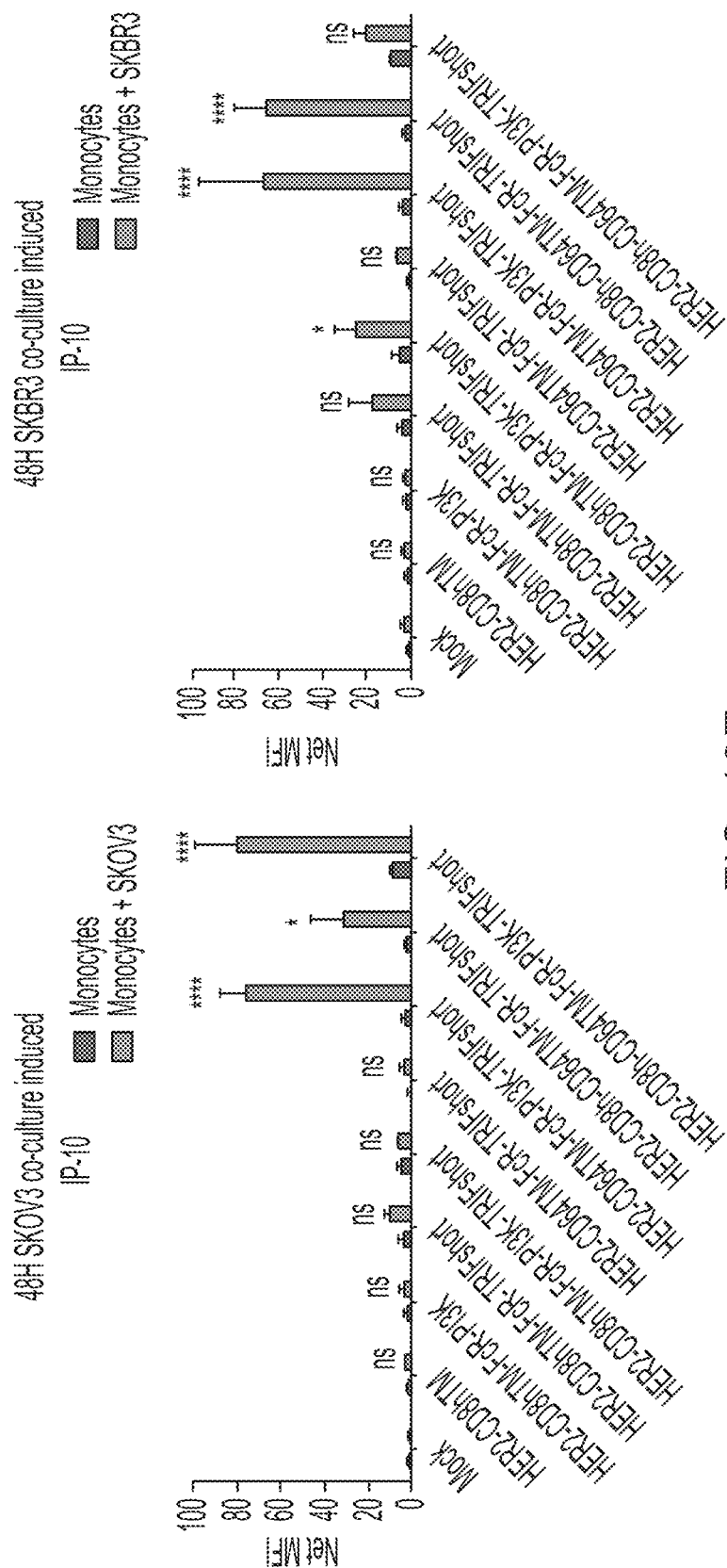

FIG. 13E shows graphs of IP10 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 13A.

Figure 13F:
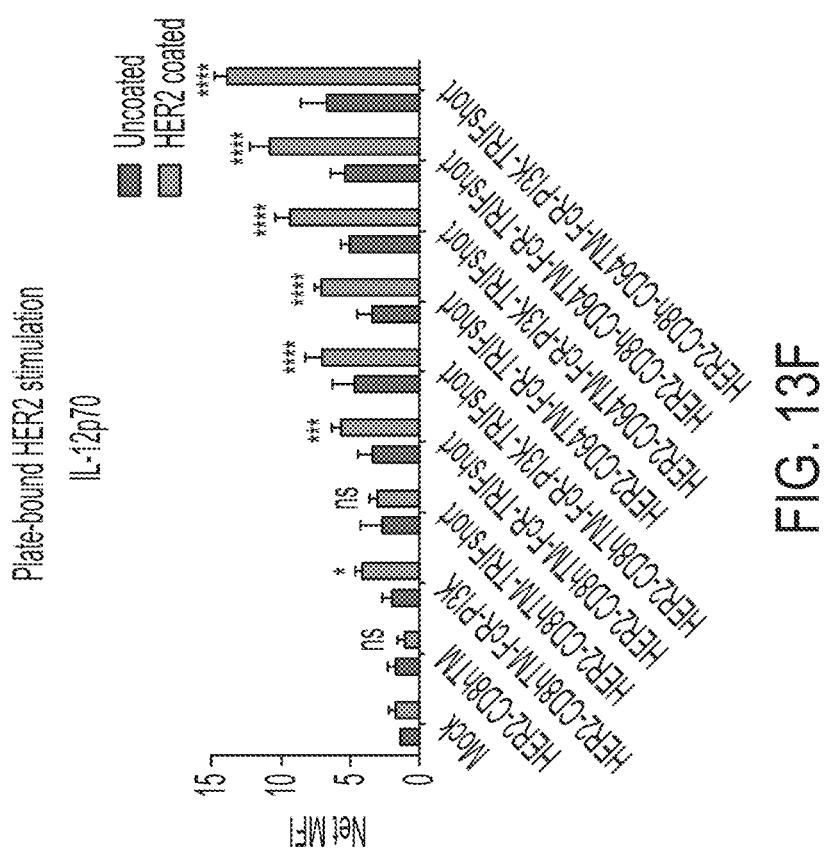
Figure 13F:
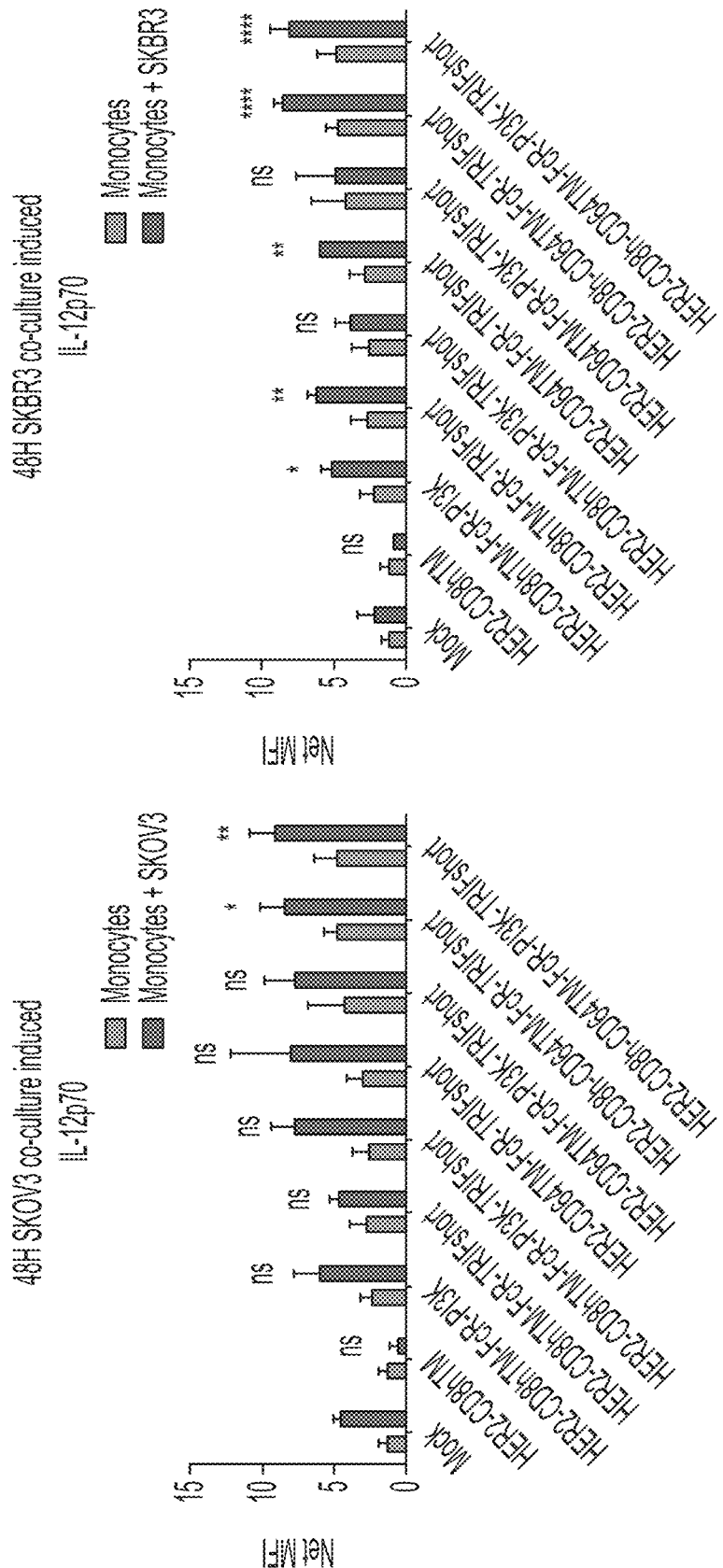

FIG. 13F shows graphs of IL-12 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 13A.

Figure 14:
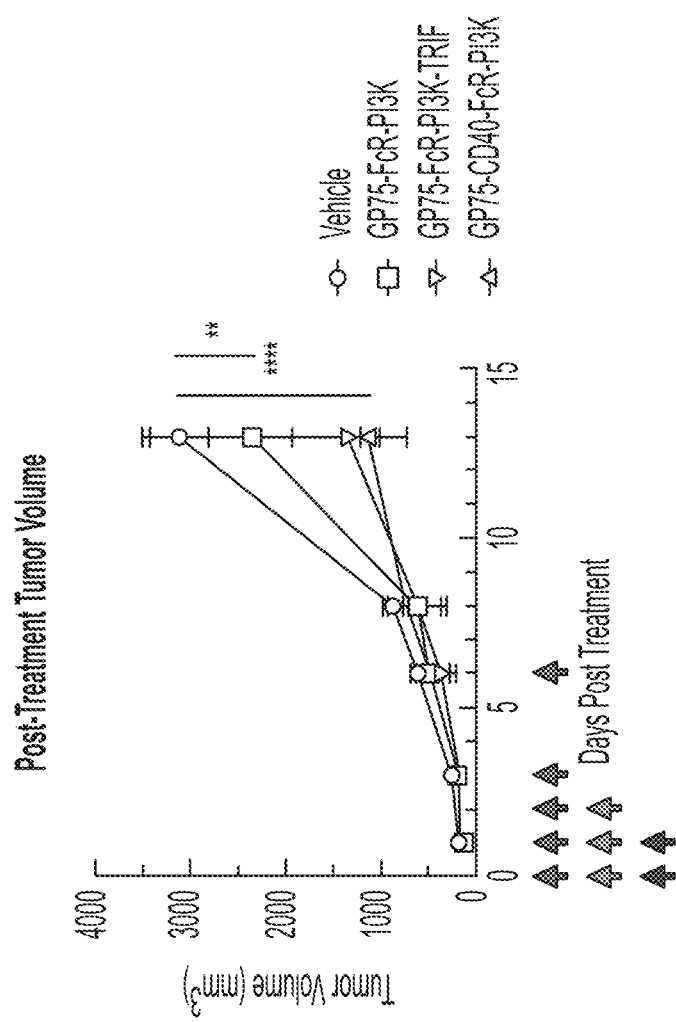
Figure 14:
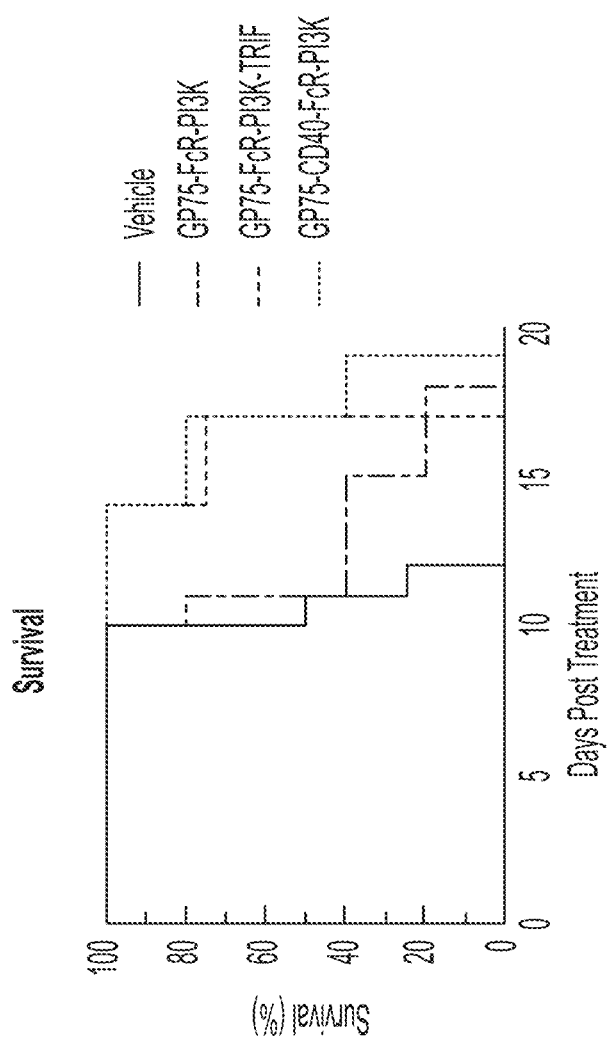

FIG. 14 shows graphs indicating tumor regression (left) and survival (right) comparisons in mice after administering CFP constructs having indicated intracellular domains.

DETAILED DESCRIPTION

T cells therapies have revolutionized cancer treatment for many patients. However, for the majority of patients with advanced solid tumors, sustained clinical benefit has not been achieved. Unlike T cells, myeloid cells readily accumulate in tumors, in some cases contributing up to 50% of the tumor mass. Myeloid cells can be specifically engineered to become highly effective anti-tumor cells, referred to as Activate, Target, Attack & Kill (ATAK) cells, that specifically target, phagocytize and lyse tumor cells, and orchestrate an immune activation in vivo against the tumor cells.

The present application is based on an approach towards augmenting engineered myeloid cells to evade the immunosuppressive tumor microenvironment and exhibit high tumor cell lytic/immunogenic potency. Engaging innate immune signaling sensors such as Toll-like receptors and STING-cGAS have been investigated as important pathways to upregulate pro-inflammatory anti-tumor immune response and are associated with anti-tumor immunity. These approaches, using synthetic agonists to activate these pathways, can be potent but delivering a localized and tumor specific activation of innate immune signaling is difficult to achieve. Many conventional chemotherapeutics, targeted anticancer agents, immunological adjuvants and oncolytic viruses are only fully efficient in the presence of intact type I IFN signaling Immunotherapy using recombinant type I interferons and IFN encoding vectors have been attempted. For example, TLR-9 agonist has been combined with chemotherapy to treat previously untreated stage Mb or stage IV non-small cell lung carcinoma (NSCLC) (Manegold, C., et al. Addition of PF-3512676 (CpG 7909) to a taxane/platinum regimen for first-line treatment of unresectable non-small cell lung cancer (NSCLC) improves objective response—phase II clinical trial. *Eur. J Cancer.* 3:326, 2005). Another study suggested that administration of IFN-a producing-iPSC-derived proliferating myeloid cells in combination with immune checkpoint blockade might be useful to overcome resistance to single-treatment modalities, e.g., in cancers refractory to checkpoint blockade (Tsuchiya, N., et al., Cell Reports 29, 162-175, October, 2019)

The present approach disclosed herein is to generate a new class of chimeric antigen receptors (ATAK receptors) that couple tumor recognition with innate immune signaling. Such recombinant chimeric receptors are expressed in myeloid cells described herein, such that via the chimeric receptor, the myeloid cell is targeted to a cancer cell, and then further activate innate immune response in the myeloid cell upon tumor recognition, leading to phagocytic lysis of the tumor cell, and further activation of the lymphocytic immune response. By combining cancer recognition domains with intracellular signaling domains from innate immune receptors such as FcRg, TLR and cytokine receptors, the chimeric antigen receptors as designed and described herein demonstrate that myeloid cells can be programmed to recognize cancer and elicit a broad and tunable immune response. The data show the versatility of building ATAK receptors by harnessing innate immune pathways and support their clinical development in cell and direct in vivo therapies.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−30% or less, +/−20% or less, +/−10% or less, +/−5% or less, or +/−1% or less of and from the specified value, insofar such variations are appropriate to perform in the present disclosure. It is to be understood that the value to which the modifier "about" or "approximately" refers is itself also specifically disclosed.

An "agent" can refer to any cell, small molecule chemical compound, antibody or fragment thereof, nucleic acid molecule, or polypeptide.

An "alteration" or "change" can refer to an increase or decrease. For example, an alteration can be an increase or decrease of 1%, 2%, 3%, 4%, 5%, 10%, 20%, 30%, or by 40%, 50%, 60%, or even by as much as 70%, 75%, 80%, 90%, or 100%. For example, an alteration can be an increase or decrease of 1-fold, 2-fold, 3-fold, 4-fold, 5-fold, 10-fold, 20-fold, 30-fold, or by 40-fold, 50-fold, 60-fold, or even by as much as 70-fold, 75-fold, 80-fold, 90-fold, or 100-fold.

An "antigen presenting cell" or "APC" as used herein includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). An APC can express Major Histocompatibility complex (MHC) molecules and can display antigens complexed with MHC on its surface which can be recognized by T cells and trigger T cell activation and an immune response. Professional antigen-presenting cells, notably dendritic cells, play a key role in stimulating naive T cells. Nonprofessional antigen-presenting cells, such as fibroblasts, may also contribute to this process. APCs can also cross-present peptide antigens by processing exogenous antigens and presenting the processed antigens on class I MHC molecules. Antigens that give rise to proteins that are recognized in association with class I MHC molecules are generally proteins that are produced within the cells, and these antigens are processed and associate with class I MHC molecules.

A "biological sample" can refer to any tissue, cell, fluid, or other material derived from an organism.

The term "epitope" can refer to any protein determinant, such as a sequence or structure or amino acid residues, capable of binding to an antibody or binding fragment thereof, a T cell receptor, and/or an antibody-like molecule. Epitopic determinants typically consist of chemically active surface groups of molecules such as amino acids or sugar side chains and generally have specific three dimensional structural characteristics as well as specific charge characteristics. A "T cell epitope" can refer to peptide or peptide-MHC complex recognized by a T cell receptor.

An engineered cell, such as an engineered myeloid cell, can refer to a cell that has at least one exogenous nucleic acid sequence in the cell, even if transiently expressed. Expressing an exogenous nucleic acid may be performed by various methods described elsewhere, and encompasses methods known in the art. The present disclosure relates to preparing and using engineered cells, for example, engineered myeloid cells, such as engineered phagocytic cells. The present disclosure relates to, inter alia, an engineered cell comprising an exogenous nucleic acid encoding, for example, a chimeric fusion protein (CFP).

The term "immune response" includes, but is not limited to, T cell mediated, NK cell mediated and/or B cell mediated immune responses. These responses may be influenced by modulation of T cell costimulation and NK cell costimulation. Exemplary immune responses include T cell responses, e.g., cytokine production, and cellular cytotoxicity. In addition, immune responses include immune responses that are indirectly affected by NK cell activation, B cell activation and/or T cell activation, e.g., antibody production (humoral responses) and activation of cytokine responsive cells, e.g., macrophages. Immune responses include adaptive immune responses. The adaptive immune system can react to foreign molecular structures, such as antigens of an intruding organism. Unlike the innate immune system, the adaptive immune system is highly specific to a pathogen. Adaptive immunity can also provide long-lasting protection. Adaptive immune reactions include humoral immune reactions and cell-mediated immune reactions. In humoral immune reactions, antibodies secreted by B cells into bodily fluids bind to pathogen-derived antigens leading to elimination of the pathogen through a variety of mechanisms, e.g. complement-mediated lysis. In cell-mediated immune reactions, T cells capable of destroying other cells are activated. For example, if proteins associated with a disease are present in a cell, they can be fragmented proteolytically to peptides within the cell. Specific cell proteins can then attach themselves to the antigen or a peptide formed in this manner, and transport them to the surface of the cell, where they can be presented to molecular defense mechanisms, such as T cells. Cytotoxic T cells can recognize these antigens and kill cells that harbor these antigens.

A "ligand" can refer to a molecule which is capable of binding or forming a complex with another molecule, such as a receptor. A ligand can include, but is not limited to, a protein, a glycoprotein, a carbohydrate, a lipoprotein, a hormone, a fatty acid, a phospholipid, or any component that binds to a receptor. In some embodiments, a receptor has a specific ligand. In some embodiments, a receptor may have promiscuous binding to a ligand, in which case it can bind to several ligands that share at least a similarity in structural configuration, charge distribution or any other physicochemical characteristic. A ligand may be a biomolecule. A ligand may be an abiotic material. For example, a ligand may be a negative charged particle that is a ligand for scavenger receptor MARCO. For example, a ligand may be $TiO_2$, which is a ligand for the scavenger receptor SRA1. In the context of a CFP described herein, the extracellular binding domain may bind to a ligand, which is a also designated as a target of the binding domain. In some embodiments, the target is an antigen expressed on a diseased cell, such as a cancer cell, which in this case is a target cell, in the sense that the target cell expresses on its cell surface a target antigen to which the extracellular antigen binding domain of the CFP binds. Anti-(target) binding domain or anti-(target) binding extracellular domain or anti-(target) CFP are often interchangeably used with terms such as (target) binding domain or (target) binding extracellular domain or (target) CFP respectively in the disclosure. For example, HER2 expressed on cancer cells is an antigen (ligand) to which the anti-HER2 binding extracellular domain of a CFP binds; or alternatively stated as, a HER2-binding extracellular domain of a CFP binds.

The term "major histocompatibility complex (MHC)", "MHC molecule", or "MHC protein" refers to a protein capable of binding an antigenic peptide and present the antigenic peptide to T lymphocytes. Such antigenic peptides can represent T cell epitopes. The human MHC is also called the HLA complex. Thus, the terms "human leukocyte antigen (HLA)", "HLA molecule" or "HLA protein" are used interchangeably with the terms "major histocompatibility complex (MHC)", "MHC molecule", and "MHC protein". HLA proteins can be classified as HLA class I or HLA class II. The structures of the proteins of the two HLA classes are very similar; however, they have very different functions. Class I HLA proteins are present on the surface of almost all cells of the body, including most tumor cells. Class I HLA proteins are loaded with antigens that usually originate from endogenous proteins or from pathogens present inside cells, and are then presented to naïve or cytotoxic T-lymphocytes (CTLs). HLA class II proteins are present on antigen presenting cells (APCs), including but not limited to dendritic cells, B cells, and macrophages. They mainly present peptides which are processed from external antigen sources, e.g. outside of cells, to helper T cells.

In the HLA class II system, phagocytes such as macrophages and immature dendritic cells can take up entities by phagocytosis into phagosomes—though B cells exhibit the more general endocytosis into endosomes—which fuse with lysosomes whose acidic enzymes cleave the uptaken protein into many different peptides. Autophagy is another source of HLA class II peptides. The most studied subclass II HLA genes are: HLA-DPA1, HLA-DPB1, HLA-DQA1, HLA-DQB1, HLA-DRA, and HLA-DRB1.

Presentation of peptides by HLA class II molecules to CD4+ helper T cells can lead to immune responses to foreign antigens. Once activated, CD4+ T cells can promote B cell differentiation and antibody production, as well as CD8+ T cell (CTL) responses. CD4+ T cells can also secrete cytokines and chemokines that activate and induce differentiation of other immune cells. HLA class II molecules are typically heterodimers of α- and β-chains that interact to form a peptide-binding groove that is more open than class I peptide-binding grooves.

HLA alleles are typically expressed in codominant fashion. For example, each person carries 2 alleles of each of the 3 class I genes, (HLA-A, HLA-B and HLA-C) and so can express six different types of class II HLA. In the class II HLA locus, each person inherits a pair of HLA-DP genes (DPA1 and DPB1, which encode α and β chains), HLA-DQ (DQA1 and DQB1, for α and β chains), one gene HLA-DRα (DRA1), and one or more genes HLA-DRβ (DRB1 and DRB3, –4 or –5). HLA-DRB1, for example, has more than nearly 400 known alleles. That means that one heterozygous individual can inherit six or eight functioning class II HLA alleles: three or more from each parent. Thus, the HLA genes are highly polymorphic; many different alleles exist in the different individuals inside a population. Genes encoding HLA proteins have many possible variations, allowing each person's immune system to react to a wide range of foreign invaders. Some HLA genes have hundreds of identified versions (alleles), each of which is given a particular number. In some embodiments, the class I HLA alleles are HLA-A*02:01, HLA-B*14:02, HLA-A*23:01, HLA-E*01:01 (non-classical). In some embodiments, class II HLA alleles are HLA-DRB*01:01, HLA-DRB*01:02, HLA-DRB*11:01, HLA-DRB*15:01, and HLA-DRB*07:01.

A "myeloid cell" can refer broadly to cells of the myeloid lineage of the hematopoietic cell system, and can exclude, for example, the lymphocytic lineage. Myeloid cells comprise, for example, cells of the granulocyte lineage and monocyte lineages. Myeloid cells are a major cellular compartment of the immune system comprising monocytes, dendritic cells, tissue macrophages, and granulocytes. Models of cellular ontogeny, activation, differentiation, and tissue-specific functions of myeloid cells have been revisited during the last years with surprising results. However, their enormous plasticity and heterogeneity, during both homeostasis and disease, are far from understood. Although myeloid cells have many functions, including phagocytosis and their ability to activate T cells, harnessing these functions for therapeutic uses has remained elusive. Newer avenues are therefore sought for using other cell types towards development of improved therapeutics, including but not limited to T cell malignancies.

Myeloid cells are differentiated from common progenitors derived from the hematopoietic stem cells in the bone marrow. Commitment to myeloid cell lineages may be governed by activation of distinct transcription factors, and accordingly myeloid cells may be characterized as cells having a level of plasticity, which may be described as the ability to further differentiate into terminal cell types based on extracellular and intracellular stimuli. Myeloid cells can be rapidly recruited into local tissues via various chemokine receptors on their surface. Myeloid cells are responsive to various cytokines and chemokines.

A myeloid cell, for example, may be a cell that originates in the bone marrow from a hematopoietic stem cell under the influence of one or more cytokines and chemokines, such as G-CSF, GM-CSF, Flt3L, CCL2, VEGF and S100A8/9. In some embodiments, the myeloid cell is a precursor cell. In some embodiments, the myeloid cell may be a cell having characteristics of a common myeloid progenitor, or a granulocyte progenitor, a myeloblast cell, or a monocyte-dendritic cell progenitor or a combination thereof. A myeloid can include a granulocyte or a monocyte or a precursor cell thereof. A myeloid can include an immature granulocyte, an immature monocyte, an immature macrophage, an immature neutrophil, and an immature dendritic cell. A myeloid can include a monocyte or a pre-monocytic cell or a monocyte precursor. In some cases, a myeloid cell as used herein may refer to a monocyte having an M0 phenotype, an M1 phenotype or an M2 phenotype. A myeloid can include a dendritic cell (DC), a mature DC, a monocyte derived DC, a plasmacytoid DC, a pre-dendritic cell, or a precursor of a DC. A myeloid can include a neutrophil, which may be a mature neutrophil, a neutrophil precursor, or a polymorphonucleocyte (PMN). A myeloid can include a macrophage, a monocyte-derived macrophage, a tissue macrophage, a macrophage of an M0, an M1 or an M2 phenotype. A monocyte or a macrophage exhibit polarization. "Polarization" as used herein may refer to a process by which macrophages exhibit distinct functional phenotypes in response to specific microenvironmental stimuli and signals, often referred to as physiological states. In some cases, macrophages can pass from one polarization state to another. For example, macrophages can be polarized into classically activated (M1) and alternatively activated (M2) macrophages. M2 macrophages are divided into M2a, M2b, M2c, and M2d subcategories. These macrophages differ in their cell surface markers, secreted cytokines and biological functions. M1 macrophages are typically characterized by phenotypes in which the cells express TLR-2, TLR-4, CD80, CD86, iNOS, and MHC-II on the surface. These cells release various cytokines and chemokines e.g., TNF-α, IL-1α, IL-1β, IL-6, IL-12, CXCL9, and CXCL10, and typically exhibit activation of transcription factors, such as NF-kB, STAT1, STATS, IRF3, and IRF5 that regulate the expression of M1 genes. It is believed that NF-κB and STAT1 are the two major pathways involved in M1 macrophage polarization. The M1 phenotype is associated with microbicidal and tumoricidal functions of macrophages, exhibiting high phagocytic and inflammatory function. On the other hand, tumor associated macrophages subject to immunosuppressive environment become generally more M2 polarized. A myeloid can include a tumor infiltrating monocyte (TIM). A myeloid can include a tumor associated monocyte (TAM). A myeloid can include a myeloid derived suppressor cell (MDSC). A myeloid can include a tissue resident macrophage. A myeloid can include a tumor associated DC (TADC). Accordingly, a myeloid cell may express one or more cell surface markers, for example, CD11b, CD14, CD15, CD16, CD38, CCR5, CD66, Lox-1, CD11c, CD64, CD68, CD163, CCR2, CCR5, HLA-DR, CD1c, CD83, CD141, CD209, MHC-II, CD123, CD303, CD304, a SIGLEC family protein and a CLEC family protein. In some cases, a myeloid cell may be characterized by a high or a low expression of one or more of cell surface markers, for example, CD11b, CD14, CD15, CD16, CD66, Lox-1, CD11c, CD64, CD68, CD163, CCR2, CCR5, HLA-DR, CD1c, CD83, CD141, CD209, MHC-II, CD123, CD303, CD304 or a combination thereof.

In one embodiment, activating the M1 polarization of macrophages are desirable using the methods described herein.

"Phagocytosis" is used interchangeably with "engulfment" and can refer to a process by which a cell engulfs a particle, such as a cancer cell or an infected cell. This process can give rise to an internal compartment (phagosome) containing the particle. This process can be used to ingest and or remove a particle, such as a cancer cell or an infected cell from the body. A phagocytic receptor may be involved in the process of phagocytosis. The process of phagocytosis can be closely coupled with an immune response and antigen presentation. The processing of exogenous antigens follows their uptake into professional antigen presenting cells by some type of endocytic event. Phagocytosis can also facilitate antigen presentation. For example, antigens from phagocytosed cells or pathogens, including cancer antigens, can be processed and presented on the cell surface of APCs.

A "polypeptide" can refer to a molecule containing amino acids linked together via a peptide bond, such as a glycoprotein, a lipoprotein, a cellular protein or a membrane protein. A polypeptide may comprise one or more subunits of a protein. A polypeptide may be encoded by a recombinant nucleic acid. In some embodiments, polypeptide may comprise more than one peptide sequence in a single amino acid chain, which may be separated by a spacer, a linker or peptide cleavage sequence. A polypeptide may be a fused polypeptide. A polypeptide may comprise one or more domains, modules or moieties.

A "receptor" can refer to a chemical structure composed of a polypeptide, which transduces a signal, such as a polypeptide that transduces an extracellular signal to a cell. A receptor can serve to transmit information in a cell, a cell formation or an organism. A receptor comprises at least one receptor unit and can contain two or more receptor units, where each receptor unit comprises a protein molecule, e.g., a glycoprotein molecule. A receptor can contain a structure that binds to a ligand and can form a complex with the ligand. Signaling information can be transmitted by a conformational change of the receptor following binding with the ligand on the surface of a cell.

The term "antibody" refers to a class of proteins that are generally known as immunoglobulins, including, but not limited to IgG1, IgG2, IgG3, and IgG4), IgA (including IgA1 and IgA2), IgD, IgE, IgM, and IgY, The term "antibody" includes, but is not limited to, full length antibodies, single-chain antibodies, single domain antibodies (sdAb) and antigen-binding fragments thereof. Antigen-binding antibody fragments include, but are not limited to, Fab, Fab' and F(ab')2, Fd (consisting of $V_H$ and $C_H1$), single-chain variable fragment (scFv), single-chain antibodies, disulfide-linked variable fragment (dsFv) and fragments comprising a $V_L$ and/or a $V_H$ domain. Antibodies can be from any animal origin. Antigen-binding antibody fragments, including single-chain antibodies, can comprise variable region(s) alone or in combination with tone or more of a hinge region, a CH1 domain, a CH2 domain, and a CH3 domain. Also included are any combinations of variable region(s) and hinge region, CH1, CH2, and CH3 domains. Antibodies can be monoclonal, polyclonal, chimeric, humanized, and human monoclonal and polyclonal antibodies which, e.g., specifically bind an HLA-associated polypeptide or an HLA-peptide complex.

The term "recombinant nucleic acid" refers a nucleic acid prepared, expressed, created or isolated by recombinant means. A recombinant nucleic acid can contain a nucleotide sequence that is not naturally occurring. A recombinant nucleic acid may be synthesized in the laboratory. A recombinant nucleic acid may be prepared by using recombinant DNA technology, for example, enzymatic modification of DNA, such as enzymatic restriction digestion, ligation, and DNA cloning. A recombinant nucleic acid can be DNA, RNA, analogues thereof, or a combination thereof. A recombinant DNA may be transcribed ex vivo or in vitro, such as to generate a messenger RNA (mRNA). A recombinant mRNA may be isolated, purified and used to transfect a cell. A recombinant nucleic acid may encode a protein or a polypeptide. Throughout the specification, nucleic acid sequences are described which may comprise deoxyribonucleotides (DNA), ribonucleotides (RNA), or in some embodiments, modified deoxyribonucleotides, or modified ribonucleotides. For example, a modified nucleotide may be a 5-hydroxymethylcytosine (5hmC), a 5-formylacytosine (5fC), a 7-methylguanosine, a pseudouridine, a dihydrouridine etc. One of skill in the art can determine an RNA sequence, e.g., an mRNA sequence from a given polynucleotide sequence without difficulty. Sequences may be codon optimized.

The process of introducing or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the introduction of small molecules such as DNA, RNA, or antibodies into eukaryotic cells. Transfection may also refer to the introduction of bacteriophage into bacterial cells. 'Transduction' is mostly used to describe the introduction of recombinant viral vector particles into target cells, while 'infection' refers to natural infections of humans or animals with wild-type viruses.

The term "vector", can refer to a nucleic acid molecule capable of autonomous replication in a host cell, and which allow for cloning of nucleic acid molecules. As known to those skilled in the art, a vector includes, but is not limited to, a plasmid, cosmid, phagemid, viral vectors, phage vectors, yeast vectors, mammalian vectors and the like. For example, a vector for exogenous gene transformation may be a plasmid. In certain embodiments, a vector comprises a nucleic acid sequence containing an origin of replication and other elements necessary for replication and/or maintenance of the nucleic acid sequence in a host cell. In some embodiments, a vector or a plasmid provided herein is an expression vector. Expression vectors are capable of directing the expression of genes and/or nucleic acid sequence to which they are operatively linked. In some embodiments, an expression vector or plasmid is in the form of circular double stranded DNA molecules. A vector or plasmid may or may not be integrated into the genome of a host cell. In some embodiments, nucleic acid sequences of a plasmid are not integrated in a genome or chromosome of the host cell after introduction. For example, the plasmid may comprise elements for transient expression or stable expression of the nucleic acid sequences, e.g. genes or open reading frames harbored by the plasmid, in a host cell. In some embodiments, a vector is a transient expression vector. In some embodiments, a vector is a stably expressed vector that replicates autonomously in a host cell. In some embodiments, nucleic acid sequences of a plasmid are integrated into a genome or chromosome of a host cell upon introduction into the host cell. Expression vectors that can be used in the methods as disclosed herein include, but are not limited to, plasmids, episomes, bacterial artificial chromosomes, yeast artificial chromosomes, bacteriophages or viral vectors. A vector can be a DNA or RNA vector. In some embodiments, a vector provide herein is a RNA vector that is capable of integrating into a host cell's genome upon introduction into the host cell (e.g., via reverse transcription), for example, a retroviral vector or a lentiviral vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

In some embodiments, nucleic acid may be delivered into a living system in the form of nanoparticles. Nucleic acid sequences disclosed herein may be delivered in vivo via suitable nanoparticles, e.g., liposomes, lipid nanoparticles, or polymeric nanoparticles. A lipid nanoparticle may comprise a polar lipid. In some embodiments, the lipid nanoparticle comprises a cationic lipid. In some embodiments, the lipid nanoparticle comprises a cationic lipid and a non-cationic lipid. In some embodiments, the lipid nanoparticle comprises a neutral lipid. In some embodiments, the lipid nanoparticle comprises a PEGylated lipid.

Alternatively, in some embodiments, the nucleic acid can be electroporated in a living cell ex vivo for preparation of a cellular therapy, wherein the cell is a myeloid cell.

The terms "spacer" or "linker" as used in reference to a fusion protein refers to a peptide sequence that joins two other peptide sequences of the fusion protein. In some embodiments, a linker or spacer has no specific biological activity other than to join or to preserve some minimum distance or other spatial relationship between the proteins or RNA sequences. In some embodiments, the constituent amino acids of a spacer can be selected to influence some property of the molecule such as the folding, flexibility, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. In some embodiments, a linker is used to separate two or more polypeptides, e.g. two antigenic peptides by a distance sufficient to ensure that each antigenic peptide properly folds. Exemplary peptide linker sequences adopt a flexible extended conformation and do not exhibit a propensity for developing an ordered secondary structure. Amino acids in flexible linker protein region may include Gly, Asn and Ser, or any permutation of amino acid sequences containing Gly, Asn and Ser. Other near neutral amino acids, such as Thr and Ala, also can be used in the linker sequence.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which can refer to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated. The term "prevent", "preventing", "prevention" and their grammatical equivalents as used herein, can refer to avoiding or delaying the onset of symptoms associated with a disease or condition in a subject that has not developed such symptoms at the time the administering of an agent or compound commences. In certain embodiments, treating a subject or a patient as described herein comprises administering a therapeutic composition, such as a drug, a metabolite, a preventive component, a nucleic acid, a peptide, or a protein that encodes or otherwise forms a drug, a metabolite or a preventive component. In some embodiments, treating comprises administering a cell or a population of cells to a subject in need thereof. In some embodiments, treating comprises administering to the subject one or more of engineered cells described herein, e.g. one or more engineered myeloid cells, such as phagocytic cells. Treating comprises treating a disease or a condition or a syndrome, which may be a pathological disease, condition or syndrome, or a latent disease, condition or syndrome. In some cases, treating, as used herein may comprise administering a therapeutic vaccine. In some embodiments, the engineered phagocytic cell is administered to a patient or a subject. In some embodiments, a cell administered to a human subject results in reduced immunogenicity. For example, an engineered phagocytic cell may lead to no or reduced graft versus host disease (GVHD) or fratricide effect. In some embodiments, an engineered cell administered to a human subject is immunocompatible to the subject (i.e. having a matching HLA subtype that is naturally expressed in the subject). Subject specific HLA alleles or HLA genotype of a subject can be determined by any method known in the art. In exemplary embodiments, the methods include determining polymorphic gene types that can comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

A "fragment" can refer to a portion of a protein or nucleic acid. In some embodiments, a fragment retains at least 50%, 75%, or 80%, or 90%, 95%, or even 99% of the biological activity of a reference protein or nucleic acid.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

The terms "neoplasia" or "cancer" refers to any disease that is caused by or results in inappropriately high levels of cell division, inappropriately low levels of apoptosis, or both. Glioblastoma is one non-limiting example of a neoplasia or cancer. The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell.

The term "vaccine" is to be understood as meaning a composition for generating immunity for the prophylaxis and/or treatment of diseases (e.g., neoplasia/tumor/infectious agents/autoimmune diseases). Accordingly, vaccines as used herein are medicaments which comprise recombinant nucleic acids, or cells comprising and expressing a recombinant nucleic acid and are intended to be used in humans or animals for generating specific defense and protective substance by vaccination. A "vaccine composition" can include a pharmaceutically acceptable excipient, carrier or diluent. Aspects of the present disclosure relate to use of the technology in preparing a phagocytic cell-based vaccine.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Nucleic acid molecules useful in the methods of the disclosure include, but are not limited to, any nucleic acid molecule with activity or that encodes a polypeptide. Polynucleotides having substantial identity to an endogenous sequence are typically capable of hybridizing with at least one strand of a double-stranded nucleic acid molecule. "Hybridize" refers to when nucleic acid molecules pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152:507). For example, stringent salt concentration can ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions can ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an exemplary embodiment, hybridization can occur at 30° C. in 750 mM NaCl, 75 mM trisodium citrate, and 1% SDS. In another exemplary embodiment, hybridization can occur at 37° C. in 500 mM NaCl, 50 mM trisodium citrate, 1% SDS, 35% formamide, and 100 µg/ml denatured salmon sperm DNA (ssDNA). In another exemplary embodiment, hybridization can occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or at least about 68° C. In exemplary embodiments, wash steps can occur at 25° C. in 30 mM NaCl, 3 mM trisodium citrate, and 0.1% SDS. In other exemplary embodiments, wash steps can occur at 42° C. in 15 mM NaCl, 1.5 mM trisodium citrate, and 0.1% SDS. In another exemplary embodiment, wash steps can occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95%, 96%, 97%, 98%, or even 99% or more identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program can be used, with a probability score between e-3 and e-m° indicating a closely related sequence. A "reference" is a standard of comparison. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment to a reference sequence and determination of homologous residues.

The term "subject" or "patient" refers to an organism, such as an animal (e g, a human) which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The term "therapeutic effect" refers to some extent of relief of one or more of the symptoms of a disorder (e.g., a neoplasia, tumor, or infection by an infectious agent or an autoimmune disease) or its associated pathology. On one hand it may indicate a reduction of a symptom of the disease, e.g., a 10%, 20%, 30% and so on reduction in tumor mass following administration of the therapeutic composition. On another embodiment, it can relate to partial or complete remission of one or more symptoms, or amelioration of the disease. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required.

Provided herein are engineered myeloid cells (including, but not limited to, neutrophils, monocytes, myeloid dendritic cells (mDCs), mast cells and macrophages), designed to specifically bind a target antigen. The target antigen may be expressed only on a target cell, such as an infected cell, a damaged cell, a malignant cell, a leukemia cell or a tumor cell. The engineered myeloid cells can attack and kill target cells directly (e.g., by phagocytosis) and/or indirectly (e.g., by activating T cells). In some embodiments, the target cell is a cancer cell.

While cancer is one exemplary embodiment described in detail in the instant disclosure, the methods and technologies described herein are contemplated to be useful in targeting an infected or otherwise diseased cell inside the body. Similarly, therapeutic and vaccine compositions using the engineered cells are described herein.

Myeloid effector cells may be generated from the isolated myeloid cells from a human biological sample and modified ex vivo to prepare cells of therapeutic interest using methods to engineer such cells and such that the modifications do not alter the plasticity of these cells. Monocytic lineage cells are phagocytic and are efficient antigen presenter cells. In one aspect, the present invention stems from an important finding that engineered myeloid cells can be a highly efficient therapeutic modality in treating a number of diseases including cancer. Myeloid cells may be engineered to express a chimeric antigen receptor that enhances a myeloid cell's immune function in which the cells are highly phagocytic and can attack and kill a diseased cell or an infected cell in the body. The chimeric antigen receptor is a recombinant construct that is designed, and specifically modified as described herein, to be (a) highly target specific, specifically directed to bind to a target antigen, having an extracellular antigen binding domain, and (b) an intracellular domain that is highly specialized to activate a myeloid cell to attain an activate phagocytic cell phenotype. For example, highly specialized intracellular domains are designed to generate chimeric receptors that, upon activation by binding of the extracellular region of the receptor to the target, can generate signaling cues inside the cell that activate intracellular interferon signaling cascade, and transcription factors, namely, directs the activation of transcription factor IRFs (IFN regulatory factors). In addition, the methods and compositions described herein are also useful in gene therapy in which a recombinant nucleic acid encoding a chimeric antigen receptor is administered locally or systemically in a subject in need thereof, such that the recombinant nucleic acid is specifically expressed in a myeloid cell in vivo, and thereby generates activated myeloid cells having the therapeutic ability. In some embodiments, the nucleic acid is mRNA. In some embodiments the mRNA is delivered in an LNP.

Phagocytes are the natural sentinels of the immune system and form the first line of defense in the body. They engulf a pathogen, a pathogen infected cell, a foreign body, or a cancerous cell and remove it from the body. Most potential pathogens are rapidly neutralized by this system before they can cause, for example, a noticeable infection or a disease. This can involve receptor-mediated uptake through the clathrin-coated pit system, pinocytosis, particularly macropinocytosis as a consequence of membrane ruffling and phagocytosis. The phagocytes therefore can be activated by a variety of non-self (and self) elements and exhibit a level of plasticity in recognition of their "targets". Most phagocytes express scavenger receptors on their surface which are pattern recognition molecules and can bind to a wide range of foreign particles as well as dead cell, debris and unwanted particles within the body. In one aspect, recombinant nucleic acids encoding chimeric antigen receptors (CAR) may be expressed in the cells. The CARs may be variously designed to attack specific tumor cells, and myeloid effector cells expressing CARs can be activated to phagocytose and kill tumor cells. The CARs may be designed to generate phagocytic receptors that are activated specifically in response to the target engagement, and the phagocytic potential of a macrophage is enhanced by specifically engineered intracellular domains of the receptor. The CAR platform for myeloid cells as described herein is designed such that no tonic signaling is detected in the myeloid cells at the time of administering in the body, or any time before the myeloid cell engages with its target via the CAR. This is often tested ex vivo. At the same time, the myeloid cells expressing the CAR can be further differentiated into M0, M1 or M2 phenotypes in presence of the suitable stimulus, and retain the cellular plasticity to do so at least at the time of administration. In addition, CAR-expressing myeloid effector cells can migrate to lymph nodes and cross-present antigens to naïve T cells in the lymph node thereby activating the adaptive response.

In some embodiments, disclosed herein are compositions and methods for generating myeloid cells that are isolated from a biological sample and engineered ex vivo to express a recombinant protein, and formulated into a pharmaceutical composition, such that the myeloid cells of the composition are "effector" myeloid cells efficient in induction of immune activation in vivo. In some embodiments, the myeloid cells of the composition are termed 'ATAK' myeloid cells where the cells are myeloid efficient in attacking and destroying target cells. The ATAK myeloid cells disclosed herein is an engineered myeloid cell that expresses a recombinant protein, e.g., a chimeric receptor, e.g., a chimeric antigen receptor, comprising at least one intracellular signaling domain that is derived from an interferon inducing protein in an immune cell. In some embodiments, the methods and compositions described herein are directed to render an engineered myeloid cell to exhibit the effector phenotype. In some embodiments, the engineered myeloid cells, e.g., monocytes are M0 or M1 phenotype monocytes, and the activation of the chimeric antigen receptor expressed in the myeloid cell renders the cells to exhibit the M1 phenotype. The M1 phenotype exhibited by the engineered cell renders the cell to be highly tumoricidal when designed to be targeted to a tumor cell.

Provided herein are compositions and methods for treating diseases or conditions, such as cancer. The compositions and methods provided herein utilize human myeloid cells, including, but not limited to, neutrophils, monocytes, myeloid dendritic cells (mDCs), mast cells and macrophages, to target diseased cells, such as cancer cells. The compositions and methods provided herein can be used to eliminate diseased cells, such as cancer cells and or diseased tissue, by a variety of mechanisms, including T cell activation and recruitment, effector immune cell activation (e.g., CD8 T cell and NK cell activation), antigen cross presentation, enhanced inflammatory responses, reduction of regulatory T cells and phagocytosis. For example, the myeloid cells can be used to sustain immunological responses against cancer cells.

Applicants previously described compositions comprising a recombinant nucleic acid encoding a chimeric fusion protein (CFP), such as a phagocytic receptor (PR) fusion protein (PFP), a scavenger receptor (SR) fusion protein (SFP), an integrin receptor (IR) fusion protein (IFP) or a caspase-recruiting receptor (caspase-CAR) fusion protein. A CFP encoded by the recombinant nucleic acid can comprise an extracellular domain (ECD) comprising an antigen binding domain that binds to an antigen of a target cell. The extracellular domain can be fused to a hinge domain or an extracellular domain derived from a receptor, such as CD2, CD8, CD28, CD68, a phagocytic receptor, a scavenger receptor or an integrin receptor. The CFP encoded by the recombinant nucleic acid can further comprise a transmembrane domain, such as a transmembrane domain derived from CD2, CD8, CD28, CD68, a phagocytic receptor, a scavenger receptor or an integrin receptor. In some embodiments, a CFP encoded by the recombinant nucleic acid further comprises an intracellular domain comprising an intracellular signaling domain, such as an intracellular signaling domain derived from a phagocytic receptor, a scavenger receptor or an integrin receptor. For example, the intracellular domain can comprise one or more intracellular signaling domains derived from a phagocytic receptor, a scavenger receptor or an integrin receptor. For example, the intracellular domain can comprise one or more intracellular signaling domains that promote phagocytic activity, inflammatory response, nitric oxide production, integrin activation, enhanced effector cell migration (e.g., via chemokine receptor expression), antigen presentation, and/or enhanced cross presentation. In some embodiments, the CFP is a phagocytic receptor fusion protein (PFP). In some embodiments, the CFP is a phagocytic scavenger receptor fusion protein (PFP). In some embodiments, the CFP is an integrin receptor fusion protein (IFP). In some embodiments, the CFP is an inflammatory receptor fusion protein. In some embodiments, a CFP encoded by the recombinant nucleic acid further comprises an intracellular domain comprising a recruitment domain. For example, the intracellular domain can comprise one or more PI3K recruitment domains, caspase recruitment domains or caspase activation and recruitment domains (CARDs).

Provided herein are improved immunogenic CAR compositions, for example, recombinant nucleic acid encoding a chimeric fusion protein (CFP, interchangeably termed chimeric antigen receptor, CAR) comprising an intracellular domain that activates interferon response in a cell expressing the CAR. Provided herein are immunogenic CFPs that comprise at least one intracellular domain comprising a pLxIS motif. The recombinant nucleic acid may be DNA or RNA. The recombinant nucleic acid encoding the CAR may be comprised in a vector. The recombinant CAR when expressed in a cell activates Type I interferon production in the cell. Such a cell is a mammalian cell, that is capable of Type 1 Interferon response. Such cell is an immune cell, e.g. a lymphocyte cell or a myeloid cell.

In some embodiments the recombinant nucleic acid encoding the chimeric receptor comprises a specific sequence therein that encodes a pro-inflammatory intracellular domain of the chimeric receptor. In some embodiments, the chimeric receptor protein described herein comprises an intracellular domain capable of activating an interferon response gene or a signaling cascade leading to induction of Type I interferon production in the cell that expresses the chimeric antigen receptor upon engagement with its target at the extracellular domain. In some embodiments, the chimeric receptor protein described herein comprises a domain from an innate immune pathway adaptor protein, e.g., Mitochondrial antiviral-signaling protein (MAVS), Stimulator of interferon genes (STING), Toll/IL-1R domain-containing adaptor inducing IFN (TRIF), and TLR adaptor interacting with endolysosomal SLC15A4 protein (TASL), or a portion thereof. In some embodiments, a domain or fragment of an innate immune pathway adaptor protein e.g., MAVS, STING, TRIF or TASL proteins may be incorporated by recombinant DNA technology in the intracellular domain of the CFP or CAR as described herein, wherein the domain or fragment comprises a pLxIS motif (in which p represents the hydrophilic residue, x represents any residue, and S represents the phosphorylation site), that is phosphorylated by TBK1 or IKKε and mediates the recruitment of IRF-3 to the signaling complexes.

In some embodiments, the chimeric receptor protein described herein comprises an intracellular domain capable of activating nuclear factor kappa B responsive gene or a signaling cascade leading to induction of NF-kappa B response in the cell that expresses the chimeric antigen receptor upon engagement with its target at the extracellular domain.

Effector Myeloid Cells and Interferon Activation

Type I and Type II interferons (IFNs) play important roles in regulating immune responses during infections and cancer. Type I is represented by multiple subtypes including numerous IFNα family members, IFNβ, IFNδ, IFNε, IFNκ, IFNτ and IFNω, and all these utilize the same cell surface receptor, IFNαR, which is a heterodimer comprised of IFNαR1 and IFNαR2 proteins. Type II IFN is represented by IFNγ. These two IFN types bind to distinct cell surface receptors that are expressed by nearly all cells to trigger signal transduction events and elicit diverse cellular responses. Myeloid cells are key targets of interferons. During early immune responses to intracellular bacterial infections. Activated natural killer (NK) and T cells are the sources of IFNγ production. During early stages of infection, production of the cytokines interleukin (IL)-12 and IL-18 drives antigen-nonspecific IFNγ production by these lymphocyte populations. Antigen-specific CD4$^+$ and CD8$^+$ T cells also can produce IFNγ in response to these pathogens. There are a large number of individual type I IFNs, including ~20 IFNα proteins and a single IFNβ. Each of these type I IFNs signals to host cells by binding the conserved cell surface type I IFN receptor, IFNαR. Ligation of cell surface IFNαR induces expression of numerous antiviral immune stimulated gene (ISG) products and thus protects the host from certain viral infections (Sadler A J, Interferon-inducible antiviral effectors. (Review) *Nat Rev Immunol.* 2008 July; 8(7):559-68). However, responsiveness to type I IFNs also correlates dramatically with increased susceptibility to a number of intracellular bacterial infections (Rayamajhi M, et al., Antagonistic crosstalk between type I and II interferons and increased host susceptibility to bacterial infections. *Virulence.* 2010 September-October; 1(5):418-22), including *Listeria monocytogenes, Mycobacterium tuberculosis, Francisella tularensis*, and others. IFNγ is secreted as a homodimer and acts on host cells by ligating cell surface receptors. Each IFNγ receptor is a heterodimer comprised of two type I integral membrane subunits, IFNγR1 and IFNγR2. Binding of an IFNγ homodimer to the cell causes the aggregation of two receptor complexes, such that there are two IFNγR1 subunits and two IFNγR2 subunits, as well as additional signaling components. While both subunits are required for signal transduction, the actual binding site for IFNγ is located on IFNγR1 (Kearney S. et al., *Differential effects of type I and II interferons on myeloid cells and resistance to intracellular bacterial infections. Immunol Res.* 2013 March; 55(0): 187-200). When IFNγ interacts with an IFNγR1 subunit, it induces a conformational change that permits a closer association of the IFNγR1 and IFNγR2 subunits. These rearrangements in the receptor induce auto- and cross-phosphorylation of Janus-associated kinases (JAKs) that are constitutively associated with the receptor. IFNγR1 contains a binding motif for JAK1, and IFNγR2 contains a binding motif for JAK2. Phosphorylation of the JAK proteins stimulates their catalytic activity and they then phosphorylate a tyrosine residue ($Y_{440}$) at the C-terminus of IFNγR1. This phosphorylated tyrosine residue provides a docking site for the SH2 domain on the Signal Transducer and Activator of Transcription-1 (STAT-1) protein. Because each receptor complex contains two IFNγR1 subunits, two STAT-1 proteins are able to bind to the receptor. JAK1 and JAK2 remain receptor-associated and phosphorylate each recruited STAT-1 protein at tyrosine residue 701 ($Y_{701}$). This phosphorylation allows release of the STAT-1 monomers from the receptor and their formation of homodimers. STAT-1 homodimers translocate to the nucleus and bind Gamma-Activated Sequences (GAS) in the promoter DNA of IFN-stimulated genes (ISGs), resulting in their increased transcription. Type I IFNs signal through a canonical JAK/STAT pathway, similar to that activated by IFNγ. Ligand binding to the IFNαR initiates dimerization of the two receptor subunits and trans-phosphorylation of their associated TYK2 and JAK1 kinases. The kinases phosphorylate residues in the cytoplasmic tails of IFNαR1 and IFNαR2 to recruit STAT1 and STAT2 proteins via their SH2 domains. Docking of these STAT proteins to the receptor subunits allows their phosphorylation by the activated JAK proteins at $Y_{701}$ on STAT-1 and $Y_{690}$ on STAT-2. Phosphorylation of the STAT monomers releases them from their docking site, allowing them to dimerize and combine in a homodimeric or heterodimeric form with IRF9 to produce the transcription factor ISG factor 3 (ISGF3). ISGF3 translocates into the nucleus to identify ISGs and induces their transcription. ISGs induced by type I IFN signaling typically contain interferon stimulated response element (ISRE) or a gamma activated sequence (GAS) elements within their promoters, although there is a clear preference for genes containing an ISRE. Some examples of ISGs transcribed as a result of type I IFNs are ISRE containing genes ISG15, IP-10, IRF-7 and PKR [66], and GAS containing genes IRF-1, IRF-2, IRF-8 and IRF-9 (Kearney S. et al., *Differential effects of type I and II interferons on myeloid cells and resistance to intracellular bacterial infections. Immunol Res.* 2013 March; 55(0): 187-200).

Recombinant Chimeric Receptor Proteins

Provided herein is a class of phagocytic or tethering receptor (PR) subunit (e.g., a phagocytic receptor fusion protein (PFP)) comprising: (i) a transmembrane domain, and (ii) an intracellular domain comprising a phagocytic receptor intracellular signaling domain; and an antigen binding domain specific to an antigen, e.g., an antigen of or presented on a target cell; wherein the transmembrane domain and the antigen binding domain are operatively linked such that antigen binding to the target by the antigen binding domain of the fused receptor activated in the intracellular signaling domain of the phagocytic receptor.

In some embodiments, the extracellular domain of a CFP comprises an Ig binding domain. In some embodiments, the extracellular domain comprises an IgA, IgD, IgE, IgG, IgM, FcRγI, FcRγIIA, FcRγIIB, FcRγIIC, FcRγIIIA, FcRγIIIB, FcRn, TRIM21, FcRL5 binding domain. In some embodiments, the extracellular domain of a CFP comprises an FcR extracellular domain. In some embodiments, the extracellular domain of a CFP comprises an FcRα, FcRβ, FcRε or FcRγ extracellular domain. In some embodiments, the extracellular domain comprises an FcRα (FCAR) extracellular domain. In some embodiments, the extracellular domain comprises an FcRβ extracellular domain. In some embodiments, the extracellular domain comprises an FCER1A extracellular domain. In some embodiments, the extracellular domain comprises an FDGR1A, FCGR2A, FCGR2B, FCGR2C, FCGR3A, or FCGR3B extracellular domain. In some embodiments, the extracellular domain comprises an integrin domain or an integrin receptor domain. In some embodiments, the extracellular domain comprises one or more integrin α1, α2, αIIb, α3, α4, α5, α6, α7, α8, α9, α10, α11, αD, αE, αL, αM, αV, αX, β1, β2, β3, β4, β5, β6, α7, or β8 domains.

In some embodiments, the CFP further comprises an extracellular domain comprising an antigen binding domain operatively linked to the transmembrane domain. In some embodiments, the extracellular domain further comprises an extracellular domain of a receptor, a hinge, a spacer and/or a linker. In some embodiments, the extracellular domain comprises an extracellular portion of a phagocytic receptor. In some embodiments, the extracellular portion of the CFP is derived from the same receptor as the receptor from which the intracellular signaling domain is derived. In some embodiments, the extracellular domain comprises an extracellular domain of a scavenger receptor. In some embodiments, the extracellular domain comprises an immunoglobulin domain. In some embodiments, the immunoglobulin domain comprises an extracellular domain of an immunoglobulin or an immunoglobulin hinge region. In some embodiments, the extracellular domain comprises a phagocytic engulfment domain. In some embodiments, the extracellular domain comprises a structure capable of multimeric assembly. In some embodiments, the extracellular domain comprises a scaffold for multimerization. In some embodiments, the extracellular domain is at least 10, 20, 30, 40, 50, 60, 70, 80, 90, 100, 150, 200, 300, 300, 400, or 500 amino acids in length. In some embodiments, the extracellular domain is at most 500, 400, 300, 200, or 100 amino acids in length. In some embodiments, the antigen binding domain specifically binds to the antigen of a target cell. In some embodiments, the antigen binding domain comprises an antibody domain. In some embodiments, the antigen binding domain comprises a receptor domain, antibody domain, wherein the antibody domain comprises a functional antibody fragment, a single chain variable fragment (scFv), an Fab, a single-domain antibody (sdAb), a nanobody, a $V_H$ domain, a $V_L$ domain, a VNAR domain, a $V_{HH}$ domain, a bispecific antibody, a diabody, or a functional fragment or a combination thereof. In some embodiments, the antigen binding domain comprises a ligand, an extracellular domain of a receptor or an adaptor. In some embodiments, the antigen binding domain comprises a single antigen binding domain that is specific for a single antigen. In some embodiments, the antigen binding domain comprises at least two antigen binding domains, wherein each of the at least two antigen binding domains is specific for a different antigen.

In some embodiments, the antigen is a cancer associated antigen, a lineage associated antigen, a pathogenic antigen or an autoimmune antigen. In some embodiments, the antigen comprises a viral antigen. In some embodiments, the antigen is a T lymphocyte antigen. In some embodiments, the antigen is an extracellular antigen. In some embodiments, the antigen is an intracellular antigen. In some embodiments, the antigen is selected from the group consisting of an antigen from Thymidine Kinase (TK1), Hypoxanthine-Guanine Phosphoribosyltransferase (HPRT), Receptor Tyrosine Kinase-Like Orphan Receptor 1 (ROR1), Mucin-1, Mucin-16 (MUC16), MUC1, Epidermal Growth Factor Receptor vIII (EGFRvIII), Mesothelin, Human Epidermal Growth Factor Receptor 2 (HER2), EBNA-1, LEMD1, Phosphatidyl Serine, Carcinoembryonic Antigen (CEA), B-Cell Maturation Antigen (BCMA), Glypican 3 (GPC3), Follicular Stimulating Hormone receptor, Fibroblast Activation Protein (FAP), Erythropoietin-Producing Hepatocellular Carcinoma A2 (EphA2), EphB2, a Natural Killer Group 2D (NKG2D) ligand, Disialoganglioside 2 (GD2), CD2, CD3, CD4, CD5, CD7, CD8, CD19, CD20, CD22, CD24, CD30, CD33, CD38, CD44v6, CD45, CD56CD79b, CD97, CD117, CD123, CD133, CD138, CD171, CD179a, CD213A2, CD248, CD276, PSCA, CS-1, CLECL1, GD3, PSMA, FLT3, TAG72, EPCAM, IL-1, an integrin receptor, PRSS21, VEGFR2, PDGFRβ, SSEA-4, EGFR, NCAM, prostase, PAP, ELF2M, GM3, TEM7R, CLDN6, TSHR, GPRC5D, ALK, Dsg1, Dsg3, IGLL1 and combinations thereof. In some embodiments, the antigen is an antigen of a protein selected from the group consisting of CD2, CD3, CD4, CD5, CD7, CCR4, CD8, CD30, CD45, and CD56. In some embodiments, the antigen is an ovarian cancer antigen or a T lymphoma antigen. In some embodiments, the antigen is an antigen of an integrin receptor. In some embodiments, the antigen is an antigen of an integrin receptor or integrin selected from the group consisting of α1, α2, αIIb, α3, α4, α5, α6, α7, α8, α9, α10, α11, αD, αE, αL, αM, αV, αX, β 1, β 2, β 3, β 4, β 5, β 6, β 7, and β8. In some embodiment, the antigen is an antigen of an integrin receptor ligand. In some embodiments, the antigen is an antigen of fibronectin, vitronectin, collagen, or laminin. In some embodiments, the antigen binding domain can bind to two or more different antigens.

In some embodiments, the antigen binding domain comprises a sequence of an antigen binding domain provided herein, such as a sequence of an antigen binding domain in a Table provided herein.

In some embodiments, the target protein is CD70. In some embodiments, the antigen binding domain comprises an anti-CD70 antibody or binding fragment thereof, wherein the antigen binding domain comprises a heavy chain variable domain (VH) comprising a heavy chain complementarity determining region 3 (HC CDR3) that is the HC CDR3 of any one of the VH sequences selected from the group consisting of

```
                                          (SEQ ID NO: 112)
QVQLQESGGGLVQAGGSLRLSCAAPRSIFSINAMGWYRQAPGKQRELVAA

ITSGGSPTYADSVKGRFTISRDNAKNTVYLQMNSLKAEDTAVYYCATGPY

GLDNALDAWGQGTQVTVSS
and
                                          (SEQ ID NO: 113)
QVQLQESGGGLVQTGGSLRLACTASGFTFDDYAIAWFRQAPGKEREFVAA

ISWSGGTTHYADSVKGRFTISRDNAKNTLYLQMSSLKPEDTAVYFCAKSL

RSSPSSRWFGSRGQGTQVTVSS.
```

In some embodiments, the VH of the anti-CD70 antibody or binding fragment thereof further comprises a heavy chain complementarity determining region 1 (HC CDR1) that is the HC CDR1 of any one of the VH sequences selected from the group consisting of

```
                                          (SEQ ID NO: 112)
QVQLQESGGGLVQAGGSLRLSCAAPRSIFSINAMGWYRQAPGKQRELVAA

ITSGGSPTYADSVKGRFTISRDNAKNTVYLQMNSLKAEDTAVYYCATGPY

GLDNALDAWGQGTQVTVSS
and
                                          (SEQ ID NO: 113)
QVQLQESGGGLVQTGGSLRLACTASGFTFDDYAIAWFRQAPGKEREFVAA

ISWSGGTTHYADSVKGRFTISRDNAKNTLYLQMSSLKPEDTAVYFCAKSL

RSSPSSRWFGSRGQGTQVTVSS.
```

In some embodiments, the VH of the anti-CD70 antibody or binding fragment thereof further comprises a heavy chain complementarity determining region 2 (HC CDR2) that is the HC CDR2 of any one of the VH sequences selected from the group consisting of QVQLQESGGGLVQAGGSLRLSCAAPRSIFSINAMGWYRQAPGKQRELVAAITSGGSPTYADSVKGRFTISRDNAKNTVYLQMNSLKAEDTAVYYCATGPYGLDNALDAWGQGTQVTVSS (SEQ ID NO: 112)
and
QVQLQESGGGLVQTGGSLRLACTASGFTFDDYAIAWFRQAPGKEREFVAAISWSGGTTHYADSVKGRFTISRDNAKNTLYLQMSSLKPEDTAVYFCAKSLRSSPSSRWFGSRGQGTQVTVSS. (SEQ ID NO: 113)

In some embodiments, the VH of the anti-CD70 antibody or binding fragment thereof comprises with 70-100% sequence identity to any one of the sequences selected from the group consisting of QVQLQESGGGLVQAGGSLRLSCAAPRSIFSINAMGWYRQAPGKQRELVAAITSGGSPTYADSVKGRFTISRDNAKNTVYLQMNSLKAEDTAVYYCATGPYGLDNALDAWGQGTQVTVSS (SEQ ID NO: 112)
and
QVQLQESGGGLVQTGGSLRLACTASGFTFDDYAIAWFRQAPGKEREFVAAISWSGGTTHYADSVKGRFTISRDNAKNTLYLQMSSLKPEDTAVYFCAKSLRSSPSSRWFGSRGQGTQVTVSS (SEQ ID NO: 113)

In some embodiments, the VH is a single domain antibody domain. In some embodiments, the VH is a VHH.

In some embodiments the target protein is GPC3. In some embodiments, the antigen binding domain comprises an anti-GPC3 antibody or binding fragment thereof, wherein the antigen binding domain comprises a heavy chain variable domain (VH) comprising a heavy chain complementarity determining region 3 (HC CDR3) of any one of the sequences selected from the group consisting of

ATACADTTQYAYDY, (SEQ ID NO: 114)

ATACADTTLYEYDY, (SEQ ID NO: 115)

ATACVDTTQYEYDY, (SEQ ID NO: 116)

ATACADATQHEYDY, (SEQ ID NO: 117)

ATACADTTQYDYDY, (SEQ ID NO: 118)

ATACADTTQYEYDY, (SEQ ID NO: 119)

ATACADTTHYEYDY, (SEQ ID NO: 120)

ATACVITTLYEYDY, (SEQ ID NO: 121)

ATACAETTLYEYDY, (SEQ ID NO: 122)

ATACADTTQHEYDY, (SEQ ID NO: 123)

ATACVDTTHYEYDY, (SEQ ID NO: 124)

ATACASTTLYEYDY, (SEQ ID NO: 125)

ATACVVTTLYEYDY, (SEQ ID NO: 126)

ATACGGATGPYDY, (SEQ ID NO: 127)

ATACAGAIGPYDY, (SEQ ID NO: 128)

ATACVVVGDQNDY, (SEQ ID NO: 129)

ATACVVVGDRNDY, (SEQ ID NO: 130)

ATDCAGGTSTPYDY, (SEQ ID NO: 131)

ATDCAGGTATPYDY, (SEQ ID NO: 132)

ATACVVADRNEYDY, (SEQ ID NO: 133)

ATSCVVVTKNEYDY, (SEQ ID NO: 134)

ATACSGLTHEYDY, (SEQ ID NO: 135)

ATTCSGLTHEYDY, (SEQ ID NO: 136)

ATACANWSSLGPYDY, (SEQ ID NO: 137)

ATACANWSTLGPYDY, (SEQ ID NO: 138)

ATACSDPRVYEYDY, (SEQ ID NO: 139)

ATTCASPEKYEYDY, (SEQ ID NO: 140)

ATHCGGTSWGTSYDY, (SEQ ID NO: 141)

ATHCGGSSWSNEYDY, (SEQ ID NO: 142)

YARYSGRTY, (SEQ ID NO: 143)

ASSAWPAGPKHQVEYDY, (SEQ ID NO: 144)

ATACGSLVGMYDY, (SEQ ID NO: 145)

ATACGSAVHEYDY, (SEQ ID NO: 146)

ATDCVGFGSNWFDY, (SEQ ID NO: 147)

ATACASPVIYEYDY, (SEQ ID NO: 148)

ATDCAGGVGHEYDY, (SEQ ID NO: 149)

ATDCSLHGSDYPYDY
and (SEQ ID NO: 150)

AVRIYSGSFDNTLAYDY. (SEQ ID NO: 151)

In some embodiments, the VH of the anti-GPC3 antibody or binding fragment thereof further comprises a heavy chain complementarity determining region 1 (HC CDR1) of any one of the sequences selected from the group consisting of SEQ ID NOs: GFPLAYYA (SEQ ID NO: 152), GFSLDYYA (SEQ ID NO: 153), GFPLDYYA (SEQ ID NO: 154), GFTLDYYA (SEQ ID NO: 155), GFSLNYYA (SEQ ID NO: 156), GFTLAYYA (SEQ ID NO: 157), GFTLGYYA (SEQ ID NO: 158), GFPLNYYA (SEQ ID NO: 159), GFPLHYYA (SEQ ID NO: 160), GFSLGYYA (SEQ ID NO: 161), GFPLGYYA (SEQ ID NO: 162), GFPLEYYA (SEQ ID NO: 163), GSDFRADA (SEQ ID NO: 164), GRTFSSYG (SEQ ID NO: 165), GFSLAYYA (SEQ ID NO: 166) and GLTFRSVG (SEQ ID NO: 167). In some embodiments, the VH of the anti-GPC3 antibody or binding fragment thereof further comprises a heavy chain complementarity determining region 2 (HC CDR2) of any one of the sequences selected from the group consisting of SEQ ID NOs: ISNSDGST (SEQ ID NO: 168), ISASDGST (SEQ ID NO: 169), ISSSDGST (SEQ ID NO: 170), ISSSDGNT (SEQ ID NO: 171), ISSADGST (SEQ ID NO: 172), ISSSGGST (SEQ ID NO: 173), ISSGDGST (SEQ ID NO: 174), ISAGDGNT (SEQ ID NO: 175), ISSSDDST (SEQ ID NO: 176), ISSNDGST (SEQ ID NO: 177), ISSPDGST (SEQ ID NO: 178), ISSRTGGT (SEQ ID NO: 179), ISAGDGSST (SEQ ID NO: 180), ISSSDGSSSDGNT (SEQ ID NO: 181), ISSGDGNT (SEQ ID NO: 182), ISSGDGKT (SEQ ID NO: 183), ISSSDGGT (SEQ ID NO: 184), ISSRTGST (SEQ ID NO: 185), ISSRTGNT (SEQ ID NO: 186), ISSSDGHSST (SEQ ID NO: 187), ISSSSDGNT (SEQ ID NO: 188), ISASNGNT (SEQ ID NO: 189), ISSGSDGNT (SEQ ID NO: 190), ISASDGNT (SEQ ID NO: 191), IDSITSI (SEQ ID NO: 192), ISWSGG-STIAASVGST (SEQ ID NO: 193), ISSSDGSDGNT (SEQ ID NO: 194) and ASPSGVIT (SEQ ID NO: 195). In some embodiments, the VH of the anti-GPC3 antibody or binding fragment thereof comprises with 70-100% sequence identity to any one of the sequences selected from the group consisting of (SEQ ID NO: 196)
QVQLQESGGGLVHSGGSLRLSCAASGFPLAYYAIGWFRQAPGKEREGVSCISSSDGNTYYADAV

KGRFTISRDNAKNTVYLQMNSLKPEDTAVYYCATACADTTQHEYDYWGQGTQVTVSS, (SEQ ID NO: 197)
QVQLQESGGGLVHSGGSLRLSCAASGFPLDYYAIGWFRQAPGKEREGVSCISSADGSTYYADSV

KGRFTISRDNAKNTVYLQMNSLGPEDTAVYYCATACADTTQYDYDYWGQGTQVTVSS, (SEQ ID NO: 198)
QVQLQESGGGLVHSGGSLRLSCAASGFTLDYYAIGWFRRAPGKEREGVSCISSGDGKTYYADSV

KGRFTISRDNAKNTVYLQMNSLKPEDTAVYYCATACAGAIGPYDYWGQGTQVTVSS, (SEQ ID NO: 199)
QVQLQESGGGLVPPGGSLRLSCAASGFPLDYYAIGWFRQAPGKEREGVSCISSADGSTYYADSV

KGRFTISRDNAKNTVYLQMNSLGPEDTAVYYCATACADTTQYDYDYWGQGTQVTVSS, (SEQ ID NO: 200)
QVQLQESGGGLVQAGGSLRLSCAASGFSLGYYAIGWFRQAPGKEREGVSCISSSDGHSSTYYAD

SVKGRFTISRDNAKNTVYLQMNNLKPEDTAVYYCATDCAGGTATPYDYWGQGTQVTVSS, (SEQ ID NO: 201)
QVQLQESGGGLVQAGGSLRLSCAASGRTFSSYGMGWFRQAPGKEREFVAAISWSGGSTYYADS

VKGRFTISRDNAKNTVYLQMNSLKPEDTAVYYCASSAWPAGPKHQVEYDYWGQGTQVTVSS, (SEQ ID NO: 202)
QVQLQESGGGLVQAGGSLRLSCTASGFSLDYYAIGWFRQAPGKEREGVACISSRTGSTYYADSV

KGRFTISRDNAKNTVALQMNSLKPEDTAVYYCATACVVVGDQNDYWGQGTQVTVSS, (SEQ ID NO: 203)
QVQLQESGGGLVQDGGSLRLSCAASGFPLAYYAIGWFRQAPGKEREGVSCISASDGSTYYADSV

KGRFTISRDNAKNTVYLQMNSLKPEDTAVYYCATACAETTLYEYDYWGQGTQVTVSS, (SEQ ID NO: 204)
QVQLQESGGGLVQPGESLRLSCAASGFPLAYYAIGWFRQAPGKEREGVSCISSSDGSTYYADSV

KGRFTISRDNAKNTVYLQMNSLKPEDTAVYYCATACANWSTLGPYDYWGQGTQVTVSS,

-continued (SEQ ID NO: 205)
QVQLQESGGGLVQPGESLRLSCAASGFTLAYYAIGWFRQAPGKEREGVSCISSSDGNTYYADSV
KGRFTISRDNAKNTVYLQMNRLKPEDTAVYYCATACADTTQYEYDYWGQGTQVTVSS, (SEQ ID NO: 206)
QVQLQESGGGLVQPGGSLKLSCAASGSDFRADAMGWYRQAPGKEREPVAIDSITSIYYVDSVEG
RFTISRDNTKNTVYLQMTSLKPEDTAVYYCYARYSGRTYWGRGTQVTVSS, (SEQ ID NO: 207)
QVQLQESGGGLVQPGGSLRLSCAASGFPLAYYAIGWFRQAPGKEREGVSCISASDGSTYYADSV
KGRFTISRDNAKNTVYLQMNSLRPEDTAVYYCATACADTTLYEYDYWGQGTQVTVSS, (SEQ ID NO: 208)
QVQLQESGGGLVQPGGSLRLSCAASGFPLAYYAIGWFRQAPGKEREGVSCISSSDGNTYYADAV
KGRFAISRDNAKNTVYLQMNSLKPEDTAVYYCATACSDPRVYEYDYWGQGTQVTVSS, (SEQ ID NO: 209)
QVQLQESGGGLVQPGGSLRLSCAASGFPLAYYAIGWFRQAPGKEREGVSCISSSDGNTYYADAV
KGRFTISRDNAKNTVYLQMNSLKPEDTAVYYCATACADTTQHEYDYWGQGTQVTVSS, (SEQ ID NO: 210)
QVQLQESGGGLVQPGGSLRLSCAASGFPLAYYAIGWFRQAPGKEREGVSCISSSDGNTYYADAV
KGRFTISRDNAKNTVYLQMNSLKPEDTAVYYCATACVDTTHYEYDYWGQGTQVTVSS, (SEQ ID NO: 211)
QVQLQESGGGLVQPGGSLRLSCAASGFPLAYYAIGWFRQAPGKEREGVSCISSSDGNTYYADSV
KGRFTISRDNAKNTVYLQMNSLKPEDTAVYYCATACADATQHEYDYWGQGTQVTVSS, (SEQ ID NO: 212)
QVQLQESGGGLVQPGGSLRLSCAASGFPLAYYAIGWFRQAPGKEREGVSCISSSDGSTYYADSV
KGRFTISRDNAKNTVYLQMNSLGPEDTAVYYCATACADTTQYDYDYWGQGTQVTVSS, (SEQ ID NO: 213)
QVQLQESGGGLVQPGGSLRLSCAASGFPLAYYAIGWFRQAPGKEREGVSCISSSDGSTYYADSV
KGRFTISRDNAKNTVYLQMNSLKPEDTAVYYCATACADTTQYEYDYWGQGTQVTVSS, (SEQ ID NO: 214)
QVQLQESGGGLVQPGGSLRLSCAASGFPLAYYAIGWFRQAPGKEREGVSCISSSDGSTYYADSV
KGRFTISRDNAKNTVYLQMNSLKPEDTAVYYCATACGGATGPYDYWGQGTQVTVSS, (SEQ ID NO: 215)
QVQLQESGGGLVQPGGSLRLSCAASGFPLAYYAIGWFRRAPGKEREGVSCISSSDGNTYYADAV
KGRFTISRDNAKNTVYLQMNSLKPEDTAVYYCATACADTTQHEYDYWGQGTQVTVSS, (SEQ ID NO: 216)
QVQLQESGGGLVQPGGSLRLSCAASGFPLDYYAIGWFRQAPGKEREGVSCISAGDGSSTYYADS
VKGRFTISRDNAKNTVYLQMNSLKPEDTAVYYCATACASTTLYEYDYWGQGTQVTVSS, (SEQ ID NO: 217)
QVQLQESGGGLVQPGGSLRLSCAASGFPLDYYAIGWFRQAPGKEREGVSCISSADGSTYYADSV
KGRFTISRDNAKNAVYLQMNSLGPEDTAVYYCATACADTTQYDYDYWGQGTQVTVSS, (SEQ ID NO: 218)
QVQLQESGGGLVQPGGSLRLSCAASGFPLDYYAIGWFRQAPGKEREGVSCISSADGSTYYADSV
KGRFTISRDNAKNTVYLQMNSLGPEDTAVYYCATACADTTQYDYDYWGQGTQVTVSS, (SEQ ID NO: 219)
QVQLQESGGGLVQPGGSLRLSCAASGFPLDYYAIGWFRQAPGKEREGVSCISSADGSTYYADSV
KGRFTISRDNAKNTVYLQMNSLKPEDTAVYYCATACVDTTQYEYDYWGQGTQVTVSS, (SEQ ID NO: 220)
QVQLQESGGGLVQPGGSLRLSCAASGFPLDYYAIGWFRQAPGKEREGVSCISSPDGSTYYADSV
KGRFTISRDNAKNTVYLQMNSLKPEDTAVYYCATACVDTTQYEYDYWGQGTQVTVSS, -continued

```
                                       (SEQ ID NO: 221)
QVQLQESGGGLVQPGGSLRLSCAASGFPLDYYAIGWFRQAPGKEREGVSCISSSDGSDGNTYYA

DSVKGRFTISRDNAKNTVYLQMNSLKPEDTAVYYCATDCSLHGSDYPYDYWGQGTQVTVSS, (SEQ ID NO: 222)
QVQLQESGGGLVQPGGSLRLSCAASGFPLDYYAIGWFRQAPGKEREGVSCISSSDGSTYYADSV

KGRFTISRDNAKNTVYLQMNSLKPEDTAVYYCATACADTTQYEYDYWGQGTQVTVSS, (SEQ ID NO: 223)
QVQLQESGGGLVQPGGSLRLSCAASGFPLEYYAIGWFRQAPGKEREGVSCISSSDGSTYYADSV

KGRFTISRDNAKNTVYLQMNSLKPEDTAVYYCATACSDPRVYEYDYWGQGTQVTVSS, (SEQ ID NO: 224)
QVQLQESGGGLVQPGGSLRLSCAASGFPLGYYAIGWFRQAPGKEREGVSCISSSDDSTYYADSV

KGRFTISRDNDKNTVYLQMNSLKPEDTAVYYCATDCAGGTSTPYDYWGQGTQVTVSS, (SEQ ID NO: 225)
QVQLQESGGGLVQPGGSLRLSCAASGFPLHYYAIGWFRQAPGKEREGVSCISSGDGSTYYADSV

KGRFTISRDNAKNTVYLQMNSLKPEDTAVYYCATSCVVVTKNEYDYWGQGTQVTVSS, (SEQ ID NO: 226)
QVQLQESGGGLVQPGGSLRLSCAASGFPLHYYAIGWFRQAPGKEREGVSCISSSDGSTYYADSV

KGRFTISRDNAKNTVYLQMNSLKPEDTAVYYCATACGGATGPYDYWGQGTQVTVSS, (SEQ ID NO: 227)
QVQLQESGGGLVQPGGSLRLSCAASGFPLHYYAIGWFRQAPGKEREGVSCISSSDGSTYYADSV

KGRFTISRDNAKNTVYLQMNSLKPEDTAVYYCATACVVADRNEYDYWGQGTQVTVSS, (SEQ ID NO: 228)
QVQLQESGGGLVQPGGSLRLSCAASGFPLHYYAIGWFRQAPGKEREGVSCISSSDGSTYYADSV

KGRFTISRDNAKNTVYLQMNSLRPEDTAVYYCATACVVADRNEYDYWGQGTQVTVSS, (SEQ ID NO: 229)
QVQLQESGGGLVQPGGSLRLSCAASGFPLNYYAIGWFRQAPGKEREGVSCISASDGNTYYADSV

KGRFTISRDNAKNTVYLQMNSLKPEDTAVYYCATTCASPEKYEYDYWGQGTQVTVSS, (SEQ ID NO: 230)
QVQLQESGGGLVQPGGSLRLSCAASGFPLNYYAIGWFRQAPGKEREGVSCISSSDGSTYYADSV

KGRFIISRDNAKNTVYLQMNSLKPEDTAVYYCATACGGATGPYDYWGQGTQVTVSS, (SEQ ID NO: 231)
QVQLQESGGGLVQPGGSLRLSCAASGFPLNYYAIGWFRQAPGKEREGVSCISSSDGSTYYADSV

KGRFTISRDNAKNTVYLQMNSLKPEDTAVYYCATACGSAVHEYDYWGQGTQVTVSS, (SEQ ID NO: 232)
QVQLQESGGGLVQPGGSLRLSCAASGFSLAYYAIGWFRQAPGKEREGVSCIAASVGSTYYADSV

KGRFTISRDDAKNTVYLQMNSLKPEDTAVYYCATDCAGGVGHEYDYWGQGTQVTVSS, (SEQ ID NO: 233)
QVQLQESGGGLVQPGGSLRLSCAASGFSLDYYAIGWFRQAPGKEREGVSCISSSDGSTYYADSV

KGRFTISRDNAKNAVYLQMNSLKPEDTAVYYCATACGGATGPYDYWGQGTQVTVSS, (SEQ ID NO: 234)
QVQLQESGGGLVQPGGSLRLSCAASGFSLDYYAIGWFRQAPGKEREGVSCISSSDGSTYYADSV

KGRFTISRDNAKNAVYLQMNSLKPEDTAVYYCATACVDTTQYEYDYWGQGTQVTVSS, (SEQ ID NO: 235)
QVQLQESGGGLVQPGGSLRLSCAASGFSLDYYAIGWFRQAPGKEREGVSCISSSDGSTYYADSV

KGRFTISRDNAKNTVYLQMNSLKPEDTAVYYCATDCAGGTSTPYDYWGQGTQVTVSS, (SEQ ID NO: 236)
QVQLQESGGGLVQPGGSLRLSCAASGFSLNYYAIGWFRQAPGKEREGVSCISAGDGNTYYADS

VKGRFTISRDNAANTVSLQMDSLKPEDTAVYYCATACVITTLYEYDYWGQGTQVTVSS,
```

```
                                                       (SEQ ID NO: 237)
QVQLQESGGGLVQPGGSLRLSCAASGFTLAYYAIGWFRQAPGKEREGVSCISSSDGSTYYADSV

KGRFTISRDNAKNTVYLQMNSLKPEDTAVYYCATACADTTQHEYDYWGQGTQVTVSS, (SEQ ID NO: 238)
QVQLQESGGGLVQPGGSLRLSCAASGFTLAYYAIGWFRQAPGKEREGVSCISSSDGSTYYADSV

KGRFTISRDNAKNTVYLQMNSLKPEDTAVYYCATACADTTQYEYDYWGQGTQVTVSS, (SEQ ID NO: 239)
QVQLQESGGGLVQPGGSLRLSCAASGFTLDYYAIGWFRQAPGKEREGVACISSSDGSTYYADSV

KGRFTISRDNAKNTVYLQMNSLKPEDTAVYYCATACGGATGPYDYWGQGTQVTVSS, (SEQ ID NO: 240)
QVQLQESGGGLVQPGGSLRLSCAASGFTLDYYAIGWFRQAPGKEREGVACISSSDGSTYYADSV

KGRFTISRDNAKNTVYLQMNSLKPQDTAVYYCATACGSLVGMYDYWGQGTQVTVSP, (SEQ ID NO: 241)
QVQLQESGGGLVQPGGSLRLSCAASGFTLDYYAIGWFRQAPGKEREGVSCISASDGNTYYADSV

KGRFTISRDNAKNTVYLQMNSLKPEDTAVYYCATTCASPEKYEYDYWGQGTQVTVSS, (SEQ ID NO: 242)
QVQLQESGGGLVQPGGSLRLSCAASGFTLDYYAIGWFRQAPGKEREGVSCISASNGNTYYADSV

KGRFTISRDSAKNTVYLQMNSLKPEDTAVYYCATTCSGLTHEYDYWGQGTQVTVSS, (SEQ ID NO: 243)
QVQLQESGGGLVQPGGSLRLSCAASGFTLDYYAIGWFRQAPGKEREGVSCISSGDGNTYYADSV

KGRFTISRDNAKNTVYLQMNSLKPEDTAVYYCATACGGATGPYDYWGQGTQVTVSS, (SEQ ID NO: 244)
QVQLQESGGGLVQPGGSLRLSCAASGFTLDYYAIGWFRQAPGKEREGVSCISSGDGSTYYADSV

KGRFTISRDNAKNTVYLQMNSLKPEDTAVYYCATHCGGSSWSNEYDYWGQGTQVTVSS, (SEQ ID NO: 245)
QVQLQESGGGLVQPGGSLRLSCAASGFTLDYYAIGWFRQAPGKEREGVSCISSNDGSTYYADSV

KGRFTISRDNAKNTVYLQMNSLKPEDTAVYYCATACADTTQHEYDYWGQGTQVTVSS, (SEQ ID NO: 246)
QVQLQESGGGLVQPGGSLRLSCAASGFTLDYYAIGWFRQAPGKEREGVSCISSSDGGTYYADSV

KGRFTISRDNAKNTVYLQMNSLKPEDTAVYYCATACGGATGPYDYWGQGTQVTVSS, (SEQ ID NO: 247)
QVQLQESGGGLVQPGGSLRLSCAASGFTLDYYAIGWFRQAPGKEREGVSCISSSDGSSSDGNTY

YADSVKGRFTISRDNAKNTVYLQMNNLKPEDTAVYYCATACVVTTLYEYDYWGQGTQVTVSS, (SEQ ID NO: 248)
QVQLQESGGGLVQPGGSLRLSCAASGFTLDYYAIGWFRQAPGKEREGVSCISSSDGSTYYADSV

KGRFTISRDNAKNTVYLQMNSLKPEDTAVYYCATACADTTQYEYDYWGQGTQVTVSP, (SEQ ID NO: 249)
QVQLQESGGGLVQPGGSLRLSCAASGFTLDYYAIGWFRQAPGKEREGVSCISSSDGSTYYADSV

KGRFTISRDNAKNTVYLQMNSLKPEDTAVYYCATACGGATGPYDYWGQGTQVTVSS, (SEQ ID NO: 250)
QVQLQESGGGLVQPGGSLRLSCAASGFTLDYYAIGWFRQAPGKEREGVSCISSSGGSTYYADSV

KGRFTISRDNAKNTVYLQMNMLKPEDTAVYYCATACADTTQYEYDYWGQGTQVTVSS, (SEQ ID NO: 251)
QVQLQESGGGLVQPGGSLRLSCAASGFTLDYYAIGWFRQAPGKEREGVSCISSSGGSTYYADSV

KGRFTISRDNAKNTVYLQMNSLKPEDTAVYYCATACASPVIYEYDYWGQGTQVTVSS, (SEQ ID NO: 252)
QVQLQESGGGLVQPGGSLRLSCAASGFTLDYYAIGWFRQAPGKEREGVSCISSSGGSTYYADSV

KGRFTISRDNAKNTVYLQMNSLKPEDTAVYYCATDCAGGTSTPYDYWGQGTQVTVSS,
```

-continued (SEQ ID NO: 253)
QVQLQESGGGLVQPGGSLRLSCAASGFTLGYYAIGWFRQAPGKEREGVSCISSSDGSTYYADSV

KGRFTISRDNAKNTVYLQMNSLKPEDTAVYYCATACADTTQYEYDYWGQGTQVTVSS, (SEQ ID NO: 254)
QVQLQESGGGLVQPGGSLRLSCAASGFTLGYYAIGWFRQAPGKEREGVSCISSSDGSTYYADSV

KGRFTISRDNAKNTVYLQMNSLKPEDTAVYYCATACANWSSLGPYDYWGQGTQVTVSS, (SEQ ID NO: 255)
QVQLQESGGGLVQPGGSLRLSCAASGFTLGYYAIGWFRQAPGKEREGVSCISSSDGSTYYADSV

KGRFTISRDNAKNTVYLQMNSLKPEDTGVYYCATACGGATGPYDYWGQGTQVTVSS, (SEQ ID NO: 256)
QVQLQESGGGLVQPGGSLRLSCEGSGFSLDYYAIGWFRQAPGKEREGVSCISSGDGNTYYADSV

KGRFTISRDNAKNTVYLQMNSLKPEDTAVYYCATDCVGFGSNWFDYWGQGTQVTVSS, (SEQ ID NO: 257)
QVQLQESGGGLVQPGGSLRLSCTASGFSLDYYAIGWFRQAPGKEREGVACISSRTGSTYYADSV

KGRFTISRDNAKNTVALQMNSLKPEDTAVYYCATACVVVGDQNDYWGQGTQVTVSS, (SEQ ID NO: 258)
QVQLQESGGGLVQPGGSLRLSCTASGFSLDYYAIGWFRQAPGKEREGVSCISSRTGGTYYADSV

KGRFTISRDDAKNTVYLQMNSLKPEDTAVYYCATACVVVGDRNDYWGQGTQVTVSS, (SEQ ID NO: 259)
QVQLQESGGGLVQPGGSLRLSCTASGFSLDYYAIGWFRQAPGKEREGVSCISSRTGGTYYADSV

KGRFTISRDNAKNTVYLQMNSLKPEDTAVYYCATACVDTTQYEYDYWGQGTQVTVSS, (SEQ ID NO: 260)
QVQLQESGGGLVQPGGSLRLSCTASGFSLDYYAIGWFRQAPGKEREGVSCISSRTGGTYYADSV

KGRFTISRDNAKNTVYLQMNSLKPEDTAVYYCATACVVVGDQNDYWGQGTQVTVSS, (SEQ ID NO: 261)
QVQLQESGGGLVQPGGSLRLSCTASGFSLDYYAIGWFRQAPGKEREGVSCISSRTGNTYYADSV

KGRFTISRDDAKNMVYLQMNSLKPEDTAVYYCATACVVVGDQNDYWGQGTQVTVSS, (SEQ ID NO: 262)
QVQLQESGGGLVQPGGSLRLSCTASGFSLDYYAIGWFRQAPGKEREGVSCISSRTGSTYYADSV

KGRFTISRDDAKNTVYLQMNSLKPEDTAVYYCATACVVVGDQNDYWGQGTQVTVSS, (SEQ ID NO: 263)
QVQLQESGGGLVQPGGSLRLSCTASGFSLGYYAIGWFRQALGKEREGVSCISSRTGSTYYADSV

KGRFTVSRDDAKNTVYLQMNSLKPEDTAVYYCATACVVVGDQNDYWGQGTQVTVSS, (SEQ ID NO: 264)
QVQLQESGGGLVQPGGSLRLSCTASGFSLGYYAIGWFRQAPGKEREGVSCISSRTGSTYYADSV

KGRFAISRDDAKNTVYLQMNSLKPEDTAVYYCATACVVVGDQNDYWGQGTQVTVSS, (SEQ ID NO: 265)
QVQLQESGGGLVQPGGSLRLSCTASGFSLGYYAIGWFRQAPGKEREGVSCISSRTGSTYYADSV

KGRFTISRDDAKNTVYLQMNSLKPEDTAVYYCATACVVVGDQNDYWGQGTQVTVSS, (SEQ ID NO: 266)
QVQLQESGGGLVQPGGSLRLSCTASGFSLGYYAIGWFRQAPGKEREGVSCISSRTGSTYYADSV

KGRFTVSRDDAKNTVYLQMNSLKPEDTAVYYCATACVVVGDQNDYWGQGTQVTVSS, (SEQ ID NO: 267)
QVQLQESGGGLVQPGGSLRLSCVASGFPLDYYAIGWFRQAPGKEREGVSCISSSDGSTYYADSV

KGRFTISRDNAKNTVYLQMNSLKPEDTAVYYCATACGGATGPYDYWGQGTQVTVSS, (SEQ ID NO: 268)
QVQLQESGGGLVQPGGSLRLSCVASGFSLDYYAIGWFRQAPGKEREGVSCISNSDGSTYYADSV

KGRFTISRDNAKNTVYLQMNSLKPEDTAVYYCATACADTTQYAYDYWGQGTQVTVSS,

```
                                                   (SEQ ID NO: 269)
QVQLQESGGGLVQPGGSLRLSCVASGFTLDYYAIGWFRQAPGKEREGVSCISSGSDGNTYYADS

VKGRFTISRDNAKNTVYLQMNSLKPEDTAVYYCATACSGLTHEYDYWGQGTQVTVSS, (SEQ ID NO: 270)
QVQLQESGGGLVQPGGSLRLSCVASGFTLDYYAIGWFRQAPGKEREGVSCISSSDDSTYYADSV

KGRFTISRDNAKNTVYLQMNSLKPEDTAVYYCATACADTTQYEYDYWGQGTQVTVSS, (SEQ ID NO: 271)
QVQLQESGGGLVQPGGSLRLSCVASGFTLDYYAIGWFRQAPGKEREGVSCISSSSDGNTYYADS

VKGRFTISRDNAKNTVYLQMNSLKPEDTAVYYCATTCSGLTHEYDYWGQGTQVTVSS, (SEQ ID NO: 272)
QVQLQESGGGLVQPGGSLRLSCVASGFTLGYYAIGWFRQAPGKEREGVSCISSSDGSTYYADSV

KGRFTISRDNAKNTVYLQMNSLKPEDTAVYYCATACADTTQYDYDYWGQGTQVTVSS, (SEQ ID NO: 273)
QVQLQESGGGLVQPGGSLRLSCVGSGFTLDYYAIGWFRQAPGKEREGVSCISSNDGSTYYADSV

KGRFTISRDNAKNTVYLQMNSLKPEDTAVYYCATACGGATGPYDYWGQGTQVTVSS, (SEQ ID NO: 274)
QVQLQESGGGLVQSGGSLRLSCAASGFPLAYYAIGWFRQAPGKEREGVSCISASDGSTYYADSV

KGRFTISRDNAKNTVYLQMNSLKPEDTAVYYCATACAETTLYEYDYWGQGTQVTVSS, (SEQ ID NO: 275)
QVQLQESGGGLVQTGGSLRLSCAASGFTLDYYAIGWFRQAPGKEREGVSCISSSDGSTYYADSV

KGRFTISRDNAKNTVYLQMNSLKPEDTAVYYCATACGGATGPYDYWGQGTQVTVSS, (SEQ ID NO: 276)
QVQLQESGGGMVQAGESLRLSCAASGFPLAYYAIGWFRQAPGKEREGVSCISSSDGNTYYADS

VKGRFTISRDNAKNTVYLQMNSLKPEDTAVYYCATACADATQHEYDYWGQGTQVTVSS, (SEQ ID NO: 277)
QVQLQESGGGSVQPGESLRLSCAASGFPLDYYAIGWFRQAPGKEREGVSCISASDGSTYYADSV

KGRFTISRDNAKNTVYLQMNSLKPEDTAVYYCATACADTTLYEYDYWGQGTQVTVSS, (SEQ ID NO: 278)
QVQLQESGGGSVQPGGSLRLSCAASGFTLDYYAIGWFRQAPGKEREGVSCISSGDGSTYYADSV

KGRFTISRDNAKNTVYLQMNSLKPEDTAVYYCATACADTTHYEYDYWGQGTQVTVSS, (SEQ ID NO: 279)
QVQLQESGGGSVQSGGSLRLSCTASGFSLGYYAIGWFRQAPGKEREGVSCISSRTGSTYYADSV

KGRFTVSRDDAKNTVYLQMNSLKPEDTAVYYCATACVVVGDQNDYWGQGTQVTVSS, (SEQ ID NO: 280)
QVQLQESGGGSVRPGGSLRLSCAASGFPLAYYAIGWFRQAPGKEREGVSCISSSDGNTYYADAV

KGRFTISRDNAKNAVYLQMNSLKPEDTAVYYCATACADTTQHEYDYWGQGTQVTVSS, (SEQ ID NO: 281)
QVQLQESGGGVAQPGGSLRLSCAASGFPLDYYAIGWFRQAPGKEREGVSCISASDGSTYYADSV

KGRFTISRDNAKNTVYLQMNSLKPEDTAVYYCATACADTTLYEYDYWGQGTQVTVSS, (SEQ ID NO: 282)
QVQLQESGGGVVQAGGSLKLSCAASGSDFRADAMGWYRQAPGKEREPVAIDSITSIYYVDSVE

GRFTISRDNTKNTVYLQMTSLKPEDTAVYYCYARYSGRTYWGRGTQVTVSS, (SEQ ID NO: 283)
QVQLQESGGGVVQPGGSLRLSCAASGFSLDYYAIGWFRQAPGKEREGVSCISSGDGSTYYADSV

KGRFTISRDNAKNTVYLQMNSLKPEDTAVYYCATHCGGTSWGTSYDYWGQGTQVTVSS, (SEQ ID NO: 284)
QVQLQESGGGVVQPGGSLRLSCAASGLTFRSVGMGWFRRAPGKEREFVATASPSGVITYYADS

VKGRFTISRDNAKNTVYLEMNSLKPEDTAVYYCAVRIYSGSFDNTLAYDYWGQGTQVTVSS,
```

-continued (SEQ ID NO: 285)
QVQLQESGGGVVQPGGSLRLSCTASGFSLGYYAIGWFRQAPGKEREGVSCISSRTGSTYYADSV KGRFTVSRDDAKNTVYLQMNSLKPEDTAVYYCATACVVVGDQNDYWGQGTQVTVSS,
and (SEQ ID NO: 286)
QVQLQESGGGVVQSGGSLRLSCTASGFSLDYYAIGWFRQAPGKEREGVSCISSRTGSTYYADSV

KGRFTISRDDAKNTVYLQMNSLKPEDTAVYYCATACVVVGDQNDYWGQGTQVTVSS.

In some embodiments, the VH is a single domain antibody domain. In some embodiments, the VH is a VHH.

In some embodiments, the antigen binding domain comprises an autoantigen or fragment thereof, such as Dsg1 or Dsg3. In some embodiments, the antigen binding domain comprises a receptor domain or an antibody domain wherein the antibody domain binds to an auto antigen, such as Dsg1 or Dsg3.

In some embodiments, the transmembrane domain and the antigen binding domain are operatively linked through a linker. In some embodiments, the transmembrane domain and the antigen binding domain are operatively linked through a linker such as a hinge region of CD8a, IgG1 or IgG4.

In some embodiments, the extracellular domain comprises a multimerization scaffold.

In some embodiments, the transmembrane domain comprises a CD8 transmembrane domain. In some embodiments, the transmembrane domain comprises a CD28 transmembrane domain. In some embodiments, the transmembrane domain comprises a CD68 transmembrane domain. In some embodiments, the transmembrane domain comprises a CD2 transmembrane domain. In some embodiments, the transmembrane domain comprises an FcR transmembrane domain. In some embodiments, the transmembrane domain comprises an FcRγ transmembrane domain. In some embodiments, the transmembrane domain comprises an FcRα transmembrane domain. In some embodiments, the transmembrane domain comprises an FcRβ transmembrane domain. In some embodiments, the transmembrane domain comprises an FGRε transmembrane domain. In some embodiments, the transmembrane domain comprises a transmembrane domain from a syntaxin, such as syntaxin 3 or syntaxin 4 or syntaxin 5. In some embodiments, the transmembrane domain oligomerizes with a transmembrane domain of an endogenous receptor when the CFP is expressed in a cell. In some embodiments, the transmembrane domain oligomerizes with a transmembrane domain of an exogenous receptor when the CFP is expressed in a cell. In some embodiments, the transmembrane domain dimerizes with a transmembrane domain of an endogenous receptor when the CFP is expressed in a cell. In some embodiments, the transmembrane domain dimerizes with a transmembrane domain of an exogenous receptor when the CFP is expressed in a cell. In some embodiments, the transmembrane domain is derived from a protein that is different than the protein from which the intracellular signaling domain is derived. In some embodiments, the transmembrane domain is derived from a protein that is different than the protein from which the extracellular domain is derived. In some embodiments, the transmembrane domain comprises a transmembrane domain of a phagocytic receptor. In some embodiments, the transmembrane domain and the extracellular domain are derived from the same protein. In some embodiments, the transmembrane domain is derived from the same protein as the intracellular signaling domain. In some embodiments, the recombinant nucleic acid encodes a DAP12 recruitment domain. In some embodiments, the transmembrane domain comprises a transmembrane domain that oligomerizes with DAP12.

In some embodiments, the transmembrane domain is at least 12, 13, 14, 15, 16, 17, 18, 19, 20, 21, 22, 23, 24, 25, 26, 27, 28, 29, 30, 31 or 32 amino acids in length. In some embodiments, the transmembrane domain is at most 12, 13, 14, 15, 16, 17, 18, 19, 20, 21, 22, 23, 24, 25, 26, 27, 28, 29, 30, 31 or 32 amino acids in length.

In some embodiments, the intracellular signaling domain comprises an intracellular signaling domain derived from a phagocytic receptor. In some embodiments, the intracellular signaling domain comprises an intracellular signaling domain derived from a phagocytic receptor other than a phagocytic receptor selected from Megf10, MerTk, FcRα, or Bai1. In some embodiments, the intracellular signaling domain comprises an intracellular signaling domain derived from a phagocytic receptor selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fc-alpha receptor I, CR1, CD35, CD3ζ, CR3, CR4, Tim-1, Tim-4 and CD169. In some embodiments, the intracellular signaling domain comprises a PI3K recruitment domain. In some embodiments, the intracellular signaling domain comprises an intracellular signaling domain derived from a scavenger receptor. In some embodiments, the intracellular domain comprises a CD47 inhibition domain. In some embodiments, the intracellular domain comprises a Rac inhibition domain, a Cdc42 inhibition domain or a GTPase inhibition domain. In some embodiments, the Rac inhibition domain, the Cdc42 inhibition domain or the GTPase inhibition domain inhibits Rac, Cdc42 or GTPase at a phagocytic cup of a cell expressing the PFP. In some embodiments, the intracellular domain comprises an F-actin disassembly activation domain, a ARHGAP12 activation domain, a ARHGAP25 activation domain or a SH3BP1 activation domain. In some embodiments, the intracellular domain comprises a phosphatase inhibition domain. In some embodiments, the intracellular domain comprises an ARP2/3 inhibition domain. In some embodiments, the intracellular domain comprises at least one ITAM domain. In some embodiments, the intracellular domain comprises at least 1, 2, 3, 4, 5, 6, 7, 8, 9, 10, or more ITAM domains. In some embodiments, the intracellular domain comprises at least one ITAM domain select from an ITAM domain of CD3 zeta, CD3 epsilon, CD3 gamma, CD3 delta, Fc epsilon receptor 1 chain, Fc epsilon receptor 2 chain, Fc gamma receptor 1 chain, Fc gamma receptor 2a chain, Fc gamma receptor 2b 1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some embodiments, the at least one ITAM domain comprises a Src-family kinase phosphorylation site. In some embodiments, the at least one ITAM domain comprises a Syk recruitment domain. In some embodiments, the intracellular domain comprises an F-actin depolymerization activation domain. In some embodiments, the intracellular domain lacks enzymatic activity.

In some embodiments, the intracellular domain does not comprise a domain derived from a CD3 zeta intracellular domain. In some embodiments, the intracellular domain does not comprise a domain derived from a MerTK intracellular domain. In some embodiments, the intracellular domain does not comprise a domain derived from a TLR4 intracellular domain. In some embodiments, the intracellular domain comprises a CD47 inhibition domain. In some embodiments, the intracellular signaling domain comprises a domain that activates integrin, such as the intracellular region of PSGL-1

In some embodiments, the intracellular signaling domain comprises a domain that activates Rap1 GTPase, such as that from EPAC and C3G. In some embodiments, the intracellular signaling domain is derived from paxillin. In some embodiments, the intracellular signaling domain activates focal adhesion kinase. In some embodiments, the intracellular signaling domain is derived from a single phagocytic receptor. In some embodiments, the intracellular signaling domain is derived from a single scavenger receptor. In some embodiments, the intracellular domain comprises a phagocytosis enhancing domain.

In some embodiments, the intracellular domain comprises a pro-inflammatory signaling domain. In some embodiments, the pro-inflammatory signaling domain comprises a kinase activation domain or a kinase binding domain. In some embodiments, the pro-inflammatory signaling domain comprises an IL-1 signaling cascade activation domain. In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, STING, an NLRP family member, NLRP1-14, NOD1, NOD2, Pyrin, AIM2, NLRC4, FCGR3A, FCERIG, CD40, Tank1-binding kinase (TBK), a caspase domain, a procaspase binding domain or any combination thereof.

In some embodiments, the intracellular domain comprises a signaling domain, such as an intracellular signaling domain, derived from a connexin (Cx) protein. For example, the intracellular domain can comprise a signaling domain, such as an intracellular signaling domain, derived from Cx43, Cx46, Cx37, Cx40, Cx33, Cx50, Cx59, Cx62, Cx32, Cx26, Cx31, Cx30.3, Cx31.1, Cx30, Cx25, Cx45, Cx47, Cx31.3, Cx36, Cx31.9, Cx39, Cx40.1 or Cx23. For example, the intracellular domain can comprise a signaling domain, such as an intracellular signaling domain, derived from Cx43.

In some embodiments, the intracellular domain comprises a signaling domain, such as an intracellular signaling domain, derived from a SIGLEC protein. For example, the intracellular domain can comprise a signaling domain, such as an intracellular signaling domain, derived from Siglec-1 (Sialoadhesin), Siglec-2 (CD22), Siglec-3 (CD33), Siglec-4 (MAG), Siglec-5, Siglec-6, Siglec-7, Siglec-8, Siglec-9, Siglec-10, Siglec-11, Siglec-12, Siglec-13, Siglec-14, Siglec-15, Siglec-16 or Siglec-17.

In some embodiments, the intracellular domain comprises a signaling domain, such as an intracellular signaling domain, derived from a TLR protein. In some embodiments, the intracellular domain may comprise an intracellular signaling domain of the endo-lysosomal TLR, e.g., TLR3, TLR7, TLR8, or TLR9. In some embodiments, the intracellular signaling domain may be derived from a TLR3 protein. In some embodiments, the intracellular signaling domain may be derived from a TLR7, 8, or 9 protein. In some embodiments, the intracellular domain may comprise an intracellular signaling domain of the cell surface TLRs 1, 2, 4, 5, 6, and 10.

In some embodiments, an intracellular signaling domain is specifically paired with another intracellular domain or a transmembrane domain for maximizing the efficiency and phagocytic potential of the myeloid cell expressing the construct. For example, in some embodiments, a TM domain comprising CD64 TM or a part thereof may be specifically paired with an intracellular signaling domain comprising an innate immune adaptor protein ICD or a PI3kinase recruitment domain, or both. In some embodiments, the combination of domains of the chimeric receptor intracellular domain(s) and/or the transmembrane domains are directed towards maximizing the phagocytosis index of the cell expression the construct, e.g., a myeloid cell. In some embodiments, the combination of domains of the chimeric receptor intracellular domain(s) and/or the transmembrane domains are directed towards maximizing the inflammatory potential of the cell expression the construct such that the cell is capable of lysing the target cell, and activating an immune response pathway for rendering long term immune responsiveness. In some embodiments, the combination of domains of the chimeric receptor intracellular domain(s) and/or the transmembrane domains are directed towards minimizing or obliterating any tonic signaling by the cell expressing the chimeric protein. In some embodiments, the combination of domains of the chimeric receptor intracellular domain(s) and/or the transmembrane domains are directed towards maximizing specificity of the immune response.

In some embodiments, the intracellular domain comprises a signaling domain, such as an intracellular signaling domain, derived from a C-type lectin protein. For example, the intracellular domain can comprise a signaling domain, such as an intracellular signaling domain, derived from a mannose receptor protein. For example, the intracellular domain can comprise a signaling domain, such as an intracellular signaling domain, derived from an asialoglycoprotein receptor protein. For example, the intracellular domain can comprise a signaling domain, such as an intracellular signaling domain, derived from macrophage galactose-type lectin (MGL), DC-SIGN (CLEC4L), Langerin (CLEC4K), Myeloid DAP12 associating lectin (MDL)-1 (CLEC5A), a DC associated C type lectin 1 (Dectin1) subfamily protein, dectin 1/CLEC7A, DNGR1/CLEC9A, Myeloid C type lectin like receptor (MICL) (CLEC12A), CLEC2 (CLEC1B), CLEC12B, a DC immunoreceptor (DCIR) subfamily protein, DCIR/CLEC4A, Dectin 2/CLEC6A, Blood DC antigen 2 (BDCA2) (CLEC4C), Mincle (macrophage inducible C type lectin) (CLEC4E), a NOD-like receptor protein, NOD-like receptor MHC Class II transactivator (CIITA), IPAF, BIRC1, a RIG-I-like receptor (RLR) protein, RIG-I, MDA5, LGP2, NAIP5/Birc1e, an NLRP protein, NLRP1, NLRP2, NLRP3, NLRP4, NLRP5, NLRP6, NLRP7, NLRP89, NLRP9, NLRP10, NLRP11, NLRP12, NLRP13, NLRP14, an NLR protein, NOD1 or NOD2, or any combination thereof.

In some embodiments, the intracellular domain comprises a signaling domain, such as an intracellular signaling domain, derived from a cell adhesion molecule. For example, the intracellular domain can comprise a signaling domain, such as an intracellular signaling domain, derived from an IgCAMs, a cadherin, an integrin, a C-type of lectin-like domains protein (CTLD) and/or a proteoglycan molecule. For example, the intracellular domain can comprise a signaling domain, such as an intracellular signaling domain, derived from an E-cadherin, a P-cadherin, an N-cadherin, an R-cadherin, a B-cadherin, a T-cadherin, or an M-cadherin. For example, the intracellular domain can comprise a signaling domain, such as an intracellular signaling domain, derived from a selectin, such as an E-selectin, an L-selectin or a P-selectin.

In some embodiments, the CFP does not comprise a full length intracellular signaling domain. In some embodiments, the intracellular domain is at least 5, 10, 20, 30, 40, 50, 60, 70, 80, 90, 100, 150, 200, 300, 300, 400, or 500 amino acids in length. In some embodiments, the intracellular domain is at most 10, 20, 30, 40, 50, 60, 70, 80, 90, 100, 150, 200, 300, 300, 400, or 500 amino acids in length.

In some embodiments, the recombinant nucleic acid encodes an FcRα chain extracellular domain, an FcRα chain transmembrane domain and/or an FcRα chain intracellular domain. In some embodiments, the recombinant nucleic acid encodes an FcRβ chain extracellular domain, an FcRβ chain transmembrane domain and/or an FcRβ chain intracellular domain. In some embodiments, the FcRα chain or the FcRβ chain forms a complex with FcRγ when expressed in a cell. In some embodiments, the FcRα chain or FcRβ chain forms a complex with endogenous FcRγ when expressed in a cell. In some embodiments, the FcRα chain or the FcRβ chain does not incorporate into a cell membrane of a cell that does not express FcRγ. In some embodiments, the CFP does not comprise an FcRα chain intracellular signaling domain. In some embodiments, the CFP does not comprise an FcRβ chain intracellular signaling domain. In some embodiments, the recombinant nucleic acid encodes a TREM extracellular domain, a TREM transmembrane domain and/or a TREM intracellular domain. In some embodiments, the TREM is TREM1, TREM 2 or TREM 3.

In some embodiments, the recombinant nucleic acid comprises a sequence encoding a pro-inflammatory polypeptide. In some embodiments, the composition further comprises a proinflammatory nucleotide or a nucleotide in the recombinant nucleic acid, for example, an ATP, ADP, UTP, UDP, and/or UDP-glucose.

Intracellular Interferon Responsive Domains

Most TLRs activate an adaptor protein called MyD88 activates the transcription-factor protein NF-κB, which drives expression of pro-inflammatory genes as part of the immune response. A subgroup of TLRs (TLR3 and TLR4) can engage the protein TRIF, which acts as a scaffold enabling a kinase enzyme to add a phosphate group to the transcription factor IRF3. This phosphorylation activates IRF3, a member of a family of transcription factors termed interferon regulatory factors (IRFs), which activate broad gene-expression programs. A hallmark of these programs is the production of type I interferon molecules Interferons are potent drivers of a branch of the immune system termed the adaptive immune response, and their presence therefore runs the risk of contributing to autoimmunity. To prevent such an attack by the host's own immune system, an interferon response must be tightly regulated. As a safeguard, a particular sequence of amino-acid residues in TRIF, the pLxIS motif, must be phosphorylated before IRF3 can be activated. This control mechanism provides a 'licensing step' that is not specific just for TRIF as an adaptor protein for TLR signaling, but is a general hallmark of sensing pathways that engage IRF3, or the related protein IRF7, to drive interferon expression. Every identified innate sensing pathway connecting the recognition of nucleic acids to the production of type I interferons, with one exception, had been shown previously to signal through one of the three adaptor proteins known so far to contain a pLxIS motif: TRIF, MAVS and STING. Thus, pLxIS-motif-containing adaptor proteins specifically hardwire nucleic-acid recognition to antiviral defenses. In some embodiments, the intracellular signaling domain of the CFP comprises an ICD of an innate immune response protein. In some embodiments, the innate immune response protein is selected from a an intracellular signaling domain derived from TLR3, TLR4, TLR7, TLR 9, TRIF, RIG-1, MYD88, MAL, IRAK1, MDA-5, an IFN-receptor, STING, MAVS, TRIF, TASL, NLRP1, NLRP2, NLRP3, NLRP4, NLRP5, NLRP6, NLRP7, NLRP89, NLRP9, NLRP10, NLRP11, NLRP12, NLRP13, NLRP1-14, NOD1, NOD2, Pyrin, AIM2, NLRC4, FCGR3A, FCERIG, CD40, Tank1-binding kinase (TBK), TNFR1, a chemokine, MHC Class II transactivator (CIITA), IPAF, BIRC1, a RIG-I-like receptor (RLR) protein, macrophage galactose-type lectin (MGL), DC-SIGN (CLEC4L), Langerin (CLEC4K), Myeloid DAP12 associating lectin (MDL)-1 (CLEC5A), a DC associated C type lectin 1 (Dectin1) subfamily protein, dectin 1/CLEC7A, DNGR1/CLEC9A, Myeloid C type lectin like receptor (MICL) (CLEC12A), CLEC2 (CLEC1B), CLEC12B, a DC immunoreceptor (DCIR) subfamily protein, DCIR/CLEC4A, Dectin 2/CLEC6A, Blood DC antigen 2 (BDCA2) (CLEC4C), and Mincle (macrophage inducible C type lectin) (CLEC4E). In some embodiments, the CFP comprises at least one intracellular signaling domain that comprises an amino acid sequence motif, pLxIS. In some embodiments, the intracellular interferon inducing moiety comprises an amino acid sequence selected from SEQ ID NOs. 36-41. Provided herein is a chimeric antigen receptor fusion protein for enhancing phagocytosis, comprising an antigen binding domain and an MDA5 intracellular signaling domain of SEQ ID NO: 30. Provided herein is a chimeric antigen receptor fusion protein for enhancing phagocytosis, comprising an antigen binding domain and an RIG1 intracellular signaling domain of SEQ ID NO: 36. Provided herein is a chimeric antigen receptor fusion protein for enhancing phagocytosis, comprising an antigen binding domain and an Myd88 intracellular signaling domain of SEQ ID NO: 37. Provided herein is a chimeric antigen receptor fusion protein for enhancing phagocytosis, comprising an antigen binding domain and an intracellular signaling domain comprising a STING moiety of SEQ ID NO: 38. Provided herein is a chimeric antigen receptor fusion protein for enhancing phagocytosis, comprising an antigen binding domain and an intracellular signaling domain comprising a MAVS moiety of SEQ ID NO: 39. Provided herein is a chimeric antigen receptor fusion protein for enhancing phagocytosis, comprising an antigen binding domain and an intracellular signaling domain comprising a TRIF moiety of SEQ ID NO: 40. Provided herein is a chimeric antigen receptor fusion protein for enhancing phagocytosis, comprising an antigen binding domain and an intracellular signaling domain comprising a TASL moiety of SEQ ID NO: 41.

In some embodiments, the composition further comprises a pro-inflammatory polypeptide. In some embodiments, the pro-inflammatory polypeptide is a chemokine, cytokine. In some embodiments, the chemokine is selected from the group consisting of IL-1, IL3, IL5, IL-6, i18, IL-12, IL-13, IL-23, TNF, CCL2, CXCL9, CXCL10, CXCL11, IL-18, IL-23, IL-27, CSF, MCSF, GMCSF, IL17, IP-10, RANTES, and interferon. In some embodiments, the cytokine is selected from the group consisting of IL-1, IL3, IL5, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, and interferon.

In some embodiments, the intracellular signaling domains from intracellular adaptor proteins known to be highly active in innate immune defense are incorporated in the chimeric receptor protein. In some embodiments, on or more mutations are introduced in one or more intracellular domains to reduce responsiveness of the intracellular domain to intracellular stimulus that is characteristic of the native intracellular adaptor protein domain, without compromising the effectiveness of the chimeric protein. In some embodiments, such effectiveness is referred to as the enhanced phagocytic potential compared to an identical cell that does not express a chimeric protein. In some embodiments, such effectiveness is referred to as the enhanced inflammatory potential compared to an identical cell that does not express a chimeric protein. In some embodiments, such effectiveness is referred to as the enhanced NF-kappa B activation, or interferon activation in the cell expressing the chimeric protein, compared to an identical cell that does not express a chimeric protein.

In some embodiments, the myeloid cells are specifically targeted for delivery. Myeloid cells can be targeted using specialized biodegradable polymers, such as PLGA (poly (lactic-co-glycolic) acid and/or polyvinyl alcohol (PVA). In some embodiments, one or more compounds can be selectively incorporated in such polymeric structures to affect the myeloid cell function. In some embodiments, the targeting structures are multilayered, e.g., of one or more PLGA and one or more PVA layers. In some embodiments, the targeting structures are assembled in an order for a layered activity. In some embodiments, the targeted polymeric structures are organized in specific shaped components, such as labile structures that can adhere to a myeloid cell surface and deliver one or more components such as growth factors and cytokines, such as to maintain the myeloid cell in a microenvironment that endows a specific polarization. In some embodiments, the polymeric structures are such that they are not phagocytosed by the myeloid cell, but they can remain adhered on the surface. In some embodiments the one or more growth factors may be M1 polarization factors, such as a cytokine. In some embodiments the one or more growth factors may be an M2 polarization factor, such as a cytokine. In some embodiments, the one or more growth factors may be a macrophage activating cytokine, such as IFNγ. In some embodiments the polymeric structures are capable of sustained release of the one or more growth factors in an in vivo environment, such as in a solid tumor.

In some embodiments, the recombinant nucleic acid comprises a sequence encoding a homeostatic regulator of inflammation. In some embodiments, the homeostatic regulator of inflammation is a sequence in an untranslated region (UTR) of an mRNA. In some embodiments, the sequence in the UTR is a sequence that binds to an RNA binding protein. In some embodiments, translation is inhibited or prevented upon binding of the RNA binding protein to the sequence in an untranslated region (UTR). In some embodiments, the sequence in the UTR comprises a consensus sequence of WWWU(AUUUA)UUUW, wherein W is A or U (SEQ ID NO: 287). In some embodiments, the recombinant nucleic acid is expressed on a bicistronic vector.

In some embodiments, the target cell is a mammalian cell. In some embodiments, the target cell is a human cell. In some embodiments, the target cell comprises a cell infected with a pathogen. In some embodiments, the target cell is a cancer cell. In some embodiments, the target cell is a cancer cell that is a lymphocyte. In some embodiments, the target cell is a cancer cell that is an ovarian cancer cell. In some embodiments, the target cell is a cancer cell that is a breast cell. In some embodiments, the target cell is a cancer cell that is a pancreatic cell. In some embodiments, the target cell is a cancer cell that is a glioblastoma cell.

In some embodiments, the recombinant nucleic acid is DNA. In some embodiments, the recombinant nucleic acid is RNA. In some embodiments, the recombinant nucleic acid is mRNA. In some embodiments, the recombinant nucleic acid is an unmodified mRNA. In some embodiments, the recombinant nucleic acid is a modified mRNA. In some embodiments, the recombinant nucleic acid is a circRNA. In some embodiments, the recombinant nucleic acid is a tRNA. In some embodiments, the recombinant nucleic acid is a microRNA.

Also provided herein is a vector comprising a recombinant nucleic acid sequence encoding a CFP described herein. In some embodiments, the vector is viral vector. In some embodiments, the viral vector is retroviral vector or a lentiviral vector. In some embodiments, the vector further comprises a promoter operably linked to at least one nucleic acid sequence encoding one or more polypeptides. In some embodiments, the vector is polycistronic. In some embodiments, each of the at least one nucleic acid sequence is operably linked to a separate promoter. In some embodiments, the vector further comprises one or more internal ribosome entry sites (IRESs). In some embodiments, the vector further comprises a 5'UTR and/or a 3'UTR flanking the at least one nucleic acid sequence encoding one or more polypeptides. In some embodiments, the vector further comprises one or more regulatory regions.

Also provided herein is a polypeptide encoded by the recombinant nucleic acid of a composition described herein.

Provided herein is a composition comprising a recombinant nucleic acid sequence encoding a CFP comprising a phagocytic or tethering receptor (PR) subunit (e.g., a phagocytic receptor fusion protein (PFP)) comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein upon binding of the CFP to the antigen of the target cell, the killing or phagocytosis activity of a myeloid cell, such as a neutrophil, monocyte, myeloid dendritic cell (mDC), mast cell or macrophage expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP.

Table 1 shows exemplary sequences of chimeric fusion protein domains and/or fragments thereof that are meant to be non-limiting for the disclosure. Underlines denote the CDR sequences in sequential order of CDR1, CDR2 and CDR3 for the respective heavy and light chains in accordance to the Kabat numbering system.

TABLE 1

Exemplary Chimeric Fusion Proteins and Receptor Domains

| SEQ ID NO | CFP/ Domain | Sequence |
|---|---|---|
| 1 | CD5-FcR-PI3K | MWLQSLLLLGTVACSISEIQLVQSGGGLVKPGGSVRISCAASGY TFTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIKSG GGGSGALSNSIMYFSHFVPVFLPAKPTTTPAPRPPTPAPTIASQP LSLRPEACRPAAGGAVHTRGLDIYIWAPLAGTCGVLLLSLVITLY CRRLKIQVRKAAITSYEKSDGVYTGLSTRNQETYETLKHEKPPQ GSGSYEDMRGILYAAPQLRSIRGQPGPNHEEDADSYENM |
| 2 | HER2-FCR-PI3K | MWLQSLLLLGTVACSISDIQMTQSPSSLSASVGDRVTITCRASQ DVNTAVAWYQQKPGKAPKLLIYSASFLYSGVPSRFSGSRSGTDF TLTISSLQPEDFATYYCQQHYTTPPTFGQGTKVEIKRTGSTSGSG KPGSGEGSEVQLVESGGGLVQPGGSLRLSCAASGFNIKDTYIHW VRQAPGKGLEWVARIYPTNGYTRYADSVKGRFTISADTSKNTA YLQMNSLRAEDTAVYYCSRWGGDGFYAMDVWGQGTLVTVSSSG GGGSGALSNSIMYFSHFVPVFLPAKPTTTPAPRPPTPAPTIASQ PLSLRPEACRPAAGGAVHTRGLDIYIWAPLAGTCGVLLLSLVIT LYCRRLKIQVRKAAITSYEKSDGVYTGLSTRNQETYETLKHEKP PQGSGSYEDMRGILYAAPQLRSIRGQPGPNHEEDADSYENM |
| 3 | CD5-FcR-CD40 | MWLQSLLLLGTVACSISEIQLVQSGGGLVKPGGSVRISCAASG TFYTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIKSG GGGSGALSNSIMYFSHFVPVFLPAKPTTTPAPRPPTPAPTIASQP LSLRPEACRPAAGGAVHTRGLDIYIWAPLAGTCGVLLLSLVITLY CRLKIQVRKAAITSYEKSDGVYTGLSTRNQETYETLKHEKPPQK KVAKKPTNKAPHPKQEPQEINFPDDLPGSNTAAPVQETLHGCQP VTQEDGKESRISVQERQ |
| 4 | CD5-FcR-MDA5 | MWLQSLLLLGTVACSISEIQLVQSGGGLVKPGGSVRISCAASG YTFTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIKSG GGGSGALSNSIMYFSHFVPVFLPAKPTTTPAPRPPTPAPTIASQP LSLRPEACRPAAGGAVHTRGLDIYIWAPLAGTCGVLLLSLVITLY CRRLKIQVRKAAITSYEKSDGVYTGLSTRNQETYETLKHEKPPQG SGSMSNGYSTDENFRYLISCFRARVKMYIQVEPVLDYLTFLPAE VKEQIQRTVATSGNMQAVELLLSTLEKGVWHLGWTREFVEAL RRTGSPLAARYMNPELTDLPSPSFENAHDEYLQLLNLLQPTLVD KLLVRDVLDKCMEEELLTIEDRNRIAAAENNGNESGVRELLKRI VQKENWFSAFLNVLRQTGNNELVQELTGSDCSESNAEIEN |
| 5 | CD5-FcR-TNFR1 | MWLQSLLLLGTVACSISEIQLVQSGGGLVKPGGSVRISCAASGY TFTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIKSG GGGSGALSNSIMYFSHFVPVFLPAKPTTTPAPRPPTPAPTIASQPL SLRPEACRPAAGGAVHTRGLDIYIWAPLAGTCGVLLLSLVITLY CRLKIQVRKAAITSYEKSDGVYTGLSTRNQETYETLKHEKPPQG SGSQRWKSKLYSIVCGKSTPEKEGELEGTTTKPLAPNPSFSPTPG FTPTLGFSPVPSSTFTSSSTYTPGDCPNFAAPRREVAPPYQGADPI LATALASDPIPNPLQKWEDSAHKPQSLDTDDPATLYAVVENVP PLRWKEFVRRLGLSDHEIDRLELQNGRCLREAQYSMLATWRRR TPRREATLELLGRVLRDMDLLGCLEDIEEALCGPAALPPAPSLL R |
| 6 | CD5-FcR-TNFR2 | MWLQSLLLLGTVACSISEIQLVQSGGGLVKPGGSVRISCAASGY TFTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIKSG GGGSGALSNSIMYFSHFVPVFLPAKPTTTPAPRPPTPAPTIASQPL SLRPEACRPAAGGAVHTRGLDIYIWAPLAGTCGVLLLSLVITLY CRLKIQVRKAAITSYEKSDGVYTGLSTRNQETYETLKHEKPPQG |

TABLE 1-continued

Exemplary Chimeric Fusion Proteins and Receptor Domains

| SEQ ID NO | CFP/ Domain | Sequence |
|---|---|---|
| | | SGSPLCLQREAKVPHLPADKARGTQGPEQQHLLITAPSSSSSSLE SSSASALDRRAPTRNQPQAPGVEASGAGEARASTGSSDSSPGGH GTQVNVTCIVNVCSSSDHSSQCSSQASSTMGDTDSSPSESPKDE QVPFSKEECAFRSQLETPETLLGSTEEKPLPLGVPDAGMKPS |
| 7 | GMCSF Signal peptide | MWLQSLLLLGTVACSIS |
| 8 | Anti-CD5 heavy chain variable domain | EIQLVQSGGGLVKPGGSVRISCAASGYTFTNYGMNWVRQAPGK GLEWMGWINTHTGEPTYADSFKGRFTFSLDDSKNTAYLQINSL RAEDTAVYFCTRRGYDWYFDVWGQGTTVTV |
| 91 | Anti-CD5 heavy chain variable domain | EIQLVQSGGGLVKPGGSVRISCAASGYTFTNYGMNWVRQAPGK GLEWMGWINTHTGEPTYADSFKGRFTFSLDDSKNTAYLQINSL RAEDTAVYFCTRRGYDWYFDVWGQGTTVTVSS |
| 9 | Anti-CD5 light chain variable domain | DIQMTQSPSSLSASVGDRVTITCRASQDINSYLSWFQQKPGKAP KTLIYRANRLESGVPSRFSGSGSGTDYTLTISSLQYEDFGIYYC QQYDESPWTFGGGTKLEIK |
| 10 | Anti-CD5 scFv | EIQLVQSGGGLVKPGGSVRISCAASGYTFTNYGMNWVRQAPGK GLEWMGWINTHTGEPTYADSFKGRFTFSLDDSKNTAYLQINSL RAEDTAVYFCTRRGYDWYFDVWGQGTTVTVSSGGGGSGGGGS GGGGSDIQMTQSPSSLSASVGDRVTITCRASQDINSYLSWFQQK PGKAPKTLIYRANRLESGVPSRFSGSGSGTDYTLTISSLQYEDF GIYYCQQYDESPWTFGGGTKLEIK |
| 11 | Anti-CD5 scFv with leader sequence | MWLQSLLLLGTVACSISEIQLVQSGGGLVKPGGSVRISCAASGY TFTNYGMNWVRQAPGKGLEWMGWINTHTGEPTYADSFKGRF TFSLDDSKNTAYLQINSLRAEDTAVYFCTRRGYDWYFDVWGQ GTTVTVSSGGGGSGGGGSGGGGSDIQMTQSPSSLSASVGDRVTI TCRASQDINSYLSWFQQKPGKAPKTLIYRANRLESGVPSRFSGS GSGTDYTLTISSLQYEDFGIYYCQQYDESPWTFGGGTKLEIK |
| 12 | Anti-HER2 light chain variable domain | DIQMTQSPSSLSASVGDRVTITCRASQDVNTAVAWYQQKPGKA PKLLIYSASFLYSGVPSRFSGSRSGTDFTLTISSLQPEDFATYY CQQHYTTPPTFGQGTKVEIKRTGSTSGSGKPGSGEGSEVQLVE |
| 92 | Anti-HER2 light chain variable domain | DIQMTQSPSSLSASVGDRVTITCRASQDVNTAVAWYQQKPGKA PKLLIYSASFLYSGVPSRFSGSRSGTDFTLTISSLQPEDFATYY CQQHYTTPPTFGQGTKVEIK |
| 13 | Anti-HER2 heavy chain variable domain | LVQPGGSLRLSCAASGFNIKDTYIHWVRQAPGKGLEWVARIYP TNGYTRYADSVKGRFTISADTSKNTAYLQMNSLRAEDTAVYYC SRWGGDGFYAMDVWGQGTLVTV |
| 93 | Anti-HER2 heavy chain variable domain | EVQLVESGGGLVQPGGSLRLSCAASGFNIKDTYIHWVRQAPGK GLEWVARIYPTNGYTRYADSVKGRFTISADTSKNTAYLQMNSL RAEDTAVYYCSRWGGDGFYAMDVWGQGTLVTVSS |
| 14 | Anti-HER2 scFv | DIQMTQSPSSLSASVGDRVTITCRASQDVNTAVAWYQQKPGKAP KLLIYSASFLYSGVPSRFSGSRSGTDFTLTISSLQPEDFATYYCQ QHYTTPPTFGQGTKVEIKRTGSTSGSGKPGSGEGSEVQLVESSG GGGSGGGGSGGGGSLVQPGGSLRLSCAASGFNIKDTYIHWVRQ APGKGLEWVARIYPTNGYTRYADSVKGRFTISADTSKNTAYLQ MNSLRAEDTAVYYCSRWGGDGFYAMDVWGQGTLVTV |
| 94 | Anti-HER2 scFv | DIQMTQSPSSLSASVGDRVTITCRASQDVNTAVAWYQQKPGKA PKLLIYSASFLYSGVPSRFSGSRSGTDFTLTISSLQPEDFATYYCQ QHYTTPPTFGQGTKVEIKRTGSTSGSGKPGSGEGSEVQLVESGG GLVQPGGSLRLSCAASGFNIKDTYIHWVRQAPGKGLEWVARIY PTNGYTRYADSVKGRFTISADTSKNTAYLQMNSLRAEDTAVYY CSRWGGDGFYAMDVWGQGTLVTVSS |
| 105 | Anti-HER2 scFv | DIQMTQSPSSLSASVGDRVTITCRASQDVNTAVAWYQQKPGKA PKLLIYSASFLYSGVPSRFSGSRSGTDFTLTISSLQPEDFATYYCQ QHYTTPPTFGQGTKVEIKRTGSTSGSGKPGSGEGSEVQLVESGG GLVQPGGSLRLSCAASGFNIKDTYIHWVRQAPGKGLEWVARIY PTNGYTRYADSVKGRFTISADTSKNTAYLQMNSLRAEDTAVYY CSRWGGDGFYAMDVWGQGTLVTVSS |

TABLE 1-continued

Exemplary Chimeric Fusion Proteins and Receptor Domains

| SEQ ID NO | CFP/ Domain | Sequence |
|---|---|---|
| 31 | Anti-CD137 binding domain | MEFGLSWLFLVAILKGVQCGLLDLRQGMFAQLVAQNVLLIDGP LSWYSDPGLAGVSLTGGLSYKEDTKELVVAKAGVYYVFFQLEL RRVVAGEGSGSVSLALHLQPLRSAAGAAALALTVDLPPASSEA RNSAFGFQGRLLHLSAGQRLGVHLHTEARARHAWQLTQGATV LGLFRVTPEIPAGLPSPRSE |
| 32 | Anti-CD70 binding domain | QVQLVQSGAEVKKPGASVKVSCKASGYTFTNYGMNWVRQAP GQGLEWMGWINTYTGEPTYADAFKGRVTMTTDTSTSTAYMEL RSLRSDDTAVYYCARDYGDYGMDYWGQGTTVTVSSGSTSGSG KPGSSEGSTKGDIVMTQSPDSLAVSLGERATINCRASKSVSTSG YSFMHWYQQKPGQPPKLLIYLASNLESGVPDRFSGSGSGTDFTL TISSLQAEDVAVYYCQHSREVPWTFGQGTKVEIK |
| 33 | Anti-Claudin 18.2 binding domain (scFv) | QVQLQESGPGLVKPSQTLSLTCTVSGGSISSGYNWHWIRQPPGK GLEWIGYIHYTGSTNYNPALRSRVTISVDTSKNQFSLKLSSVTA ADTAVYYCARIYNGNSFPYWGQGTTVTVSSGGGGSGGGGSGG GGSDIVMTQSPDSLAYSLGERATINCKSSQSLFNSGNQKNYLTW YQQKPGQPPKLLIYWASTRESGVPDRFSGSGSGTDIFITISSLQAE DVAVYYCQNAYSFPYTFGGGTKLEIKR |
| 34 | Anti-Trop-2 binding domain (scFv) | DIQLTQSPSSLSASVGDRVSITCKASQDVSIAVAWYQQKPGKAP KLLIYSASYRYTGVPDRFSGSGSGTDFTLTISSLQPEDFAVYYCQ QHYITPLTFGAGTKVEIKRGGGGSGGGGSGGGGSQVQLQQSGS ELKKPGASVKVSCKASGYTFTNYGMNWVKQAPGQGLKWMG WINTYTGEPTYTDDFKGRFAFSLDTSVSTAYLQISSLKADDTAV YFCARGGFGSSYWYFDVWGQGSLVTVSS |
| 35 | Anti-Trop-2 binding domain (scFv) | QUQLQQSGSELKKPGASVKVSCKASGYTFTNYGMNWVKQAPG QGLKWMGWINTYTGEPTYTDDFKGRFAFSLDTSVSTAYLQISS LKADDTAVYFCARGGFGSSYWYFDVWGQGSLVTVSSGGGGSG GGGSGGGGSDIQLTQSPSSLSASVGDRVSITCKASQDVSIAVAW YQQKPGKAPKLLIYSASYRYTGVPDRFSGSGSGTDFTLTISSLQP EDFAVYYCQQHYITPLTFGAGTKVEIKR |
| 95 | Anti-Trop-2 VH domain | QVQLQQSGSELKKPGASVKVSCKASGYTFTNYGMNWVKQAPG QGLKWMGWINTYTGEPTYTDDFKGRFAFSLDTSVSTAYLQISS LKADDTAVYFCARGGFGSSYWYFDVWGQGSLVTVSS |
| 96 | Anti-TROP2 VL domain | DIQLTQSPSSLSASVGDRVSITCKASQDVSIAVAWYQQKPGKAP KLLIYSASYRYTGVPDRFSGSGSGTDFTLTISSLQPEDFAVYYCQ QHYITPLTFGAGTKVEIKR |
| 97 | Anti-GPC3 binding domain variable heavy chain | QVQLVQSGAEVKKPGASVKVSCKASGYTFTDYEMHWVRQAP GQGLEWMGALDPKTGDTAYSQKFKGKATLTADKSTSTAYMEL SSLTSEDTAVYYCTRFYSYTYWGQGTLVTVSS |
| 98 | Anti-GPC3 binding domain variable light chain | DVVMTQSPLSLPVTPGEPASISCRSSQSLVHSNRNTYLHWYLQK PGQSPQLLIYKVSNRFSGVPDRFSGSGSGTDFTLKISRVEAEDVG VYYCSQNTHVPPTFGQGTKLEIK |
| 106 | Anti-GPC3 binding domain (scFv) | QVQLVQSGAEVKKPGASVKVSCKASGYTFTDYEMHWVRQAP GQGLEWMGALDPKTGDTAYSQKFKGKATLTADKSTSTAYMEL SSLTSEDTAVYYCTRFYSYTYWGQGTLVTVSSGGGGSGGGGSG GGGSDVVMTQSPLSLPVTPGEPASISCRSSQSLVHSNRNTYLHW YLQKPGQSPQLLIYKVSNRFSGVPDRFSGSGSGTDFTLKISRVEA EDVGVYYCSQNTHVPPTFGQGTKLEIK |
| 15 | CD8a transmembrane domain | IYIWAPLAGTCGVLLLSLVIT |
| 16 | CD8a transmembrane domain | IYIWAPLAGTCGVLLLSLVITLYC |
| 17 | CD2 Transmembrane domain | TYLIIGICGGGSLLMVFVALLVFYIT |

TABLE 1-continued

Exemplary Chimeric Fusion Proteins and Receptor Domains

| SEQ ID NO | CFP/ Domain | Sequence |
|---|---|---|
| 18 | CD28 transmembrane domain | FWVLVVVGGVLACYSLLVTVAFIIFWV |
| 19 | CD68 transmembrane domain | ILLPLIIGLILLGLLALVLIAFCII |
| 46 | Mutant CD68 transmembrane domain | ILLPLIIGLILLGLLALVLIAFAII |
| 20 | CD8α hinge domain + transmembrane domain | ALSNSIMYFSHFVPVFLPAKPTTTPAPRPPTPAPTIASQPLSLRPE ACRPAAGGAVHTRGLDIYIWAPLAGTCGVLLLSLVITLYC |
| 21 | CD8α hinge domain + transmembrane domain | ALSNSIMYFSHFVPVFLPAKPTTTPAPRPPTPAPTIASQPLSLRPE ACRPAAGGAVHTRGLDIYIWAPLAGTCGVLLLSLVIT |
| 22 | FcRγ-chain intracellular signaling domain | LYCRRLKIQVRKAAITSYEKSDGVYTGLSTRNQETYETLKHEKP PQ |
| 23 | FcRγ-chain intracellular signaling domain | LYCRLKIQVRKAAITSYEKSDGVYTGLSTRNQETYETLKHEKPP Q |
| 24 | FcRγ-chain intracellular signaling domain | RLKIQVRKAAITSYEKSDGVYTGLSTRNQETYETLKHEKPPQ |
| 25 | FcRγ-chain intracellular signaling domain | RRLKIQVRKAAITSYEKSDGVYTGLSTRNQETYETLKHEKPPQ |
| 26 | PI3K recruitment domain | YEDMRGILYAAPQLRSIRGQPGPNHEEDADSYENM |
| 27 | CD40 intracellular domain | KKVAKKPTNKAPHPKQEPQEINFPDDLPGSNTAAPVQETLHGC QPVTQEDGKESRISVQERQ |
| 28 | TNFR1 intracellular domain | QRWKSKLYSIVCGKSTPEKEGELEGTTTKPLAPNPSFSPTPGFTP TLGFSPVPSSTFTSSSTYTPGDCPNFAAPRREVAPPYQGADPILA TALASDPIPNPLQKWEDSAHKPQSLDTDDPATLYAVVENVPPLR WKEFVRRLGLSDHEIDRLELQNGRCLREAQYSMLATWRRRTPR REATLELLGRVLRDMDLLGCLEDIEEALCGPAALPPAPSLLR |
| 29 | TNFR2 intracellular domain | PLCLQREAKVPHLPADKARGTQGPEQQHLLITAPSSSSSSLESSA SALDRRAPTRNQPQAPGVEASGAGEARASTGSSDSSPGGHGTQ VNVTCIVNVCSSSDHSSQCSSQASSTMGDTDSSPSESPKDEQVPF SKEECAFRSQLETPETLLGSTEEKPLPLGVPDAGMKPS |
| 90 | CLEC9A (1-35) intracellular signaling domain | MHEEEIYTSLQWDSPAPDTYQKCLSSNKCSGACCL |

Provided herein is a composition comprising a recombinant nucleic acid sequence encoding a CFP comprising a phagocytic or tethering receptor (PR) subunit (e.g., a phagocytic receptor fusion protein (PFP)) comprising: an extracellular domain comprising an antigen binding domain specific to an antigen of a target cell; a transmembrane domain; and an intracellular domain comprising an intracellular signaling domain; and wherein the transmembrane domain and the extracellular domain are operatively linked; and wherein upon binding of the CFP to the antigen on the target cell, the killing or phagocytosis activity of the myeloid cell, such as a neutrophil, monocyte, myeloid dendritic cell (mDC), mast cell or macrophage cell expressing the CFP is increased by at least 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, -fold, 17-fold, 18-fold, 19-fold, 20-fold, 25-fold, 30-fold, 40-fold, 50-fold, 75-fold, or 100-fold compared to a cell not expressing the CFP.

Provided herein is a recombinant nucleic acid sequence encoding a CFP as described in the immediate above paragraph, wherein the intracellular domain comprises at least one innate immune activating intracellular domain, e.g., a pattern recognition receptor intracellular signaling domain, a TLR intracellular signaling domain, an FcR intracellular signaling domain, an intracellular adapter protein signaling domain, or fragments thereof, that is capable of activating innate immune response of the myeloid cell, activating its phagocytic potential, activating inflammatory cytokine and chemokine response, antigen presentation and T cell activation of the myeloid cell that expresses the CFP, and upon contact with its target antigen, e.g., upon engagement of the antigen binding domain with the target antigen.

In some embodiments, the pro-inflammatory signaling domain comprises an intracellular signaling domain derived from TLR3, TLR4, TLR7, TLR 9, TRIF, RIG-1, MYD88, MAL, IRAK1, MDA-5, an IFN-receptor, STING, MAVS, TRIF or TASL intracellular domains, an NLRP family member, NLRP1-14, NOD1, NOD2, Pyrin, AIM2, NLRC4, FCGR3A, FCERIG, IL-1, IL3, IL5, IL-6, IL-12, IL-13, IL-23, TNF, IL-18, IL-23, IL-27, CSF, MCSF, GMCSF, IL17, IP-10, or RANTES.

In some embodiments, the CFP comprises an intracellular signaling domain comprising a sequence derived from protein that activates interferon responsive transcription factors IRF1, IRF2, IRF3, IRF4, IRF5, IRF6, IRF7, IRF8, or IRF9.

In some embodiments, the CFP comprises intracellular signaling domain comprising a sequence derived from an intracellular adaptor protein. In some embodiments, the adaptor protein may comprise a transmembrane that anchors it to a organelle, such as mitochondria, endoplasmic reticulum or a lysosomal compartment. In some embodiments, the intracellular adaptor protein is a cytosolic protein.

TABLE 2

Interferon Regulatory Factor (IRF)-activating intracellular domains

| SEQ ID NO | CFP/Domain | Sequence |
|---|---|---|
| 30 | MDA5 intracellular domain (CARD domains) | MSNGYSTDENFRYLISCFRARVKMYIQVEPVLDYLTFLPA EVKEQIQRTVATSGNMQAVELLLSTLEKGVWHLGWTREF VEALRRTGSPLAARYMNPELTDLPSPSFENAHDEYLQLLN LLQPTLVDKLLVRDVLDKCMEEELLTIEDRNRIAAAENNG NESGVRELLKRIVQKENWFSAFLNVLRQTGNNELVQELTG SDCSESNAEIEN |
| 36 | RIG-1 intracellular domain (CARD domains) | MTTEQRRSLQAFQDYIRKTLDPTYILSYMAPWFREEEVQY IQAEKNNKGPMEAATLFLKFLLELQEEGWFRGFLDALDHA GYSGLYEAIESWDFKKIEKLEEYRLLLKRLQPEFKTRIIP TDIISDLSECLINQECEEILQICSTKGMMAGAEKLVECLL RSDKENWPKTLKLALEKERNKFSELW |
| 37 | Myd88 intracellular domain | MAAGGPGAGSAAPVSSTSSLPLAALNMRVRRRLSLFLNVR TQVAADWTALAEEMDFEYLEIRQLETQADPTGRLLDAWQG RPGASVGRLLELLTKLGRDDVLLELGPSIEEDCQKYILKQ QQEEAEKPLQVAAVDSSVPRTAELAGITTLDDPLGHMPER FDAFICYCPSDIQFVQEMIRQLEQTNYRLKLCVSDRDVLP GTCVWSIASELIEKRCRRMVVVVSDDYLQSKECDFQTKFA LSLSPGAHQKRLIPIKYKAMKKEFPSILRFITVCDYTNPC TKSWFWTRLAKALSLP |
| 38 | STING (341-379) | VTVGSLKTSAVPSTSTMSQEPELLISGMEKPLPLRTDFS |
| 39 | MAVS (138-152) | PSYPMPVQETQAPES |
| 40 | MAVS (401-450) | SSAWLDSSSENRGLGSELSKPGVLASQVDSPFSGCFEDLAI SASTSLGMG |
| 45 | MAVS (138-152)-gggs linker-MAVS (401-450) | PSYPMPVQETQAPESGGGSSSAWLDSSSENRGLGSELSKP GVLASQVDSPFSGCFEDLAISASTSLGMG |
| 41 | TRIF (1-255) | MACTGPSLPSAFDILGAAGQDKLLYLKHKLKTPRPGCQG QDLLHAMVLLKLGQETEARISLEALKADAVARLVARQWA GVDSTEDPEEPPDVSWAVARLYHLLAEEKLCPASLRDVA YQEAVRTLSSRDDHRLGELQDEARNRCGWDIAGDPGSIR TLQSNLGCLPPSSALPSGTRSLPRPIDGVSDWSQGCSLR STGSPASLASNLEISQSPTMPFLSLHRSPHGPSKLCDDP QASLVPEPVPGGCQEPEEMSW |
| 43 | TRIF (short) (153-387) | GSIRTLQSNLGCLPPSSALPSGTRSLPRPIDGVSDWSQGCSL RSTGSPASLASNLEISQSPTMPFLSLHRSPHGPSKLCDDPQA SLVPEPVPGGCQEPEEMSWPPSGEIASPPELPSSPPPGLPEV APDATSTGLPDTPAAPETSTNYPVECTEGSAGPQSLPLPILE |

TABLE 2-continued

Interferon Regulatory Factor (IRF)-activating intracellular domains

| SEQ ID NO | CFP/Domain | Sequence |
|---|---|---|
| | | PVKNPCSVKDQTPLQLSVEDTTSPNTKPCPPTPTTPETSPPP<br>PPPPPSSTPCSAHLTPSSLFPSSLE |
| 44 | TRIF (long)<br>(153-545) | GSIRTLQSNLGCLPPSSALPSGTRSLPRPIDGVSDWSQGCSL<br>RSTGSPASLASNLEISQSPTMPFLSLHRSPHGPSKLCDDPQA<br>SLVPEPVPGGCQEPEEMSWPPSGEIASPPELPSSPPPGLPEV<br>APDATSTGLPDTPAAPETSTNYPVECTEGSAGPQSLPLPILE<br>PVKNPCSVKDQTPLQLSVEDTTSPNTKPCPPTPTTPETSPPP<br>PPPPPSSTPCSAHLTPSSLFPSSLESSSEQKFYNFVILHARA<br>DEHIALRVREKLEALGVPDGATFCEDFQVPGRGELSCLQDAI<br>DHSAFIILLLTSNFDCRLSLHQVNQAMMSNLTRQGSPDCVIP<br>FLPLESSPAQLSSDTASLLSGLVRLDEHSQIFARKVANTFKP<br>HRLQARKAMWRKEQD |
| 42 | TASL<br>(279-301) | MSTEITEISTPSLHISQYSNVNP |

A CFP, as described herein may comprise any one of the sequences listed in Table 1, in combination with an intracellular domain listed in Table 2.

In some embodiments, for example, the intracellular signaling domain of a CFP described herein comprises an intracellular signaling domain derived from an MDA5 intracellular signaling domain having an amino acid sequence of SEQ ID NO: 30 or at least 85% sequence identity to SEQ ID NO: 30. In some embodiments, the intracellular signaling domain comprises a sequences that has at least at least 86%, or at least 87%, or at least 88% or at least 89% sequence identity to SEQ ID NO: 30. In some embodiments, the intracellular signaling domain comprises an intracellular signaling domain derived from an MDA5 intracellular signaling domain having at least 90% sequence identity to SEQ ID NO: 30. In some embodiments, the intracellular signaling domain comprises a sequences that has at least at least 91%, or at least 92%, or at least 93% or at least 94% sequence identity to SEQ ID NO: 30. In some embodiments, the intracellular signaling domain comprises an intracellular signaling domain derived from an MDA5 intracellular signaling domain having at least 95% sequence identity to SEQ ID NO: 30. In some embodiments, the intracellular signaling domain comprises a sequences that has at least at least 96%, or at least 97%, or at least 98% or at least 99% sequence identity to SEQ ID NO: 30. In some embodiments, the intracellular domain of a CFP comprises an intracellular signaling domain derived from an MDA5 intracellular signaling domain having at least 90% sequence identity to SEQ ID NO: 30; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an MDA5 intracellular signaling domain having at least 90% sequence identity to SEQ ID NO: 30; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an MDA5 intracellular signaling domain having at least 90% sequence identity to SEQ ID NO: 30; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 30.

In some embodiments, the intracellular signaling domain comprises an intracellular signaling domain derived from an RIG-1 intracellular domain having an amino acid sequence of SEQ ID NO: 36 or at least 85% sequence identity to SEQ ID NO: 36. In some embodiments, the intracellular signaling domain comprises an intracellular signaling domain derived from an RIG-1 intracellular domain intracellular signaling domain having at least 90% sequence identity to SEQ ID NO: 36. In some embodiments, the intracellular signaling domain comprises an intracellular signaling domain derived from an RIG-1 intracellular domain intracellular signaling domain having at least 95% sequence identity to SEQ ID NO: 36. In some embodiments, the intracellular domain of a CFP comprises an intracellular signaling domain derived from an RIG-1 intracellular signaling domain having at least 90% sequence identity to SEQ ID NO: 36; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an RIG-1 intracellular signaling domain having at least 90% sequence identity to SEQ ID NO: 36; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an RIG-1 intracellular signaling domain having at least 90% sequence identity to SEQ ID NO: 36; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 36.

In some embodiments, the intracellular signaling domain of a CFP comprises an intracellular signaling domain derived from an MyD88 intracellular domain having an amino acid sequence of SEQ ID NO: 37 or at least 85% sequence identity to SEQ ID NO: 37. In some embodiments, the intracellular signaling domain comprises an intracellular signaling domain derived from an MyD88 intracellular domain intracellular signaling domain having at least 90% sequence identity to SEQ ID NO: 37. In some embodiments, the intracellular signaling domain comprises a sequence having at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 37. In some embodiments, the intracellular signaling domain comprises an intracellular signaling domain derived from an MyD88 intracellular domain intracellular signaling domain having at least 95% sequence identity to SEQ ID NO: 37. In some embodiments, the intracellular domain of a CFP comprises an intracellular signaling domain derived from an MyD88 intracellular signaling domain having at least 90% sequence identity to SEQ ID NO: 37; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an MyD88 intracellular signaling domain having at least 90% sequence identity to SEQ ID NO: 37; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an MyD88 intracellular signaling domain having at least 90% sequence identity to SEQ ID NO: 37; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 37.

In some embodiments, the intracellular signaling domain comprises an intracellular signaling domain derived from a STING intracellular domain having an amino acid sequence of SEQ ID NO: 38 or at least 85% sequence identity to SEQ ID NO:38. In some embodiments, the intracellular signaling domain comprises an intracellular signaling domain derived from STING intracellular domain intracellular signaling domain having at least 90% sequence identity to SEQ ID NO: 38. In some embodiments, the intracellular signaling domain comprises a sequence having at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 38. In some embodiments, the intracellular signaling domain comprises an intracellular signaling domain derived from STING intracellular domain intracellular signaling domain having at least 95% sequence identity to SEQ ID NO: 38. In some embodiments, the intracellular domain of a CFP comprises an intracellular signaling domain derived from an STING intracellular signaling domain having at least 90% sequence identity to SEQ ID NO: 38; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an STING intracellular signaling domain having at least 90% sequence identity to SEQ ID NO: 38; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an STING intracellular signaling domain having at least 90% sequence identity to SEQ ID NO: 38; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 38.

In some embodiments, the intracellular signaling domain comprises an intracellular signaling domain derived from a MAVS intracellular domain having an amino acid sequence of SEQ ID NO: 39 or 40 or an amino acid sequence with at least 85% sequence identity to SEQ ID NO: 39 or 40. In some embodiments, the intracellular signaling domain comprises an intracellular signaling domain derived from MAVS intracellular domain intracellular signaling domain having at least 90% sequence identity to SEQ ID NO: 39 or 40. In some embodiments, the intracellular signaling domain comprises an intracellular signaling domain derived from MAVS intracellular domain intracellular signaling domain having at least 95% sequence identity to SEQ ID NO: 39 or 40. In some embodiments, the intracellular domain of a CFP comprises an intracellular signaling domain derived from an MAVS intracellular signaling domain having at least 90% sequence identity to SEQ ID NO: 39 or 40; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an MAVS intracellular signaling domain having at least 90% sequence identity to SEQ ID NO: 39 or 40; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an MAVS intracellular signaling domain having at least 90% sequence identity to SEQ ID NO: 39 or 40; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 39 or 40.

In some embodiments, the intracellular signaling domain comprises an intracellular signaling domain derived from a MAVS intracellular domain having an amino acid sequence of SEQ ID NO: 45 or a sequence with at least 85% sequence identity to SEQ ID NO: 45. In some embodiments, the intracellular signaling domain comprises an intracellular signaling domain derived from MAVS intracellular domain intracellular signaling domain having at least 90% sequence identity to SEQ ID NO: 45. In some embodiments, the intracellular signaling domain comprises an intracellular signaling domain derived from MAVS intracellular domain intracellular signaling domain having at least 95% sequence identity to SEQ ID NO: 45. In some embodiments, the intracellular signaling domain comprises a sequence having at least 86%, at least 87%, at least 88%, at least 89%, at least 90%, at least 91%, at least 92%, at least 93%, at least 94%, at least 95%, at least 96%, at least 97%, at least 98% or at least 99% sequence identity to SEQ ID NO: 45. In some embodiments, the intracellular domain of a CFP comprises an intracellular signaling domain derived from an MAVS intracellular signaling domain having at least 90% sequence identity to SEQ ID NO: 45; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an MAVS intracellular signaling domain having at least 90% sequence identity to SEQ ID NO: 45; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an MAVS intracellular signaling domain having at least 90% sequence identity to SEQ ID NO: 45; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 45.

In some embodiments, the intracellular signaling domain comprises an intracellular signaling domain derived from a TRIF intracellular domain having an amino acid sequence of SEQ ID NO: 41 or at least 85% sequence identity to SEQ ID NO: 41. In some embodiments, the intracellular signaling domain comprises a sequences that has at least at least 86%, or at least 87%, or at least 88% or at least 89% sequence identity to SEQ ID NO: 41. In some embodiments, the intracellular signaling domain comprises an intracellular signaling domain derived from an TRIF intracellular signaling domain having at least 90% sequence identity to SEQ ID NO: 41. In some embodiments, the intracellular signaling domain comprises a sequences that has at least at least 91%, or at least 92%, or at least 93% or at least 94% sequence identity to SEQ ID NO: 41. In some embodiments, the intracellular signaling domain comprises an intracellular signaling domain derived from an TRIF intracellular signaling domain having at least 95% sequence identity to SEQ ID NO: 41. In some embodiments, the intracellular domain of a CFP comprises an intracellular signaling domain derived from an TRIF intracellular signaling domain having at least 90% sequence identity to SEQ ID NO: 41; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an TRIF intracellular signaling domain having at least 90% sequence identity to SEQ ID NO: 41; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an TRIF intracellular signaling domain having at least 90% sequence identity to SEQ ID NO: 41; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 41.

In some embodiments, the intracellular signaling domain comprises an intracellular signaling domain derived from a TRIF intracellular domain having an amino acid sequence of SEQ ID NO: 43 or at least 85% sequence identity to SEQ ID NO: 43. In some embodiments, the intracellular signaling domain comprises a sequences that has at least at least 86%, or at least 87%, or at least 88% or at least 89% sequence identity to SEQ ID NO: 43. In some embodiments, the intracellular signaling domain comprises an intracellular signaling domain derived from an TRIF intracellular signaling domain having at least 90% sequence identity to SEQ ID NO: 43. In some embodiments, the intracellular signaling domain comprises a sequences that has at least at least 91%, or at least 92%, or at least 93% or at least 94% sequence identity to SEQ ID NO: 43. In some embodiments, the intracellular signaling domain comprises an intracellular signaling domain derived from an TRIF intracellular signaling domain having at least 95% sequence identity to SEQ ID NO: 43. In some embodiments, the intracellular domain of a CFP comprises an intracellular signaling domain derived from an TRIF intracellular signaling domain having at least 90% sequence identity to SEQ ID NO: 43; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an TRIF intracellular signaling domain having at least 90% sequence identity to SEQ ID NO: 43; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an TRIF intracellular signaling domain having at least 90% sequence identity to SEQ ID NO: 43; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 43.

In some embodiments, the intracellular signaling domain comprises an intracellular signaling domain derived from a TRIF intracellular domain having an amino acid sequence of SEQ ID NO: 44 or at least 85% sequence identity to SEQ ID NO: 44. In some embodiments, the intracellular signaling domain comprises a sequences that has at least at least 86%, or at least 87%, or at least 88% or at least 89% sequence identity to SEQ ID NO: 44. In some embodiments, the intracellular signaling domain comprises an intracellular signaling domain derived from an TRIF intracellular signaling domain having at least 90% sequence identity to SEQ ID NO: 44. In some embodiments, the intracellular signaling domain comprises a sequences that has at least at least 91%, or at least 92%, or at least 93% or at least 94% sequence identity to SEQ ID NO: 44. In some embodiments, the intracellular signaling domain comprises an intracellular signaling domain derived from an TRIF intracellular signaling domain having at least 95% sequence identity to SEQ ID NO: 44.

In some embodiments, the intracellular domain of a CFP comprises an intracellular signaling domain derived from an TRIF intracellular signaling domain having at least 90% sequence identity to SEQ ID NO: 44; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an TRIF intracellular signaling domain having at least 90% sequence identity to SEQ ID NO: 44; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an TRIF intracellular signaling domain having at least 90% sequence identity to SEQ ID NO: 44; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 44.

In some embodiments, the intracellular signaling domain comprises an intracellular signaling domain derived from a TASL intracellular domain having an amino acid sequence of SEQ ID NO: 42 or at least 85% sequence identity to SEQ ID NO: 42. In some embodiments, the intracellular domain of a CFP comprises an intracellular signaling domain derived from an TASL intracellular signaling domain having at least 90% sequence identity to SEQ ID NO: 42; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell. In some embodiments, the intracellular domain of a CFP comprises an intracellular signaling domain derived from an TASL intracellular signaling domain having at least 90% sequence identity to SEQ ID NO: 42; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD68 transmembrane domain or a CD64 transmembrane domain or a CD16 transmembrane domain, or a CD89 transmembrane domain, and a hinge domain. In some embodiments, the intracellular domain of a CFP comprises an intracellular signaling domain derived from an TASL intracellular signaling domain having at least 90% sequence identity to SEQ ID NO: 42; wherein the CFP comprises and extracellular binding domain capable of binding a CD5 molecule on a target cell, a HER2 molecule on a target cell, a CD19 molecule on a target cell, a TROP2 molecule on a target cell, a GPC3 molecule on a target cell, a CD70 molecule on a target cell, a CD137 molecule on a target cell, a CD7 molecule on a target cell, a Claudin molecule on a target cell, a CD22 molecule on a target cell or GP75 molecule on a target cell; with a CD8 transmembrane domain or a CD28 transmembrane domain, or a CD64 transmembrane domain or a CD16 transmembrane domain, or a CD89 transmembrane domain, and one or more additional intracellular signaling domains such as PI3kinase recruitment domain or a CD40 intracellular signaling domain. For example, an exemplary CFP molecule disclosed herein comprises an extracellular CD5 binding domain having an amino acid sequence comprising the sequence of SEQ ID NO: 8, or SEQ ID NO: 9 or both, or that of SEQ ID NO: 10 or SEQ ID NO: 11; and an intracellular domain comprising a sequence having at least 90% sequence identity to SEQ ID NO: 42.

In some embodiments, an exemplary anti-CD5-binding CFP described herein comprises an extracellular antigen binding domain having a sequence of SEQ ID NO: 10, or SEQ ID NO: 11, or at least a heavy chain variable domain comprising a CDR3 sequence of RGYDWYFDV (SEQ ID NO: 99), and/or a light chain variable domain comprising a CDR3 sequence of QQYDESPWT (SEQ ID NO: 100) and further comprises an intracellular domain of SEQ ID NO: 41. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 43. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 44. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 30. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 36. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 37. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 38. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 39. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 40. In some embodiments, an exemplary CFP described herein comprises an extracellular antigen binding domain having a sequence of SEQ ID NO: 10, or SEQ ID NO: 11, or at least a VH domain comprising a CDR3 sequence of RGYDWYFDV (SEQ ID NO: 99), and/or a VL domain comprising a CDR3 sequence of SEQ ID NO: 100; and further comprises an intracellular domain of SEQ ID NO: 45.

In some embodiments, an exemplary anti-HER2-binding CFP described herein comprises an extracellular antigen binding domain having a sequence of SEQ ID NO: 14, or SEQ ID NO: 94, or at least a heavy chain variable domain comprising a CDR3 sequence of WGGDGFYAMDV (SEQ ID NO: 101), and/or a light chain variable domain comprising a CDR3 sequence of QQHYTTPPT (SEQ ID NO: 102) and further comprises an intracellular domain of SEQ ID NO: 41. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 43. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 44. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 30. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 36. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 37. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 38. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 39. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 40. In some embodiments, an exemplary CFP described herein comprises an extracellular antigen binding domain having a sequence of SEQ ID NO: 14, or SEQ ID NO: 94, or at least a VH domain comprising a CDR3 sequence of WGGDGFYAMDV (SEQ ID NO: 101), and/or a VL domain comprising a CDR3 sequence of SEQ ID NO: 102; and further comprises an intracellular domain of SEQ ID NO: 45.

In some embodiments, an exemplary anti-TROP2-binding CFP described herein comprises an extracellular antigen binding domain having a sequence of SEQ ID NO: 34, or SEQ ID NO: 35, or at least a heavy chain variable domain comprising a CDR3 sequence of GGFGSSYWYFDV (SEQ ID NO: 103), and/or a light chain variable domain comprising a CDR3 sequence of QQHYITPLT (SEQ ID NO: 104) and further comprises an intracellular domain of SEQ ID NO: 41. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 43. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 44. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 30. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 36. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 37. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 38. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 39. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 40. In some embodiments, an exemplary CFP described herein comprises an extracellular antigen binding domain having a sequence of SEQ ID NO: 34, or SEQ ID NO: 35, or at least a VH domain comprising a CDR3 sequence of GGFGSSYWYFDV (SEQ ID NO: 103), and/or a VL domain comprising a CDR3 sequence of SEQ ID NO: 104; and further comprises an intracellular domain of SEQ ID NO: 45.

IRF Inducible Proteins and IRF Activation Pathways

Type I IFNs are key cytokines mediating innate antiviral immunity and therefore drive a pro-inflammatory response. Type I IFNs are readily induced by cGMP-AMP synthase, retinoic acid-inducible protein 1 (RIG-I)-like receptors, and Toll-like receptors that recognize microbial double-stranded (ds)DNA, dsRNA, and LPS. These signaling pathways converge at the recruitment and activation of the transcription factor IRF-3 (IFN regulatory factor 3). The adaptor proteins STING (stimulator of IFN genes), MAVS (mitochondrial antiviral signaling), and TRIF (TIR domain-containing adaptor inducing IFN-β) mediate the recruitment of IRF-3 through a conserved pLxIS motif. The pLxIS motif of phosphorylated STING, MAVS, and TRIF generally binds to IRF-3 in a similar manner, whereas residues upstream of the motif confer specificity. Type I IFNs, such as IFN-α and -β, are a major family of cytokines mediating antiviral immunity Microbial dsDNA in the cytosol binds to and activates the enzyme cGAS (cGMP-AMP synthase), which catalyzes the synthesis of a cyclic dinucleotide, cGAMP (cyclic [G(2',5')pA(3',5')p]). As a second messenger, cGAMP binds to the adaptor protein STING (stimulator of IFN genes) located on the endoplasmic reticulum (ER) membrane and directs the activation of transcription factor IRF-3 (IFN regulatory factor 3) through the protein kinase TBK1 (TANK-binding kinase 1). Phosphorylated IRF-3 dimerizes and translocates to the nucleus to initiate the transcription of the IFN-β gene. In contrast, viral dsRNA in the cytosol is sensed by the RLRs [retinoic acid-inducible protein 1 (RIG-I)-like receptors] to activate IRF-3 via the adaptor protein MAVS (mitochondrial antiviral signaling). Moreover, the TLRs (Toll-like receptors) TLR3 and TLR4, which recognize viral dsRNA in the endosome and bacterial cell wall component LPS, respectively, also mediate the induction of type I IFNs and inflammatory cytokines (1). These two TLRs use the adaptor protein TRIF (TIR domain-containing adaptor inducing IFN-β) to mediate the recruitment and activation of IRF-3. Strikingly, the signaling pathways of these three families of innate immune sensors converge at the activation of TBK1 and IRF-3. Mechanistically, the adaptor proteins STING, MAVS, and TRIF contain a conserved motif, pLxIS (in which p represents the hydrophilic residue, x represents any residue, and S represents the phosphorylation site), that is phosphorylated by TBK1 or IKKε and mediates the recruitment of IRF-3 to the signaling complexes. The induced proximity between TBK1 and IRF-3 results in IRF-3 phosphorylation and activation. Moreover, IRF-3 itself also contains a pLxIS motif that is crucial for phosphorylation-induced dimerization and activation of IRF-3. Mutations of the phosphorylation site serine in the pLxIS motif of STING, MAVS, and TRIF abolish the induction of type I IFNs in their respective signaling pathways. However, the exact molecular mechanisms of IRF-3 recruitment and activation remain unknown. To elucidate the structural bases of IRF-3 recruitment by phosphorylated STING (pSTING), MAVS (pMAVS), and TRIF (pTRIF), we expressed peptides containing the pLxIS motif from the three adaptor proteins, phosphorylated them in vitro with TBK1, and determined the crystal structures of their complexes with the IRF-3 C-terminal domain (CTD).

Mechanisms of IRF-3 Recruitment by pMAVS and pTRIF.

In contrast to dsDNA sensing through the cGAS-STING pathway, the RLRs sense dsRNA in the cytosol and activate IRF-3 via the adaptor MAVS, and TLR3 and TLR4 use the adaptor TRIF to recruit IRF-3. Phosphorylation of the pLxIS motif of MAVS or TRIF is required for the recruitment and activation of IRF-3.

TRAF Interacting Proteins:

The presence of the TRAF domain, a ~180 amino acid protein-interacting domain, is a distinct feature of TRAF family proteins and six TRAF proteins (TRAF1-TRAF6) among the seven in the family, in accordance with this criterion, have been identified as the TRAF family in mammals. The TRAF domain can be subdivided into two distinct regions: the TRAF-N domain and TRAF-C domain. Various receptors bind to the TRAF-C domain, while various intracellular signaling molecules bind to the TRAF-N domain. Despite the structural similarity of TRAF domains, each TRAF protein has specific biological functions with specificity to the interacting partners: upstream receptors and downstream effector molecules. The structure of the TRAF domain of TRAF2 was first reported by Dr. Wu's group around 1999, and the structure of TRAF6's TRAF domain was reported 3 years later by the same group. Since then, the structures of the TRAF domain of TRAF3, TRAF5, TRAF4, and TRAF1 have been reported. The TRAF structures revealed that the TRAF-N domain is a coiled-coil structure, and TRAF-C is composed of seven to eight anti-parallel β-sheet folds. Structural alignment of all six TRAF family members shows that the TRAF-C domain is well-aligned, while the location and length of TRAF-N varies among TRAF family members. Sequence analysis indicates that the length of TRAF-N varies in the family, whereas that of the TRAF-C domain is conserved: the length of TRAF-N of TRAF4 and TRAF6 is relatively shorter, while TRAF3 and TRAF5 are relatively longer. Although the overall structures are nearly identical, obvious structural differences have been observed. For example, the length and position of some loops in the TRAF domain of TRAF4 and TRAF6 differ from those of other TRAF family members. TRAF4 contains a more negatively charged surface in the middle of the receptor-binding region, whereas TRAF6 contains a more positively charged surface in the receptor-binding region. Because the surface features often determine their mode of interactions with partners, the similar electrostatic surface of the TRAF domain among TRAF1, TRAF2, TRAF3, and TRAF5, namely, diversely charged surfaces, has been shown to be important for accommodating diverse receptors in the same binding pocket with similar modes of interaction. In contrast, different features on the binding surface of functionally different TRAFs, TRAF4, and TRAF6, indicate that TRAF4 and TRAF6 can accommodate different receptors with different modes of interactions.

For the purpose of this disclosure, any pathway, signaling intermediate, or activating moiety discussed in the paragraphs above may be considered as activable or functional as it applies, upon induction of the CFP disclosed herein. Likewise, the CFP disclosed herein may be useful in targeting any of the applicable targets that are described in the pathways discussed. Any pathway or part thereof readily known to one of skill in the art as of date from existing literature that relates to the signaling domain, signaling pathways, signaling intermediates, transcription factors of activated genes is understood to be within the prevue of this disclosure.

Chimeric Proteins with TLR Intracellular Domains, TLR Intracellular Signaling Pathways and NF-Kappa B Activation:

In some embodiments, the intracellular signaling domain comprises an intracellular signaling domain derived from a TLR protein. In some embodiments, the CFP designed to comprise an intracellular signaling domain derived from a TLR intracellular signaling domains can activate NF-kappa B upon engagement of the receptor's extracellular domain to its target. In some embodiments, the intracellular signaling domain may comprise an intracellular signaling domain of the endolysosomal TLR, e.g., TLR3, TLR7, TLR8, or TLR9. In some embodiments, the intracellular signaling domain may be derived from a TLR3 protein. In some embodiments, the intracellular signaling domain may be derived from a TLR7, 8, or 9 protein. In some embodiments, the intracellular domain may comprise an intracellular signaling domain of the cell surface TLRs 1, 2, 4, 5, 6, and 10. In some embodiments, the cytoplasmic domain for inflammatory response comprises an intracellular signaling domain of TLR3, TLR4, TLR9, MYD88, TRIF, RIG-1, MDA5, CD40, IFN receptor, NLRP-1, NLRP-2, NLRP-3, NLRP-4, NLRP-5, NLRP-6, NLRP-7, NLRP-8, NLRP-9, NLRP-10, NLRP-11, NLRP-12, NLRP-13, NLRP-14, NOD1, NOD2, Pyrin, AIM2, NLRC4 and/or CD40.

In some embodiments, the phagocytic scavenger receptor (PR) fusion protein (PFP) comprises a pro-inflammatory cytoplasmic domain for activation of IL-1 signaling cascade.

In some embodiments, the cytoplasmic portion of the chimeric receptor (for example, phagocytic receptor (PR) fusion protein (PFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9).

In general TLRs have a diverse cellular localization, pathways of generation, activation, recognition and mode of action. TLRs are expressed in innate immune cells such as dendritic cells (DCs) and macrophages as well as non-immune cells such as fibroblast cells and epithelial cells. Cell surface TLRs mainly recognize microbial membrane components such as lipids, lipoproteins, and proteins. TLR4 recognizes bacterial lipopolysaccharide (LPS). TLR2 along with TLR1 or TLR6 recognizes a wide variety of PAMPs including lipoproteins, peptidoglycans, lipoteichoic acids, zymosan, mannan, and tGPI-mucin. TLR5 recognizes bacterial flagellin. TLR10 is pseudogene in mouse due to an insertion of a stop codon, but human TLR10 collaborates with TLR2 to recognize ligands from *listeria*. TLR10 can also sense influenza A virus infection.

Intracellular TLRs recognize nucleic acids derived from bacteria and viruses, and also recognize self-nucleic acids in disease conditions such as autoimmunity. TLR3 recognizes viral double-stranded RNA (dsRNA), small interfering RNAs, and self-RNAs derived from damaged cells. TLR7 is predominantly expressed in plasmacytoid DCs (pDCs) and recognizes single-stranded (ss)RNA from viruses. It also recognizes RNA from *streptococcus* B bacteria in conventional DCs (cDCs). Human TLR8 responds to viral and bacterial RNA. Structural analysis revealed that unstimulated human TLR8 exists as a preformed dimer, and although the Z-loop between LRR14 and LRR15 is cleaved, the N- and C-terminal halves remain associated with each other and participate in ligand recognition and dimerization. Ligand binding induces reorganization of the dimer to bring the two C termini into close proximity. TLR13 recognizes bacterial 23S rRNA and unknown components of vesicular stomatitis virus. TLR9 recognizes bacterial and viral DNA that is rich in unmethylated CpG-DNA motifs; it also recognizes hemozoin, an insoluble crystalline byproduct generated by *Plasmodium falciparum* during the process of detoxification after host hemoglobin is digested. TLR11 is localized in the endolysosome and recognizes flagellin or an unknown proteinaceous component of uropathogenic *Escherichia coli* (UPEC) as well as a profilin-like molecule derived from *Toxoplasma gondii*. TLR12 is predominantly expressed in myeloid cells and is highly similar to TLR11 and recognizes profilin from *T. gondii*. TLR12 functions either as a homodimer or a heterodimer with TLR11. All TLRs are synthesized in the ER, traffic to the Golgi, and are recruited to the cell surface or to intracellular compartments such as endosomes. Intracellular localization of TLRs is thought to be critical for ligand recognition as well as for preventing TLRs from coining into contact with self-nucleic acids, which could cause autoimmunity.

Individual TLRs differentially recruit members of a set of TIR domain-containing adaptors such as MyD88, TRIF, TIRAP/MAL, or TRAM. MyD88 is utilized by all TLRs and activates NF-κB and MAPKs for the induction of inflammatory cytokine genes. TIRAP is a sorting adaptor that recruits MyD88 to cell surface TLRs such as TLR2 and TLR4. TIRAP also participates in signaling through endosomal TLRs such as TLR9. The lipid-binding domain of TIRAP binds to $PI(4,5)P_2$ at the plasma membrane and to PI(3)P on endosomes, which mediates the formation of functional TLR4 and TLR9 signaling complexes at their respective sites. Thus, TIRAP associates with both cell surface and endosomal TLRs by binding to different lipids. TRIF is recruited to TLR3 and TLR4 and promotes an alternative pathway that leads to the activation of IRF3, NF-κB, and MAPKs for induction of type I IFN and inflammatory cytokine genes. TRAM is selectively recruited to TLR4 but not TLR3 to link between TRIF and TLR4. TLR3 directly interacts with TRIF, and this interaction requires phosphorylation of the two tyrosine residues in the cytoplasmic domain of TLR3 by the epidermal growth factor ErbB1 and Btk. After TLR engagement, MyD88 forms a complex with IRAK kinase family members. IRAK4 activates IRAK1, which is then autophosphorylated at several sites and released from MyD88. IRAK1 associates with the RING-domain E3 ubiquitin ligase TRAF6. TRAF6, along with ubiquitin-conjugating enzyme UBC13 and UEV1A, promotes K63-linked polyubiquitination of both TRAF6 itself and the TAK1 protein kinase complex. TAK1 is a member of the MAPKKK family and forms a complex with the regulatory subunits TAB1, TAB2, and TAB3, which interact with polyubiquitin chains generated by TRAF6 to drive TAK1 activation. TAK1 then activates two different pathways that lead to activation of the IKK complex-NE-κB pathway and -MAPK pathway. The IKK complex is composed of the catalytic subunits IKKα and IKKβ and the regulatory subunit NEMO (also called IKKγ). TAK1 binds to the IKK complex through ubiquitin chains, which allows it to phosphorylate and activate IKKβ. The IKK complex phosphorylates the NF-κB inhibitory protein IκBα, which undergoes proteasome degradation, allowing NF-κB to translocate into the nucleus to induce proinflammatory gene expression. TAK1 activation also results in activation of MAPK family members such as ERK1/2, p38 and JNK, which mediates activation of AP-1 family transcription factors or stabilization of mRNA to regulate inflammatory responses.

In some embodiments, an intracellular domain described herein may be specifically paired with another domain, e.g., a structural domain such as another intracellular domain, a transmembrane domain or an extracellular domain; a functional domain such as a signaling domain. In some embodiments, the intracellular domain described in the section herein, such as a MyD88, TRIF, TIRAP/MAL, TLR, MAVS, MDA5, STING, RIG1, TASL or am other domain mentioned herein may be adjusted or modified for pairing with another domain or component thereof. By pairing it is intended to mean inclusion of the part of the domain or domains in consideration, or a fragment or component thereof within the CFP design, as any part of the CEP protein molecular structure. In some embodiments, the adjustment may be structural alignment or placement of the domain within the CFP molecule, for example two domains in consideration are juxtaposed, or separated by one or more domains in between or separated by one or more amino acids in between. The one or more amino acids may be linkers. The one or more amino acids may provide structural distancing between two adjacent domains, flexibility between two adjacent domains or confer a three dimensional orientation than a molecular structure comprising the domains without the one or more amino acids. In some embodiments, the adjustment or modification may comprise a modification within the domain, such as a mutation.

In some embodiments, the intracellular domain described in the section herein, such as a MyD88, TRIF, TIRAP/MAL, TLR, MAVS, MDA5, STING, RIG1, TASL or any other domain mentioned herein may be adjusted or modified for pairing or inclusion with another intracellular domain within the CFP, such as a kinase recruitment domain, such as a PI3 kinase recruitment domain. In some embodiments, the PI3kinase recruitment domain is modified to mask tonic signaling. In some embodiments one of the other intracellular domains, such as any one or more of the MyD88, TRIF, TIRAP/MAL, TLR, MAVS, MDA5, STING, RIG1, TASL domains or fragments thereof are modified to reduce or eliminate tonic signaling.

In some embodiments, the intracellular domain described in the section herein, such as a MyD88, TRIF, TIRAP/MAL, TLR, MAVS, MDA5, STING, RIG1, TASL or any other domain mentioned herein may be adjusted or modified for pairing or inclusion with another structural domain such as a transmembrane domain. In some embodiments, the transmembrane domain is a CD68 domain. In some embodiments, the transmembrane domain is a CD64 domain. In some embodiments the transmembrane domain is a CD89 domain. In some embodiments, a mutated CD68 domain may be used, e.g., SEQ ID NO: 46.

For the purpose of this disclosure, any pathway, signaling intermediate, or activating moiety discussed in the paragraphs above may be considered as activable or functional as it applies, upon induction of the CFP disclosed that comprises a TLR intracellular signaling domain as disclosed herein. Likewise, the CFP disclosed herein may be useful in targeting any of the applicable targets that are described in the pathways discussed. Any pathway or part thereof readily known to one of skill in the art as of date from existing literature that relates to the signaling domain, signaling pathways, signaling intermediates, transcription factors of activated genes is understood to be within the prevue of this disclosure.

Therapeutic Compositions

Provided herein, in one aspect, is a myeloid cell, such as a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell. In some embodiments, provided herein is a therapeutic composition comprising at least 20%, at least 30%, at least 40% or at least 50% CD14+ cells. In some embodiments, the therapeutic composition comprises at least 20%, at least 30%, at least 40% or at least 50% CD14+/CD16− cells. In some embodiments, provided herein is a therapeutic composition comprising less than 20%, less than 15%, less than 10% or less than 5% dendritic cells. The myeloid cell for the therapeutic composition as described herein, comprises a recombinant nucleic acid that encodes a chimeric fusion protein encoding a CFP receptor protein or an engager protein as described herein. The myeloid cell for the therapeutic composition as described herein, expresses the CFP encoded by the recombinant nucleic acid or expresses an engager protein encoded by the recombinant nucleic acid as described herein.

In some embodiments, provided herein is a therapeutic composition comprising a chimeric fusion protein, such as a chimeric fusion receptor protein (CFP), the CFP comprises: (a) an extracellular domain comprising: (i) a scFv that specifically binds any one of the targets disclosed herein, and (ii) a hinge domain derived from CD8, a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRγ or FORε, (ii) a second intracellular signaling domain e.g., intracellular signaling domain derived from TLR3, TLR4, TLR7, TLR 9, TRIF, RIG-1, MYD88, MAL, IRAK1, MDA-5, an IFN-receptor, STING, MAVS, TRIF or TASL intracellular domains, an NLRP family member, NLRP1-14, NOD1, NOD2, Pyrin, AIM2, NLRC4, FCGR3A, FCERIG, IL-1, IL3, IL5, IL-6, IL-12, IL-13, IL-23, TNF, IL-18, IL-23, IL-27, CSF, MCSF, GMCSF, IL17, IP-10, or RANTES and a second intracellular signaling domain, that comprises a PI3K recruitment domain, or a domain that is derived from CD40.

In some embodiments, the pharmaceutical composition comprises a population of cells comprising therapeutically effective dose of the myeloid cells. In some embodiments, the population of cells: differentiate into effector cells in the subject after administration; infiltrate into a diseased site of the subject after administration or migrate to a diseased site of the subject after administration; and/or have a life-span of at least 5 days in the subject after administration.

In some embodiments, myeloid cells may be further modified or manipulated to develop a therapeutically effective myeloid cells. Isolated cells can be manipulated by expressing a gene or a fragment thereof in the cell, without altering its functional and developmental plasticity, differential potential and cell viability.

In some embodiments, myeloid cells may be further modified or manipulated to develop a therapeutically effective myeloid cells by expressing a non-endogenous polynucleotide into the cell. A non-endogenous polynucleotide may encode for a protein or a peptide. Alternatively, a non-endogenous polypeptide may be a non-coding sequence, such as an inhibitory RNA, or a morpholino.

In some embodiments, myeloid cells may be further modified or manipulated to develop a therapeutically effective myeloid cells by stably altering the genomic sequence of the cell. In some embodiments, the myeloid cell is manipulated by editing the myeloid cell genome using a CRISPR-CAS system. In some embodiments, one or more genes may be edited to silence the gene expression. In some embodiments, the myeloid cell is manipulated to delete a gene. In some embodiments, one or more genes may be edited to enhance the gene expression. In some embodiments, the genetic material is introduced into a myeloid cell in the form of a messenger RNA, wherein the messenger RNA encodes a protein or a peptide, thereby rendering the myeloid cell therapeutically effective. In some embodiments, naked DNA or messenger RNA (mRNA) may be used to introduce the nucleic acid inside the myeloid cell. In some embodiments, DNA or mRNA encoding the chimeric antigen receptor is introduced into the phagocytic cell by lipid nanoparticle (LNP) encapsulation. mRNA is single stranded and may be codon optimized. In some embodiments the mRNA may comprise one or more modified or unnatural bases such as 5'-Methylcytosine, or Pseudouridine or methyl pseudouridine. In some embodiments greater than or about 50% uridine ('U') residues of the mRNA may be converted to methyl-pseudouridine. In some embodiments, the mRNA may be 50-10,000 bases long. In one aspect the transgene is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. LNP encapsulated DNA or RNA can be used for transfecting a macrophage or can be administered to a subject. In some embodiments, the mRNA is incorporated into an effector myeloid cell population by transient transfection. In some embodiments the transient transfection method comprises electroporation of the mRNA. In some embodiments, the transient transfection comprises chemical transfection. In some embodiments, 1-5,000 micrograms/ml of the mRNA may be used for transfection using a suitable protocol for the methods described above. In some embodiments, 1-2,000 micrograms/ml of the mRNA may be used for transfection. In some embodiments, 1-1,000 micrograms/ml of the mRNA may be used for transfection. In some embodiments, 1-1,000 micrograms/ml of the mRNA may be used for transfection. In some embodiments, 1-500 micrograms/ml of the mRNA may be used for transfection. In some embodiments, 1-250 micrograms/ml of the mRNA may be used for transfection. In some embodiments, about 500 micrograms/ml of the mRNA or less may be used for transfection. In some embodiments, about 250 micrograms/ml of the mRNA or less may be used for transfection. In some embodiments, about 10 micrograms/ml of the mRNA is used. In some embodiments, about 20 micrograms/ml of the mRNA is used. In some embodiments, about 30 micrograms/ml of the mRNA is used. In some embodiments, about 40 micrograms/ml of the mRNA is used. In some embodiments, about 50 micrograms/ml of the mRNA is used. In some embodiments, about 60 micrograms/ml of the mRNA is used. In some embodiments, about 80 micrograms/ml of the mRNA is used. In some embodiments, about 100 micrograms/ml of the mRNA is used. In some embodiments, about 150 micrograms/ml of the mRNA is used. In some embodiments, about 200 micrograms/ml of the mRNA is used. In some embodiments, 20, 50, 100, 150, 200, 250, 300, 400, 500 or about 1000 micrograms/ml of the mRNA is used. A suitable cell density is selected for a transfection, based on the method and instrument and/or reagent manufacturer's instructions, or as is well-known to one of skill in the art.

In some embodiments the recombinant nucleic acid is an mRNA. mRNA constructs may be thawed on ice and gently pipetted to monocytes and pre-mixed. In some embodiments, the mRNA is electroporated into the cells. Cells following elutriation may be pooled, centrifuged and may be subjected to electroporation with mRNA using MaxCyte ATX system optimized for the said purpose. In some embodiments, optimized electroporation buffer, cell density, and/or mRNA concentration is used for each protocol for each construct.

In some embodiments, a polynucleotide may be introduced into a myeloid cell in the form of a circular RNA (circRNAs). In circular RNAs (circRNAs) the 3' and 5' ends are covalently linked. CircRNA may be delivered inside a cell using LNPs.

In some embodiments, a stable integration of transgenes into macrophages and other phagocytic cells may be accomplished via the use of a transposase and transposable elements, in particular, mRNA-encoded transposase. In one embodiment, Long Interspersed Element-1 (L1) RNAs may be contemplated for retrotransposition of the transgene and stable integration into a macrophage or a phagocytic cell. Retrotransposon may be used for stable integration of a recombinant nucleic acid encoding a phagocytic or tethering receptor (PR) fusion protein (PFP).

In some embodiments, the myeloid cell may be modified by expressing a transgene via incorporation of the transgene in a transient expression vector. In some embodiments expression of the transgene may be temporally regulated by a regulator from outside the cell. Examples include the Tet-on Tet-off system, where the expression of the transgene is regulated via presence or absence of tetracycline.

In some embodiments, the myeloid cell may be modified to develop a therapeutically effective cell by contacting the cell with a compound, which compound may be an inhibitor or an activator of a protein or enzyme within the myeloid cell.

In some embodiments, a polynucleotide encoding a chimeric antigen receptor may be introduced into an isolated myeloid cell that is obtained by the method described in the preceding section, where the chimeric antigen receptor upon expression in the myeloid cell augments an innate immune response function of the myeloid cell. In some embodiments, the chimeric antigen receptor expression can direct a myeloid cell to a specific target in vivo or in vitro. In some embodiments, the chimeric antigen receptor may increase the phagocytic potential of the myeloid cell. In some embodiments, the chimeric antigen receptor increases the immunogenicity of the myeloid cell. In some embodiments, the chimeric antigen receptor may increase augment intracellular signaling. In some embodiments, the chimeric antigen receptor may function cooperatively with one or more proteins within the cell. In some embodiments, the chimeric antigen receptor may dimerize or multimerize with a second receptor or transmembrane protein inside the myeloid cell, where the second receptor or transmembrane protein is an endogenous protein. In some embodiments, the cells are cultured ex vivo briefly after thawing or after incorporation of the nucleic acid. In some embodiments, the ex vivo culture is performed in presence of a suitable medium, that may comprise a regulated serum component, e.g., human serum albumin (HSA). In some embodiments, the ex vivo culture and manipulation may be performed in low serum containing media. In some embodiment, the serum is specifically treated for compliment deactivation. In some embodiments, the myeloid cells may be cultured ex vivo as described above, in the presence of M-CSF. In some embodiments, the myeloid cells may be cultured ex vivo as described above, in the presence of GM-CSF. In some embodiments, the myeloid cells may be cultured in the presence of one or more cytokines. In some embodiments, the myeloid cells may be cultured or manipulated ex vivo in the absence of growth factor or cytokines for a period. In some embodiments, the method provided herein comprises isolation or enrichment and manipulation of a myeloid cell in less than 72 hours, 70 hours, 65 hours, 60 hours, 55 hours, 50 hours, 45 hours, 40 hours, or 35 hours, or 30 hours, or 28 hours, or 26 hours or 24 hours. In some embodiments, the myeloid cell may be culture for less than 24 hours, or less than 20 hours or less than 16 hours, or less than 14 hours, or less than 12 hours, or less than 10 hours, or less than 8 hours, or less than 6 hours or less than about 4 hours. The myeloid cell following isolation or enrichment and manipulation may be cultured briefly and frozen till further use. In some embodiments, the myeloid cell is thawed once or at the most twice.

In some embodiments, the therapeutically competent cells are cells that have been electroporated with a recombinant nucleic acid encoding a polypeptide, frozen and thawed, culture stabilized for less than 24 hours, and wherein the cells in the cell population at the time of administration exhibit (i) greater than at least 70% viability, (ii) greater than at least 50% CD14+ and CD16− cells; and/or greater than 50% CD11b+/CD14+/CD16− cells; (iii) less than 5% CD3+ cells, less than 5% CD19+ cells, less than about 10% CD56+ cells, less than about 10% CD42b+ cells (iv) greater than 50% cells express the polypeptide encoded by the electroporated nucleic acid. In some embodiments, the therapeutically competent cells are cells that have been electroporated with a recombinant nucleic acid encoding a polypeptide, culture stabilized for less than 24 hours, frozen and thawed, and wherein the cells in the cell population at the time of administration exhibit (i) greater than at least 70% viability, (ii) greater than at least 50% CD14+ and CD16− cells; and/or greater than 50% CD11b+/CD14+/CD16− cells; (iii) less than 5% CD3+ cells, less than 5% CD19+ cells, less than about 10% CD56+ cells, less than about 10% CD42b+ cells (iv) greater than 50% cells express the polypeptide encoded by the electroporated nucleic acid. In some embodiments, the therapeutically competent cells are cells that have been culture stabilized for less than 24 hours, that have been electroporated with a recombinant nucleic acid encoding a polypeptide, frozen and thawed, and wherein the cells in the cell population at the time of administration exhibit (i) greater than at least 70% viability, (ii) greater than at least 50% CD14+ and CD16− cells; and/or greater than 50% CD11b+/CD14+/CD16− cells; (iii) less than 5% CD3+ cells, less than 5% CD19+ cells, less than about 10% CD56+ cells, less than about 10% CD42b+ cells (iv) greater than 50% cells express the polypeptide encoded by the electroporated nucleic acid. Cells must be pathogen free. In the above embodiments, the therapeutically competent cells may have been frozen and thawed not more than twice, preferably once, and may be administered within 24 hours of thawing, within 18 hours of thawing, within 8 hours of thawing, or within 2 hours of thawing. Cells are tested for quality assurance to meet the standards as described herein in the disclosure prior to administering.

Provided herein are methods for treating cancer in a subject using a pharmaceutical composition comprising engineered phagocytic cells, particularly macrophages, expressing recombinant nucleic acid encoding a phagocytic receptor (PR) fusion protein (PFP), which is specifically designed to target, attack and kill cancer cells. The PFP is also designated as a chimeric antigenic receptor for phagocytosis (CAR-P), and both the terms may be used interchangeably herein. The engineered phagocytic cells are also designated as CAR-P cells in the descriptions herein.

Cancers include, but are not limited to, T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells. In some aspects a patient or a subject having cancer, is treated with autologous cells, the method comprising, isolation or enrichment of PBMC-derived macrophages, modifying the macrophages ex vivo to generate highly phagocytic macrophages capable of tumor lysis by introducing into the macrophages a recombinant nucleic acid encoding chimeric antigenic receptor for phagocytosis which is a phagocytic receptor fusion protein (PFP), and administering the modified macrophages into the patient or the subject.

In one aspect, a subject is administered one or more doses of a pharmaceutical composition comprising therapeutic phagocytic cells, wherein the cells are allogeneic. An HLA may be matched for compatibility with the subject, and such that the cells do not lead to graft versus Host Disease, GVHD. A subject arriving at the clinic is HLA typed for determining the HLA antigens expressed by the subject, prior to determining a therapeutic or therapeutic regimen.

In some embodiments a therapeutically effective dose ranges between $10^7$ cells to $10^{12}$ myeloid cells for one infusion. The cell number may vary according to the age, body weight and other subject-related parameters and can be determined by a medical practitioner. In some embodiments, a therapeutically effective dose is about $10^7$ myeloid cells. In some embodiments, a therapeutically effective dose is about $2\times10^7$ myeloid cells. In some embodiments, a therapeutically effective dose is about $3\times10^7$ myeloid cells. In some embodiments, a therapeutically effective dose is about $4\times10^7$ myeloid cells. In some embodiments, a therapeutically effective dose is about $5\times10^7$ myeloid cells. In some embodiments, a therapeutically effective dose is about $6\times10^7$ myeloid cells. In some embodiments, a therapeutically effective dose is about $7\times10^7$ myeloid cells. In some embodiments, a therapeutically effective dose is about $8\times10^7$ myeloid cells. In some embodiments, a therapeutically effective dose is about $9\times10^7$ myeloid cells. In some embodiments, a therapeutically effective dose is about $10^8$ myeloid cells. In some embodiments, a therapeutically effective dose is about $2\times10^8$ myeloid cells. In some embodiments, a therapeutically effective dose is about $3\times10^8$ myeloid cells. In some embodiments, a therapeutically effective dose is about $4\times10^8$ myeloid cells. In some embodiments, a therapeutically effective dose is about $5\times10^8$ myeloid cells. In some embodiments, a therapeutically effective dose is about $6\times10^8$ myeloid cells. In some embodiments, a therapeutically effective dose is about $7\times10^8$ myeloid cells. In some embodiments, a therapeutically effective dose is about $8\times10^8$ myeloid cells. In some embodiments, a therapeutically effective dose is about $9\times10^8$ myeloid cells. In some embodiments, a therapeutically effective dose is about $10^9$ myeloid cells. In some embodiments, a therapeutically effective dose is about $2\times10^9$ myeloid cells. In some embodiments, a therapeutically effective dose is about $3\times10^9$ myeloid cells. In some embodiments, a therapeutically effective dose is about $4\times10^9$ myeloid cells. In some embodiments, a therapeutically effective dose is about $5\times10^9$ myeloid cells. In some embodiments, a therapeutically effective dose is about $6\times10^9$ myeloid cells. In some embodiments, a therapeutically effective dose is about $7\times10^9$ myeloid cells. In some embodiments, a therapeutically effective dose is about $8\times10^9$ myeloid cells. In some embodiments, a therapeutically effective dose is about $9\times10^9$ myeloid cells. In some embodiments, a therapeutically effective dose is about $10^{10}$ myeloid cells. In some embodiments, a therapeutically effective dose is about $5\times10^{10}$ myeloid cells. In some embodiments a therapeutically effective dose is about $10^{11}$ myeloid cells. In some embodiments a therapeutically effective dose is about $5\times10^{11}$ myeloid cells. In some embodiments a therapeutically effective dose is about $10^{12}$ myeloid cells.

Provided herein, in one aspect, one or more recombinant polynucleic acid(s) encoding one or more recombinant proteins that can be a chimeric fusion protein such as a receptor, or an engager as described herein. In some embodiments, the recombinant polynucleic acid(s) is an mRNA. In some embodiments, the recombinant polynucleic acid comprises a circRNA. In some embodiments, the recombinant polynucleic acid is encompassed in a viral vector. In some embodiments, the recombinant polynucleic acid is delivered via a viral vector.

In some embodiments, provided herein is a therapeutic composition comprising a recombinant nucleic acid encoding a chimeric fusion protein, such as a chimeric fusion receptor protein (CFP), the CFP comprises: (a) an extracellular domain comprising: (i) a scFv that specifically binds any one of the targets disclosed herein, and (ii) a hinge domain derived from CD8, a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRγ or FGRε, an interferon inducing domain, and/or (ii) a third intracellular signaling domain that: (A) comprises a PI3K recruitment domain, or (B) is derived from CD40.

In some embodiments, provided herein is therapeutic composition comprising a recombinant nucleic acid encoding a bispecific or trispecific engager as disclosed herein.

Other Therapeutic Compositions for Co-Administration

In some embodiments, the therapeutic composition further comprises an additional therapeutic agent selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity, an agent that promotes sequestration of lymphocytes in primary and/or secondary lymphoid organs, an agent that increases concentration of naïve T cells and central memory T cells in secondary lymphoid organs, and any combination thereof.

In some embodiments, the myeloid cell further comprises: (a) an endogenous peptide or protein that dimerizes with the CFP, (b) a non-endogenous peptide or protein that dimerizes with the CFP; and/or (c) a second recombinant polynucleic acid sequence, wherein the second recombinant polynucleic acid sequence comprises a sequence encoding a peptide or protein that interacts with the CFP; wherein the dimerization or the interaction potentiates phagocytosis by the myeloid cell expressing the CFP as compared to a myeloid cell that does not express the CFP.

In some embodiments, the myeloid cell exhibits (i) an increase in effector activity, cross-presentation, respiratory burst, ROS production, iNOS production, inflammatory mediators, extra-cellular vesicle production, phosphatidylinositol 3,4,5-trisphosphate production, trogocytosis with the target cell expressing the antigen, resistance to CD47 mediated inhibition of phagocytosis, resistance to LILRB1 mediated inhibition of phagocytosis, or any combination thereof; and/or (ii) an increase in expression of a IL-1, IL3, IL-6, IL-10, IL-12, IL-13, IL-23, TNFα, a TNF family of cytokines, CCL2, CXCL9, CXCL10, CXCL11, IL-18, IL-23, IL-27, CSF, MCSF, GMCSF, IL-17, IP-10, RANTES, an interferon, MHC class I protein, MHC class II protein, CD40, CD48, CD58, CD80, CD86, CD112, CD155, a TRAIL/TNF Family death receptor, TGFβ, B7-DC, B7-H2, LIGHT, HVEM, TL1A, 41BBL, OX40L, GITRL, CD30L, TIM1, TIM4, SLAM, PDL1, an MMP (e.g., MMP2, MMP7 and MMP9) or any combination thereof.

In some embodiments, the intracellular signaling domain is derived from a phagocytic or tethering receptor or wherein the intracellular signaling domain comprises a phagocytosis activation domain. In some embodiments, the intracellular signaling domain is derived from a receptor other than a phagocytic receptor selected from Megf10, MerTk, FcRalpha, or Bai1. In some embodiments, the intracellular signaling domain is derived from a protein, such as receptor (e.g., a phagocytic receptor), selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3ζ, a complement receptor, CR3, CR4, Tim-1, Tim-4 and CD169. In some embodiments, the intracellular signaling domain comprises a pro-inflammatory signaling domain. In some embodiments, the intracellular signaling domain comprises a pro-inflammatory signaling domain that is not a PI3K recruitment domain.

In some embodiments, the intracellular signaling domain is derived from an ITAM domain containing receptor.

Provided herein is a composition comprising a recombinant nucleic acid encoding a CFP, such as a phagocytic or tethering receptor (PR) fusion protein (PFP), comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a phagocytic receptor other than a phagocytic receptor selected from Megf10, MerTk, FcRα, or Bai1.

In some embodiments, upon binding of the CFP to the antigen of the target cell, the killing activity of a cell expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP. In some embodiments, the CFP functionally incorporates into a cell membrane of a cell when the CFP is expressed in the cell. In some embodiments, upon binding of the CFP to the antigen of the target cell, the killing activity of a cell expressing the CFP is increased by at least 1.1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, -fold, 17-fold, 18-fold, 19-fold, 20-fold, 25-fold, 30-fold, 40-fold, 50-fold, 75-fold, or 100-fold compared to a cell not expressing the CFP.

In some embodiments, the intracellular signaling domain is derived from a receptor, such as a phagocytic receptor, selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3ζ, CR3, CR4, Tim-1, Tim-4 and CD169. In some embodiments, the intracellular signaling domain comprises a pro-inflammatory signaling domain.

Provided herein is a composition comprising a recombinant nucleic acid encoding a CFP, such as a phagocytic or tethering receptor (PR) fusion protein (PFP), comprising: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked; and wherein the intracellular signaling domain is derived from a receptor, such as a phagocytic receptor, selected from the group consisting of TNFR1, MDA5, CD40, lectin, dectin 1, CD206, scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSC5D, CD205, CD207, CD209, RAGE, CD14, CD64, F4/80, CCR2, CX3CR1, CSF1R, Tie2, HuCRIg(L), CD64, CD32a, CD16a, CD89, Fcα receptor I, CR1, CD35, CD3, CR3, CR4, Tim-1, Tim-4 and CD169.

In some embodiments, upon binding of the CFP to the antigen of the target cell, the killing activity of a cell expressing the CFP is increased by at least greater than 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 100%, 150%, 200%, 250%, 300%, 350%, 400%, 450%, 500%, 550%, 600%, 650%, 700%, 750%, 800%, 850%, 900%, 950%, or 1000% compared to a cell not expressing the CFP. In some embodiments, the intracellular signaling domain is derived from a phagocytic receptor other than a phagocytic receptor selected from Megf10, MerTk, FcRα, or Bai1. In some embodiments, the intracellular signaling domain comprises a pro-inflammatory signaling domain. In some embodiments, the intracellular signaling domain comprises a PI3K recruitment domain, such as a PI3K recruitment domain derived from CD19. In some embodiments, the intracellular signaling domain comprises a pro-inflammatory signaling domain that is not a PI3K recruitment domain.

In some embodiments, a cell expressing the CFP exhibits an increase in phagocytosis of a target cell expressing the antigen compared to a cell not expressing the CFP. In some embodiments, a cell expressing the CFP exhibits at least a 1.1-fold increase in phagocytosis of a target cell expressing the antigen compared to a cell not expressing the CFP. In some embodiments, a cell expressing the CFP exhibits at least a 2-fold, 3-fold, 4-fold, 5-fold, 6-fold, 7-fold, 8-fold, 9-fold, 10-fold, 20-fold, 30-fold or 50-fold increase in phagocytosis of a target cell expressing the antigen compared to a cell not expressing the CFP. In some embodiments, a cell expressing the CFP exhibits an increase in production of a cytokine compared to a cell not expressing the CFP. In some embodiments, the cytokine is selected from the group consisting of IL-1, IL3, IL-6, IL-12, IL-13, IL-23, TNF, CCL2, CXCL9, CXCL10, CXCL11, IL-18, IL-23, IL-27, CSF, MCSF, GMCSF, IL17, IP-10, RANTES, an interferon and combinations thereof. In some embodiments, a cell expressing the CFP exhibits an increase in effector activity compared to a cell not expressing the CFP. In some embodiments, a cell expressing the CFP exhibits an increase in cross-presentation compared to a cell not expressing the CFP. In some embodiments, a cell expressing the CFP exhibits an increase in expression of an MHC class II protein compared to a cell not expressing the CFP. In some embodiments, a cell expressing the CFP exhibits an increase in expression of CD80 compared to a cell not expressing the CFP. In some embodiments, a cell expressing the CFP exhibits an increase in expression of CD86 compared to a cell not expressing the CFP. In some embodiments, a cell expressing the CFP exhibits an increase in expression of MHC class I protein compared to a cell not expressing the CFP. In some embodiments, a cell expressing the CFP exhibits an increase in expression of TRAIL/TNF Family death receptors compared to a cell not expressing the CFP. In some embodiments, a cell expressing the CFP exhibits an increase in expression of B7-H2 compared to a cell not expressing the CFP. In some embodiments, a cell expressing the CFP exhibits an increase in expression of LIGHT compared to a cell not expressing the CFP. In some embodiments, a cell expressing the CFP exhibits an increase in expression of HVEM compared to a cell not expressing the CFP. In some embodiments, a cell expressing the CFP exhibits an increase in expression of CD40 compared to a cell not expressing the CFP. In some embodiments, a cell expressing the CFP exhibits an increase in expression of TL1A compared to a cell not expressing the CFP. In some embodiments, a cell expressing the CFP exhibits an increase in expression of 41BBL compared to a cell not expressing the CFP. In some embodiments, a cell expressing the CFP exhibits an increase in expression of OX40L compared to a cell not expressing the CFP. In some embodiments, a cell expressing the CFP exhibits an increase in expression of GITRL death receptors compared to a cell not expressing the CFP. In some embodiments, a cell expressing the CFP exhibits an increase in expression of CD30L compared to a cell not expressing the CFP. In some embodiments, a cell expressing the CFP exhibits an increase in expression of TIM4 compared to a cell not expressing the CFP. In some embodiments, a cell expressing the CFP exhibits an increase in expression of TIM1 ligand compared to a cell not expressing the CFP. In some embodiments, a cell expressing the CFP exhibits an increase in expression of SLAM compared to a cell not expressing the CFP. In some embodiments, a cell expressing the CFP exhibits an increase in expression of CD48 compared to a cell not expressing the CFP. In some embodiments, a cell expressing the CFP exhibits an increase in expression of CD58 compared to a cell not expressing the CFP. In some embodiments, a cell expressing the CFP exhibits an increase in expression of CD155 compared to a cell not expressing the CFP. In some embodiments, a cell expressing the CFP exhibits an increase in expression of CD112 compared to a cell not expressing the CFP. In some embodiments, a cell expressing the CFP exhibits an increase in expression of PDL1 compared to a cell not expressing the CFP. In some embodiments, a cell expressing the CFP exhibits an increase in expression of B7-DC compared to a cell not expressing the CFP. In some embodiments, a cell expressing the CFP exhibits an increase in respiratory burst compared to a cell not expressing the CFP. In some embodiments, a cell expressing the CFP exhibits an increase in ROS production compared to a cell not expressing the CFP. In some embodiments, a cell expressing the CFP exhibits an increase in iNOS production compared to a cell not expressing the CFP. In some embodiments, a cell expressing the CFP exhibits an increase in iNOS production compared to a cell not expressing the CFP. In some embodiments, a cell expressing the CFP exhibits an increase in extra-cellular vesicle production compared to a cell not expressing the CFP. In some embodiments, a cell expressing the CFP exhibits an increase in trogocytosis with a target cell expressing the antigen compared to a cell not expressing the CFP. In some embodiments, a cell expressing the CFP exhibits an increase in resistance to CD47 mediated inhibition of phagocytosis compared to a cell not expressing the CFP. In some embodiments, a cell expressing the CFP exhibits an increase in resistance to LILRB1 mediated inhibition of phagocytosis compared to a cell not expressing the CFP. In some embodiments, a cell expressing the CFP exhibits an increase in phosphatidylinositol 3,4,5-trisphosphate production.

Also provided herein is a pharmaceutical composition comprising a composition described herein, such as a recombinant nucleic acid described herein, a vector described herein, a polypeptide described herein or a cell described herein; and a pharmaceutically acceptable excipient. The engineered cell is a myeloid cell. In one aspect, a pharmaceutical composition is disclosed, comprising a recombinant nucleic acid of encoding or comprising any one of the sequences of SEQ ID NOs: 1-51, or a cell comprising the recombinant nucleic acid of encoding or comprising any one of the sequences of SEQ ID NOs: 1-51, or an engineered cell comprising the recombinant nucleic acid of encoding or comprising any one of the sequences of SEQ ID NOs: 1-51; and a pharmaceutically acceptable excipient. In one embodiment the cell comprises a recombinant nucleic acid encoding an amino acid sequence comprising at least one of the sequences selected from SEQ ID NO: 36, 37, 38, 39, 40, 41, 42, 43, 44 and 45. In one embodiment the cell is a myeloid cell. In one embodiment, the cell is a mammalian cell. In one embodiment the cell is a primary human cell. In one embodiment, the cell is a human primary immune cell. In some embodiments the cell is a precursor cell or a stem cell, or an undifferentiated cell. In some embodiments the cell is obtained from a biological sample of a human subject. In some embodiments the cell is isolated from a biological sample of a human subject, and is selected for a phenotype, such as expression of cell surface markers. In one embodiment, the isolated cell is a precursor cell, a precursor myeloid cell, a cell characterized as CD14+/CD16−.

In one embodiment, the isolated cell or the engineered cell is CD14+/CD16−.

In one aspect, a pharmaceutical composition comprises an engineered cell, wherein the engineered cell is CD14+/CD16−.

In one aspect the pharmaceutical composition comprises a population of cells wherein at least 50% of the cells are CD14+/CD16−, and less than 10% cells are dendritic cells. In one embodiment, the cells exhibit high expression of CCR2. In one embodiment, the cells do not exhibit tonal signaling and activation de novo, and exhibit M0, M1 or M2 differentiation upon activation.

Provided herein is a method of treating a cancer or a viral infection in a subject comprising: administering to the subject the pharmaceutical composition comprising the recombinant nucleic acid of encoding or comprising any one of the sequences of SEQ ID NOs: 1-51, or a cell comprising the recombinant nucleic acid of encoding or comprising any one of the sequences of SEQ ID NOs: 1-51, or an engineered cell comprising the recombinant nucleic acid of encoding or comprising any one of the sequences of SEQ ID NOs: 1-51; and a pharmaceutically acceptable excipient. In some embodiments, the pharmaceutical composition comprises a population of cells wherein at least 50% of the cells are CD14+/CD16−, with less than 10% cells that are dendritic cells; and the cells exhibit high expression of CCR2. In one embodiment, the cells do not exhibit tonal signaling and activation de novo, and exhibit M0, M1 or M2 differentiation upon activation.

In some embodiments, provided herein is a therapeutic composition comprising a cell, the cell comprising a recombinant nucleic acid as described anywhere within the specification. In some embodiments, the therapeutic composition comprising a recombinant nucleic acid expressing a chimeric protein as described anywhere herein. In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

In some embodiments, the pharmaceutical composition further comprises an additional therapeutic agent. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof. In some embodiments, the pharmaceutically acceptable excipient comprises serum free media, a lipid, or a nanoparticle.

In some embodiments, the therapeutic is a recombinant nucleic acid encoding or comprising any one of the sequences of SEQ ID NOs: 1-51, that is injected systemically or topically in a subject. In some embodiments the recombinant nucleic acid comprises at least one of the sequences encoding sequences selected from SEQ ID NO: 36, 37, 38, 39, 40, 41, 42, 43, 44 and 45. In some embodiments the recombinant nucleic acid is mRNA or circRNA. In some embodiments the recombinant nucleic acid is associated with one or more lipid components in the pharmaceutical composition. The lipid components may be associated in the form of a liposome or a lipid nanoparticle. The lipid components may comprise at least one cationic lipid. One or more lipids of the pharmaceutical composition may be conjugated or modified.

Methods for Generation of Novel Chimeric Receptors Fusion Proteins (CFP) Constructs In one aspect, provided herein is a method for generating novel chimeric receptor proteins, including, for example, identification of novel domains that can be useful in augmenting a myeloid cell function such that when the fusion receptor is expressed in a myeloid cell, it functions as an effector myeloid cell of the specifications described herein. Generation of fusion proteins as described herein can be performed using well known molecular cloning techniques, and the sequences can be verified after generating of the recombinant nucleic acid.

Preparation of Recombinant Nucleic Acid Encoding A Chimeric Antigen Receptor: Recombinant nucleic acid constructs are prepared that encode chimeric antigen receptor (CAR) designed for expression in a myeloid cell and are incorporated in plasmid vectors for amplification and/or testing expression in an eukaryotic cell. The recombinant CARs are constructed using molecular cloning techniques known in the art. A recombinant CAR protein comprises an intracellular domain, a transmembrane domain and an extracellular domain. Each domain or subsection of a domain can be encoded by a nucleic acid sequence that is generated by PCR from heterologous source sequences, and pieced together by cloning individually into the vector, or ligated into a longer nucleic acid that is then inserted into the multi-cloning sites of a suitable plasmid or vector with appropriate promoter and 3'-regulatory elements for amplification. Briefly, an exemplary CAR is prepared by incorporating a nucleic sequence encoding one or more signaling domains, (e.g., a PI3Kinase recruiting domain), a nucleic acid sequence encoding the CD8 hinge and transmembrane domain, a nucleic acid sequence encoding an extracellular domain, having a sequence encoding a target antigen binding scFv at the extracellular end. Certain constructs include a FLAG peptide sequence at the extracellular end designed such that it does not pose hindrance to the scFv binding to its target antigen. These components are ligated together into a sequence that encode a fully functional transmembrane CAR. The nucleic acid subunits encoding individual domains of the recombinant protein is designed to include intervening short flexible linker sequences between two domains. The construct is ligated in a plasmid having a promoter and 3' stabilizing structural units. In one variation, the construct is placed within an Alu retrotransposon element that encodes ORF2p and has the respective 5'- and 3'-UTR sequences, a CMV promoter. The plasmid is amplified in *E. coli*, validated by sequencing or stored in (−) 80° C.

mRNA Preparation: mRNA can be prepared by in vitro transcription using the digested plasmid as template and purified to remove contaminant DNA and polyadenylated. The RNA product is purified, resuspended to 1 mg/ml in RNase free water and stored in cryovials.

Identification of useful CFP ECD, TM, ICD and antigen binding domains for the generation of novel CFPs can be done using the method described herein. Briefly, a large number of potential candidate proteins can be screened for enhanced phagocytic properties and their respective phagocytosis related intracellular signaling. The useful domains can be then used for generation of novel CFPs. The screen can be divided in two parts: A. Screening for the phagocytic receptor (PR) domains; B. Screening for the antigen binding domains.

Screening for the PR Domains:

In one embodiment, about 5,800 plasma membrane proteins were screened for their phagocytic potential following the general method described herein. J774 macrophage cells can be transiently transfected with the library of 5800 plasma proteins. High-throughput multiplex assays (ranging from 6-well plate assay set up to up to 384-well plate assay with robotic handling) can be set up to evaluate various potential functions of the plasma membranes. Exemplary assays include, but are not limited to phagocytosis assay, cytokine production assay, inflammasome activation assay, and iNOS activation assay. Exemplary simplified methods can be described in the following paragraphs. Variations of each method can be also used and can be understood by a skilled artisan. Variations of each method can be also used and can be understood by a skilled artisan. Exemplary intracellular signaling domains tested for include but are not limited to CD40-FcRγ; FcRγ-CD40; NLRP3; FcRγ-SH2-Procaspase; FcRγ-Myd88; FcRγ-IFN receptor; FcR-TNFR1; FcRγ-TNFR2; FcR-AIM2; FcRγ-TRIFN; FcRγ-Procaspase; TRIFC; RIG1; MDA5; TBK; CD64; CD16A; CD89; FcRε; SIRPβ; (two consecutive intracellular domains can be represented as hyphenated terms, for example, FcRγ-Myd88 refers to an intracellular domain comprising an FcRγ intracellular signaling domain as signaling domain 1; and an Myd88 intracellular signaling domain as signaling domain 2). The extracellular linker domains screened include but are not limited to CD64, CD16A, CD89, SIRPα, FcRε, CD8 hinge. The transmembrane domains tested include but are not limited to CD8, CD64, CD16A, CD89, FcRε, SIRPα, TNFR1 and CD40. MDA5 domains were also screened.

Phagocytosis Assay:

Antigen-linked silica or polystyrene beads ranging in diameters 1 nm, 5 nm or 10 nm were used for a screen of macrophages. Inert beads can be coated in a supported lipid bilayer and the antigens can be ligated to the lipid bilayer. J774 macrophage cell lines can be prepare d, each cell line expressing a cloned recombinant plasma membrane protein. The recombinant plasma membrane protein may also express a fluorescent tag. The cell lines can be maintained and propagated in complete RPMI media with heat inactivated serum and antibiotics (Penicillin/Streptomycin). On the day of the assay, cells can be plated at a density of $1\times10^6$ cells/ml per well in 6 well plates or in a relative proportion in 12 or 24 well plates, and incubated for 2-6 hours. The cells can be then washed once in Phosphate Buffer Saline, and the beads can be added in serum depleted or complement depleted nutrient media. Cells can be visualized by light microscopy at 30 minutes and 2 hours after addition of the beads Immunofluorescence reaction may be performed using tagged antibody, and fluorescent confocal microscopy is used to detect the interaction and co-localization of cellular proteins at engulfment. Confidence levels can be determined by Kruskal-Wallis test with Dunn's multiple comparison correction.

In some examples, dye loaded tumor cells can be fed to macrophage cell lines and phagocytosis is assessed by microscopy.

Cytokine Production:

Macrophage cell lines can be cultured as described above. In one assay, each J774 cell line expressing a plasma membrane protein is plated in multi-wells and challenged with antigen-linked beads and cytokine production was assayed by collecting the supernatants at 4 hours and 24 hours. Cytokines can be assayed from the supernatant by ELISA. In another fraction, cells can be collected at 4 and 24 hours after incubation with the beads and flow cytometry is performed for detection of cytokines. In each case, multiple cytokines can be assayed in a multiplex format, which can be selected from: IL-1α, IL-1β, IL-6, IL-12, IL-23, TNF-α, GMCSF, CXCL1, CXCL3, CXCL9, CXCL-10, MIP1-α and MIP-2. Macrophage inflammatory cytokine array kit (R&D Systems) is used.

Intracellular signaling pathway for inflammatory gene and cytokine activation can be identified by western blot analysis for phosphorylation of MAP kinases, JNK, Akt signaling pathway, Interferon activation pathway including phosphorylation and activation of STAT-1.

Functional Assays

Inflammasome Activation Assay:

Activation of NLRP3 inflammasome is assayed by ELISA detection of increased IL-1 production and detection caspase-1 activation by western blot, detecting cleavage of procaspase to generate the shorter caspase. In a microwell plate multiplex setting, Caspase-Glo (Promega Corporation) is used for faster readout of Caspase 1 activation.

iNOS Activation Assay:

Activation of the oxidative burst potential can be measured by iNOS activation and NO production using a fluorimetric assay NOS activity assay kit (AbCAM).

Cancer Cell Killing Assay:

Raji B cells can be used as cancer antigen presenting cells. Raji cells can be incubated with whole cell crude extract of cancer cells, and co-incubated with J774 macrophage cell lines. The macrophages can destroy the cells after 1 hour of infection, which can be detected by microscopy or detected by cell death assay.

Screening for High Affinity Antigen Binding Domains:

Cancer ligands can be subjected to screening for antibody light chain and heavy chain variable domains to generate extracellular binding domains for the CFPs. Human full length antibodies or scFv libraries can be screened. Also potential ligands can be used for immunizing llama for development of novel immunoglobulin binding domains in llama, and preparation of single domain antibodies.

Specific useful domains identified from the screens can be then reverse transcribed, and cloned into lentiviral expression vectors to generate the CFP constructs. A recombinant nucleic acid encoding a CFP can generated using one or more domains from the extracellular, TM and cytoplasmic regions of the highly phagocytic receptors generated from the screen. Briefly plasma membrane receptors showing high activators of pro-inflammatory cytokine production and inflammasome activation can be identified. Bioinformatics studies can be performed to identify functional domains including extracellular activation domains, transmembrane domains and intracellular signaling domains, for example, specific kinase activation sites, SH2 recruitment sites. These screened functional domains can be then cloned in modular constructions for generating novel CFPs. These can be candidate CFPs, and each of these chimeric construct is tested for phagocytic enhancement, production of cytokines and chemokines, and/or tumor cell killing in vitro and/or in vivo. A microparticle based phagocytosis assay was used to examine changes in phagocytosis. Briefly, streptavidin coupled fluorescent polystyrene microparticles (6 μm diameter) can be conjugated with biotinylated recombinantly expressed and purified cancer ligand. Myeloid cells expressing the novel CFP can be incubated with the ligand coated microparticles for 1-4 h and the amount of phagocytosis was analyzed and quantified using flow cytometry. Plasmid or lentiviral constructions of the designer CFPs can be then prepared and tested in macrophage cells for cancer cell lysis.

Method of Manufacturing Myeloid Cells from a Subject

Myeloid Cell Isolation from PBMCs:

Peripheral blood mononuclear cells can be separated from normal donor buffy coats by density centrifugation using Histopaque 1077 (Sigma). After washing, CD14+ monocytes can be isolated from the mononuclear cell fraction using CliniMACS GMP grade CD14 microbeads and LS separation magnetic columns (Miltenyi Biotec). Briefly, cells can be resuspended to appropriate concentration in PEA buffer (phosphate-buffered saline [PBS] plus 2.5 mmol/L ethylenediaminetetraacetic acid [EDTA] and human serum albumin [0.5% final volume of Alburex 20%, Octopharma]), incubated with CliniMACS CD14 beads per manufacturer's instructions, then washed and passed through a magnetized LS column After washing, the purified monocytes can be eluted from the demagnetized column, washed and re-suspended in relevant medium for culture. Isolation of CD14+ cells from leukapheresis: PBMCs can be collected by leukapheresis from cirrhotic donors who gave informed consent to participate in the study. Leukapheresis of peripheral blood for mononuclear cells (MNCs) is carried out using an Optia apheresis system by sterile collection. A standard collection program for MNC is used, processing 2.5 blood volumes. Isolation of CD14 cells is carried out using a GMP-compliant functionally closed system (CliniMACS Prodigy system, Miltenyi Biotec). Briefly, the leukapheresis product is sampled for cell count and an aliquot taken for pre-separation flow cytometry. The percentage of monocytes (CD14+) and absolute cell number can be determined, and, if required, the volume is adjusted to meet the required criteria for selection (≤20×10$^9$ total white blood cells; <400×10$^6$ white blood cells/mL; <3.5×10$^9$ CD14 cells, volume 50-300 mL). CD14 cell isolation and separation is carried out using the CliniMACS Prodigy with CliniMACS CD14 microbeads (medical device class III), TS510 tubing set and LP-14 program. At the end of the process, the selected CD14+ positive monocytes can be washed in PBS/EDTA buffer (CliniMACS buffer, Miltenyi) containing pharmaceutical grade 0.5% human albumin (Alburex), then re-suspended in TexMACS (or comparator) medium for culture.

Cell Count and Purity:

Cell counts of total MNCs and isolated monocyte fractions can be performed using a Sysmex XP-300 automated analyzer (Sysmex). Assessment of macrophage numbers is carried out by flow cytometry with TruCount tubes (Becton Dickinson) to determine absolute cell number, as the Sysmex consistently underestimated the number of monocytes. The purity of the separation is assessed using flow cytometry (FACSCanto II, BD Biosciences) with a panel of antibodies against human leukocytes (CD45-VioBlue, CD15-FITC, CD14-PE, CD16-APC), and product quality is assessed by determining the amount of neutrophil contamination (CD45int, CD15pos).

Cell Culture—Development of Cultures with Healthy Donor Samples

Optimal culture medium for macrophage differentiation is investigated, and three candidates can be tested using for the cell product. In addition, the effect of monocyte cryopreservation on deriving myeloid cells and macrophages for therapeutic use is examined. Functional assays can be conducted to quantify the phagocytic capacity of myeloid cells and macrophages and their capacity for further polarization, and phagocytic potential as described elsewhere in the disclosure.

Full-Scale Process Validation with Subject Samples

Monocytes cultured from leukapheresis from Prodigy isolation can be cultured at 2×10$^6$ monocytes per cm$^2$ and per mL in culture bags (MACS GMP differentiation bags, Miltenyi) with GMP-grade TexMACS (Miltenyi) and 100 ng/mL M-CSF. Monocytes can be cultured with 100 ng/mL GMP-compliant recombinant human M-CSF (R&D Systems). Cells can be cultured in a humidified atmosphere at 37° C., with 5% CO$_2$ for 7 days. A 50% volume media replenishment is carried out twice during culture (days 2 and 4) with 50% of the culture medium removed, then fed with fresh medium supplemented with 200 ng/mL M-CSF (to restore a final concentration of 100 ng/mL).

Cell Harvesting:

For normal donor-derived macrophages, cells can be removed from the wells at day 7 using Cell Dissociation Buffer (Gibco, Thermo Fisher) and a pastette. Cells can be resuspended in PEA buffer and counted, then approximately 1×10$^6$ cells per test can be stained for flow cytometry. Leukapheresis-derived macrophages can be removed from the culture bags at day 7 using PBS/EDTA buffer (CliniMACS buffer, Miltenyi) containing pharmaceutical grade 0.5% human albumin from serum (HAS; Alburex). Harvested cells can be resuspended in excipient composed of two licensed products: 0.9% saline for infusion (Baxter) with 0.5% human albumin (Alburex).

Flow Cytometry Characterization:

Monocyte and macrophage cell surface marker expression can be analyzed using either a FACSCanto II (BD Biosciences) or MACSQuant 10 (Miltenyi) flow cytometer. Typically, approximately 20,000 events can be acquired for each sample. Cell surface expression of leukocyte markers in freshly isolated and day 7 matured cells is carried out by incubating cells with specific antibodies (final dilution 1:100). Cells are incubated for 5 min with FcR block (Miltenyi) then incubated at 4° C. for 20 min with antibody cocktails. Cells can be washed in PEA, and dead cell exclusion dye DRAQ7 (BioLegend) is added at 1:100. Cells can be stained for a range of surface markers as follows: CD45-VioBlue, CD14-PE or CD14-PerCP-Vio700, CD163-FITC, CD169-PE and CD16-APC (all Miltenyi), CCR2-BV421, CD206-FITC, CXCR4-PE and CD115-APC (all BioLegend), and 25F9-APC and CD115-APC (eBioscience). Both monocytes and macrophages can be gated to exclude debris, doublets and dead cells using forward and side scatter and DRAQ7 dead cell discriminator (BioLegend) and analyzed using FlowJo softwcan be (Tree Star). From the initial detailed phenotyping, a panel is developed as Release Criteria (CD45-VB/CD206-FITC/CD14-PE/25F9 APC/DRAQ7) that defined the development of a functional macrophage from monocytes. Macrophages can be determined as having mean fluorescence intensity (MFI) five times higher than the level on day 0 monocytes for both 25F9 and CD206. A second panel is developed which assessed other markers as part of an Extended Panel, composed of CCR2-BV421/CD163-FITC/CD169-PE/CD14-PerCP-Vio700/CD16-APC/DRAQ7), but is not used as part of the Release Criteria for the cell product.

Monocytes and macrophages can be isolated from withdrawing a buffy coat layer formed in a sucrose gradient centrifugation sample of isolated peripheral blood cells. CD14 cells can be tested for phagocytic uptake using pHRodo beads, which fluoresce only when taken into acidic endosomes. Briefly, monocytes or macrophages can be cultured with 1-2 uL of pHRodo *Escherichia coli* bioparticles (Life Technologies, Thermo Fisher) for 1 h, then the medium is taken off and cells are washed to remove non-phagocytosed particles. Phagocytosis is assessed using an EVOS microscope (Thermo Fisher), images captured and cellular uptake of beads quantified using ImageJ software (NIH). The capacity to polarize toward defined differentiated macrophages is examined by treating day 7 macrophages with IFNγ (50 ng/mL) or IL-4 (20 ng/mL) for 48 h to induce polarization to M1 or M2 phenotype (or M[IFNγ] versus M[IL-4], respectively). After 48 h, the cells can be visualized by EVOS bright-field microscopy, then harvested and phenotyped as before. Further analysis is performed on the cytokine and growth factor secretion profile of macrophages after generation and in response to inflammatory stimuli. Macrophages can be generated from healthy donor buffy coats as before, and either left untreated or stimulated with TNFα (50 ng/mL, Peprotech) and polyinosinic:polycytidylic acid (poly I:C, a viral homolog which binds TLR3, 1 g/mL, Sigma) to mimic the conditions present in the inflamed liver, or lipopolysaccharide (LPS, 100 ng/mL, Sigma) plus IFNγ (50 IU/mL, Peprotech) to produce a maximal macrophage activation. Day 7 macrophages can be incubated overnight and supernatants collected and spun down to remove debris, then stored at −80° C. until testing. Secretome analysis is performed using a 27-plex human cytokine kit and a 9-plex matrix metalloprotease kit run on a Magpix multiplex enzyme linked immunoassay plate reader (BioRad).

Product Stability:

Various excipients can be tested during process development including PBS/EDTA buffer; PBS/EDTA buffer with 0.5% HAS (Alburex), 0.9% saline alone or saline with 0.5%

HAS. The 0.9% saline (Baxter) with 0.5% HAS excipient is found to maintain optimal cell viability and phenotype (data not shown). The stability of the macrophages from cirrhotic donors after harvest is investigated in three process optimization runs, and a more limited range of time points assessed in the process validation runs (n=3). After harvest and re-suspension in excipient (0.9% saline for infusion, 0.5% human serum albumin), the bags can be stored at ambient temperature (21-22° C.) and samples taken at 0, 2, 4, 6, 8, 12, 24, 30 and 48 h postharvest. The release criteria antibody panel is run on each sample, and viability and mean fold change from day 0 is measured from geometric MFI of 25F9 and CD206.

Statistical Analysis:

Results can be expressed as mean±SD. The statistical significance of differences is assessed where possible with the unpaired two-tailed t-test using GraphPad Prism 6. Results can be considered statistically significant when the P value is <0.05.

Also provided herein is a cell comprising a composition described herein, a vector described herein or a polypeptide described herein. In some embodiments, the cell is a phagocytic cell. In some embodiments, the cell is a stem cell derived cell, a myeloid cell, a macrophage, a dendritic cell, a lymphocyte, a mast cell, a monocyte, a neutrophil, a microglia, or an astrocyte. In some embodiments, the cell is an autologous cell. In some embodiments, the cell is an allogeneic cell. In some embodiments, the cell is an M1 cell. In some embodiments, the cell is an M2 cell. In some embodiments, the cell is an M1 macrophage cell. In some embodiments, the cell is an M2 macrophage cell. In some embodiments, the cell is an M1 myeloid cell. In some embodiments, the cell is an M2 myeloid cell.

Also provided herein is a method of treating a disease in a subject in need thereof comprising administering to the subject a pharmaceutical composition described herein. In some embodiments, the disease is cancer. In some embodiments, the cancer is a solid cancer. In some embodiments, the solid cancer is selected from the group consisting of ovarian cancer, suitable cancers include ovarian cancer, renal cancer, breast cancer, prostate cancer, liver cancer, brain cancer, lymphoma, leukemia, skin cancer, pancreatic cancer, colorectal cancer, lung cancer. In some embodiments, the cancer is a liquid cancer. In some embodiments, the liquid cancer is leukemia or a lymphoma. In some embodiments, the liquid cancer is a T cell lymphoma. In some embodiments, the disease is a T cell malignancy.

In some embodiments, the method further comprises administering an additional therapeutic agent to the subject. In some embodiments, the additional therapeutic agent is selected from the group consisting of a CD47 agonist, an agent that inhibits Rac, an agent that inhibits Cdc42, an agent that inhibits a GTPase, an agent that promotes F-actin disassembly, an agent that promotes PI3K recruitment to the PFP, an agent that promotes PI3K activity, an agent that promotes production of phosphatidylinositol 3,4,5-trisphosphate, an agent that promotes ARHGAP12 activity, an agent that promotes ARHGAP25 activity, an agent that promotes SH3BP1 activity and any combination thereof.

In some embodiments, administering comprises infusing or injecting. In some embodiments, administering comprises administering directly to the solid cancer. In some embodiments, administering comprises a circRNA-based delivery procedure, anon-particle encapsulated mRNA-based delivery procedure, an mRNA-based delivery procedure, viral-based delivery procedure, particle-based delivery procedure, liposome-based delivery procedure, or an exosome-based delivery procedure. In some embodiments, a CD4+ T cell response or a CD8+ T cell response is elicited in the subject.

Also provided herein is a method of preparing a cell, the method comprising contacting a cell with a composition described herein, a vector described herein or a polypeptide described herein. In some embodiments, contacting comprises transducing. In some embodiments, contacting comprises chemical transfection, electroporation, nucleofection, or viral infection or transduction.

Provided herein is a method for administering a therapeutic comprising any one of the compositions described above. In some embodiments, the therapeutic is administered via a parenteral administration route.

In some embodiments, the therapeutic is administered via intramuscular administration route. In some embodiments, the therapeutic is administered via intravenous administration route. In some embodiments, the therapeutic is administered via subcutaneous administration route.

Also provided herein is a method of preparing a pharmaceutical composition comprising the one or more recombinant nucleic acids described herein and a lipid in an aqueous composition described herein. In some embodiments, the composition comprises a vector described herein. In some embodiments, the lipid comprises forming a lipid nanoparticle.

EXAMPLES

Example 1. Chimeric Antigen Receptor Protein Constructs with Intracellular Interferon Activating Domains In this example, amino acid and nucleic acid sequences of the various CFP constructs described herein having inflammatory signal transducing intracellular domains are disclosed. Nucleic acid sequences as detailed below can be easily interpreted by one of skill in the art for DNA and mRNA sequences in order to provide guidance in making and using a suitable constructs or variants therefrom using commonly used molecular cloning techniques.

TABLE 3

Amino acid sequence of exemplary CFP constructs used herein are provided below

| Name | Amino Acid Sequence |
|---|---|
| HER2-<br>CD8-<br>FcR-<br>PI3K | MWLQSLLLLGTVACSISDIQMTQSPSSLSASVGDRVTITC<u>RASQDVNTAVAWY</u><br>QQKPGKAPKLLIY<u>SASFLYS</u>GVPSRFSGSRSGTDFTLTIS<u>SLQPEDFATYYCQQ</u><br>HYTTPPTFGQGTKVEIKRTGSTSGSGKPGSGEGSEVQLVESGGGLVQPGGSLR<br>LSCAASGFNIKDTYIHWVRQAPGKGLEWVARIYPTNGYTRYADSVKGRFTISA<br>DTSKNTAYLQMNSLRAEDTAVYYCSRWGGDGFYAMDVWGQGTLVTVSSSG<br>GGGSGALSNSIMYFSHFVPVFLPAKPTTTPAPRPPTPAPTIASQPLSLRPEACRP<br>AAGGAVHTRGLDIYIWAPLAGTCGVLLLSLVITLYCRRLKIQVRKAAITSYEKS |

TABLE 3-continued

Amino acid sequence of exemplary CFP constructs used herein are provided below

| Name | Amino Acid Sequence |
|---|---|
| | DGVYTGLSTRNQETYETLKHEKPPQGSGSYEDMRGILYAAPQLRSIRGQPGPN HEEDADSYENM (SEQ ID NO: 52). |
| HER2-CD8-FcR-41BB | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAA ADYKDDDDKSGGGGSALSNSIMYFSHFVPVFLPAKPTTTPAPRPPTPAPTIAS QPLSLRPEACRPAAGGAVHTRGLDIYIWAPLAGTCGVLLLSLVITLYCRRLKIQ VRKAAITSYEKSDGVYTGLSTRNQETYETLKHEKPPQGSGSKKLLYIFKQPFM RPVQTTQEEDGCSCRFPEEEEGGCEL (SEQ ID NO: 53). |
| HER2-CD8-41BB-FcR | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAA ADYKDDDDKSGGGGSALSNSIMYFSHFVPVFLPAKPTTTPAPRPPTPAPTIAS QPLSLRPEACRPAAGGAVHTRGLDIYIWAPLAGTCGVLLLSLVITLYCKRGRK KLLYIFKQPFMRPVQTTQEEDGCSCRFPEEEEGGCELGSGSLKIQVRKAAITSY EKSDGVYTGLSTRNQETYETLKHEKPPQ (SEQ ID NO: 54). |
| HER2-CD68-CD40-FcR | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAAILL PLIIGLILLGLLALVLIAFAIIKKVAKKPTNKAPHPKQEPQEINFPDDLPGSN TAAPVQETLHGCQPVTQEDGKESRISVQERQGSRLKIQVRKAAITSYEKSDGV YTGLSTRNQETYETLKHEKPPQ (SEQ ID NO: 55). |
| HER2-CD68-FcR-MDA5 | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAAIL LPLIIGLILLGLLALVLIAFAIIRRLKIQVRKAAITSYEKSDGVYTGLSTRNQE TYETLKHEKPPQGSGSGSMSNGYSTDENFRYLISCFRARVKMYIQVEPVLDYL TFLPAEVKEQIQRTVATSGNMQAVELLLSTLEKGVWHLGWTREFVEALRRTG SPLAARYMNPELTDLPSPSFENAHDEYLQLLNLLQPTLVDKLLVRDVLDKCM EEELLTIEDRNRIAAAENNGNESGVRELLKRIVQKENWFSAFLNVLRQTGNNE LVQELTGSDCSESNAEIEN (SEQ ID NO: 56). |
| HER2-CD64 | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAA AGSQLPTPVWFHVLFYLAVGIMFLVNTVLWVTIRKELKRKKKWDLEISLDSG HEKKVISSLQEDRHLEEELKCQEQKEEQLQEGVHRKEPQGAT (SEQ ID NO: 57). |
| HER2-CD89 | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSAA AGSDSIHQDYTTQNLIRMAVAGLVLVALLAILVENWHSHTALNKEASADVAE PSWSQQMCQPGLTFARTPSVCK (SEQ ID NO: 58). |
| HER2-CD68-CD40-FcR-PI3K | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAGSDSIHQDYTTQNLIRMAVAGLVLVALLAILVENWHSHTALNKEA SADVAEPSWSQQMCQPGLTFARTPSVCKGTKKVAKKPTNKAPHPKQEPQEIN FPDDLPGSNTAAPVQETLHGCQPVTQEDGKESRISVQERQGSYEDMRGILYAA PQLRSIRGQPGPNHEEDADSYENM (SEQ ID NO: 59). |

TABLE 3-continued

Amino acid sequence of exemplary CFP constructs used herein are provided below

| Name | Amino Acid Sequence |
|---|---|
| HER2-CD68-FcR-PI3K-MDA5 | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSMSNGYSTDENFRYLISCFRARVKMYIQVEPVLDYLTFLPAEVKEQI QRTVATSGNMQAVELLLSTLEKGVWHLGWTREFVEALRRTGSPLAARYMNP ELTDLPSPSFENAHDEYLQLLNLLQPTLVDKLLVRDVLDKCMEEELLTIEDRN RIAAAENNGNESGVRELLKRIVQKENWFSAFLNVLRQTGNNELVQELTGSDC SESNAEIEN (SEQ ID NO: 60). |
| HER2-CD68-FcR-PI3K-RIGI | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSMTTEQRRSLQAFQDYIRKTLDPTYILSYMAPWFREEEVQYIQAEKN NKGPMEAATLFLKFLLELQEEGWFRGFLDALDHAGYSGLYEAIESWDFKKIE KLEEYRLLLKRLQPEFKTRIIPTDIISDLSECLINQECEEILQICSTKGMMAGAEK LVECLLRSDKENWPKTLKLALEKERNKFSELW (SEQ ID NO: 61). |
| HER2-FcR-PI3K-Myd88-CD68 | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSAAGGPGAGSAAPVSSTSSLPLAALNMRVRRRLSLFLNVRTQVAAD WTALAEEMDFEYLEIRQLETQADPTGRLLDAWQGRPGASVGRLLELLTKLGR DDVLLELGPSIEEDCQKYILKQQQEEAEKPLQVAAVDSSVPRTAELAGITTLDD PLG (SEQ ID NO: 62). |
| HER2-CD68tm-FcR-PI3K-STING | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSGGG GSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSVTVGSLKTSAVPSTSTMSQEPELLISGMEKPLPLRTDFS (SEQ ID NO: 63). |
| HER2-CD68tm-FcR-PI3K-MAVS | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSPSYPMPVQETQAPESGGGSSSAWLDSSSENRGLGSELSKPGVLASQ VDSPFSGCFEDLAISASTSLGMG (SEQ ID NO: 64). |
| HER2-CD68tm-FcR-PI3K-TRIF long | MWLQSLLLLGTVACSISDIQMTQSPSSLSASVGDRVTITCRASQDVNTAVAWY QQKPGKAPKLLIYSASFLYSGVPSRFSGSRSGTDFTLTISSLQPEDFATYYCQQ HYTTPPTFGQGTKVEIKRTGSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGGDGFYAMDVWGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSGSIRTLQSNLGCLPPSSALPSGTRSLPRPIDGVSDWSQGCSLRSTGSP ASLASNLEISQSPTMPFLSLHRSPHGPSKLCDDPQASLVPEPVPGGCQEPEEMS WPPSGEIASPPELPSSPPPGLPEVAPDATSTGLPDTPAAPETSTNYPVECTEGSA GPQSLPLPILEPVKNPCSVKDQTPLQLSVEDTTSPNTKPCPPTPTTPETSPPPPPP PPSSTPCSAHLTPSSLFPSSLESSSEQKFYNFVILHARADEHIALRVREKLEALG VPDGATFCEDFQVPGRGELSCLQDAIDHSAFIILLLTSNFDCRLSLHQVNQAM MSNLTRQGSPDCVIPFLPLESSPAQLSSDTASLLSGLVRLDEHSQIFARKVANTF KPHRLQARKAMWRKEQD (SEQ ID NO: 65). |

TABLE 3-continued

Amino acid sequence of exemplary CFP constructs used herein are provided below

| Name | Amino Acid Sequence |
|---|---|
| HER2-CD68tm-FcR-PI3K-TRIF short | MWLQSLLLLGTVACSISDIQMTQSPSSLSASVGDRVTITC<u>RASQDVNTAVAWY</u> QQKPGKAPKLLIY<u>SASFLYS</u>GVPSRFSGSRSGTDFTLTISSLQPEDFATYYC<u>QQ</u> <u>HYTTPPT</u>FGQGTK<u>VEIKRT</u>GSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGG<u>DGFYAMDV</u>WGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSGSIRTLQSNLGCLPPSSALPSGTRSLPRPIDGVSDWSQGCSLRSTGSP ASLASNLEISQSPTMPFLSLHRSPHGPSKLCDDPQASLVPEPVPGGCQEPEEMS WPPSGEIASPPELPSSPPPGLPEVAPDATSTGLPDTPAAPETSTNYPVECTEGSA GPQSLPLPILEPVKNPCSVKDQTPLQLSVEDTTSPNTKPCPPTPTTPETSPPPPPP PPSSTPCSAHLTPSSLFPSSLE (SEQ ID NO: 66). |
| HER2-CD68tm-FcR-PI3K-TASL | MWLQSLLLLGTVACSISDIQMTQSPSSLSASVGDRVTITC<u>RASQDVNTAVAWY</u> QQKPGKAPKLLIY<u>SASFLYS</u>GVPSRFSGSRSGTDFTLTISSLQPEDFATYYC<u>QQ</u> <u>HYTTPPT</u>FGQGTK<u>VEIKRT</u>GSTSGSGKPGSGEGSEVQLVESGGGLVQPGGSLR LSCAASGFNIKDTYIHWVRQAPGKGLEWVARIYPTNGYTRYADSVKGRFTISA DTSKNTAYLQMNSLRAEDTAVYYCSRWGG<u>DGFYAMDV</u>WGQGTLVTVSSSG GGGSAAAILLPLIIGLILLGLLALVLIAFAIIRRLKIQVRKAAITSYEKSDGVYTG LSTRNQETYETLKHEKPPQGSGSYEDMRGILYAAPQLRSIRGQPGPNHEEDAD SYENMGSMSTEITEISTPSLHISQYSNVNP (SEQ ID NO: 67). |

HER2-targeted PFP was designed and constructed using recombinant DNA techniques. The PFP has an extracellular domain comprising a signal peptide fused to an scFv containing a heavy chain variable domain linked to a light chain variable domain that binds to HER2 on a target cell, attached to a CD8 alpha chain hinge and CD8 alpha chain TM domain via a short linker. The TM domain is fused at the cytosolic end with an FcγR gamma intracellular domain, and a MDA5 recruitment domain separated by a short linker. Linkers are marked as italicized. The construct was sequenced. The sequence is provided below. The intracellular signaling domain of MDA5 is marked as bold.

HER2-FcR-MDA5 chimeric fused protein (CFP) amino acid sequence (CDR sequences are underlined):

```
                                       (SEQ ID NO: 47)
MWLQSLLLLGTVACSISEIQLVQSGGGLVKPGGSVRISCA

ASGYTFTNYGMNWVRQAPGKGLEWMGWINTHTGEPTYADS

FKGRFTFSLDDSKNTAYLQINSLRAEDTAVYFCTRRGYDW

YFDVWGQGTTVTVSSGGGGSGGGGSGGGGSDIQMTQSPSS

LSASVGDRVTITCRASQDINSYLSWFQQKPGKAPKTLIYR

ANRLESGVPSRFSGSGSGTDYTLTISSLQYEDFGIYYCQQ

YDESPWTFGGGTKLEIKSGGGGSGALSNSIMYFSHFVPVF

LPAKPTTTPAPRPPTPAPTIASQPLSLRPEACRPAAGGAV

HTRGLDIYIWAPLAGTCGVLLLSLVITLYCRLKIQVRKAA

ITSYEKSDGVYTGLSTRNQETYETLKHEKPPQGSGSMSNG

YSTDENFRYLISCFRARVKMYIQVEPVLDYLTFLPAEVKE

QIQRTVATSGNMQAVELLLSTLEKGVWHLGWTREFVEALR

RTGSPLAARYMNPELTDLPSPSFENAHDEYLQLLNLLQPT

LVDKLLVRDVLDKCMEEELLTIEDRNRIAAAENNGNESGV
```

-continued

RELLKRIVQKENWFSAFLNVLRQTGNNELVQELTGSDCSE

SNAEIEN.

An exemplary polynucleotide sequence encoding SEQ ID NO: 47 may comprise a sequence:

```
                                       (SEQ ID NO: 48)
atgtggctgcagagcctgctgctgctgggcaccgtgg cgtgcagcattagcgaaattcagctggtgcagagcg gcggcggcctggtgaaaccgggcggcagcgtgcgca ttagctgcgcggcgagcggctatacctttaccaact atggcatgaactgggtgcgccaggcgccgggcaaag gcctggaatggatgggctggattaacacccataccg gcgaaccgacctatgcggatagctttaaaggccgct ttacctttagcctggatgatagcaaaaacaccgcgt atctgcagattaacagcctgcgcgcggaagataccg cggtgtattttgcacccgccgcggctatgattggt attttgatgtgtggggccagggcaccaccgtgaccg tgagcagcggcggcggcggcagcggcggcggcggca gcggcggcggcggcagcgatattcagatgacccaga gcccgagcagcctgagcgcgagcgtgggcgatcgcg tgaccattacctgccgcgcgagccaggatattaaca gctatctgagctggtttcagcagaaaccgggcaaag cgccgaaaaccctgatttatcgcgcgaaccgcctgg aaagcggcgtgccgagccgctttagcggcagcggca gcggcaccgattatacccctgaccattagcagcctgc
```

-continued agtatgaagattttggcatttattattgccagcagt
atgatgaaagcccgtggacctttggcggcggcacca
aactggaaattaaaagcggcggcggcggcagcggcg
cgctgagcaacagcattatgtattttagccattttg
tgccggtgtttctgccggcgaaaccgaccaccaccc
cggcgccgcgcccgccgaccccggcgccgaccattg
cgagccagccgctgagcctgcgcccggaagcgtgcc
gcccggcggggcggcgcggtgcatacccgcggcct
ggatatttatatttgggcgccgctggcgggcacctg
cggcgtgctgctgctgagcctggtgattaccctgta
ttgccgcctgaaaattcaggtgcgcaaagcggcgat
taccagctatgaaaaagcgatggcgtgtataccgg
cctgagcacccgcaaccaggaaacctatgaaaccct
gaaacatgaaaaccgccgcagggcagcggcagcat
gagcaacggctatagcaccgatgaaaactttcgcta
tctgattagctgctttcgcgcgcgcgtgaaaatgta
tattcaggtggaaccggtgctggattatctgacctt
tctgccggcggaagtgaaagaacagattcagcgcac
cgtggcgaccagcggcaacatgcaggcggtggaact
gctgctgagcaccctggaaaaggcgtgtggcatct
gggctggaccgcgaatttgtggaagcgctgcgccg
caccggcagcccgctggcggcgcgctatatgaaccc
ggaactgaccgatctgccgagcccgagctttgaaaa
cgcgcatgatgaatatctgcagctgctgaacctgct
gcagccgaccctggtggataaactgctggtgcgcga
tgtgctggataaatgcatggaagaagaactgctgac
cattgaagatcgcaaccgcattgcggcggcggaaaa
caacggcaacgaaagcggcgtgcgcgaactgctgaa
acgcattgtgcagaaagaaaactggtttagcgcgtt
tctgaacgtgctgcgccagaccggcaacaacgaact
ggtgcaggaactgaccggcagcgattgcagcgaaag
caacgcggaaattgaaaac An exemplary nucleic acid sequence encoding a HER2-CD8hinge-FcR-MDA5 as disclosed herein, comprises a sequence as follows:

(SEQ ID NO: 68)
ATGTGGCTGCAGTCTCTGCTGCTGCTGGGAACAGT

GGCCTGCAGCATCAGCGACATCCAGATGACACAGA

GCCCTAGCAGCCTGTCTGCCTCTGTGGGCGATAGA

GTGACCATCACCTGTAGAGCCAGCCAGGATGTGAA

TACCGCCGTGGCCTGGTATCAGCAGAAGCCTGGAA

AAGCCCCTAAGCTGCTGATCTACAGCGCCAGCTTT

CTGTACAGCGGCGTGCCAAGCAGATTCAGCGGCAG

CAGATCTGGCACCGACTTCACCCTGACCATCTCTA

GCCTGCAGCCTGAGGACTTCGCCACCTACTACTGC

CAGCAGCACTACACCACACCTCCAACCTTTGGCCA

GGGCACCAAGGTGGAAATCAAGAGAACAGGCAGCA

CCAGCGGCTCTGGAAAGCCTGGATCTGGCGAAGGA

TCTGAGGTGCAGCTGGTTGAATCTGGCGGAGGACT

TGTTCAGCCTGGCGGCTCTCTGAGACTGTCTTGTG

CCGCCAGCGGCTTCAACATCAAGGACACCTACATC

CACTGGGTCCGACAGGCCCCTGGAAAGGGACTTGA

ATGGGTCGCCAGAATCTACCCCACCAACGGCTACA

CCAGATACGCCGATAGCGTGAAGGGCAGATTCACC

ATCAGCGCCGACACCAGCAAGAACACCGCCTACCT

GCAGATGAACAGCCTGAGAGCCGAGGACACCGCCG

TGTACTACTGTTCTAGATGGGGAGGCGACGGCTTC

TACGCCATGGATGTTGGGGACAGGGCACCCTGGT

CACAGTTTCTTCTAGCGGAGGCGGAGGAAGCGGAG

CCCTGAGCAATAGCATCATGTACTTCAGCCACTTC

GTGCCCGTGTTTCTGCCCGCCAAGCCTACAACAAC

ACCCGCTCCTAGACCACCTACACCAGCTCCTACAA

TCGCCAGCCAGCCTCTGTCTCTCAGACCTGAAGCC

TGTAGACCTGCAGCTGGCGGAGCTGTGCATACCAG

AGGCCTGGATATCTACATTTGGGCCCCTCTGGCTG

GCACATGTGGCGTTCTGCTGCTCTCTCTGGTCATC

ACCCTGTACTGCAGACGGCTGAAGATCCAAGTGCG

GAAGGCCGCCATCACCAGCTACGAGAAATCTGATG

GCGTGTACACCGGCCTGAGCACCCGGAATCAAGAA

ACCTACGAGACACTGAAGCACGAGAAGCCTCCACA

AATGAGTAACGGTTACAGCACGGACGAGAACTTCC

GCTATCTGATTAGCTGTTTCCGGGCTCGCGTAAAG

ATGTATATCCAGGTAGAGCCAGTGCTGGATTACCT

GACGTTCCTCCCTGCCGAGGTGAAGGAACAGATTC

AGCGAACAGTAGCGACATCAGGAAATATGCAAGCG

GTGGAGTTGCTGCTCTCTACCCTCGAAAAAGGTGT

TTGGCACCTGGGATGGACACGGGAATTCGTCGAAG

CTCTCAGGCGAACTGGATCTCCTCTTGCCGCTAGG

TACATGAACCCGGAACTCACTGATTTGCCGTCACC

GTCTTTCGAGAACGCCCATGATGAGTATCTCCAGC

TTCTGAATTTGCTTCAGCCTACCTTGGTCGACAAA

CTGTTGGTTCGGGACGTTTTGGACAAGTGTATGGA

```
GGAGGAGCTGCTGACCATCGAGGACAGAAACCGGA

TAGCTGCGGCAGAGAACAATGGCAACGAGTCAGGA

GTTCGGGAGTTGTTGAAGAGGATAGTGCAAAAGGA

GAATTGGTTCAGCGCTTTCCTTAACGTACTCCGAC

AGACAGGCAACAATGAACTCGTACAAGAGTTGACA

GGGTCAGATTGCAGTGAATCCAACGCCGAAATTGA

AAAT
```

TABLE 4

Partial nucleotide sequences denoting component sequences encoding the individual domains of the CFP: HER2-CD8hinge-FcR-MDA5 (e.g., from full length sequence SEQ ID NO: 68).

| Sequence encoding | Nucleic Acid Sequence |
|---|---|
| GMCSF signal peptide | ATGTGGCTGCAGTCTCTGCTGCTGC TGGGAACAGTGGCCTGCAGCATCAG C (SEQ ID NO: 69) |
| HER2 scFv | GACATCCAGATGACACAGAGCCCTA GCAGCCTGTCTGCCTCTGTGGGCGA TAGAGTGACCATCACCTGTAGAGCC AGCCAGGATGTGAATACCGCCGTGG CCTGGTATCAGCAGAAGCCTGGAAA AGCCCCTAAGCTGCTGATCTACAGC GCCAGCTTTCTGTACAGCGGCGTGC CAAGCAGATTCAGCGGCAGCAGATC TGGCACCGACTTCACCCTGACCATC TCTAGCCTGCAGCCTGAGGACTTCG CCACCTACTACTGCCAGCAGCACTA CACCACACCTCCAACCTTTGGCCAG GGCACCAAGGTGGAAATCAAGAGAA CAGGCAGCACCAGCGGCTCTGGAAA GCCTGGATCTGGCGAAGGATCTGAG GTGCAGCTGGTTGAATCTGGCGGAG GACTTGTTCAGCCTGGCGGCTCTCT GAGACTGTCTTGTGCCGCCAGCGGC TTCAACATCAAGGACACCTACATCC ACTGGGTCCGACAGGCCCCTGGAAA GGGACTTGAATGGGTCGCCAGAATC TACCCCACCAACGGCTACACCAGAT ACGCCGATAGCGTGAAGGGCAGATT CACCATCAGCGCCGACACCAGCAAG AACACCGCCTACCTGCAGATGAACA GCCTGAGAGCCGAGGACACCGCCGT GTACTACTGTTCTAGATGGGGAGGC GACGGCTTCTACGCCATGGATGTTT GG GGACAGGGCACCCTGGTCACAGTTT CTTCT (SEQ ID NO: 70) |
| Linker | AGCGGAGGCGGAGGAAGCGGA (SEQ ID NO: 71) |
| CD8 hinge and trans-membrane region | GCCCTGAGCAATAGCATCATGTACT TCAGCCACTTCGTGCCCGTGTTTCT GCCCGCCAAGCCTACAACAACACCC GCTCCTAGACCACCTACACCAGCTC CTACAATCGCCAGCCAGCCTCTGTC TCTCAGACCTGAAGCCTGTAGACCT GCAGCTGGCGGAGCCTGTGCATCCA GAGGCCGGATATCTACATTTGGGC CCCTCTGGCTGGCACATGTGGCGTT CTGCTGCTCTCTCTGGTCATCACCC TGTACTGC (SEQ ID NO: 72) |

TABLE 4-continued

Partial nucleotide sequences denoting component sequences encoding the individual domains of the CFP: HER2-CD8hinge-FcR-MDA5 (e.g., from full length sequence SEQ ID NO: 68).

| Sequence encoding | Nucleic Acid Sequence |
|---|---|
| FCR ICD | AGACGGCTGAAGATCCAAGTGCGGA AGGCCGCCATCACCAGCTACGAGAA ATCTGATGGCGTGTACACCGGCCTG AGCACCCGGAATCAAGAAACCTACG AGACACTGAAGCACGAGAAGCCTCC ACAA(SEQ ID NO: 73) |
| MDA5 ICD | ATGAGTAACGGTTACAGCACGGACG AGAACTTCCGCTATCTGATTAGCTG TTTCCGGGCTCGCGTAAAGATGTAT ATCCAGGTAGAGCCAGTGCTGGATT ACCTGACGTTCCTCCCTGCCGAGGT GAAGGAACGATTCAGCGAACAGTA GCGACATCAGGAAATATGCAAGCGG TGGAGTTGCTGCTCTCTACCCTCGA AAAAGGTGTTTGGCACCTGGGATGG ACACGGGAATTCGTCGAAGCTCTCA GGCGAACTGGATCTCCTCTTGCCGC TAGGTACATGAACCCGGAACTCACT GATTTGCCGTCACCGTCTTTCGAGA ACGCCCATGATGAGTATCTCCAGCT TCTGAATTTGCTTCAGCCTACCTTG GTCGACAAACTGTTGGTTCGGGACG TTTTGGACAAGTGTATGGAGGAGGA GCTGCTGACCATCGAGGACAGAAAC CGGATAGCTGCGGCAGAGAACAATG GCAACGAGTCAGGAGTTCGGGAGTT GTTGAAGAGGATAGTGCAAAAGGAG AATTGGTTCAGCGCTTTCCTTAACG TACTCCGACAGACAGGCAACAATGA ACTCGTACAAGAGTTGACAGGGTCA GATTGCAGTGAATCCAACGCCGAAA TTGAAAAT (SEQ ID NO: 74) |

Additional anti-HER2 binding sequence may comprise a VHH domain comprising a sequence:

(SEQ ID NO: 107)
EVQLVESGGGLVQAGGSLRLSCAASGITFSINTMGWYRQAPGKQRELVAL

ISSIGDTYYADSVKGRFTISRDNAKNTVYLQMNSLKPEDTAVYYCKRFRT

AAQGTDYWGQGTQVTVSS.

An additional exemplary CFP construct using MDA5 intracellular domain can be a CD5-FcR-MDA5 construct (SEQ ID NO: 4), having the amino acid sequence:

(SEQ ID NO: 4)
MWLQSLLLLGTVACSISEIQLVQSGGGLVKPGGSVRISCAASGYTFTNYG

MNWVRQAPGKGLEWMGWINTHTGEPTYADSFKGRFTFSLDDSKNTAYLQI

NSLRAEDTAVYFCTRRGYDWYFDVWGQGTTVTVSSGGGGSGGGGSGGGGS

DIQMTQSPSSLSASVGDRVTITCRASQDINSYLSWFQQKPGKAPKTLIYR

ANRLESGVPSRFSGSGSGTDYTLTISSLQYEDFGIYYCQQYDESPWTFGG

GTKLEIKSGGGGSGALSNSIMYFSHFVPVFLPAKPTTTPAPRPPTPAPTI

ASQPLSLRPEACRPAAGGAVHTRGLDIYIWAPLAGTCGVLLLSLVITLYC

RLKIQVRKAAITSYEKSDGVYTGLSTRNQETYETLKHEKPPQGSGSMSNG

YSTDENFRYLISCFRARVKMYIQVEPVLDYLTFLPAEVKEQIQRTVATSG

NMQAVELLLSTLEKGVWHLGWTREFVEALRRTGSPLAARYMNPELTDLPS

PSFENAHDEYLQLLNLLQPTLVDKLLVRDVLDKCMEEELLTIEDRNRIAA

AENNGNESGVRELLKRIVQKENWFSAFLNVLRQTGNNELVQELTGSDCSE

SNAEIEN

In this example, a CD5-targeted CFP was constructed using known molecular biology techniques having an intracellular domain comprising two caspase activation (CARD) domains of MDA-5 intracellular domain sequence (Tandem CARD ICD sequence shown in bold letters).

An exemplary polynucleotide sequence encoding a CD5-FcR-MDA5 may comprise a sequence:

(SEQ ID NO: 49)
atgtggctgcagagcctgctgctgctgggcaccgtggcgtgcagcattag cgaaattcagctggtgcagagcggcggcggcctggtgaaaccgggcggca gcgtgcgcattagctgcgcggcgagcggctataccttaccaactatggc atgaactgggtgcgccaggcgccgggcaaaggcctggaatggatgggctg gattaacacccataccggcgaaccgacctatgcggatagctttaaaggcc gctttacctttagcctggatgatagcaaaaacaccgcgtatctgcagatt aacagcctgcgcgcggaagataccgcggtgtattttgcacccgccgcgg ctatgattggtattttgatgtgtggggccagggcaccaccgtgaccgtga gcagcggcggcggcggcagcggcggcggcggcagcggcggcggcggcagc gatattcagatgacccagagcccgagcagcctgagcgcgagcgtgggcga tcgcgtgaccattacctgccgcgcgagccaggatattaacagctatctga gctggtttcagcagaaaccgggcaaagcgccgaaaaccctgatttatcgc gcgaaccgcctggaaagcggcgtgccgagccgctttagcggcagcggcag cggcaccgattataccctgaccattagcagcctgcagtatgaagattttg gcatttattattgccagcagtatgatgaaagcccgtggacctttggcggc ggcaccaaactggaaattaaaagcggcggcggcggcagcggcgcgctgag caacagcattatgtatttagccattttgtgccggtgtttctgccggcga aaccgaccaccacccggcgccgcgcccgccgaccccggcgccgaccatt gcgagccagccgctgagcctgcgcccggaagcgtgccgcccggcggcggg cggcgcggtgcatacccgcggcctggatatttatatttgggcgccgctgg cgggcacctgcggcgtgctgctgctgagcctggtgattaccctgtattgc cgcctgaaaattcaggtgcgcaaagcggcgattaccagctatgaaaaaag cgatggcgtgtataccggcctgagcacccgcaaccaggaaacctatgaaa ccctgaaacatgaaaaaccgccgcagggcagcggcagcatgagcaacggc tatagcaccgatgaaaactttcgctatctgattagctgctttcgcgcgcg cgtgaaaatgtatattcaggtggaaccggtgctggattatctgacctttc tgccggcggaagtgaaagaacagattcagcgcaccgtggcgaccagcggc aacatgcaggcggtggaactgctgctgagcacccctggaaaaggcgtgtg gcatctgggctggacccgcgaatttgtggaagcgctgcgccgccaccgca An exemplary nucleic acid sequence encoding a CD5-CD8hinge-CD8TM-FcR-MDA5 as disclosed herein, comprises a sequence as follows:

(SEQ ID NO: 75)
ATGTGGCTGCAGTCTCTGCTGCTGCTGGGAACAGTGGCCTGCAGCATCAG

CGAGATCCAGCTGGTTCAGTCTGGCGGCGGACTTGTGAAACCTGGCGGAT

CTGTCAGAATCAGCTGTGCCGCCAGCGGCTACACCTTCACCAACTACGGC

ATGAACTGGGTCCGACAGGCCCCTGGAAAAGGCCTTGAGTGGATGGGCTG

GATCAATACCCACACCGGCGAGCCAACCTACGCCGATAGCTTTAAGGGCA

GATTCACCTTCAGCCTGGACGACAGCAAGAACACCGCCTACCTGCAGATC

AACAGCCTGAGAGCCGAGGATACCGCCGTGTACTTCTGCACCAGAAGAGG

CTACGACTGGTACTTCGATGTGTGGGGCCAGGGCACCACAGTGACAGTTT

CTAGCGGAGGCGGAGGATCAGGTGGCGGTGGATCTGGCGGTGGTGGCTCT

GATATCCAGATGACACAGAGCCCTAGCAGCCTGTCTGCCTCTGTGGGCGA

TAGAGTGACCATCACCTGTAGAGCCAGCCAGGACATCAACAGCTACCTGA

GCTGGTTCCAGCAGAAGCCTGGCAAGGCCCCTAAGCACTGATCTACCGG

GCCAACAGACTGGAAAGCGGCGTGCCAAGCAGATTTTCTGGCAGCGGCTC

TGGCACCGACTACACCCTGACAATCAGCAGCCTGCAGTACGAGGACTTCG

GCATCTACTACTGCCAGCAGTACGACGAGAGCCCTTGGACATTTGGCGGA

GGCACCAAGCTGGAAATCAAAAGCGGAGGCGGAGGAAGCGGAGCCCTGAG

CAATAGCATCATGTACTTCAGCCACTTCGTGCCCGTGTTTCTGCCCGCCA

AGCCTACAACAACACCCGCTCCTAGACCACCTACACCAGCTCCTACAATC

GCCAGCCAGCCTCTGTCTCTCAGACCTGAAGCCTGTAGACCTGCAGCTGG

CGGAGCTGTGCATACCAGAGGCCTGGATATCTACATTTGGGCCCCTCTGG

CTGGCACATGTGGCGTTCTGCTGCTCTCTCTGGTCATCACCCTGTACTGC

AGACGGCTGAAGATCCAAGTGCGGAAGGCCGCCATCACCAGCTACGAGAA

ATCTGATGGCGTGTACACCGGCCTGAGCACCCGGAATCAAGAAACCTACG

AGACACTGAAGCACGAGAAGCCTCCACAAATGAGTAACGGTTACAGCACG

GACGAGAACTTCCGCTATCTGATTAGCTGTTTCCGGGCTCGCGTAAAGAT

GTATATCCAGGTAGAGCCAGTGCTGGATTACCTGACGTTCCTCCCTGCCG

AGGTGAAGGAACAGATTCAGCGAACAGTAGCGACATCAGGAAATATGCAA

GCGGTGGAGTTGCTGCTCTCTACCCTCGAAAAAGGTGTTTGGCACCTGGG

ATGGACACGGGAATTCGTCGAAGCTCTCAGGCGAACTGGATCTCCTCTTG gcccgctggcggcgcgctatatgaacccggaactgaccgatctgccgagc ccgagctttgaaaacgcgcatgatgaatatctgcagctgctgaacctgct gcagccgaccctggtggataaactgctggtgcgcgatgtgctggataaat gcatggaagaagaactgctgaccattgaagatcgcaaccgcattgcggcg gcggaaaacaacggcaacgaaagcggcgtgcgcgaactgctgaaacgcat tgtgcagaaagaaaactggtttagcgcgtttctgaacgtgctgcgccaga ccggcaacaacgaactggtgcaggaactgaccggcagcgattgcagcgaa agcaacgcggaaattgaaaac.

```
-continued
CCGCTAGGTACATGAACCCGGAACTCACTGATTTGCCGTCACCGTCTTTC

GAGAACGCCCATGATGAGTATCTCCAGCTTCTGAATTTGCTTCAGCCTAC

CTTGGTCGACAAACTGTTGGTTCGGGACGTTTTGGACAAGTGTATGGAGG

AGGAGCTGCTGACCATCGAGGACAGAAACCGGATAGCTGCGGCAGAGAAC

AATGGCAACGAGTCAGGAGTTCGGGAGTTGTTGAAGAGGATAGTGCAAAA

GGAGAATTGGTTCAGCGCTTTCCTTAACGTACTCCGACAGACAGGCAACA

ATGAACTCGTACAAGAGTTGACAGGGTCAGATTGCAGTGAATCCAACGCC

GAAATTGAAAAT
```

An additional exemplary CFP construct is CD5-FcR-TNFR1 construct, having an amino acid sequence (CDR sequences are underlined):

(SEQ ID NO: 50)
MWLQSLLLLGTVACSISEIQLVQSGGGLVKPGGSVRISCAASGYTFTNYG

MNWVRQAPGKGLEWMGWINTHTGEPTYADSFKGRFTFSLDDSKNTAYLQI

NSLRAEDTAVYFCTRRGYDWYFDVWGQGTTVTVSSGGGGSGGGGSGGGGS

DIQMTQSPSSLSASVGDRVTITCRASQDINSYLSWFQQKPGKAPKTLIYR

ANRLESGVPSRFSGSGSGTDYTLTISSLQYEDFGIYYCQQYDESPWTFGG

TABLE 5

Partial nucleotide sequences denoting component sequences encoding the individual domains of the CFP: CD5-CD8hinge-CD8TM-FcR-MDA5 (e.g., SEQ ID NO: 75).

| Sequence encoding | Nucleic Acid Sequence |
|---|---|
| GMCSF signal peptide | ATGTGGCTGCAGTCTCTGCTGCTGCTGGGAACAGTGGCCTGCAGCATC AGC (SEQ ID NO: 76) |
| CD5 scFv | GAGATCCAGCTGGTTCAGTCTGGCGGCGGACTTGTGAAACCTGGCGGA TCTGTCAGAATCAGCTGTGCCGCCAGCGGCTACACCTTCACCAACTACG GCATGAACTGGGTCCGACAGGCCCCTGGAAAAGGCCTTGAGTGGATGG GCTGGATCAATACCCACACCGGCGAGCCAACCTACGCCGATAGCTTTA AGGGCAGATTCACCTTCAGCCTGGACGACAGCAAGAACACCGCCTACC TGCAGATCAACAGCCTGAGAGCCGAGGATACCGCCGTGTACTTCTGCA CCAGAAGAGGCTACGACTGGTACTTCGATGTGTGGGGCCAGGGCACCA CAGTGACAGTTTCTAGCGGAGGCGGAGGATCAGGTGGCGGTGGATCTG GCGGTGGTGGCTCTGATATCCAGATGACACAGAGCCCTAGCAGCCTGT CTGCCTCTGTGGGCGATAGAGTGACCATCACCTGTAGAGCCAGCCAGG ACATCAACAGCTACCTGAGCTGGTTCCAGCAGAAGCCTGGCAAGGCCC CTAAGACACTGATCTACCGGGCCAACAGACTGGAAAGCGGCGTGCCAA GCAGATTTTCTGGCAGCGGCTCTGGCACCGACTACACCCTGACAATCAG CAGCCTGCAGTACGAGGACTTCGGCATCTACTACTGCCAGCAGTACGAC GAGAGCCCTTGGACATTTGGCGGAGGCACCAAGCTGGAAATCAAA (SEQ ID NO: 77) |
| Linker | AGCGGAGGCGGAGGAAGCGGA (SEQ ID NO: 78) |
| CD8 hinge and transmembrane region | GCCCTGAGCAATAGCATCATGTACTTCAGCCACTTCGTGCCCGTGTTTCT GCCCGCCAAGCCTACAACAACACCCGCTCCTAGACCACCTACACCAGCT CCTACAATCGCCAGCCAGCCTCTGTCTCTCAGACCTGAAGCCTGTAGACC TGCAGCTGGCGGAGCTGTGCATACCAGAGGCCTGGATATCTACATTTGGG CCCCTCTGGCTGGCACATGTGGCGTTCTGCTGCTCTCTCTGGTCATCACCC TGTACTGC (SEQ ID NO: 79) |
| FcR | AGACGGCTGAAGATCCAAGTGCGGAAGGCCGCCATCACCAGCTACGAG AAATCTGATGGCGTGTACACCGGCCTGAGCACCCGGAATCAAGAAACCT ACGAGACACTGAAGCACGAGAAGCCTCCACAA (SEQ ID NO: 80) |
| MDA5 | ATGAGTAACGGTTACAGCACGGACGAGAACTTCCGCTATCTGATTAGCT GTTTCCGGGCTCGCGTAAAGATGTATATCCAGGTAGAGCCAGTGCTGGA TTACCTGACGTTCCTCCCTGCCGAGGTGAAGGAACAGATTCAGCGAACA GTAGCGACATCAGGAAATATGCAAGCGGTGGAGTTGCTGCTCTCTACCC TCGAAAAAGGTGTTTGGCACCTGGGATGGACACGGGAATTCGTCGAAG CTCTCAGGCGAACTGGATCTCCTCTTGCCGCTAGGTACATGAACCCGGA ACTCACTGATTTGCCGTCACCGTCTTTCGAGAACGCCCATGATGAGTAT CTCCAGCTTCTGAATTTGCTTCAGCCTACCTTGGTCGACAAACTGTTGGT TCGGGACGTTTTGGACAAGTGTATGGAGGAGGAGCTGCTGACCATCGAG GACAGAAACCGGATAGCTGCGGCAGAGAACAATGGCAACGAGTCAGGA GTTCGGGAGTTGTTGAAGAGGATAGTGCAAAAGGAGAATTGGTTCAGCG CTTTCCTTAACGTACTCCGACAGACAGGCAACAATGAACTCGTACAAGA GTTGACAGGGTCAGATTGCAGTGAATCCAACGCCGAAATTGAAAAT (SEQ ID NO: 81) |

GTKLEIKSGGGGSGALSNSIMYFSHFVPVFLPAKPTTTPAPRPPTPAPTI
ASQPLSLRPEACRPAAGGAVHTRGLDIYIWAPLAGTCGVLLLSLVITLYC
RLKIQVRKAAITSYEKSDGVYTGLSTRNQETYETLKHEKPPQGSGSQRWK
SKLYSIVCGKSTPEKEGELEGTTTKPLAPNPSFSPTPGFTPTLGFSPVPS
STFTSSSTYTPGDCPNFAAPRREVAPPYQGADPILATALASDPIPNPLQK
WEDSAHKPQSLDTDDPATLYAVVENVPPLRWKEFVRRLGLSDHEIDRLEL
QNGRCLREAQYSMLATWRRRTPRREATLELLGRVLRDMDLLGCLEDIEEA
LCGPAALPPAPSLLR.

An exemplary polynucleotide sequence encoding a CD5-FcR-TNFR1 may comprise a sequence:

(SEQ ID NO: 51)
atgtggctgcagagcctgctgctgctgggcaccgtggcgtgcagcattag
cgaaattcagctggtgcagagcggcggcggcctggtgaaaccgggcggca
gcgtgcgcattagctgcgcggcgagcggctataccttaccaactatggc
atgaactgggtgcgccaggcgccgggcaaaggcctggaatggatgggctg
gattaacacccataccggcgaaccgacctatgcggatagctttaaaggcc
gctttacctttagcctggatgatagcaaaaacaccgcgtatctgcagatt
aacagcctgcgcgcggaagataccgcggtgtattttgcacccgccgcgg
ctatgattggtattttgatgtgtggggccagggcaccaccgtgaccgtga
gcagcggcggcggcggcagcggcggcggcggcagcggcggcggcggcagc
gatattcagatgacccagagcccgagcagcctgagcgcgagcgtgggcga
tcgcgtgaccattacctgccgcgcgagccaggatattaacagctatctga
gctggtttcagcagaaaccgggcaaagcgccgaaaaaccctgatttatcgc
gcgaaccgcctggaaagcggcgtgccgagccgctttagcggcagcggcag
cggcaccgattataccctgaccattagcagcctgcagtatgaagattttg
gcatttattattgccagcagtatgatgaaagcccgtggacctttggcggc
ggcaccaaactggaaattaaaagcggcggcggcggcagcggcgcgctgag
caacagcattatgtattttagccattttgtgccggtgtttctgccggcga
aaccgaccaccacccgggcgccgcgcccgccgaccccggcgccgaccatt
gcgagccagccgctgagcctgcgcccggaagcgtgccgcccggcggcggg
cggcgcggtgcataccgcggcctggatatttatatttgggcgccgctgg
cgggcacctgcggcgtgctgctgctgagcctggtgattaccctgtattgc
cgcctgaaaattcaggtgcgcaaagcggcgattaccagctatgaaaaaag
cgatggcgtgtataccggcctgagcacccgcaaccaggaaacctatgaaa
ccctgaaacatgaaaaaccgccgcagggcagcggcagccagcgctggaaa
agcaaactgtatagcattgtgtgcggcaaaagcaccccggaaaaagaagg
cgaactggaaggcaccaccaccaaaccgctggcgccgaacccgagcttta
gcccgacccgggctttaccccgaccctgggctttagcccggtgccgagc
agcacctttaccagcagcagcacctataccccgggcgattgcccgaactt
tgcggcgccgcgccgcgaagtggcgccgccgtatcagggcgcggatccga An exemplary nucleic acid sequence encoding CD5-CD8hinge-CD8TM-FcR-TNFR1 is as follows:

(SEQ ID NO: 82)
ATGTGGCTGCAGTCTCTGCTGCTGCTGGGAACAGTGGCCTGCAGCATCAG
CGAGATCCAGCTGGTTCAGTCTGGCGGCGGACTTGTGAAACCTGGCGGAT
CTGTCAGAATCAGCTGTGCCGCCAGCGGCTACACCTTCACCAACTACGGC
ATGAACTGGGTCCGACAGGCCCCTGGAAAAGGCCTTGAGTGGATGGGCTG
GATCAATACCCACACCGGCGAGCCAACCTACGCCGATAGCTTTAAGGGCA
GATTCACCTTCAGCCTGGACGACAGCAAGAACACCGCCTACCTGCAGATC
AACAGCCTGAGAGCCGAGGATACCGCCGTGTACTTCTGCACCAGAAGAGG
CTACGACTGGTACTTCGATGTGTGGGGCCAGGGCACCACAGTGACAGTTT
CTAGCGGAGGCGGAGGATCAGGTGGCGGTGGATCTGGCGGTGGTGGCTCT
GATATCCAGATGACACAGAGCCCTAGCAGCCTGTCTGCCTCTGTGGGCGA
TAGAGTGACCATCACCTGTAGAGCCAGCCAGGACATCAACAGCTACCTGA
GCTGGTTCCAGCAGAAGCCTGGCAAGGCCCCTAAGACACTGATCTACCGG
GCCAACAGACTGGAAAGCGGCGTGCCAAGCAGATTTTCTGGCAGCGGCTC
TGGCACCGACTACACCCTGACAATCAGCAGCCTGCAGTACGAGGACTTCG
GCATCTACTACTGCCAGCAGTACGACGAGAGCCCTTGGACATTTGGCGGA
GGCACCAAGCTGGAAATCAAAAGCGGAGGCGGAGGAAGCGGAGCCCTGAG
CAATAGCATCATGTACTTCAGCCACTTCGTGCCCGTGTTTCTGCCCGCCA
AGCCTACAACAACACCCGCTCCTAGACCACCTACACCAGCTCCTACAATC
GCCAGCCAGCCTCTGTCTCTCAGACCTGAAGCCTGTAGACCTGCAGCTGG
CGGAGCTGTGCATACCAGAGGCCTGGATATCTACATTTGGGCCCCTCTGG
CTGGCACATGTGGCGTTCTGCTGCTCTCTCTGGTCATCACCCTGTACTGC
AGACGGCTGAAGATCCAAGTGCGGAAGGCCGCCATCACCAGCTACGAGAA
ATCTGATGGCGTGTACACCGGCCTGAGCACCCGGAATCAAGAAACCTACG
AGACACTGAAGCACGAGAAGCCTCCACAAGGCAGCGGCAGCCAAAGATGG
AAGAGCAAGCTGTATAGCATCGTGTGCGGCAAGTCCACCCCTGAGAAGGA
AGGAGAGCTGGAAGGCACCACAACAAAGCCTCTGGCCCCTAACCCCTCAT
TCAGCCCTACCCCCGGCTTCACCCCCACCCTGGGATTAGCCCCGTGCCC
AGCAGCACCTTCACCAGCTCTAGCACCTACACCCCTGGCGACTGCCCCAA
CTTCGCCGCCCCTAGACGCGAGGTGGCCCCTCCTTACCAGGGCGCCGACC
CTATCCTGGCCACAGCCCTGGCTTCTGATCCGATTCCTAATCCTCTGCAG

-continued

AAGTGGGAGGACAGCGCCCACAAGCCCCAGAGCCTGGACACCGACGACCC

CGCCACCCTGTACGCCGTGGTGGAAAACGTGCCTCCACTGCGGTGGAAAG

AGTTCGTGCGGCGGCTGGGCCTGAGCGACCACGAGATCGACAGACTGGAA

CTGCAGAACGGCCGTTGCCTGAGAGAGGCCCAGTACAGCATGCTGGCAAC

ATGGCGGAGAAGAACACCCAGAAGAGAGGCCACCCTGGAACTGCTGGGCA

GAGTGCTGAGAGATATGGACCTGCTGGGTTGTCTGGAAGATATCGAGGAA

GCCCTGTGCGGTCCTGCCGCTCTGCCTCCTGCTCCATCTCTGCTGAGA

Example 2. Functional Assays for Testing CFP Constructs

The targeted constructs are tested for functional properties. THP-1 cells or CD14+/CD16− monocytes isolated from leukapheresis samples are transfected with the polynucleotide constructs encoding respecting CFPs.

Method for cell transfection and detection of transfection efficiency: THP-1 cells are harvested and washed once with MaxCyte Electroporation buffer. The cells are resuspended at 10 million/ml density and added to 100 ug of ATAK-receptor RNA in an Eppendorf tube, mixed twice and loaded into a MaxCyte processing assembly (OC-25x3). The cells

TABLE 6

Partial nucleotide sequences denoting component sequences encoding the individual domains of the CFP: CD5-CD8hinge-CD8TM-FcR-TNFR1 (e.g., SEQ ID NO: 82).

| Sequence encoding | Nucleic Acid Sequence |
| --- | --- |
| GMCSF signal peptide | ATGTGGCTGCAGTCTCTGCTGCTGCTGGGAACAGTGGCCTGCAGCAT CAGC (SEQ ID NO: 83) |
| CD5 scFv | GAGATCCAGCTGGTTCAGTCTGGCGGCGGACTTGTGAAACCTGGCGG ATCTGTCAGAATCAGCTGTGCCGCCAGCGGCTACACCTTCACCAACT ACGGCATGAACTGGGTCCGACAGGCCCCTGGAAAAGGCCTTGAGTG GATGGGCTGGATCAATACCCACACCGGCGAGCCAACCTACGCCGAT AGCTTTAAGGGCAGATTCACCTTCAGCCTGGACGACAGCAAGAACA CCGCCTACCTGCAGATCAACAGCCTGAGAGCCGAGGATACCGCCGT GTACTTCTGCACCAGAAGAGGCTACGACTGGTACTTCGATGTGTGGG GCCAGGGCACCACAGTGACAGTTTCTAGCGGAGGCGGAGGATCAGG TGGCGGTGGATCTGGCGGTGGTGGCTCTGATATCCAGATGACACAGA GCCCTAGCAGCCTGTCTGCCTCTGTGGGCGATAGAGTGACCATCACC TGTAGAGCCAGCCAGGACATCAACAGCTACCTGAGCTGGTTCCAGCA GAAGCCTGGCAAGGCCCCTAAGACACTGATCTACCGGGCCAACAGA CTGGAAAGCGGCGTGCCAAGCAGATTTTCTGGCAGCGGCTCTGGCAC CGACTACACCCTGACAATCAGCAGCCTGCAGTACGAGGACTTCGGCA TCTACTACTGCCAGCAGTACGACGAGAGCCCTTGGACATTTGGCGGA GGCACCAAGCTGGAAATCAAA (SEQ ID NO: 84) |
| Linker | AGCGGAGGCGGAGGAAGCGGA (SEQ ID NO: 85) |
| CD8 hinge and trans membrane region | GCCCTGAGCAATAGCATCATGTACTTCAGCCACTTCGTGCCCGTGTT TCTGCCCGCCAAGCCTACAACAACACCCGCTCCTAGACCACCTACAC CAGCTCCTACAATCGCCAGCCAGCCTCTGTCTCTCAGACCTGAAGCC TGTAGACCTGCAGCTGGCGGAGCTGTGCATACCAGAGGCCTGGATA TCTACATTTGGGCCCCTCTGGCTGGCACATGTGGCGTTCTGCTGCTC TCTCTGGTCATCACCCCTGTACTGC (SEQ ID NO: 86) |
| FcR | AGACGGCTGAAGATCCAAGTGCGGAAGGCCGCCATCACCAGCTACG AGAAATCTGATGGCGTGTACACCGGCCTGAGCACCCGGAATCAAGA AACCTACGAGACACTGAAGCACGAGAAGCCTCCACAA (SEQ ID NO: 87) |
| Linker | GGCAGCGGCAGC (SEQ ID NO: 88) |
| TNFR1 | CAAAGATGGAAGAGCAAGCTGTATAGCATCGTGTGCGGCAAGTCCA CCCCTGAGAAGGAAGGAGAGCTGGAAGGCACCACAACAAAGCCTC TGGCCCCTAACCCCTCATTCAGCCCTACCCCCGGCTTCACCCCCACC CTGGGATTTAGCCCCGTGCCCAGCAGCACCTTCACCAGCTCTAGCAC CTACACCCCTGGCGACTGCCCCAACTTCGCCGCCCCTAGACGCGAGG TGGCCCCTCCTTACCAGGGCGCCGACCCTATCCTGGCCACAGCCCTG GCTTCTGATCCGATTCCTAATCCTCTGCAGAAGTGGGAGGACAGCGC CCACAAGCCCCAGAGCCTGGACACCGACGACCCCGCCACCCTGTAC GCCGTGGTGGAAAACGTGCCTCCACTGCGGTGGAAAGAGTTCGTGC GGCGGCTGGGCCTGAGCGACCACGAGATCGACAGACTGGAACTGCA GAACGGCCGTTGCCTGAGAGAGGCCCAGTACAGCATGCTGGCAACA TGGCGGAGAAGAACACCCAGAAGAGAGGCCACCCTGGAACTGCTGG GCAGAGTGCTGAGAGATATGGACCTGCTGGGTTGTCTGGAAGATATC GAGGAAGCCCTGTGCGGTCCTGCCGCTCTGCCTCCTGCTCCATCTCTG CTGAGA (SEQ ID NO: 89) | are electroporated using the THP-1 program on MaxCyte. After the electroporation, cells are incubated at 37° C. for 10 mins to recover in the processing assembly and then transferred to plates containing pre-warmed media at 0.5 million cells/ml density.

After overnight incubation, the expression of ATAK-receptor in electroporated monocytes is assessed by Flow cytometry. Anti-Fab-Alexa Fluor-647 antibody (1:50 dilution) is used to detect the expression of scFv of ATAK receptor. The stained samples are acquired on Cytek Northern lights cytometer and percent of binder positive cells calculated based on increase in Anti-Fab intensity over mock-transfected control.

Method for phagocytosis assay: Target tumor cells (SKOV3) are labeled with pHrodo-Red dye (700 ng/ml final concentration) following the Sartorius Incucyte pHrodo-Red labeling kit protocol. After labeling, the SKOV3 cells are resuspended at 0.5 million cells/ml density using the culture medium. CD14-positive monocytes are isolated from donor leukopak and electroporated with 100 ug/ml of ATAK-receptor RNA using MaxCyte. After electroporation, cells are recovered overnight at 2 million cells/mL density in culture medium at 37° C. Next day, cells are counted using NC-200 and are resuspended at 2.5 million cells/ml density using the culture medium. In a low adhesion U-bottom 96-well plate, 50 uL of tumor cells (50,000 cells total) are added to 50 uL of ATAK-receptor transfected monocytes (125,000 cells total) at 5:1 E:T ratio. The cells are mixed and incubated at 37° C. overnight.

The following day, cells are stained with CD45-Alexa Fluor 700 which labels monocytes specifically. The samples are then acquired on Cytek Northern lights to detect pHrodo-Red and CD45 signal intensities. Phagocytosis is measured as percent phagocytosis index as well as specific increase in pHrodo-Red intensity in monocytes. The phagocytosis index is calculated as the percent of monocytes with high pHrodo-red signal normalized to total number of monocytes. Phagocytic activity of ATAK-monocytes is compared with the mock-transfected control to determine the efficacy of ATAK-receptor.

Figure 4A:
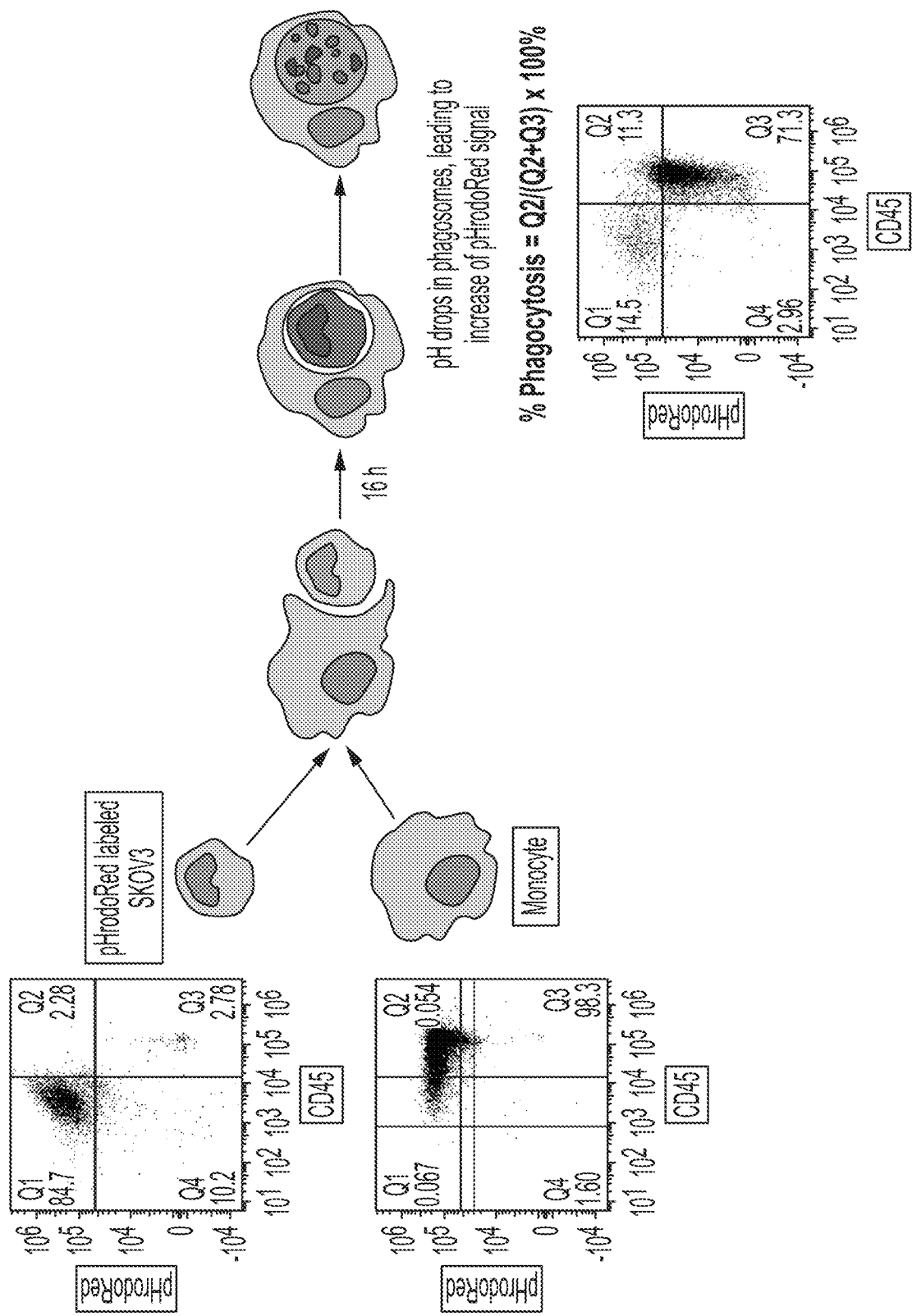
FIG. 4A shows exemplary assay set up for quantitative assessment of phagocytosis of target cells by myeloid cells expressing a CFP. SKOV3 tumor cell lines are the exemplary target cells, labeled with a cytoplasmic dye. Phagocytosis of the target cell leads to release of the dye in the myeloid cell which is then analyzed by flow cytometry. Exemplary flow cytometry data from a representative experiment are also shown.
Figure 5A:
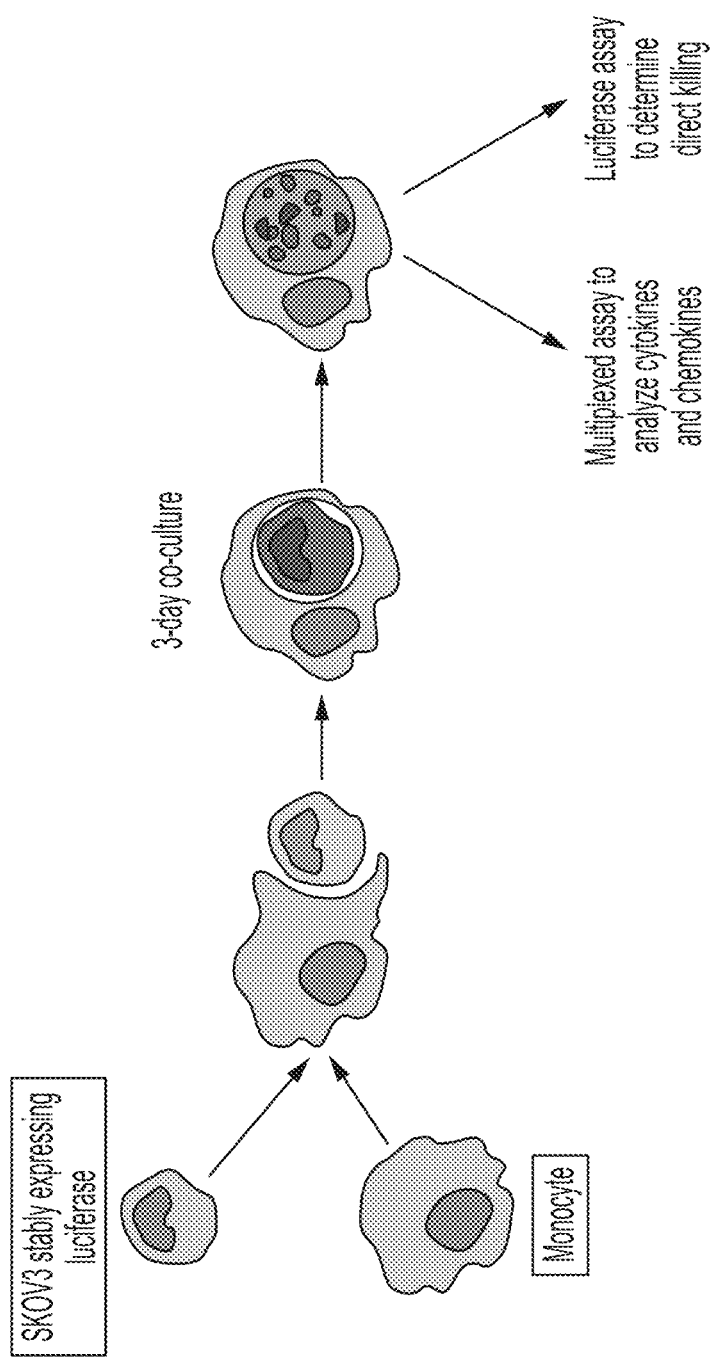
FIG. 5A shows exemplary assay set up for quantitative assessment of phagocytic lysis of target cells by myeloid cells expressing a CFP and multiplexed assay for analyzing cytokines and chemokines. Target cells express a luciferase gene, and upon engulfment and lysis of the target cell the luciferase is released in the myeloid cell which can be used to detect and quantitate direct target cell lysis.
Figure 5B:
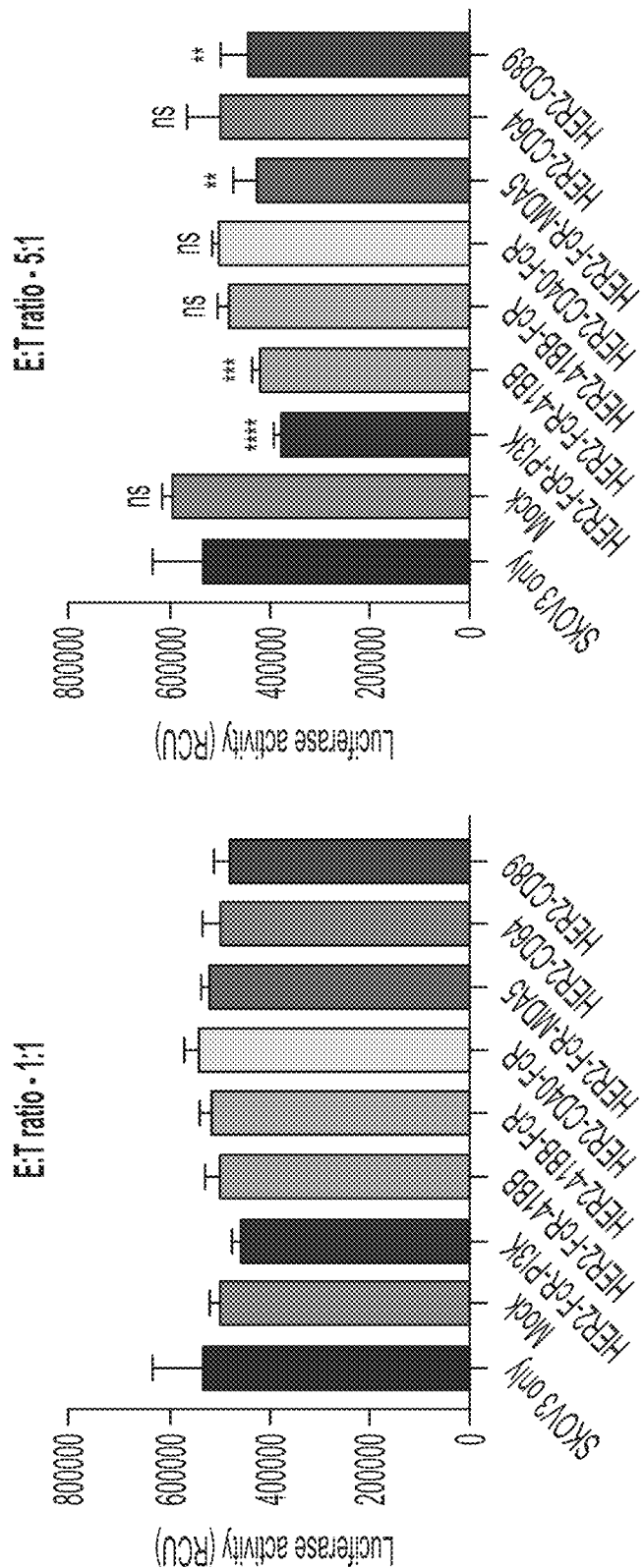
FIG. 5B shows representative data of target cell lysis by myeloid cells each set expressing a CFP construct as indicated. Left, results from experiment using effector:target cell ratio of 1:1; Right, results from experiment using effector:target cell ratio of 5:1.

Phagocytosis can be tested using labeled tumor cells as shown in FIGS. 4A and 5A.

Method for SKOV3 cell killing assay: The tumoricidal activity of ATAK receptor-transfected monocytes is tested using SKOV3-Luciferase cells. CD14-positive monocytes are isolated from donor leukopak and electroporated with 100 ug/ml of ATAK-receptor RNA using MaxCyte. After electroporation, cells are recovered for 2 hours in culture medium at 37° C. After recovery, cells are resuspended at 2.5 million cells/ml density using the culture medium. SKOV3-Luciferase cells are harvested and resuspended at density of 0.25 million cells/mL and 100 ul of cell suspension (total 25,000 cells per well) is added in a 96 well flat-bottom plate. 100 uL of ATAK-receptor transfected monocytes are added to the same well at E:T ratio of 1:1 and 10:1. The cells are mixed and incubated at 37° C. for 3 days.

On day 3, supernatant is collected and frozen to measure the cytokines and chemokines secreted by the ATAK-monocytes. The cells are lysed, and SKOV3 luciferase levels are measured using luminescence plate reader. A decrease in Luciferase level for samples containing ATAK-monocytes, compared to mock transfected control, is indicative of SKOV3 killing activity of the ATAK cells.

Polarization potential of myeloid cells is tested using the following method. These effector myeloid cells electroporated with the polynucleic acid construct and frozen for later use and testing. Upon thawing, the cells were then subject to culture in polarizing stimuli, for example in separate aliquot cultures, with (i) GMCSF (ii) IL4, IL10, and TGFbeta (M2 stimuli), (iii) activated T cell conditioned media (TCM) and (iv) MCSF. Cells were analyzed at 24, 48 and 72 hours by flow cytometry, and cytokine analysis was performed by Luminex.

Method for detecting NF-κB and IFN pathway activation using THP1-Dual cells: THP1-Dual cells have NF-κB response elements upstream of secreted Alkaline phosphatase and IFN stimulated response elements upstream of secreted Luciferase. Measuring the levels of Alkaline phosphatase in the supernatant indicates the activation of NF-κB signaling pathway, while levels of Luciferase in the supernatant indicates IFN signaling pathway activation. THP1-Dual cells are electroporated with 100 ug/ml of ATAK-receptor RNA using MaxCyte. After electroporation, cells are recovered for 2 hours in culture medium at 37° C. Post recovery, cells are resuspended at 0.5 million cells/ml density using the culture medium. SKOV3 cells are harvested and resuspended at density of 0.5 million cells/mL. In a 96-well plate, 100 ul of SKOV3 cell suspension (total 50,000 cells per well) and 100 uL of ATAK-THP1-Dual cells (50,000 cells total) are added in a 96 well flat-bottom plate at E:T ratio of 1:1. The cells are mixed and incubated for 24 hours at 37° C. After 24 hours, the cells are centrifuged, and supernatant is collected.

To detect NF-κB pathway activation, QUANTI-Blue solution (Invivogen) is added to the supernatant and incubated at 37° C. for 2 hours, after which OD is measured using an absorbance plate reader. Increase in absorbance is indicative of activation of NF-κB signaling and the OD values for ATAK-transfected THP1-Dual cells can be compared to that of mock transfected controls to determine activity of ATAK-receptors.

To detect IFN pathway activation, QUANTI-Luc solution (Invivogen) is added to the supernatant and luciferase levels are measured using luminescence plate reader. Increase in luciferase levels implies activation of IFN signaling and can be compared between the ATAK-transfected THP1-Dual cells compared to mock transfected controls.

Figure 1A:
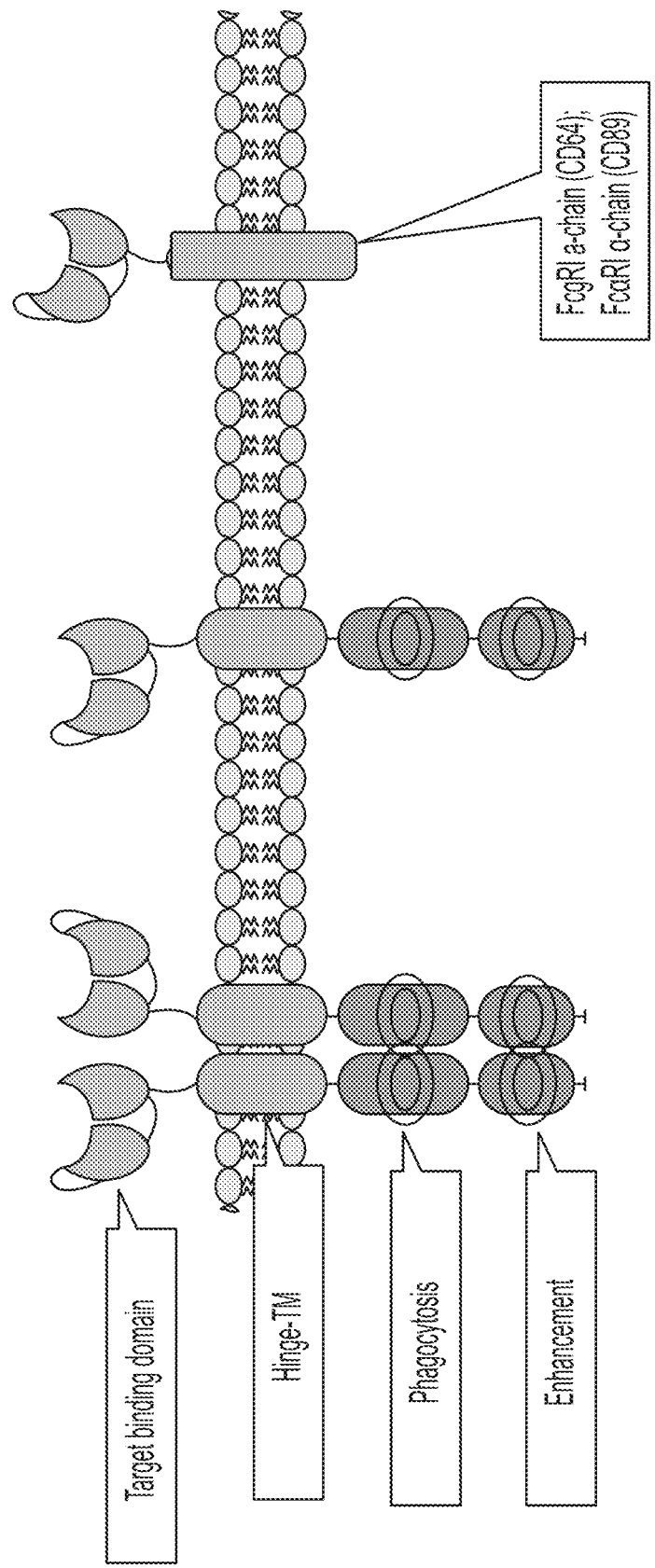
FIG. 1A depicts a schematic showing exemplary CFPs, containing an extracellular binding domain, a transmembrane domain. Left two figures represent CFP contain multiple intracellular signaling domains for augmenting intracellular signaling related to phagocytosis or other domains for intracellular signaling for augmenting immune response or inflammatory signaling inside the cell that expresses the CFP. The figure on the right exemplifies another exemplary chimeric fusion protein, that comprises a transmembrane domain derived from an Fc alpha R1 a chain (FcaR1 a chain or CD89) or an Fc gamma R1 a chain (FcgR1 a chain or CD64). Such a CFP as shown in the figure on the right can lack an intracellular domain of its own, and intracellular signaling will occur if and only if the CFP binds to an endogenous protein in the cell in which it is expressed that has an intracellular domain or otherwise trigger an intracellular signaling. As described elsewhere in the disclosure, an exemplary CFP as shown in the figure on the right side can bind to an endogenous Fc gamma receptor expressed on a myeloid cell, and thereafter it is functional in intracellular signaling and activation of the myeloid cell via the Fc gamma receptor activation. The extracellular domains are target binding domains.
Figure 1B:
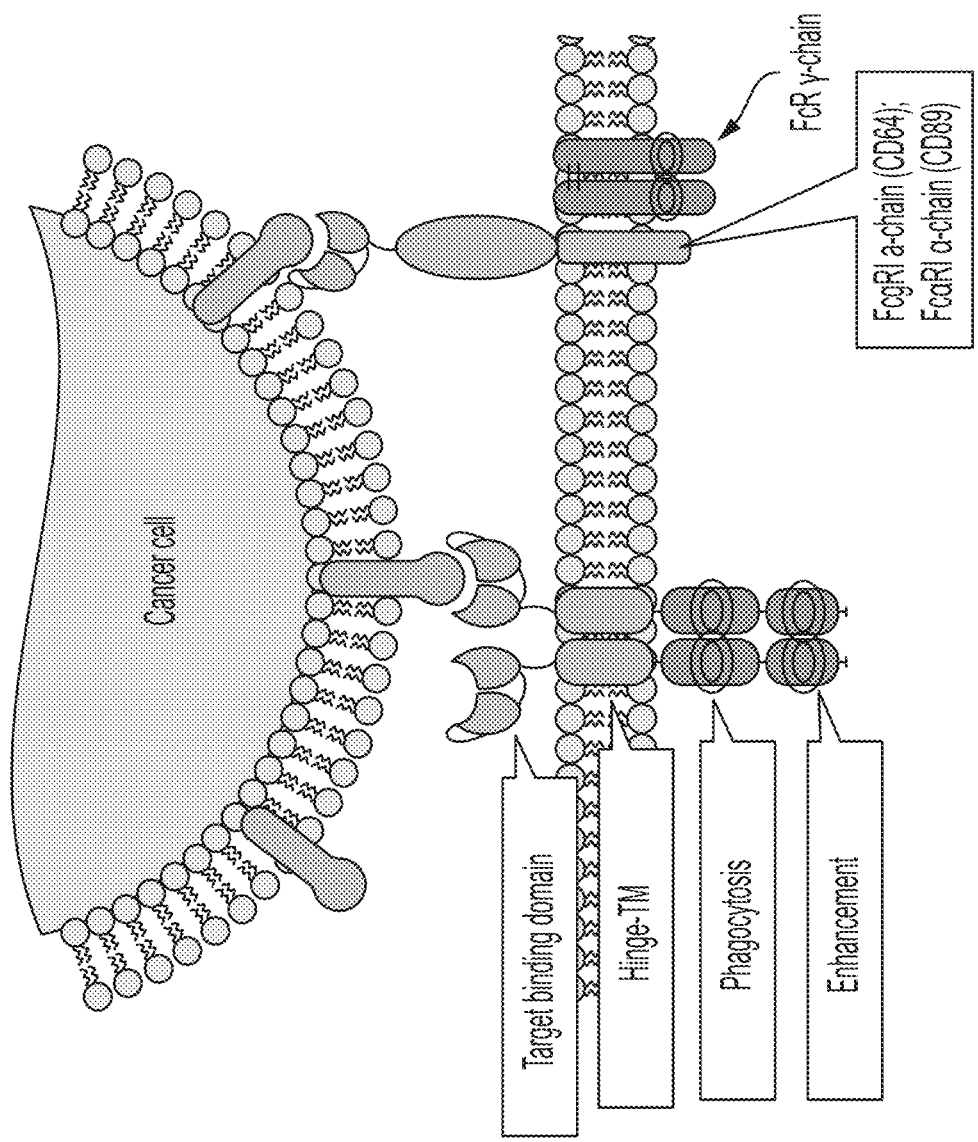
FIG. 1B is a graphical representation of an exemplary myeloid cell expressing CFP receptors and engaging a cancer cell by binding to target antigens on the cancer cell. Activation of intracellular signaling domain upon target engagement potentiates phagocytosis. TM, transmembrane domain.
Figure 1C:
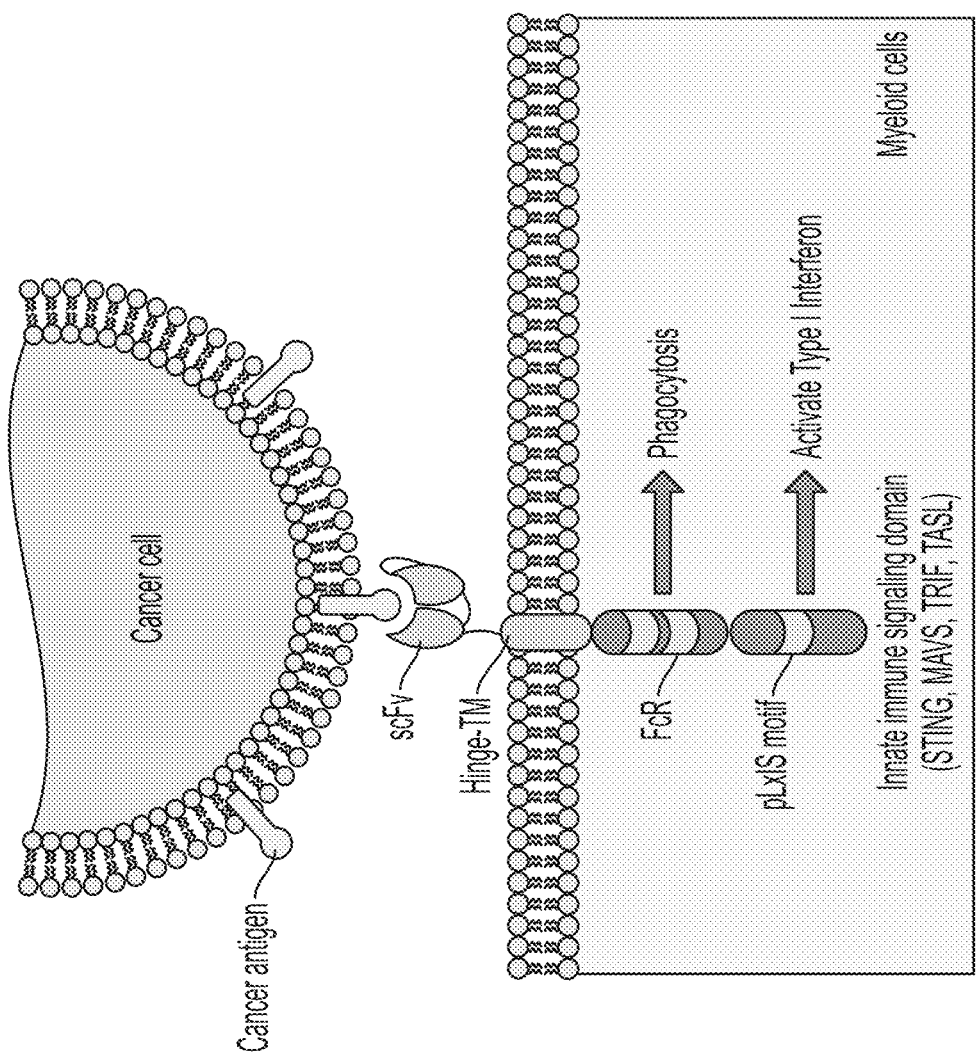
FIG. 1C shows a graphical representation of an exemplary CFP expressed on a myeloid cell, the CFP targets a cancer antigen, and has an intracellular domain capable for activating Type 1 interferon. FcR, Fc receptor.
Figure 1D:
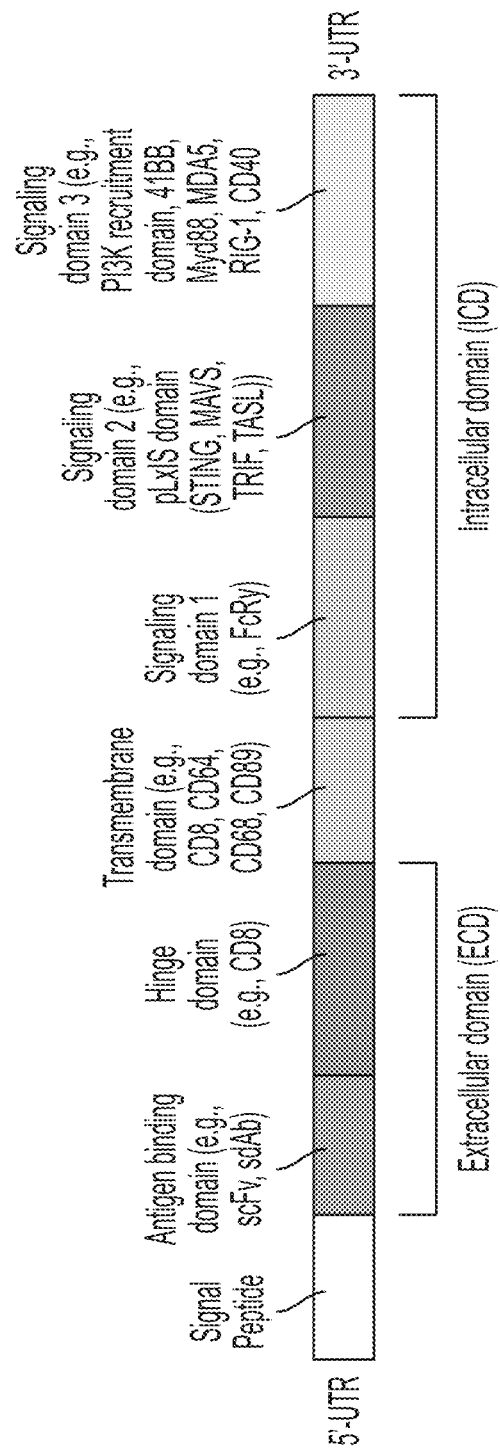
FIG. 1D shows a schematic of an exemplary nucleic acid encoding an exemplary chimeric antigen receptor construct comprising an intracellular signaling domain (ICD) having a pLxIS motif to trigger type I interferon response.
Figure 2A:
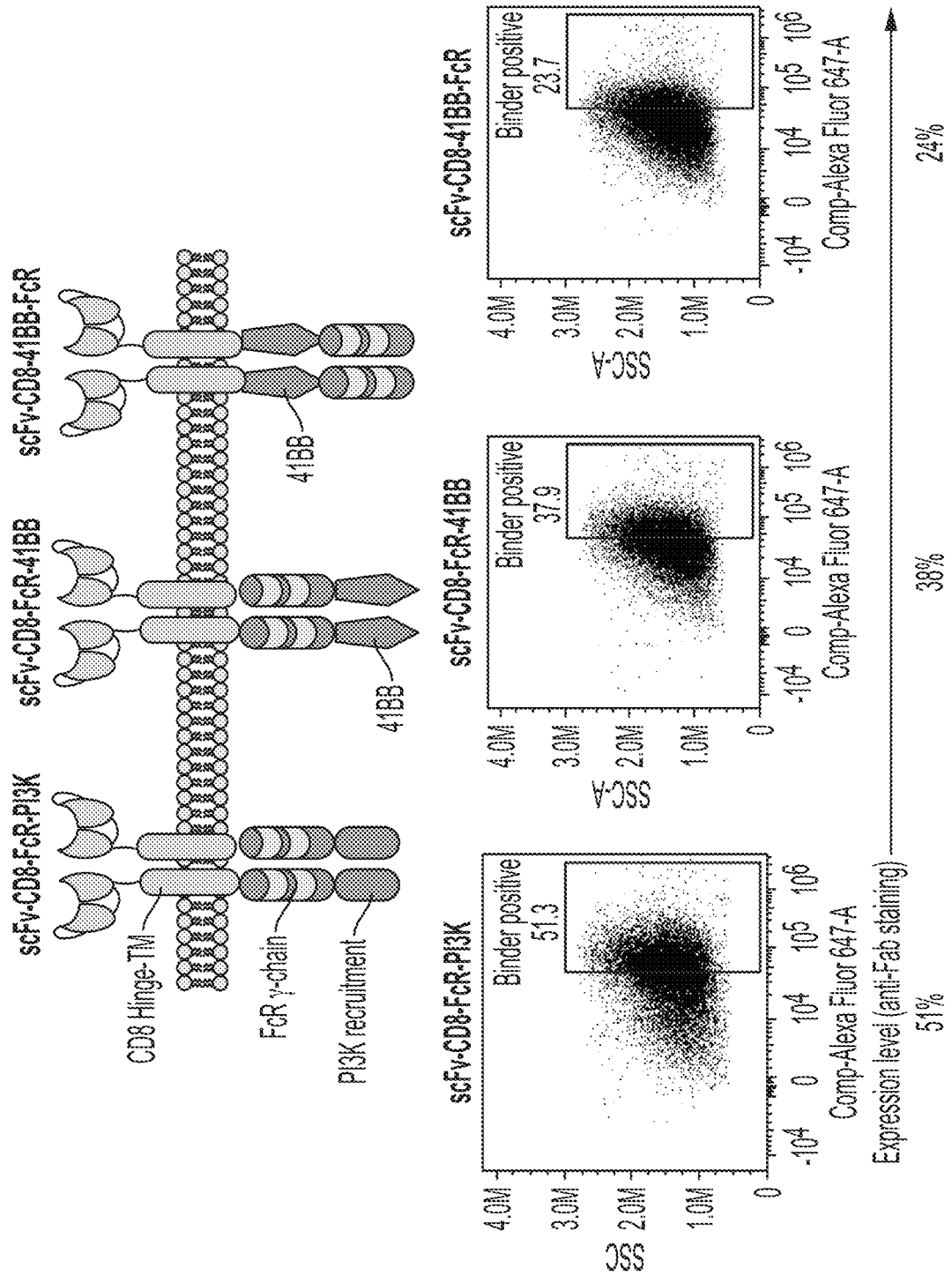
FIG. 2A upper panel depicts a schematic showing exemplary CFP construct designs with indicated domains. Each construct is generated and used for functional characterization. Each have a hinge and TM domain derived from CD8 molecule.
Figure 2B:
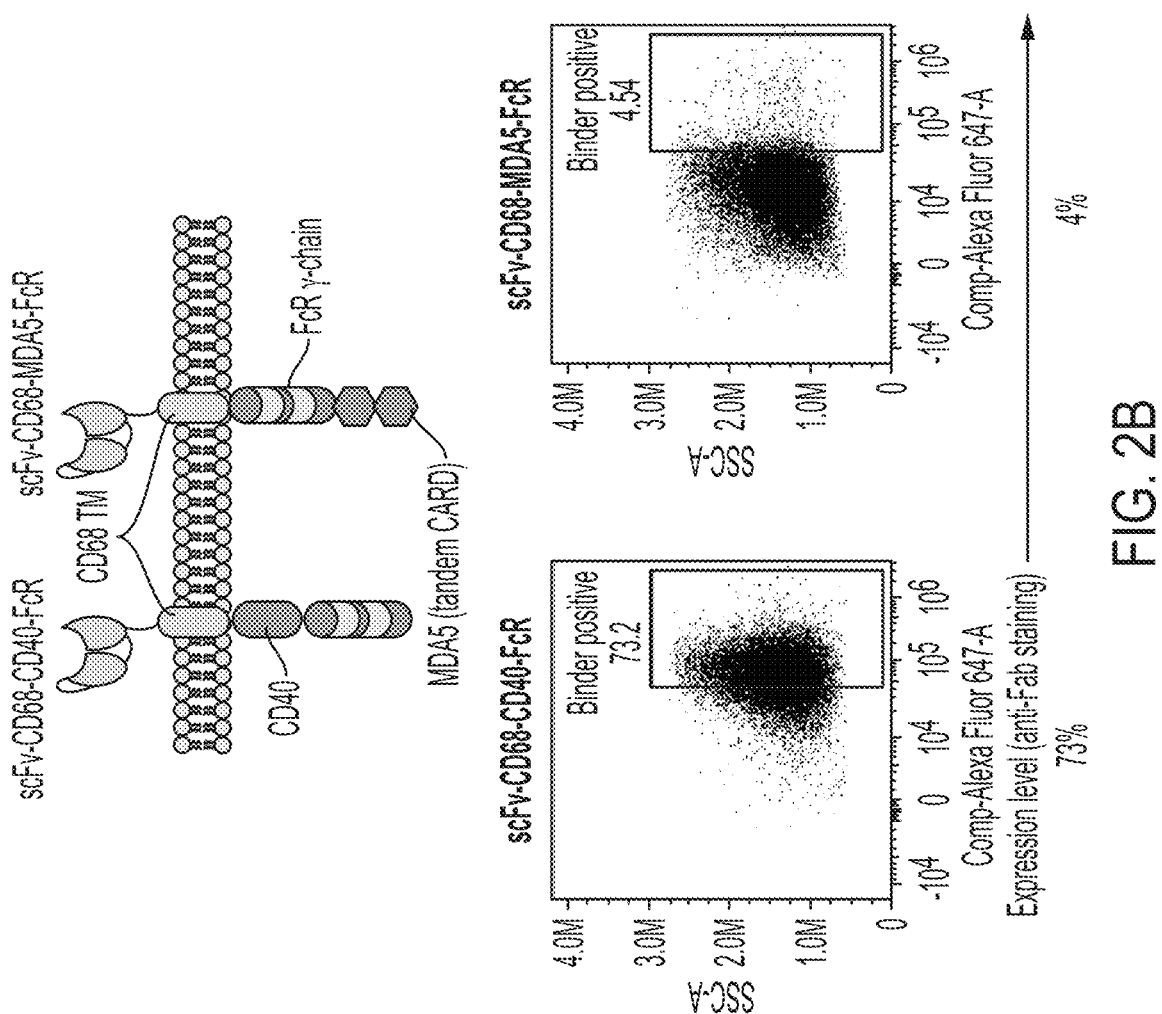
FIG. 2B upper panel depicts a schematic showing exemplary CFP construct designs with indicated domains. Each construct is generated and used for functional characterization. Each have a hinge and TM domain derived from CD68 molecule.
Figure 2C:
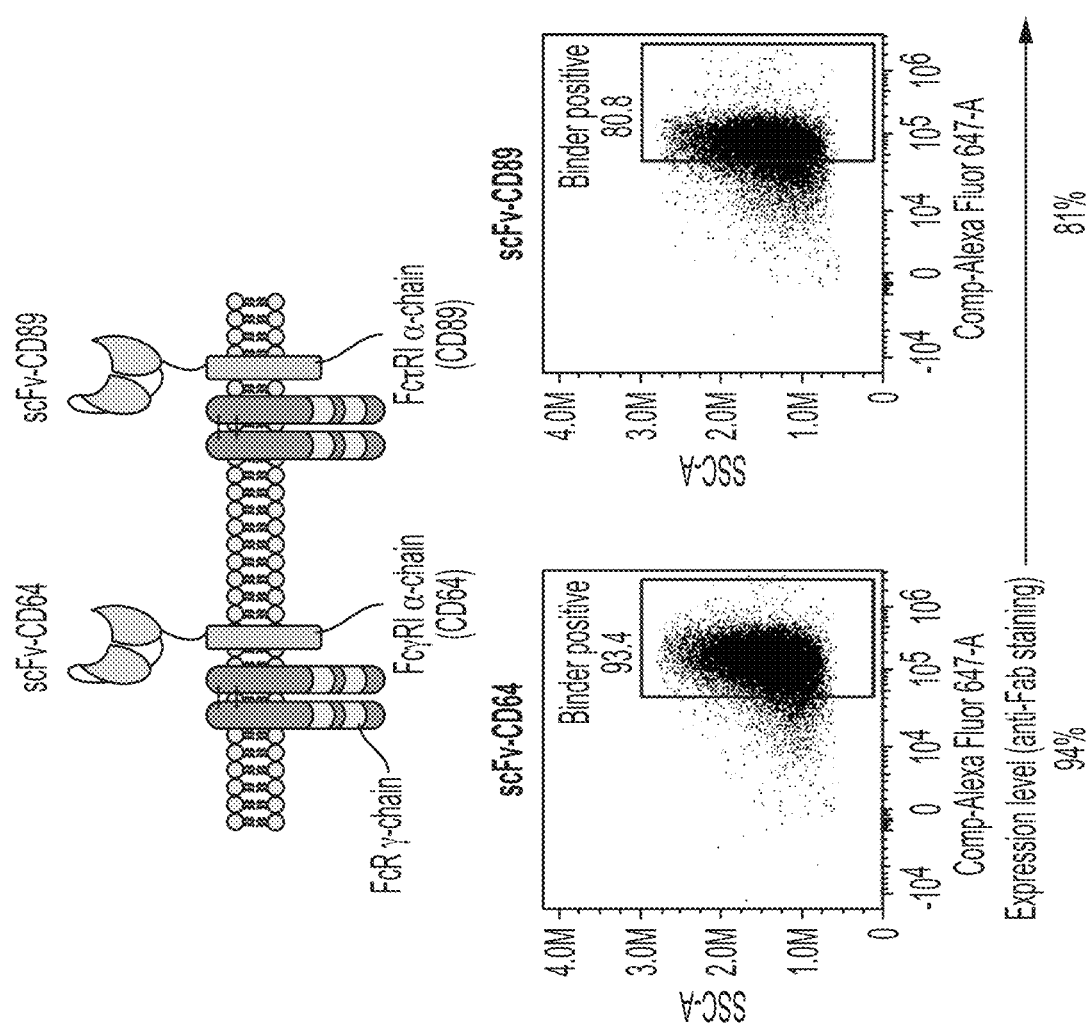
FIG. 2C upper panel depicts a schematic showing exemplary CFP construct designs with indicated domains. The construct on the left have a CD64 transmembrane domain, and the construct on the right has a CD89 transmembrane domain.
Figure 2D:
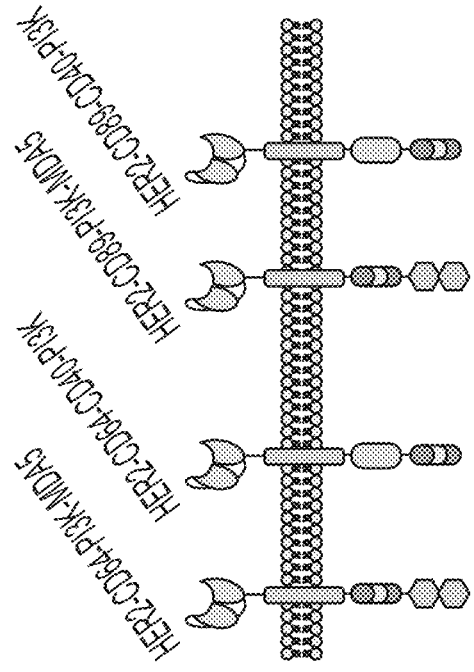
FIG. 2D upper panel depicts a schematic showing exemplary CFP construct designs with indicated domains. The two construct on the left each has a CD64 transmembrane domain and additional intracellular signaling domains as follows: the first CFP from left contains a PI3K recruitment domain and a signaling domain derived from MDA5; second from left contains a CD40 intracellular signaling domain and a PI3K recruitment domain. The two construct on the right has a CD89 transmembrane domain and additional intracellular signaling domains as follows: the third from left CFP contains a PI3K recruitment domain and a signaling domain derived from MDA5; fourth from left contains a CD40 intracellular signaling domain and a PI3K recruitment domain.
Figure 2D:
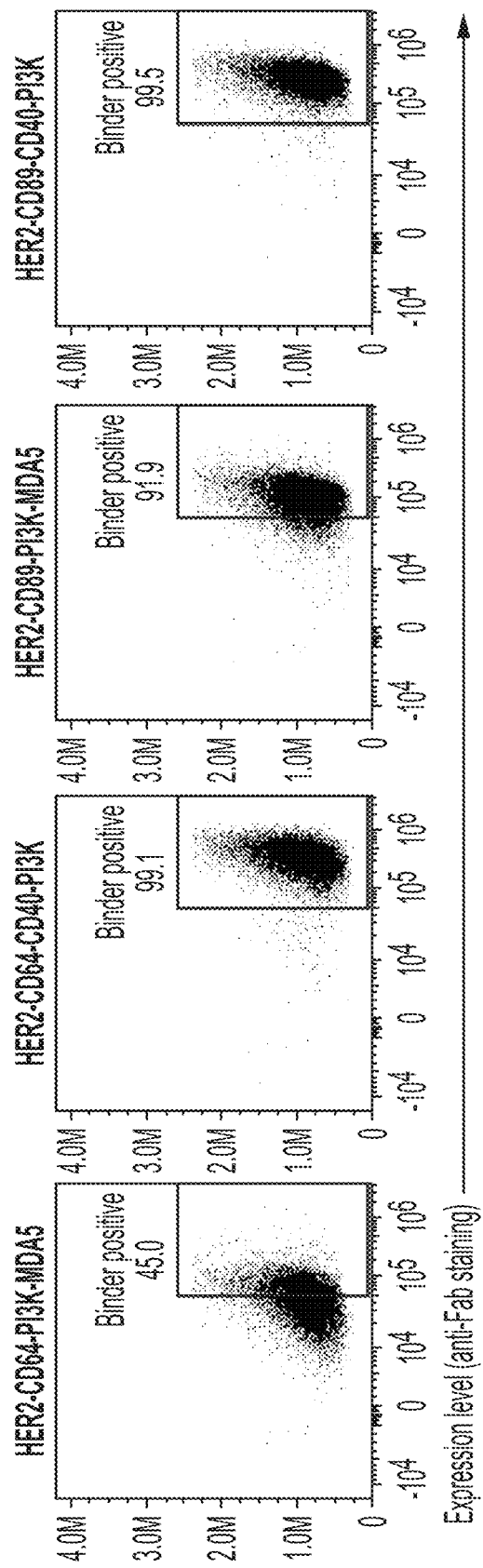
Figure 2E:
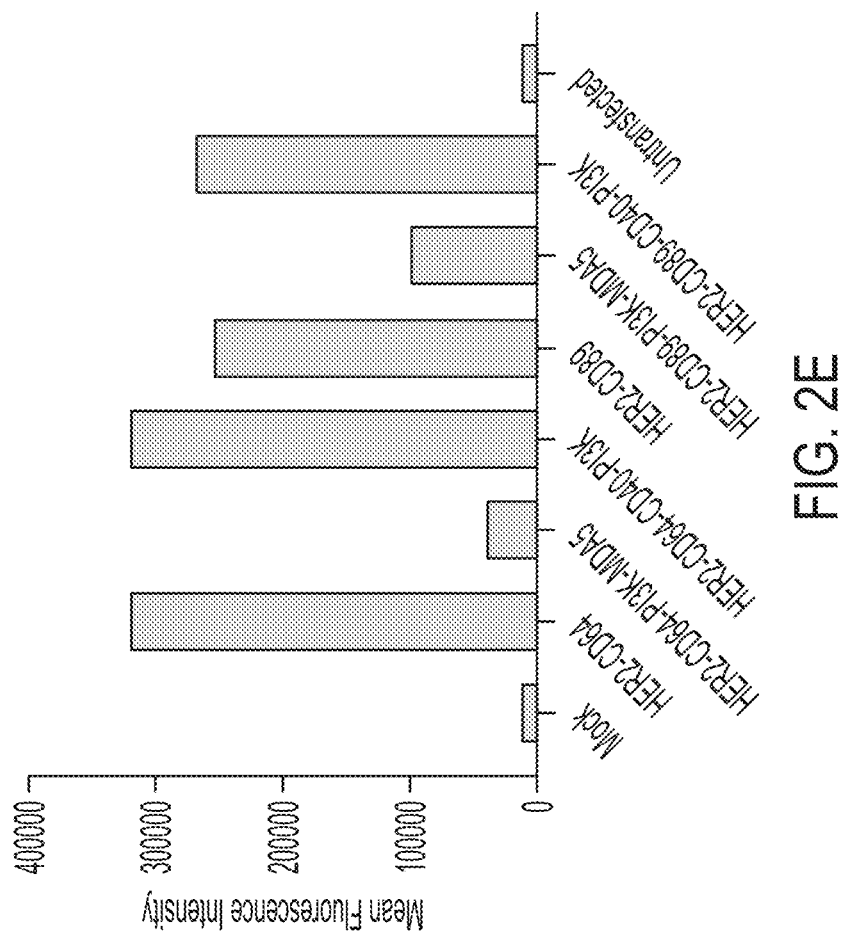
FIG. 2E shows quantitative data of relative expression levels of each of the constructs indicated in the figure in THP-1 cells from analysis of flow cytometry results.
Figure 2F:
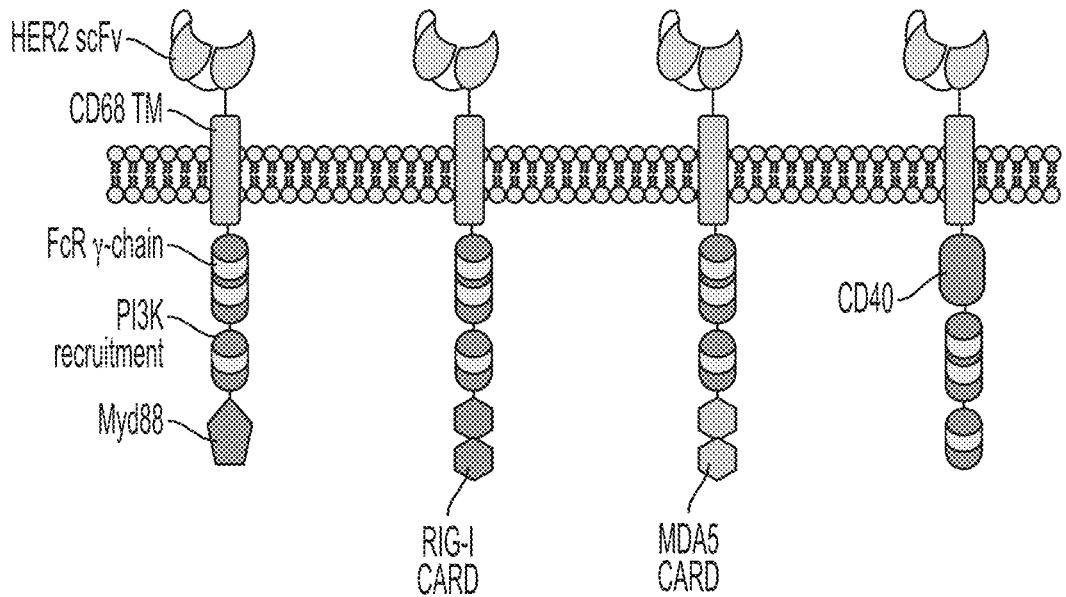
FIG. 2F shows exemplary CFP design (upper panel), and expression data (lower panel) of the constructs in THP-1 cells. The respective domains are as indicated in the figure. HER-FcR-PI3K construct has a CD8 TM domain, others have a CD68 TM domain.
Figure 2F:
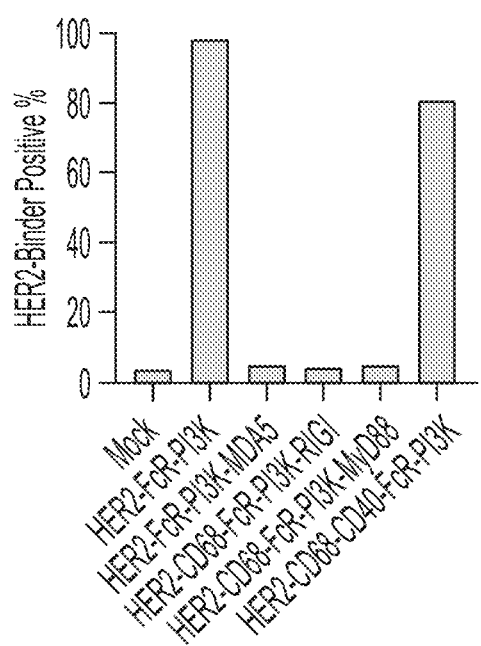
Figure 2F:
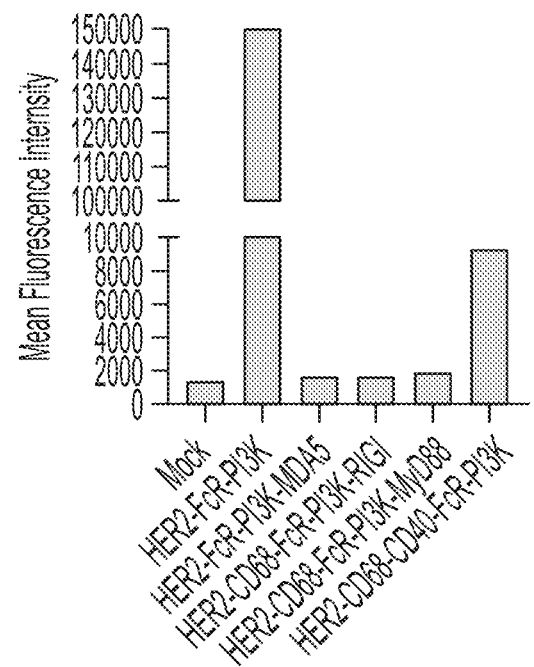
Figure 4B:
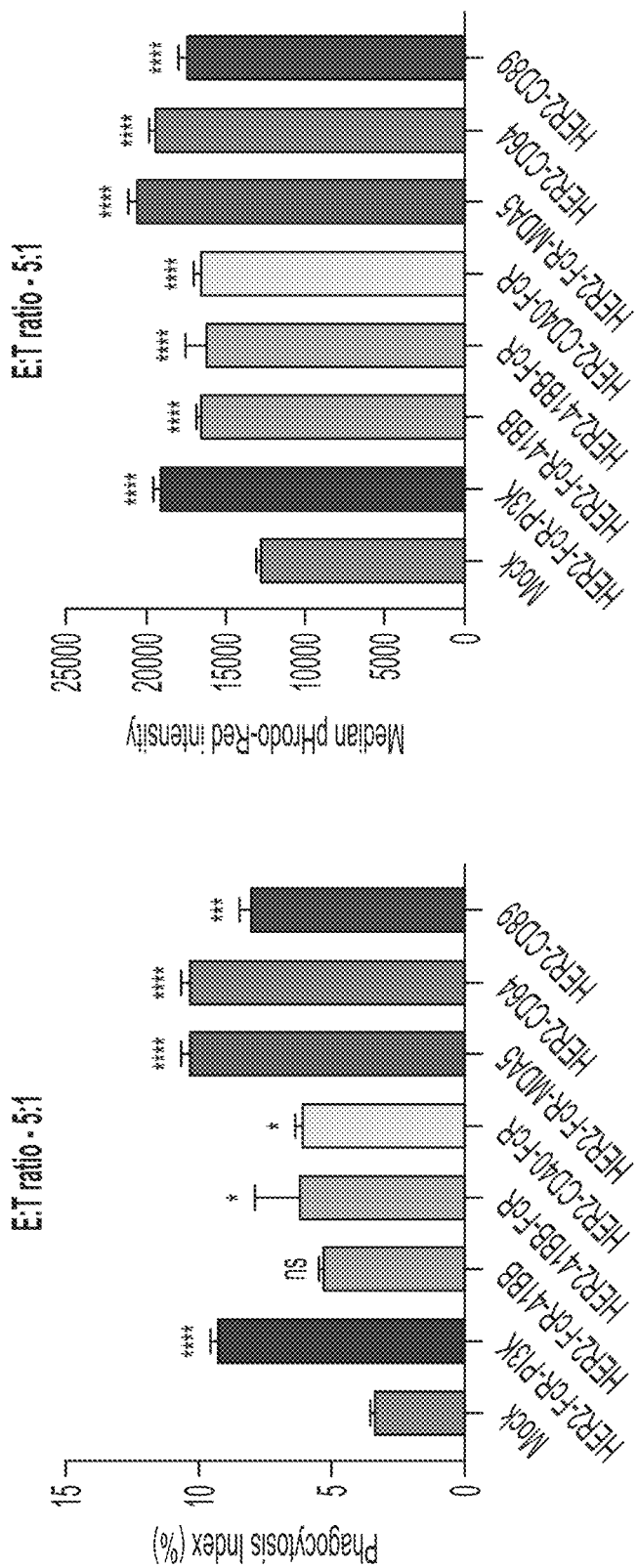
FIG. 4B depicts representative quantitative data showing phagocytosis index of myeloid cells expressing each construct as indicated. E:T ratio, effector (myeloid) cell:target cell ratio. Experimental results were analyzed according to the method of FIG. 4A.
Figure 4C:
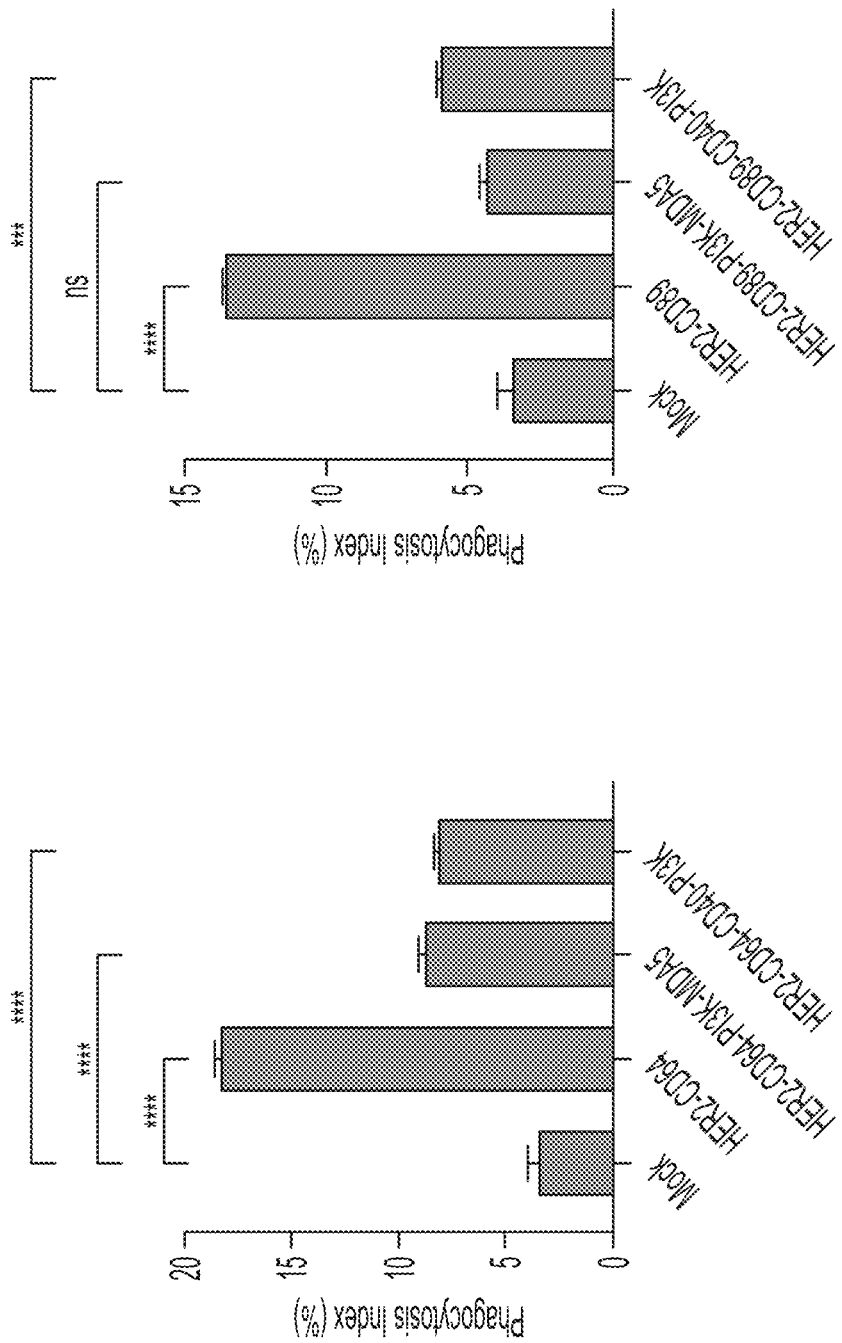
FIG. 4C depicts representative data showing phagocytosis index of myeloid cells expressing each construct as indicated.

Example 3. NF-Kappa B Activation and Inflammatory Cytokine Induction in Myeloid Cells Expressing CFP Constructs In this example, individual constructs are electroporated into THP-1 cells and expression and functional analysis were performed. Expression of various constructs (FIGS. 2A-2D) were high, other than the construct having a MDA5 intracellular domain (FIG. 2E). Likewise, constructs encoding a HER2-FcR-PI3K-MDA5, HER2-CD68-FcR-PI3K-RIG1, and HER2-CD68-FcR-PI3K-MyD88 showed poor expression in THP-1 myeloid cells (FIG. 2E, 2F). In cases where the CFP construct comprised a CD64 TM domain, or a CD89 TM domain, high CFP expression was observed, but not in otherwise identical constructs that contained additional dual or multiple intracellular signaling domains, particularly, for example a PI3K signaling ICD and a TLR signaling ICD. It was observed that fusion of additional domains to CD64 or CD89 apparently resulted in loss of function (e.g., phagocytosis, shown in FIG. 4C). Constructs having CD40 ICD with another signaling ICD, such as a PI3Kinase recruitment domain show slightly higher expression levels in parallel assays, compared to the CFP constructs with multi-ICDs that include a TLR signaling domain instead of CD40 ICD. Phagocytosis potential as indicated by phagocytic index was higher in CD40 ICD constructs relative to the TLR-ICD containing multi-ICDs (FIG. 2F, FIG. 4D). Constructs containing an MDA5 ICD with an FcR ICD (HER2-FcR-MDA5) showed higher or comparable phagocytic index with HER2-CD40-FcR CFPs as shown in FIG. 4B. When a PI3 kinase recruitment domain was placed in the intracellular region, along with an MDA5, RIG-1 or MyD88 signaling intracellular domains both expression (FIG. 2F, FIG. 2G) and phagocytosis (FIG. 4D and FIG. 4E) were lower than a construct containing FcR and PI3 kinase recruitment domains.

Figure 5C:
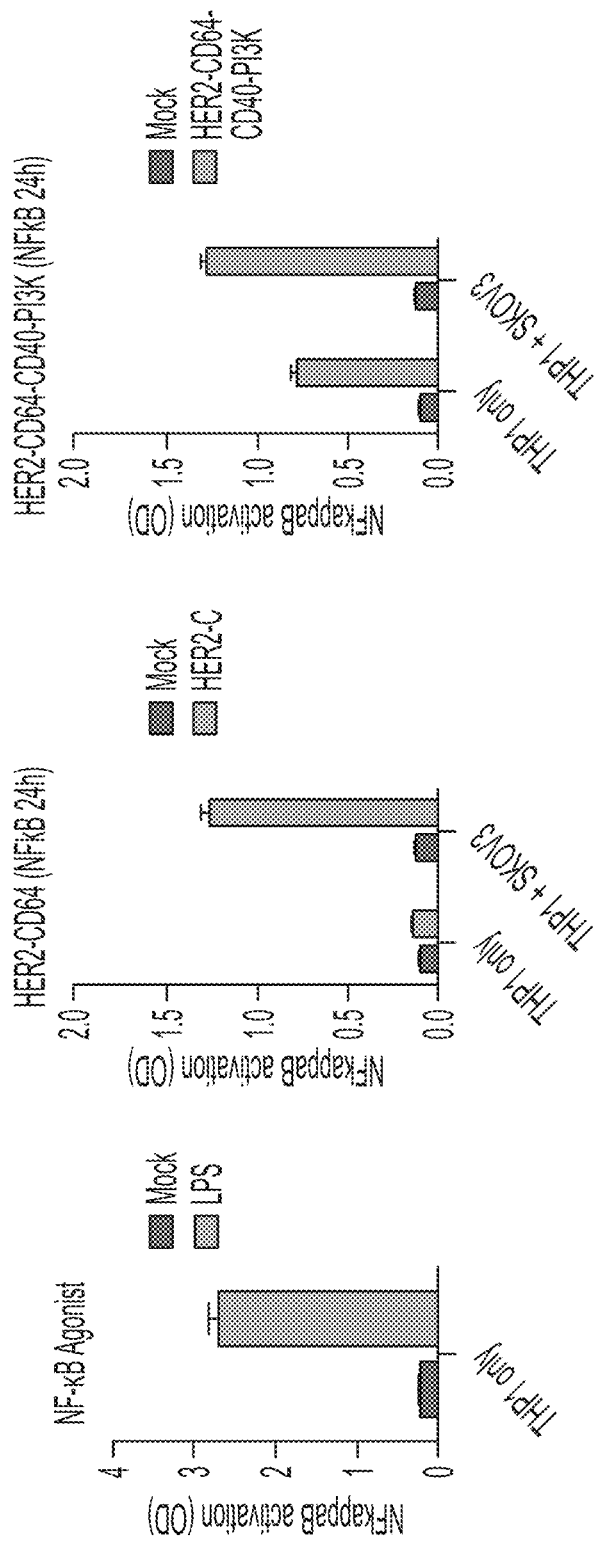
FIG. 5C shows data demonstrating NF-kappa B activation in THP-1 cells that were either mock electroporated or electroporated with the indicated CFP construct and assayed after 24 hours of transfection, in the presence or absence of target SKOV3 cells. Cells expressing constructs having CD64 intracellular domain alone show high NF-kappa B activation in presence of target cells. Constructs having both PI3 kinase recruitment domain and an innate immune response signaling domain from CD40 exhibit tonic signaling (graph at the right) for NF-kappa B activation. Positive control is shown on the left graph using NF-kappa B agonist.
Figure 5D:
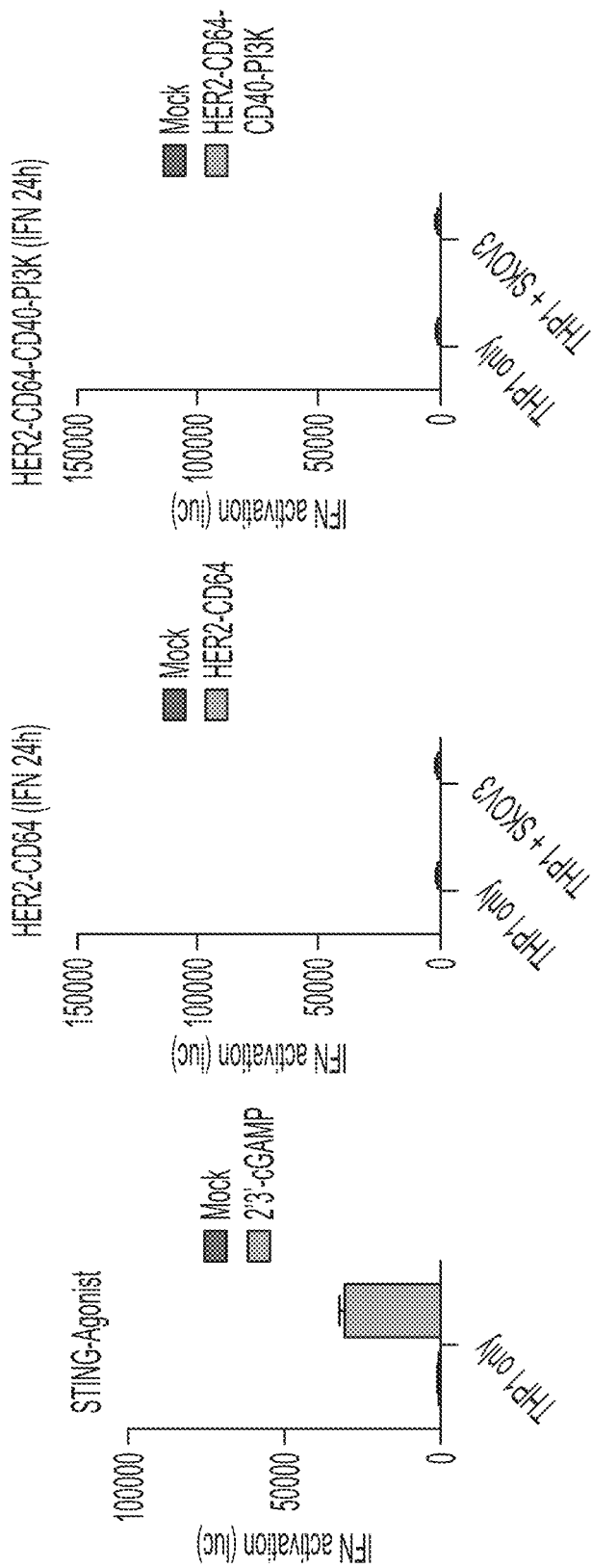
FIG. 5D shows data demonstrating IFN activation in THP-1 cells 24 hours after transfection with the CFP construct as in FIG. 5C or mock transfected. HER2-CD64 constructs do not activate IFN response. Multi-domain constructs (right graph) do not activate IFN in absence or in presence of the target cell. Positive controls are shown on the left graph using a STING agonist.
Figure 5G:
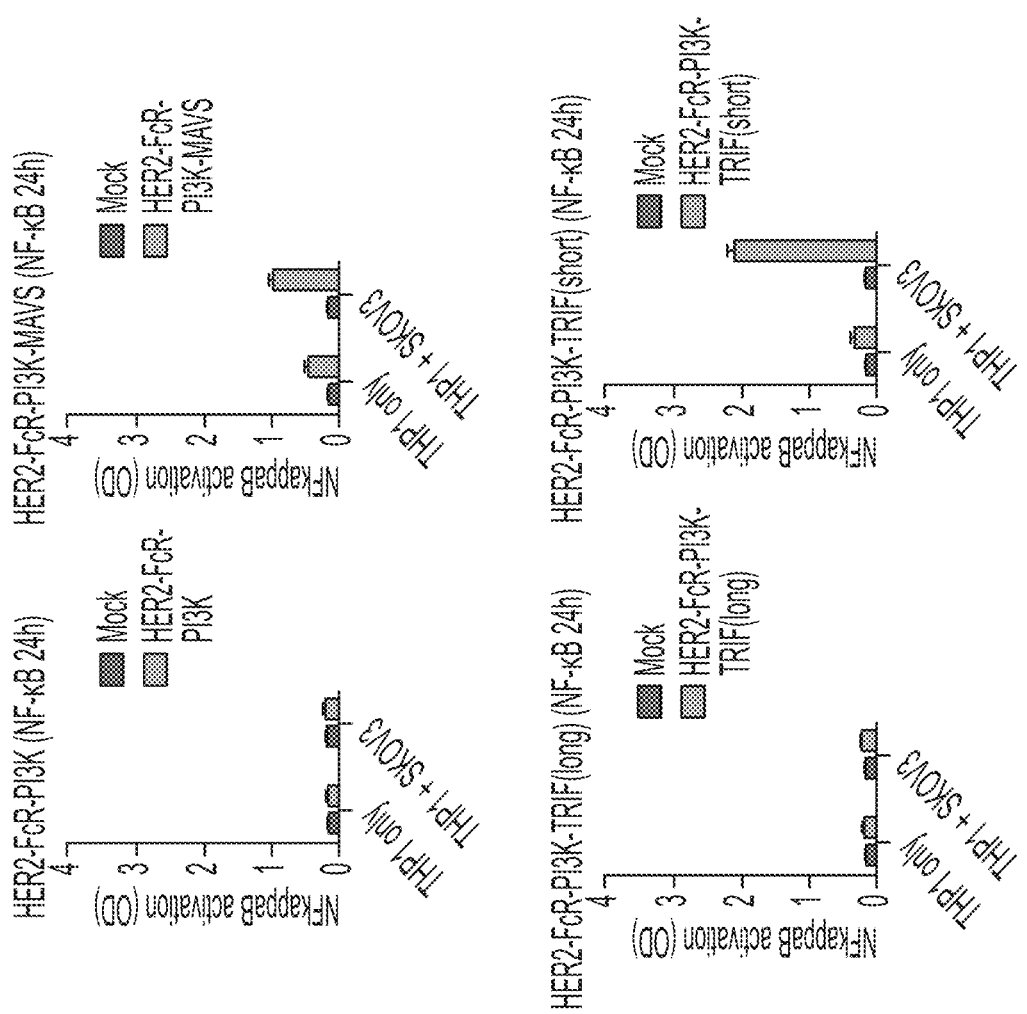
FIG. 5G shows data demonstrating NF-kappa B activation in THP-1 cells expressing individual constructs as indicated. Cells expressing constructs having FcR domain or FcR domain along with additional intracellular domains were tested and results shown.
Figure 5H:
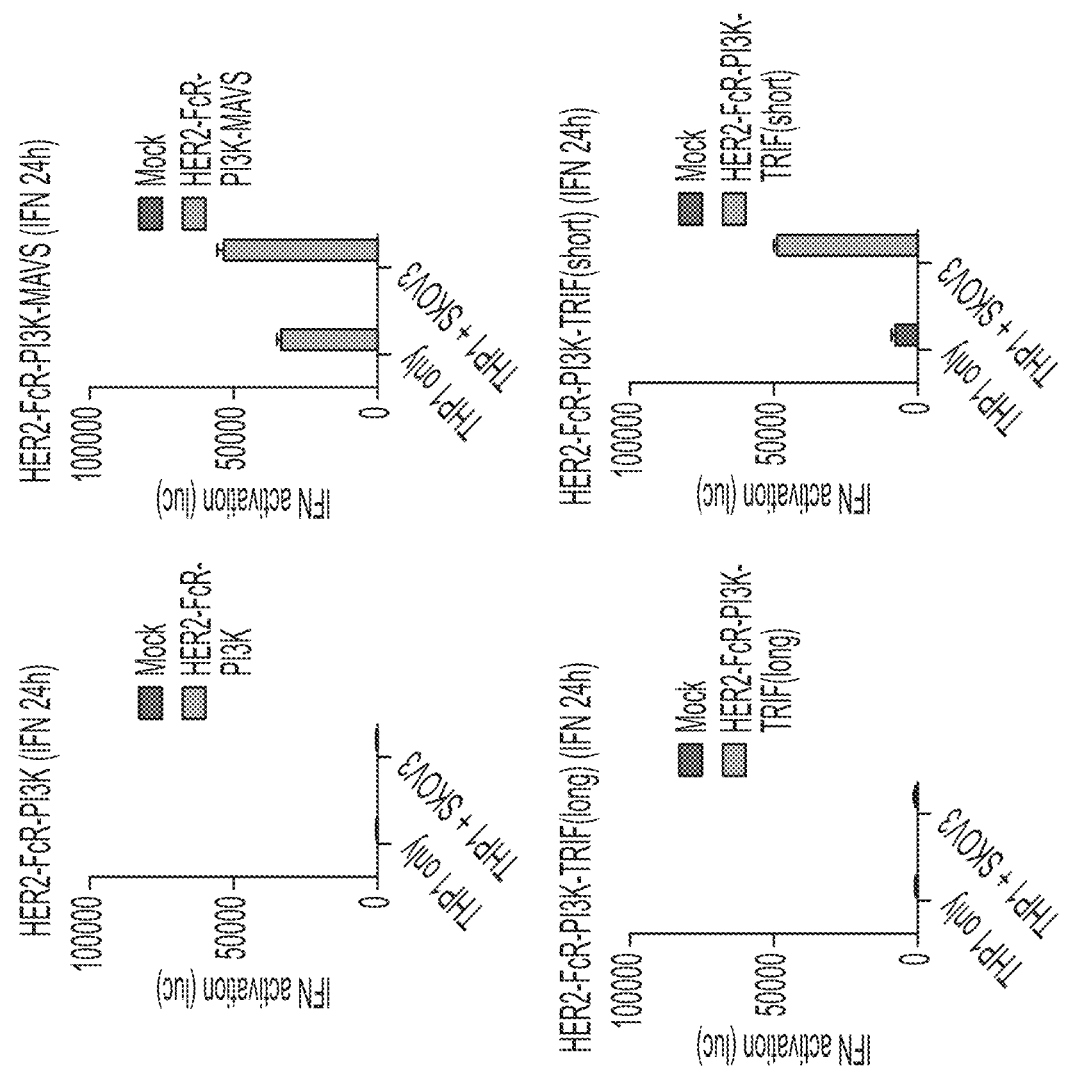
FIG. 5H shows flow cytometry data demonstrating IFN activation in THP-1 cells 24 hours after electroporation with the CFP construct as indicated.

THP-1 cells expressing some of the constructs mentioned in the preceding paragraph exhibit tonic signaling upon expression, especially when a PI3 kinase recruitment domain was placed in the intracellular region, along with an MDA5, RIG-1 or MyD88 signaling intracellular domains. Shown in FIG. 5C, HER2-CD64-CD40-PI3K construct exhibited tonic signaling. NF-kappa B activation was induced in HER2-CD64 constructs, but when CD40 ICD and PI3kinase recruitment intracellular domains were added, tonic NF-kappa B induction was observed (FIG. 5C). As is hereby understood, expression of HER2-CD64 or HER2-CD89 do not induce IFN (FIG. 5D). Similarly, with HER2-CD89 construct alone, without additional ICD, NF-kappa B was induced, but addition of CD40 and PI3K signaling ICDs to the construct decreased its ability to induce NF-kappa B upon contact with a target cell (e.g., HER2-expressing SKOV3). Addition of PI3kinase recruitment domain (PI3K) and MDA5 domains had a similar effect in HER2-CD89 construct. Likewise, HER2-FcR-PI3K-MAVS exhibited tonic NF-kappa B or IFN-gamma signaling (FIG. 5G, and FIG. 5H). These results revealed considerable unpredictability of the effects of the intracellular ICD function in the combined recombinant protein, even though the ICDs may individually, or in their native protein, function in a certain predictable manner. Therefore success in designing the constructs does not depend merely upon routine molecular cloning with the expectation that any assortment of fragments or functional domains can create a CAR with a desired function. The compatibility and functional ability of different domains with respect to each other when structured into a CAR is the crucial aspect in generating a successful CAR construct designed for improved phagocytosis of myeloid cells. Preliminary data exemplifying some ongoing findings that are not yet comprehensive are tabulated below (Table 7):

TABLE 7

| Construct Name | CD64 constructs | CD64-PI3K-MDA5 | CD64-CD40-PI3K | CD89 | CD89-PI3K-MDA5 | CD89-CD40-PI3K |
|---|---|---|---|---|---|---|
| Expression | +++ | + | ++ | ++ | + | ++ |
| Phagocytosis | +++ | + | + | ++ | – | – |
| NF-kB Activation | +++ | +++ (Tonic signaling) | +++ (Tonic signaling) | ++ | – | – |
| IFN-1 Activation | – | +++ (Tonic signaling) | | – | – | – |

Without wishing to be bound by a theory, it is plausible that the intracellular adaptor protein domains, e.g. pLxIS motif containing domains can be triggered by a host of intracellular triggers when overexpressed, and which may be augmented by a PI3kinase recruitment domain in the intracellular region of the chimeric protein.

Figure 2G:
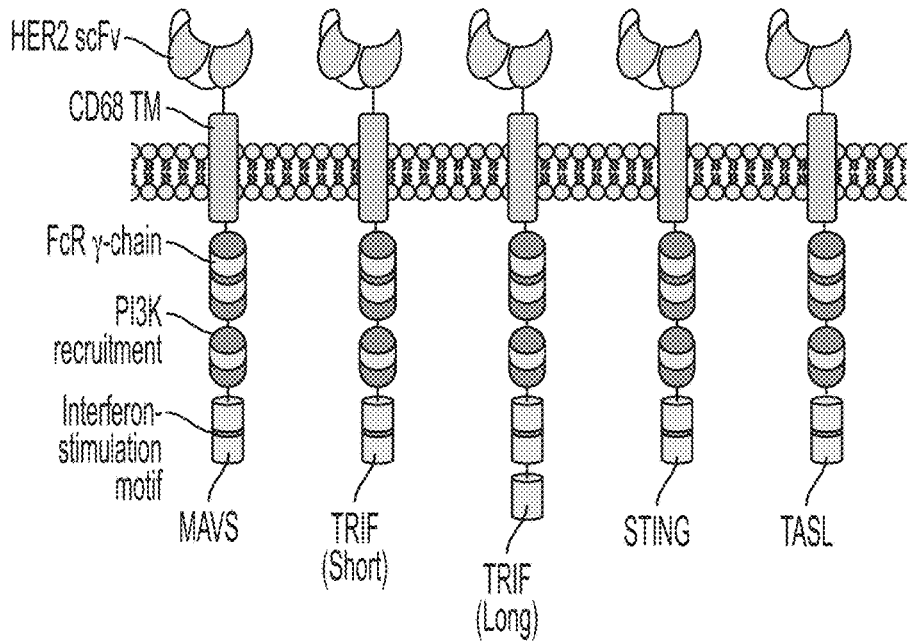
FIG. 2G shows exemplary CFP design (upper panel), and expression data (lower panel) of the constructs in THP-1 cells. The respective domains are as indicated in the figure.
Figure 2G:
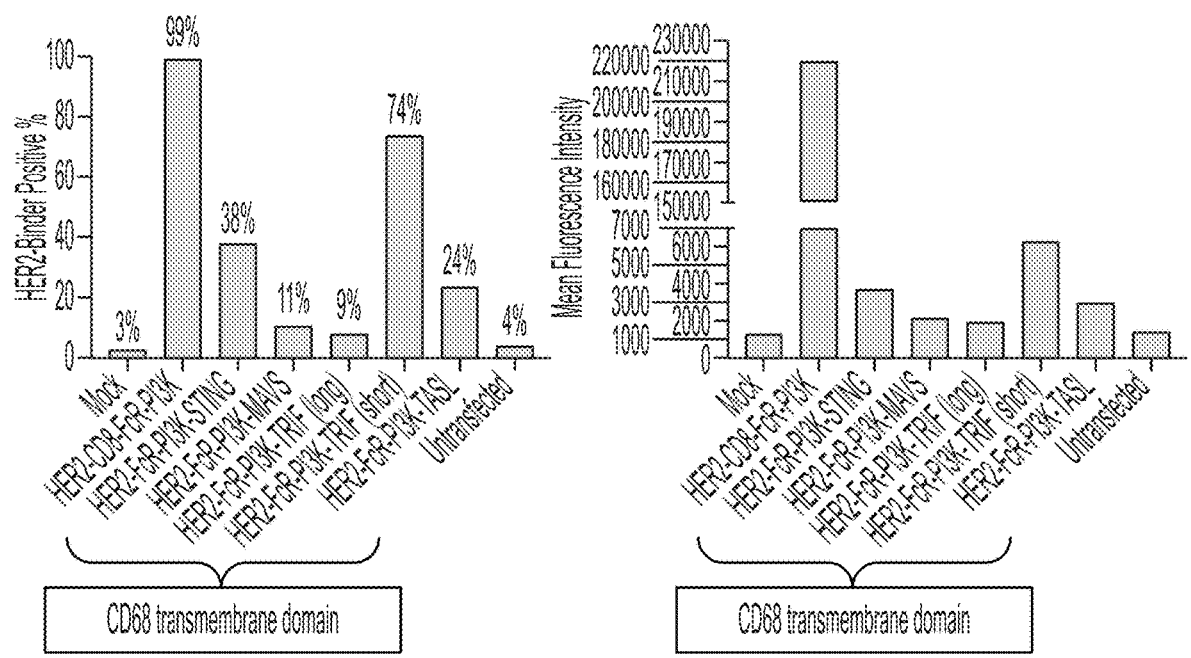
Figure 3:
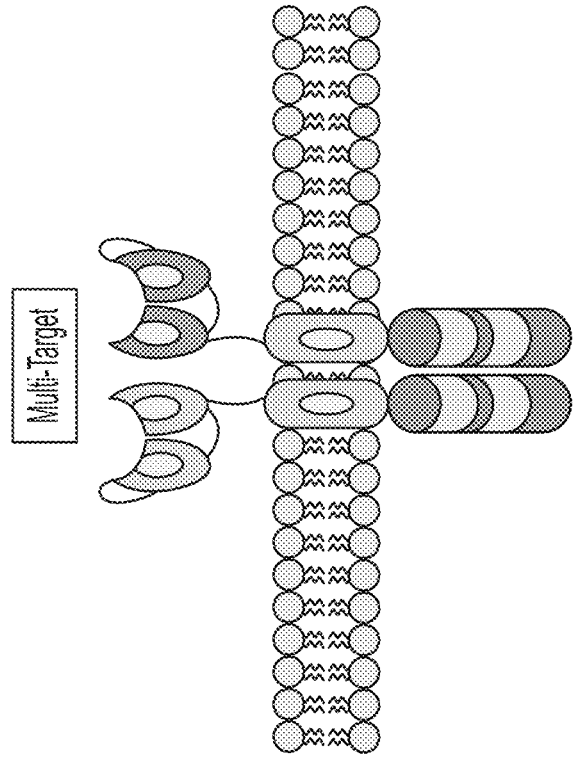
FIG. 3 shows exemplary CFP designs with extracellular domains containing one or more scFvs, directed towards binding to a single target antigen or to multiple targets, with each scFv having a different antigen specificity.
Figure 3:
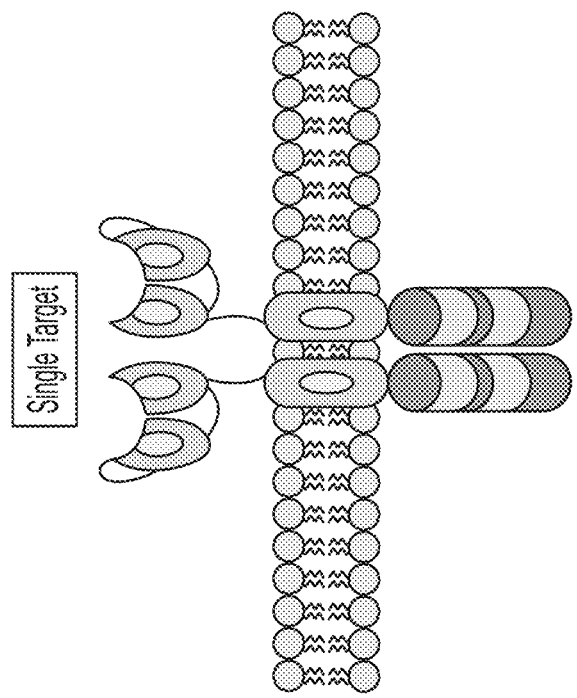
Figure 4E:
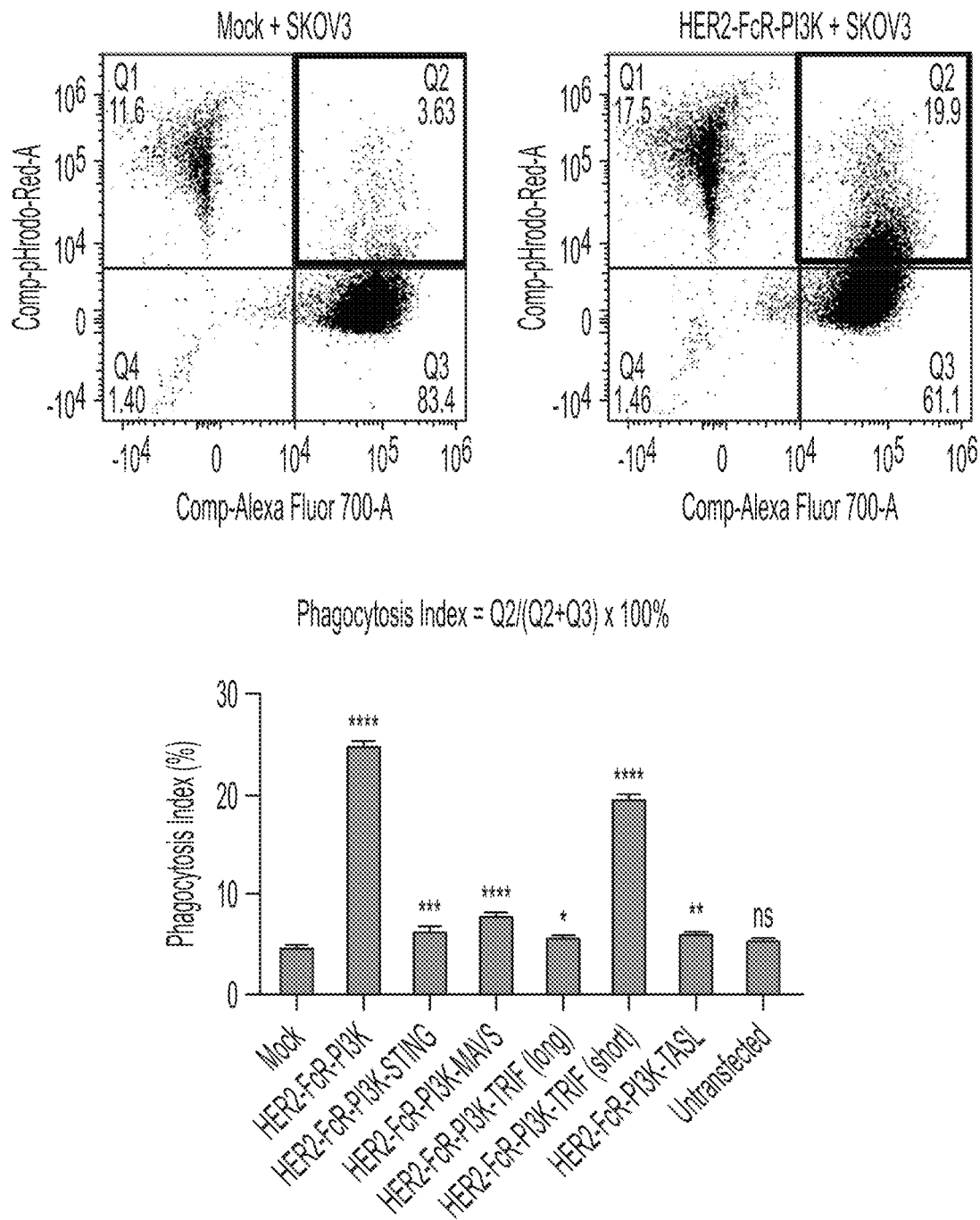
FIG. 4E depicts representative data showing phagocytosis index of myeloid cells expressing each construct as indicated. Exemplary flow cytometry plots are shown in the upper panel, and quantitative data shown in lower panel. The data demonstrated cells expressing HER2-FcR-PI3K-TRIF (short) construct show high phagocytic index compared to other constructs.
Figure 5I:
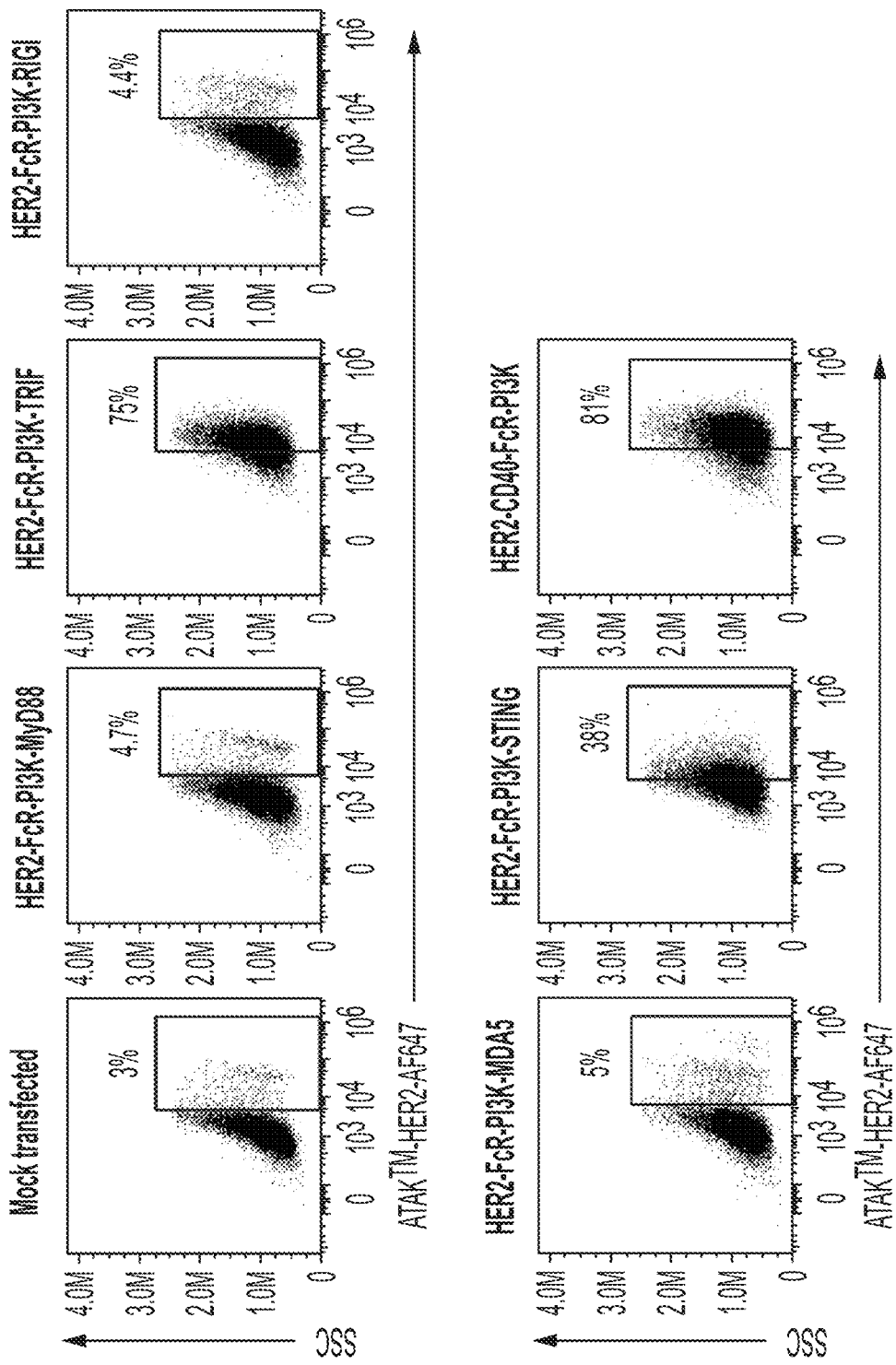
FIG. 5I shows data demonstrating expression of the different HER2-CFP constructs having different intracellular domains comprising TLR domains. Flow cytometry analysis of the cell surface expression of HER2 binder CFP using labeled antibody, anti-HER2-AF647 in mRNA electroporated THP-1 cells. Percentage of HER2-binder expressing cells are indicated in the figure.
Figure 5J:
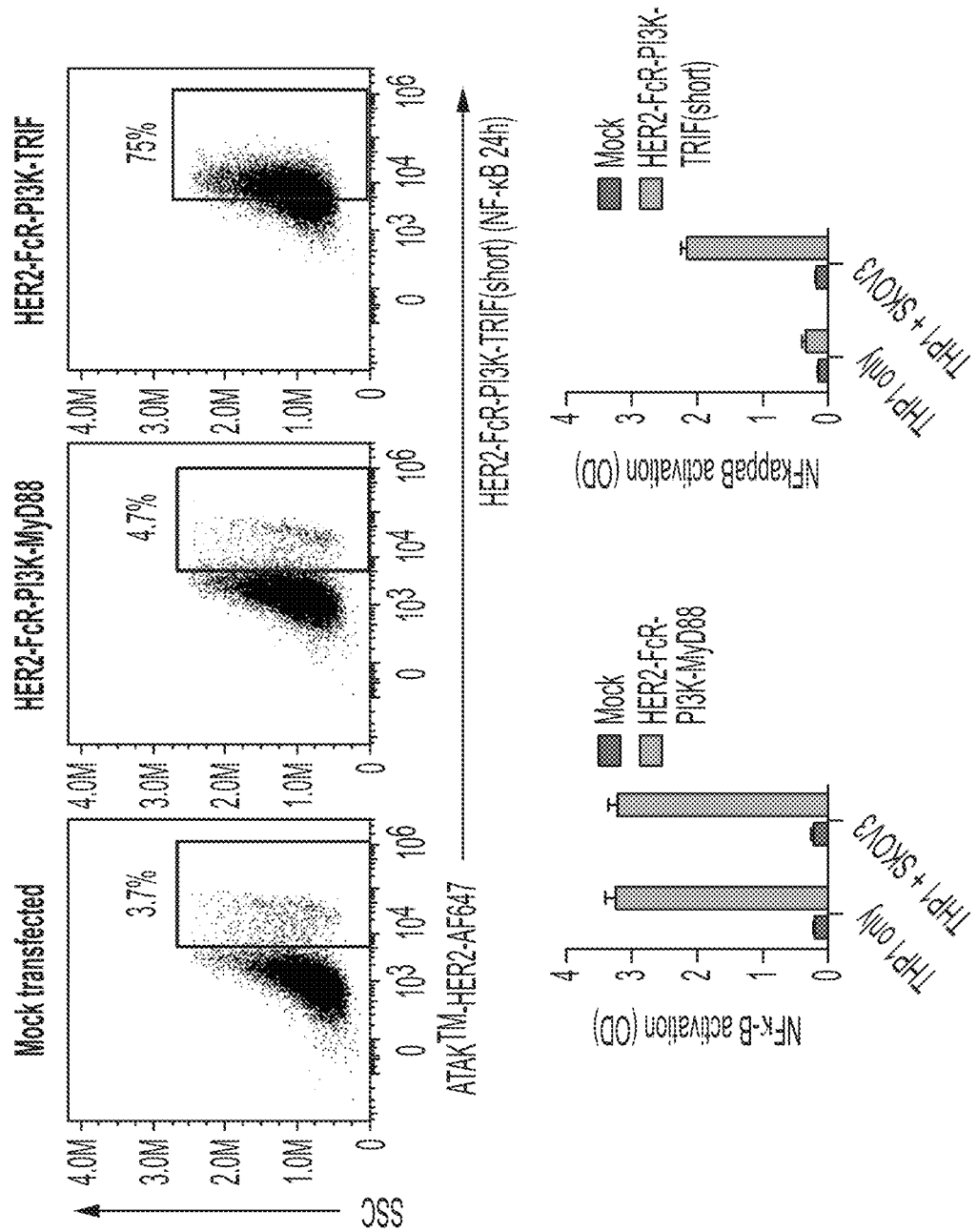
FIG. 5J shows flow cytometry data demonstrating expression of the indicated HER2-CFP constructs in THP-1 cells (top panel) and NF-kappa B activation 24 hours after electroporation with the CFP construct as indicated (bottom panel). Expression of HER2-FcR-PI3Kinase-MyD88 construct led to tonic NF-kappa B signaling (signaling in absence of the target cell SKOV3, that is, in absence of engagement of the extracellular binding domain of the CFP to the antigen on SKOV3 cells).
Figure 5K:
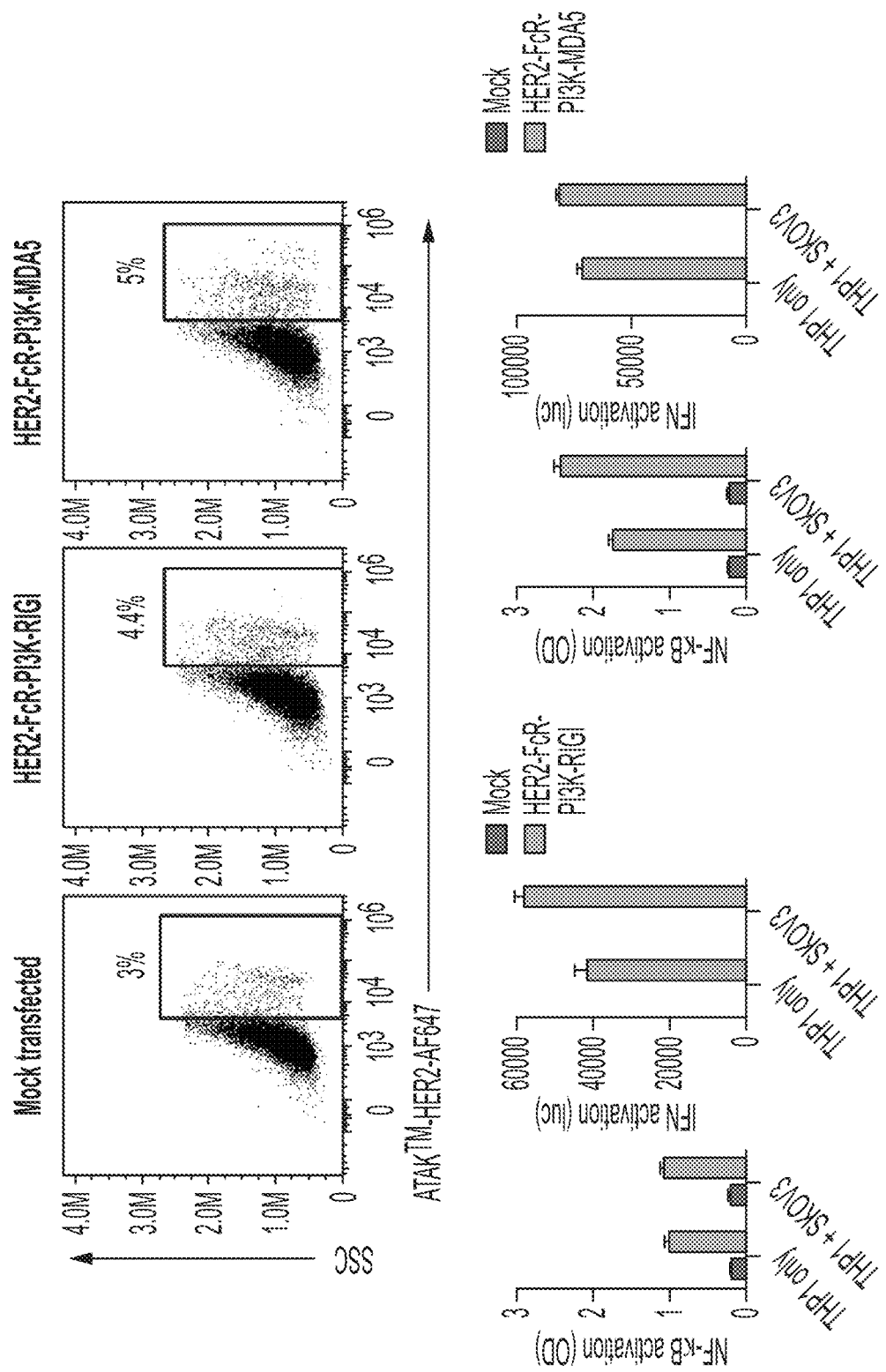
FIG. 5K shows flow cytometry data demonstrating expression of the indicated HER2-CFP constructs in THP-1 cells and NF-kappa B activation and IFN activation 24 hours after electroporation with the HER2-CFP construct as indicated. The data demonstrated that tonic NF-kappa B and IFN gamma signaling was seen in the multi-domain constructs having FcR-PI3K-RIG1 intracellular domains, or FcR-PI3K-MDA5 intracellular domains.
Figure 5L:
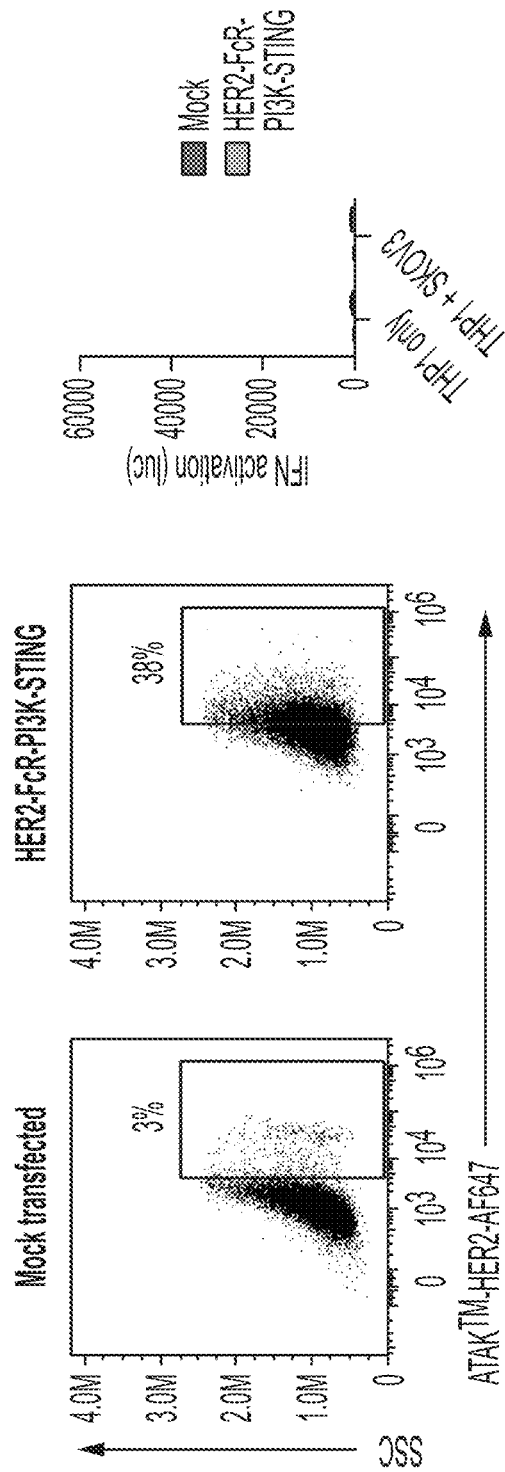
FIG. 5L shows flow cytometry data demonstrating expression of the indicated HER2-CFP constructs in THP-1 cells and IFN activation in THP-1 cells 24 hours after electroporation with the CFP constructs as indicated.
Figure 5M:
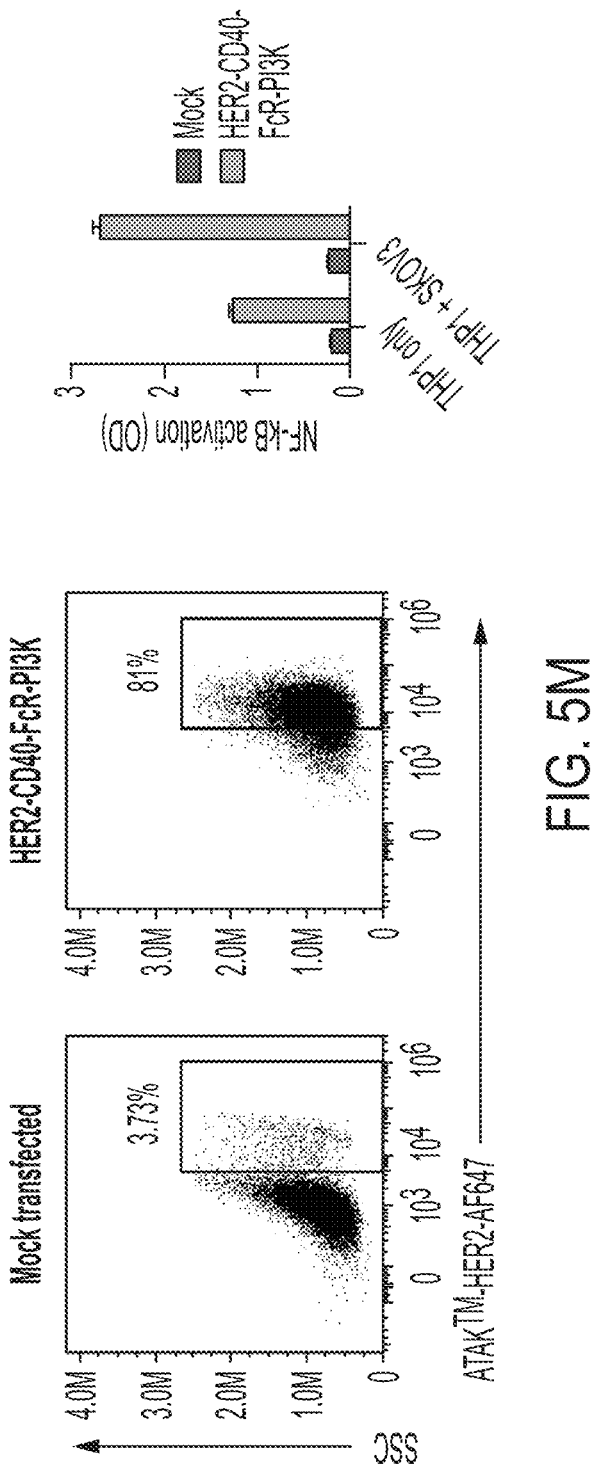
FIG. 5M shows flow cytometry data demonstrating expression of the indicated HER2-CFP constructs and NF-kappa B activation in THP-1 cells 24 hours after electroporation with the CFP construct as indicated.
Figure 5N:
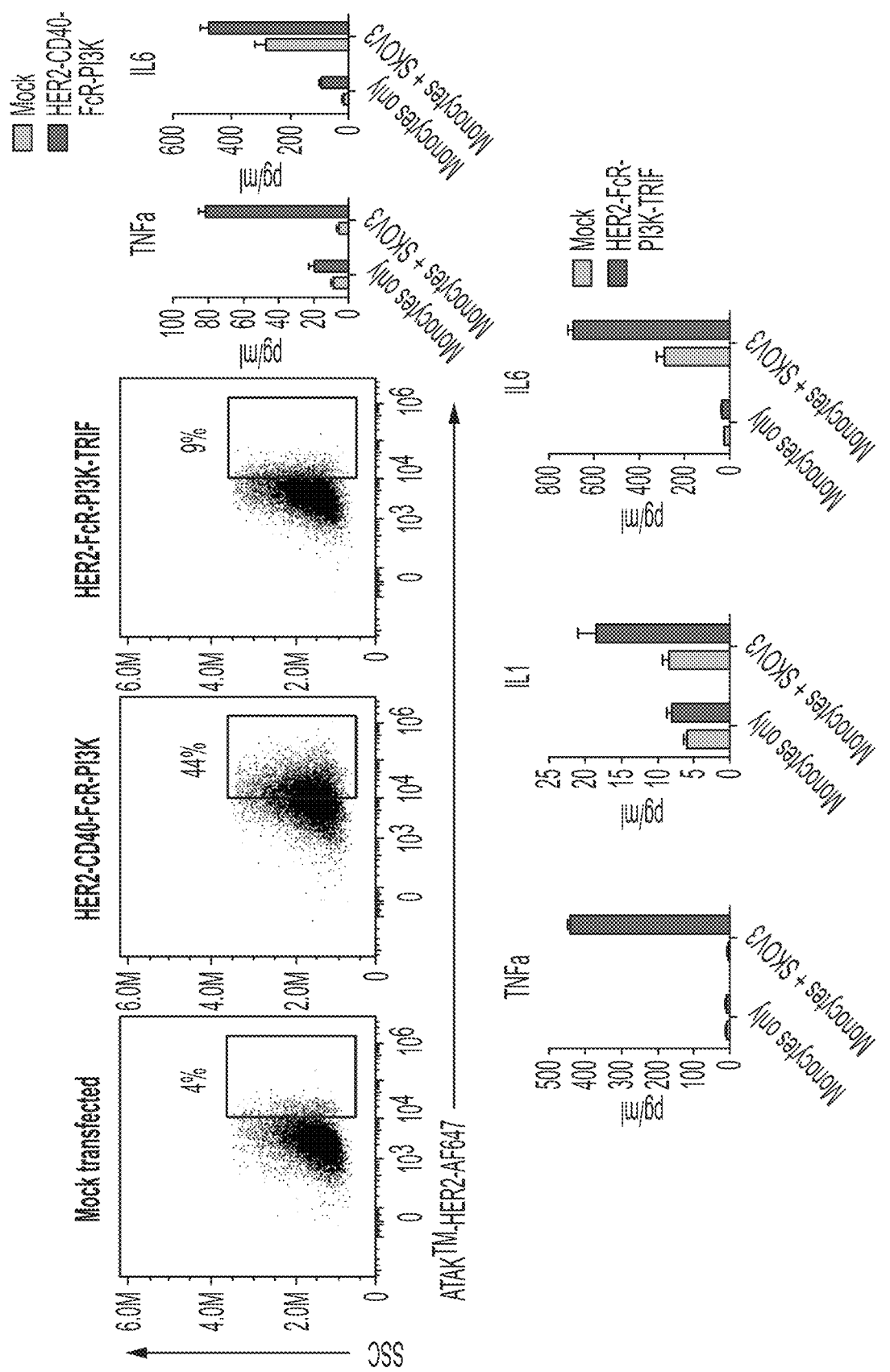
FIG. 5N shows flow cytometry data demonstrating expression of the indicated HER2-CFP constructs and cytokine expression by THP-1 cells 24 hours after electroporation with the CFP mRNA construct as indicated.

Example 4. NF-Kappa B Activation and IFN Response in Cells Expressing TRIF Long and Short Constructs In order to design constructs that exhibit sufficient level of expression, avoid tonic signaling, and would show NF-kappa B activation and IFN response upon activation of the extracellular domains several other constructs were designed and tested. FIG. 2G and FIG. 5I show representative construct designs and expression data in THP-1 cells. mRNA constructs were electroporated in THP-1 cells and expression of the HER2-CFP constructs were determined by flow cytometry. Phagocytosis was assayed following the protocol demonstrated in the schematic of FIG. 5A, NF-kappa B activation, interferon gamma activation, and cytokine expression levels were determined in these cells. Surprisingly, a construct that comprises both a PI3kinase recruitment domain and a truncated version of TRIF, called TRIF (short) (TRIF domain of SEQ ID NO: 43), demonstrated higher expression levels than in the constructs described in the previous paragraph, including the TRIF long (SEQ ID NO: 44) (FIG. 5I). THP-1 cells expressing TRIF (short) lacked tonic signaling and showed NF-kappa B and IFN activation only in presence of the target SKOV3 tumor cells (FIG. 5G-5H, FIG. 5J), showed improved phagocytosis index (FIG. 4E) of the TRIF (short) expressing cells than cells expressing other innate immune adaptor domains with PI3kinase recruitment domain. Despite 30-fold lower expression (FIG. 2G, right), TRIF short construct phagocytosis is comparable to baseline construct (HER2-FcR-PI3K) (FIG. 4E). Expression levels and NF-kappa B activation for other constructs were demonstrated in FIGS. 5J-5L. FIG. 5N shows inflammatory cytokine expression of CD40 and TRIF constructs.

Preliminary findings are tabulated below (Table 8):

TABLE 8

| Construct Name | Binder-FcR-PI3K-MAVS | Binder-FcR-PI3K-TRIF(short) | Binder-FcR-PI3K-TRIF(long) |
|---|---|---|---|
| Expression | 9% | 74% | 11% |
| Phagocytosis | – | ++ | – |
| NF-kB Activation | + | ++ | – |
| IFN-1 Activation | +++ (Tonic signaling) | +++ | – |

Figure 6A:
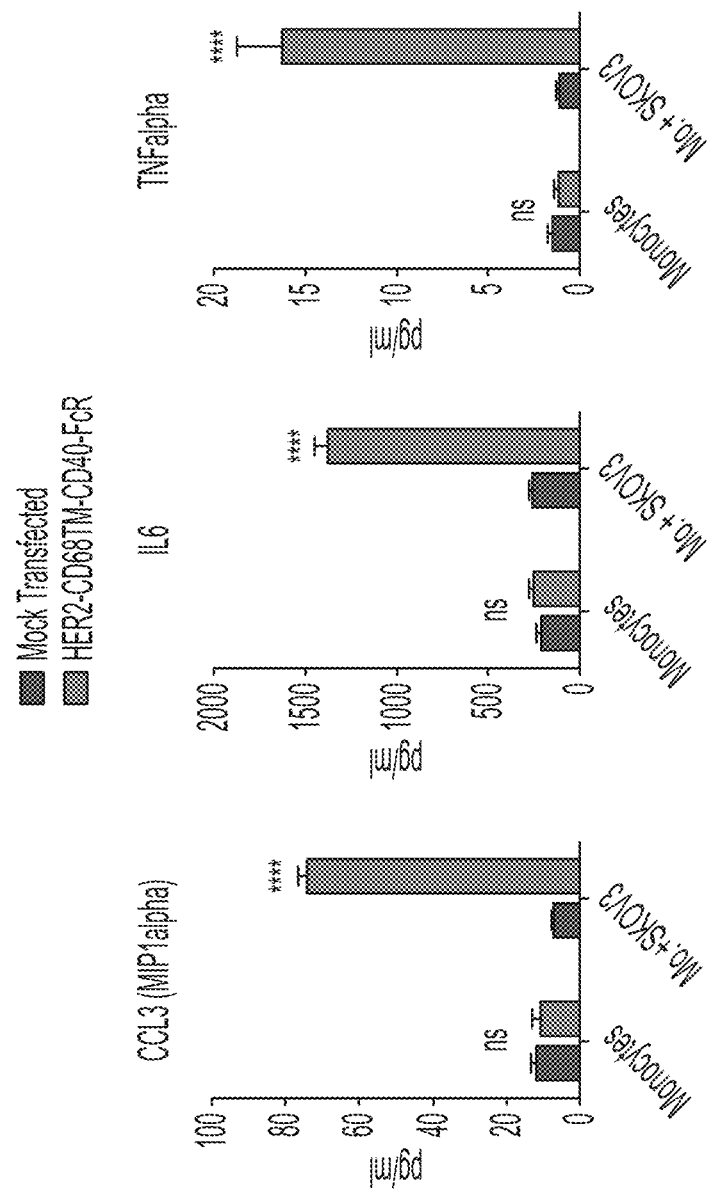
FIG. 6A shows data demonstrating baseline cytokine (IL6 and TNFalpha) and chemokine (CCL3) expression by THP-1 cells expressing the indicated constructs, compared to mock transfected cells. Negative control (mock transfected) graphs appear on the left side of each CFP transfected graph per experimental set.
Figure 6C:
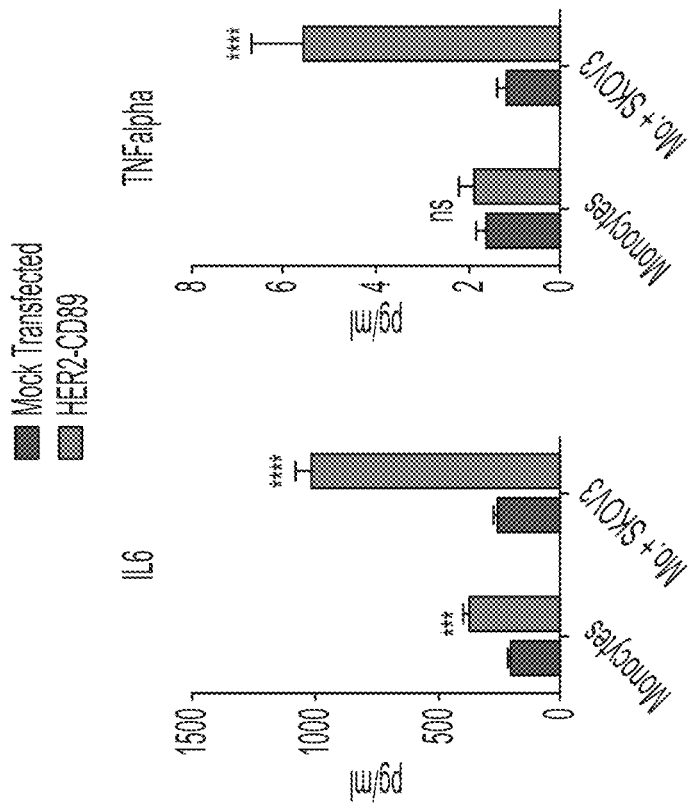
FIG. 6C shows data demonstrating baseline cytokine (IL6 and TNFalpha) expression by THP-1 cells expressing the indicated constructs, compared to mock transfected cells. Negative control (mock transfected) graphs appear on the left side of each CFP transfected graph per experimental set.
Figure 6B:
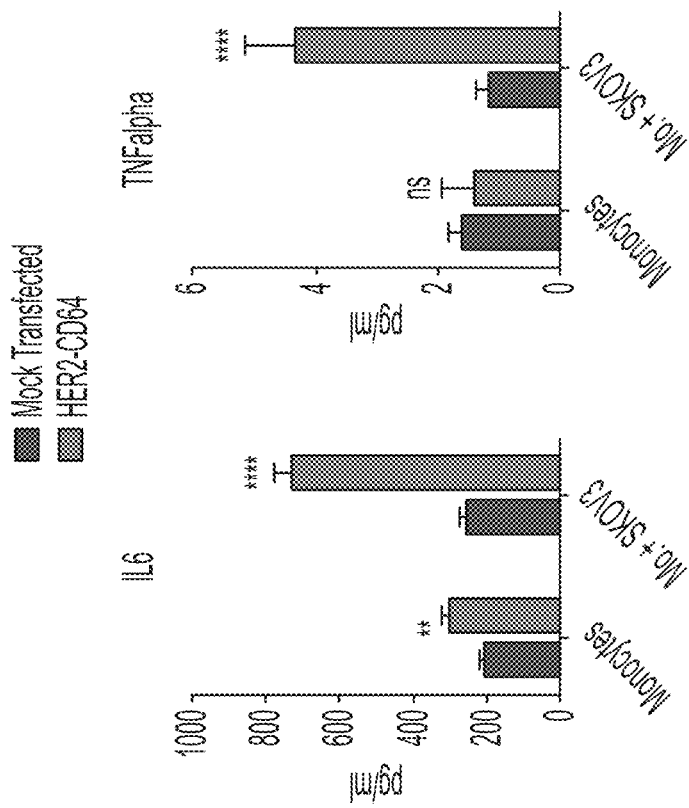
FIG. 6B shows data demonstrating baseline cytokine (IL6 and TNFalpha) expression by THP-1 cells expressing the indicated constructs, compared to mock transfected cells. Negative control (mock transfected) graphs appear on the left side of each CFP transfected graph per experimental set.
Figure 6D:
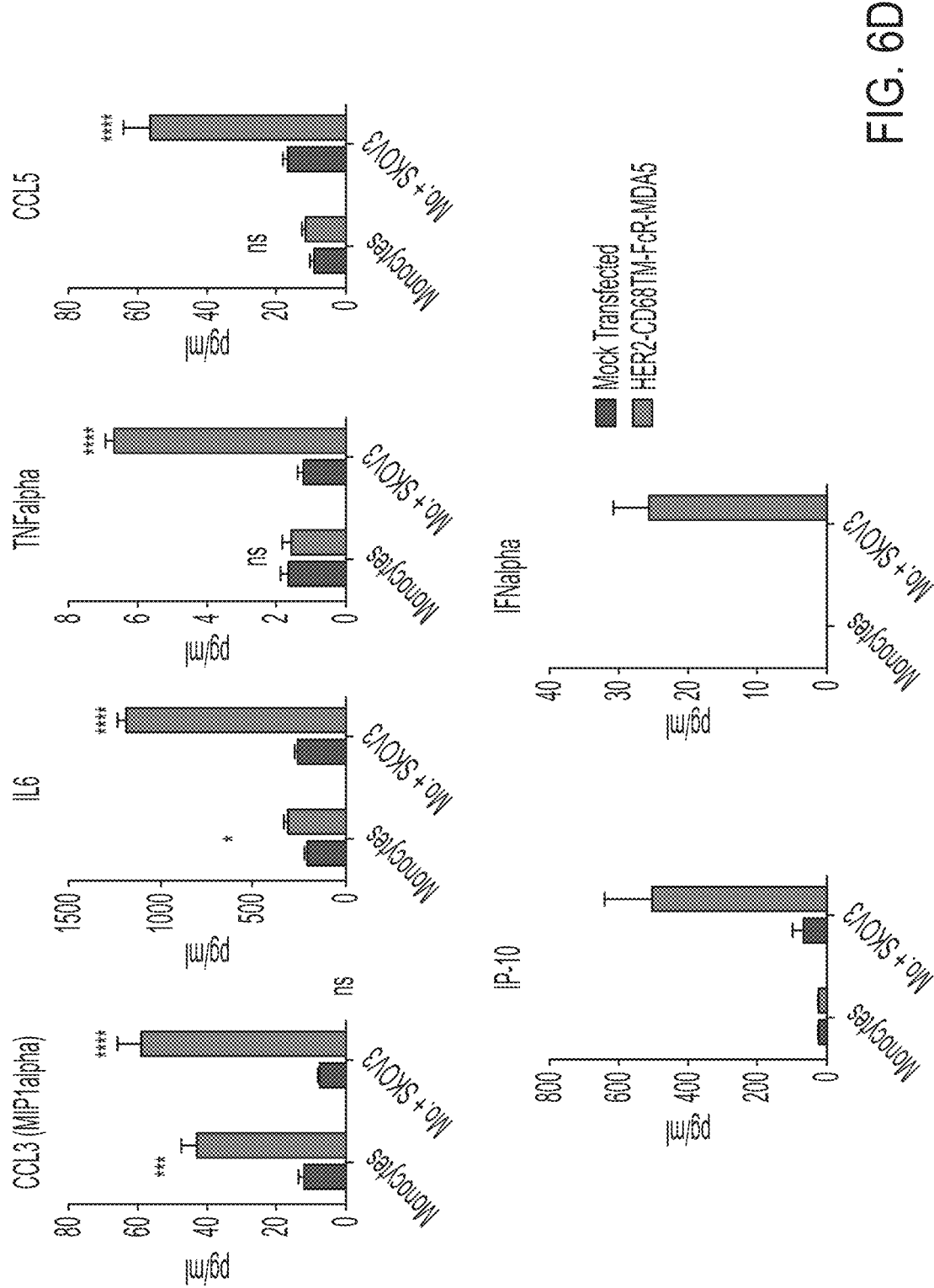
FIG. 6D shows data demonstrating baseline cytokine (IL6, TNFalpha and IFN-gamma as indicated on the respective graphs) and chemokine (CCL3, CCL5 and IP10 as indicated) expression by THP-1 cells expressing the indicated constructs, compared to mock transfected cells. Negative control (mock transfected) graphs appear on the left side of each CFP transfected graph per experimental set.
Figure 6E:
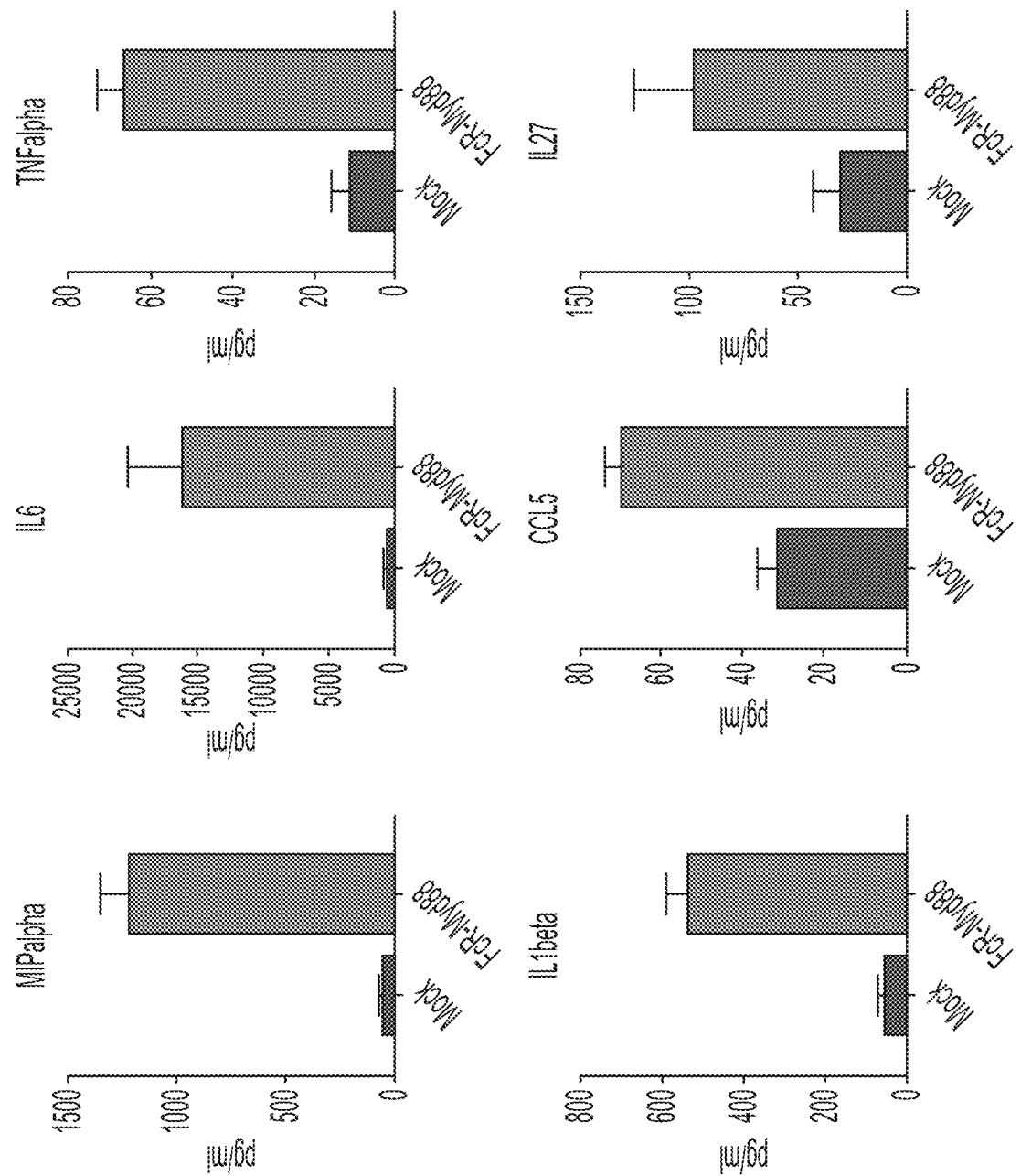
FIG. 6E shows data demonstrating cytokine and chemokine expression in cells transfected with the indicated constructs compared to mock transfected cells.
Figure 6F:
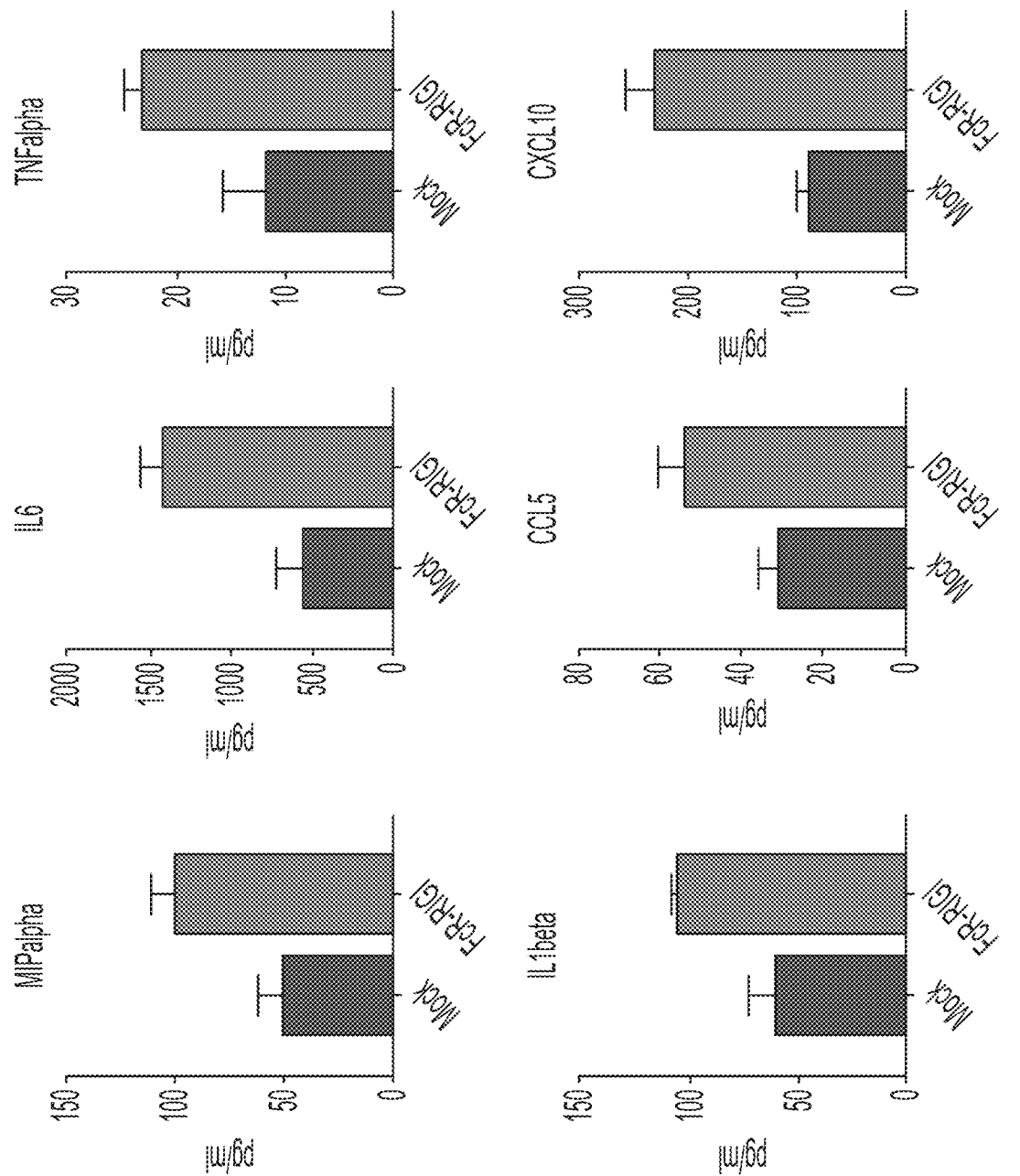
FIG. 6F shows data demonstrating cytokine and chemokine expression in cells transfected with the indicated constructs compared to mock transfected cells.
Figure 7A:
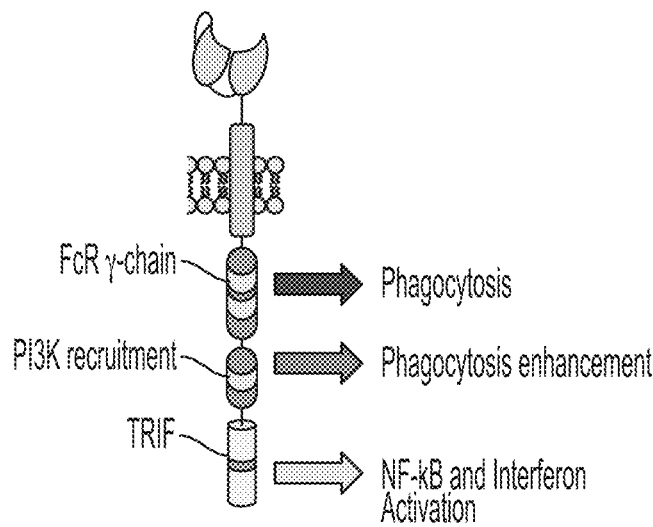
FIG. 7A shows diagrammatic representation of exemplary chimeric antigen receptor constructs with CD68 transmembrane domains.
Figure 7A:
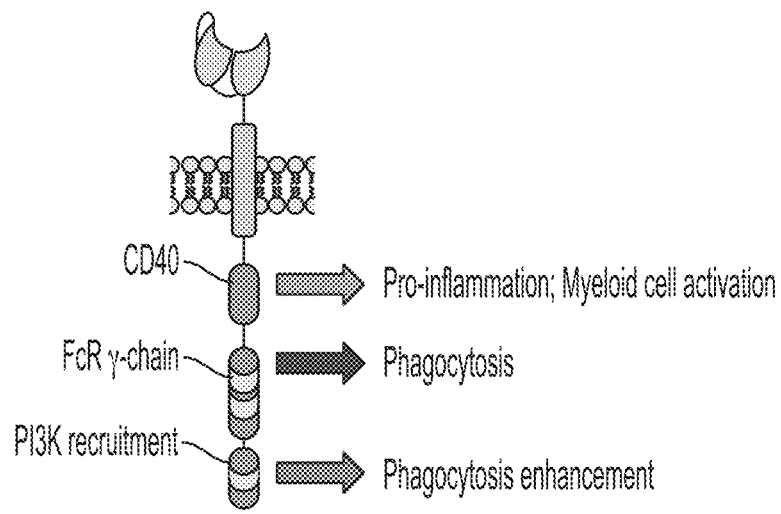
Figure 7B:
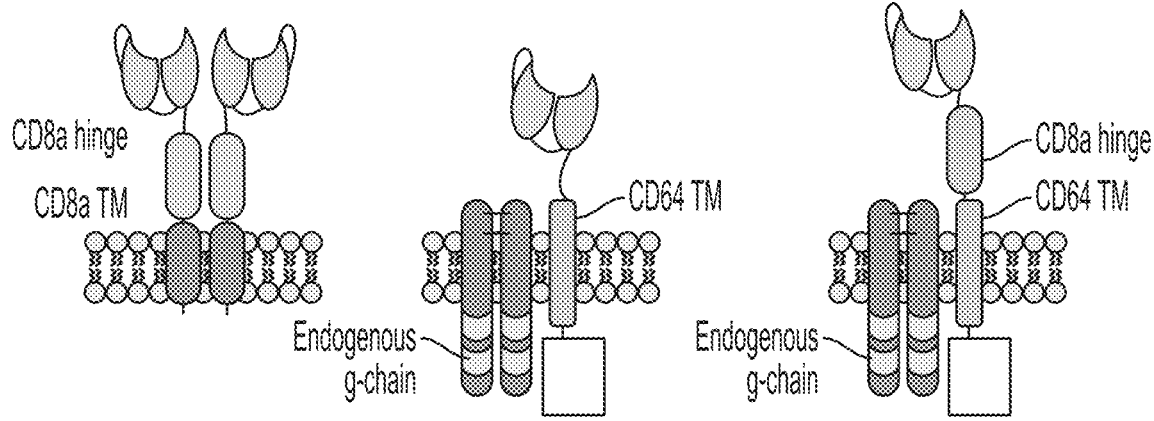
FIG. 7B shows exemplary chimeric antigen receptors with the indicated domains. Top row, middle and right figures show exemplary CFPs with CD64 transmembrane domains that oligomerize with endogenous Fc gamma, and lack intracellular domains of their own. Middle row shows exemplary intracellular domains that were paired with various combinations of domains in the recombinant CFP construct designs. Bottom row shows exemplary CFPs comprising multiple domains.
Figure 7B:
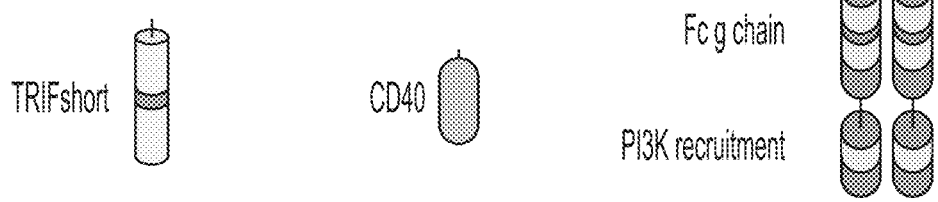
Figure 7B:
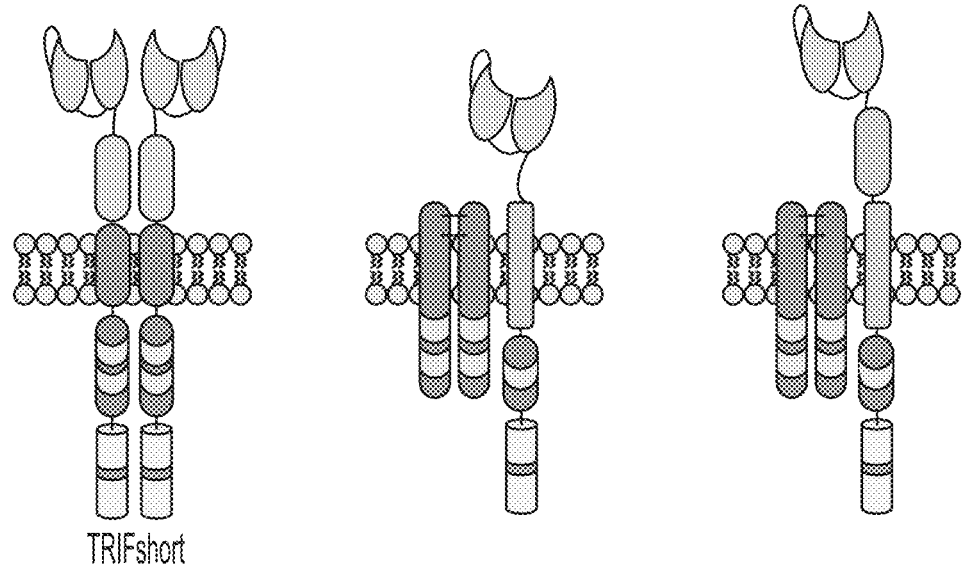

Monocytes expressing the above constructs demonstrate high inflammatory response in presence of a target cell. Data shown in FIGS. 6A-6F demonstrate the above. For example, monocytes expressing HER2-CD68TM-CD40-FcR construct shows elevated CCL3, IL6 and TNF-alpha response when co-cultured with target SKOV3 cells (FIG. 6A). Monocytes expressing a HER2-CD64 construct show greater than 2-fold increase in IL6 and TNF-alpha production compared to mock-transfected monocytes in the presence of the target SKOV3 cells (FIG. 6B); and similar results are observed in monocytes expressing HER2-CD89 (FIG. 6C). Monocytes expressing HER2-CD68TM-FcR-MDA5 construct show high induction of chemokines CCL3 and IP10, and cytokines IL6, TNF-alpha and interferon alpha (FIG. 6D). Similar results were obtained with MyD88 and RIG-1 intracellular domains (FIGS. 6E and 6F). These results clearly demonstrate that the TM and intracellular domains described here are highly functional in inducing an inflammatory response when in monocytes, in the presence of the target cell.

Example 5. Testing of Primary Human Monocytes with Various HER2-CD40 CFP Constructs Based on the results above, receptor enhancements using specific combinations of intracellular signaling domains and/or TM domains were tested in human primary monocytes, testing for expression, phagocytosis and inflammatory cytokine/chemokine release in presence of the respective CFP target. ICD signaling domains comprising domains from (i) CD40 and (ii) TRIF were leading candidates for CFP enhancements. Although high expression and activity of CD40 and TRIF constructs as demonstrated in the previous section in THP-1 cells held great promise, the expression of these constructs were lower in human primary monocytes. Therefore to improve expression and stability of the constructs, the CD68TM domains were swapped with CD64TM and CD8hinge and TM domains. To test surface expression of HER2-CD40 CFP constructs in primary monocytes, primary monocytes were harvested from two healthy human donors and electroporated with the constructs in the table below (Table 9).

TABLE 9

List of HER2-CD40 CFP Constructs tested
HER2-CD40 CFP Constructs tested

HER2-CD8h-CD8TM
HER2-CD8h-CD8TM-FcR-PI3K
HER2-CD8h-CD8TM-CD40-FcR
HER2-CD8h-CD8TM-CD40-FcR-PI3K
HER2-CD64TM-CD40-FcR
HER2-CD64TM-CD40-FcR-PI3K
HER2-CD8h-CD64TM-CD40-FcR
HER2-CD8h-CD64TM-CD40-FcR-PI3K

Figure 8A:
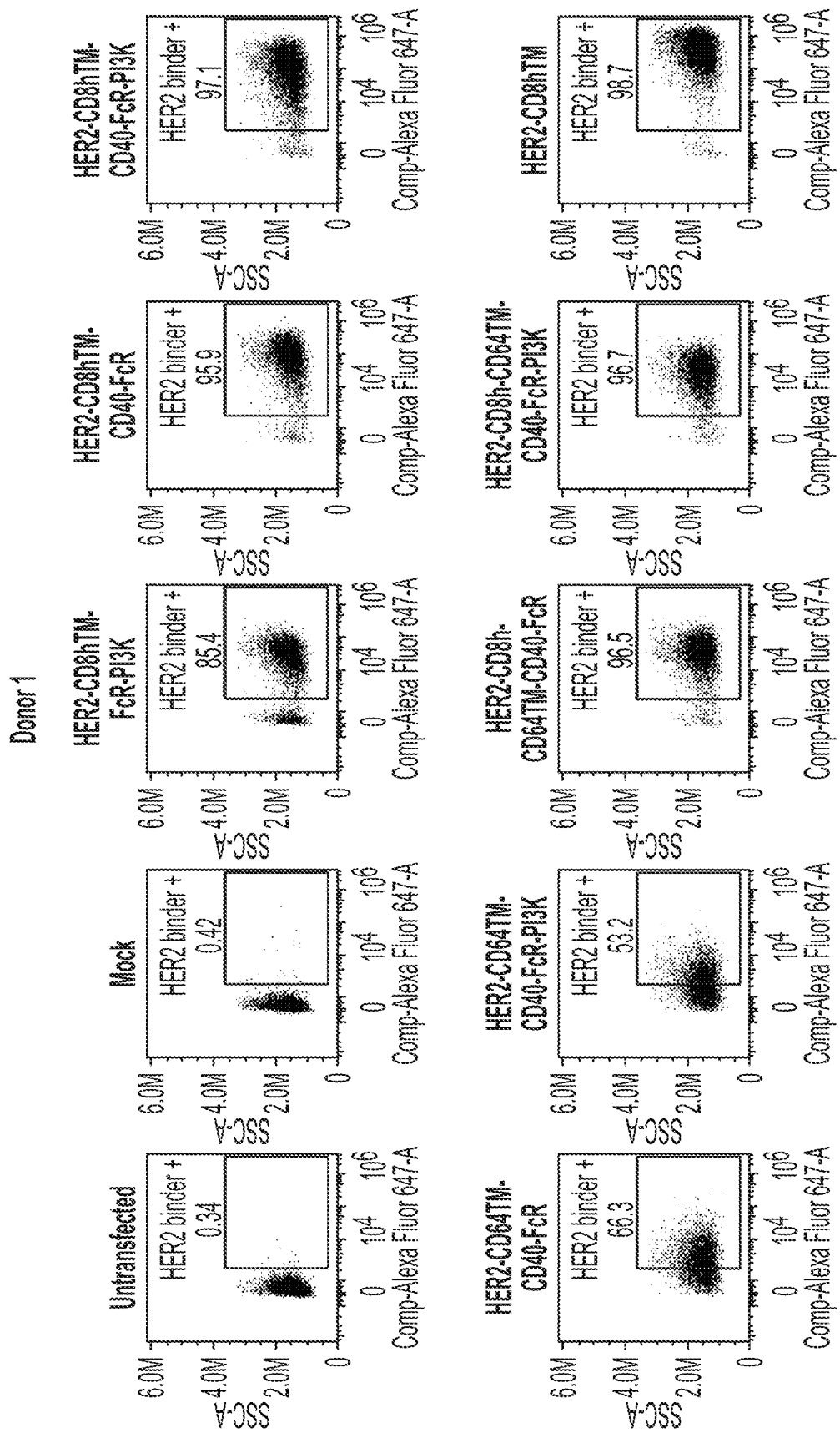
FIG. 8A shows flow cytometry data demonstrating expression of the indicated HER2-CFP constructs in primary human monocytes from a first donor after electroporation of the indicated HER2-CFP constructs. For example, HER2-CD8hTM-CD40-FcR-Pi3K signifies a construct that has anti-HER2-binding extracellular domain; CD8 hinge and transmembrane domains; and three separate intracellular domains that are derived from CD40, FcR and PI3kinase molecules.
Figure 8B:
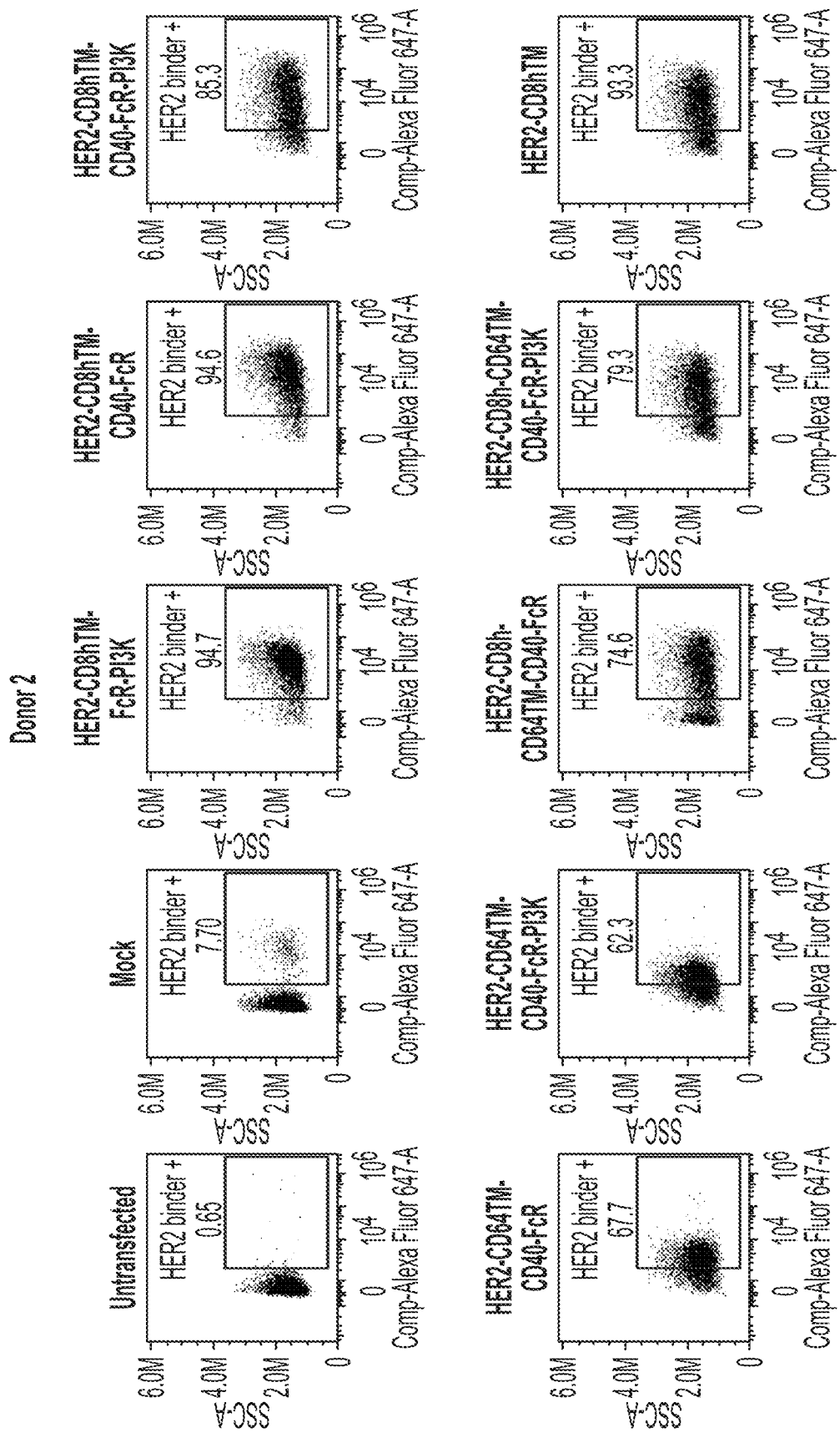
FIG. 8B shows flow cytometry data demonstrating expression of the indicated HER2-CFP constructs in primary human monocytes from a second donor after electroporation of the indicated HER2-CFP constructs.
Figure 8C:
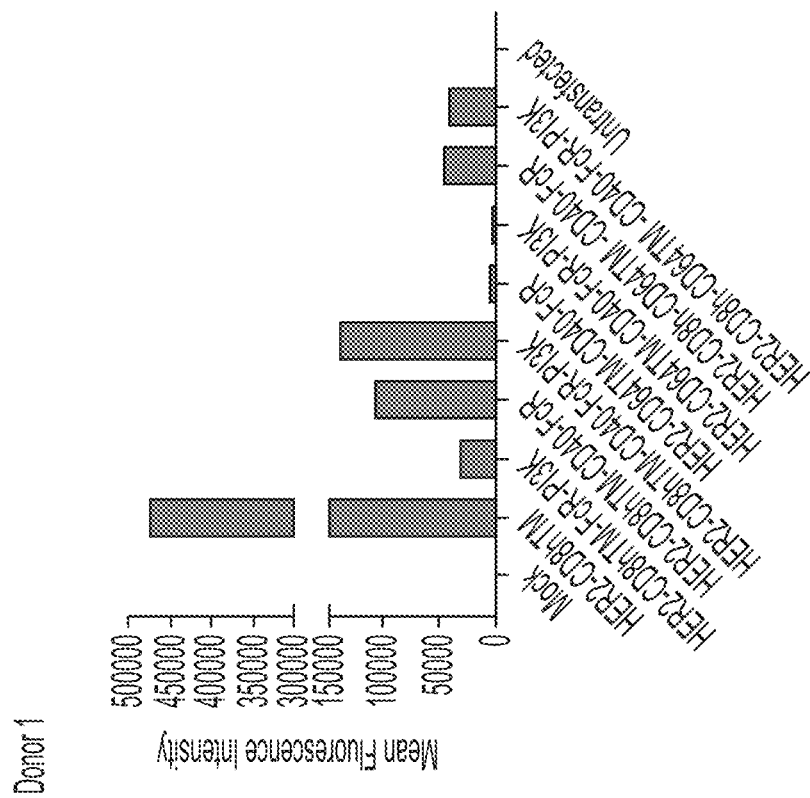
FIG. 8C shows graphs of the percentage of cells positive for the indicated HER2-CFP constructs and the mean fluorescence intensity using the data from FIG. 8A and FIG. 8B. Similar expression of the HER2-CFP constructs was observed in both donors.
Figure 8C:
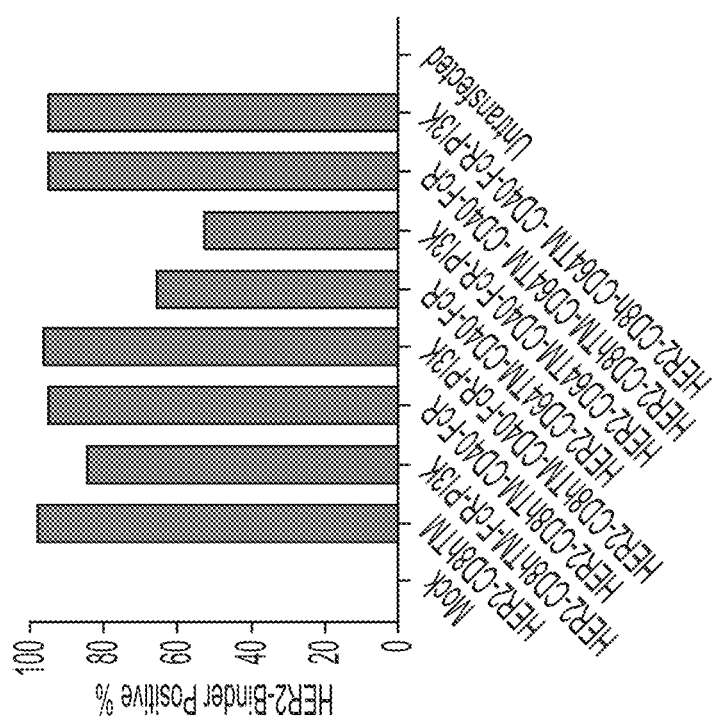
Figure 8C:
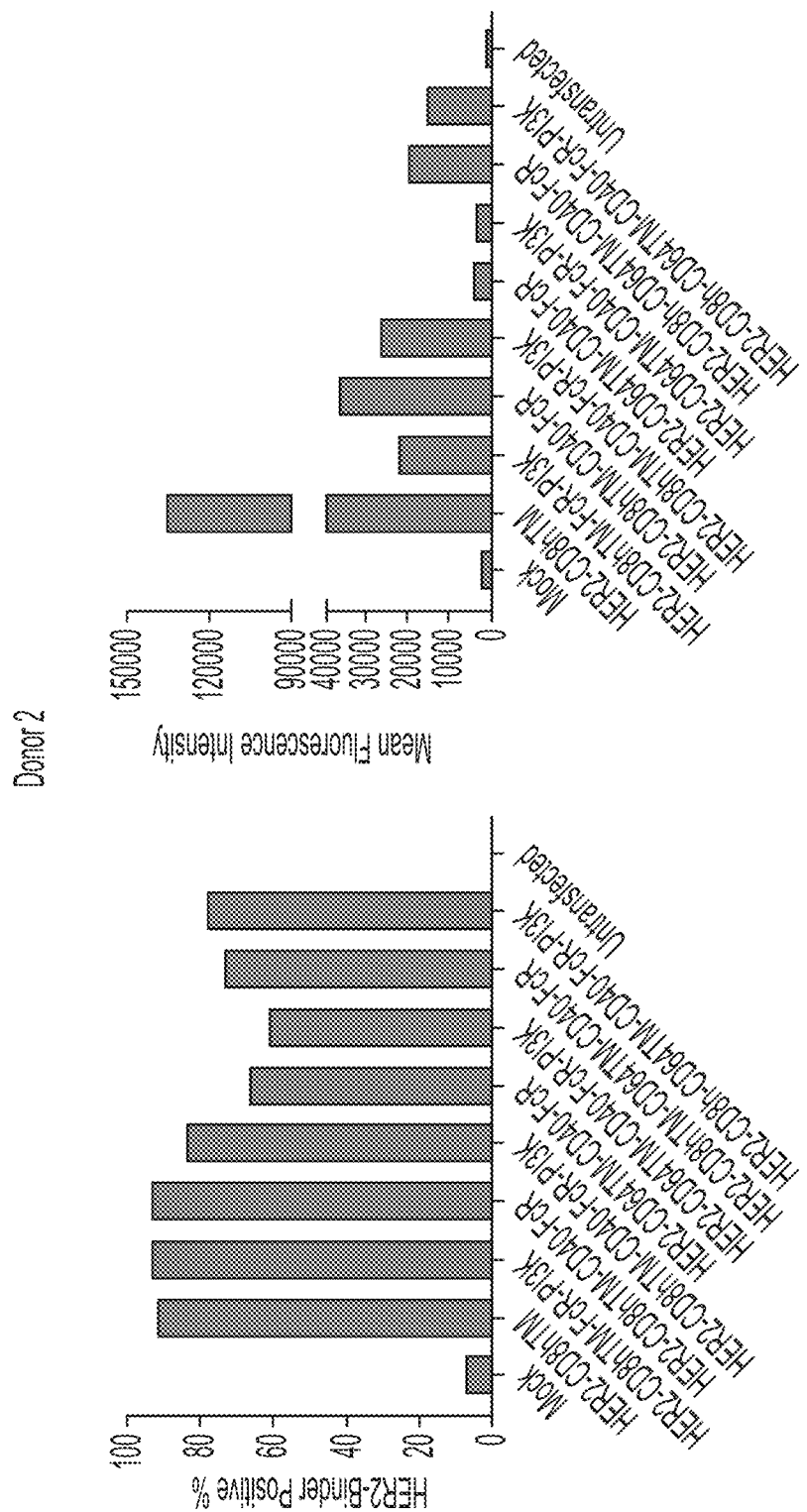

FIG. 8A shows flow cytometry data demonstrating expression of the indicated HER2-CFP constructs in primary human monocytes from a first donor after electroporation of the indicated HER2-CFP constructs. FIG. 8B shows flow cytometry data demonstrating expression of the indicated HER2-CFP constructs in primary human monocytes from a second donor after electroporation of the indicated HER2-CFP constructs. FIG. 8C shows graphs of the percentage of cells positive for the indicated HER2-CFP constructs and the mean fluorescence intensity using the data from FIG. 8A and FIG. 8B. Similar expression of the HER2-CFP constructs was observed in both donors.

Figure 9A:
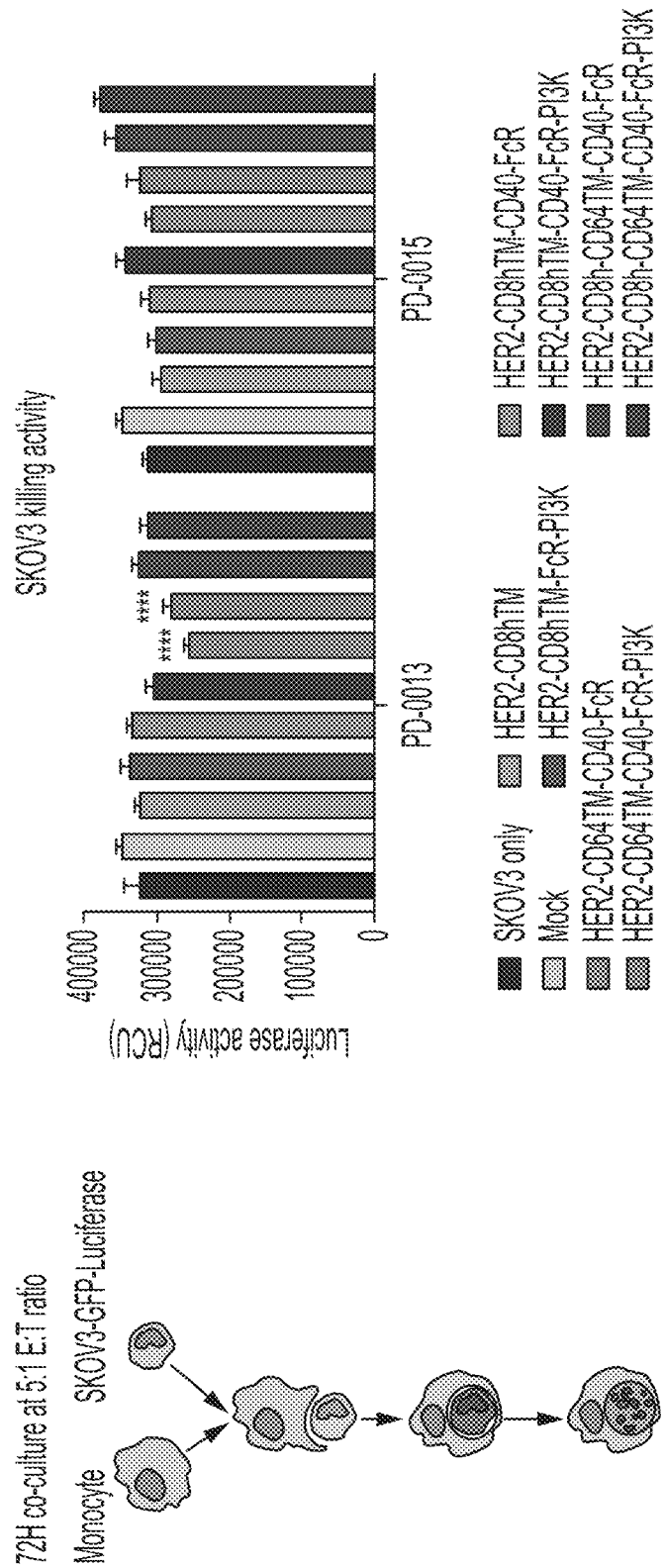
FIG. 9A shows a graph of SKOV3 killing activity by primary human monocytes from two different donors that were electroporated with the indicated HER2-CFP constructs. 100,000 primary human monocytes electroporated with the indicated HER2-CFP constructs were co-cultured with 20,000 SKOV3-GFP-Luciferase tumor cells. Luciferase activity of the tumor cells was detected after 72 hours of co-culture and killing was determined by a decrease in luciferase signal intensity.

To test SKOV3 tumor killing activity of human primary monocytes expressing the constructs above, 100,000 primary human monocytes electroporated with the indicated HER2-CFP constructs were co-cultured with 20,000 SKOV3-GFP-Luciferase tumor cells. Luciferase activity of the tumor cells was detected after 72 hours of co-culture and killing was determined by a decrease in luciferase signal intensity. FIG. 9A shows a graph of SKOV3 killing activity by primary human monocytes from two different donors that were electroporated with the indicated HER2-CFP constructs.

Figure 9B:
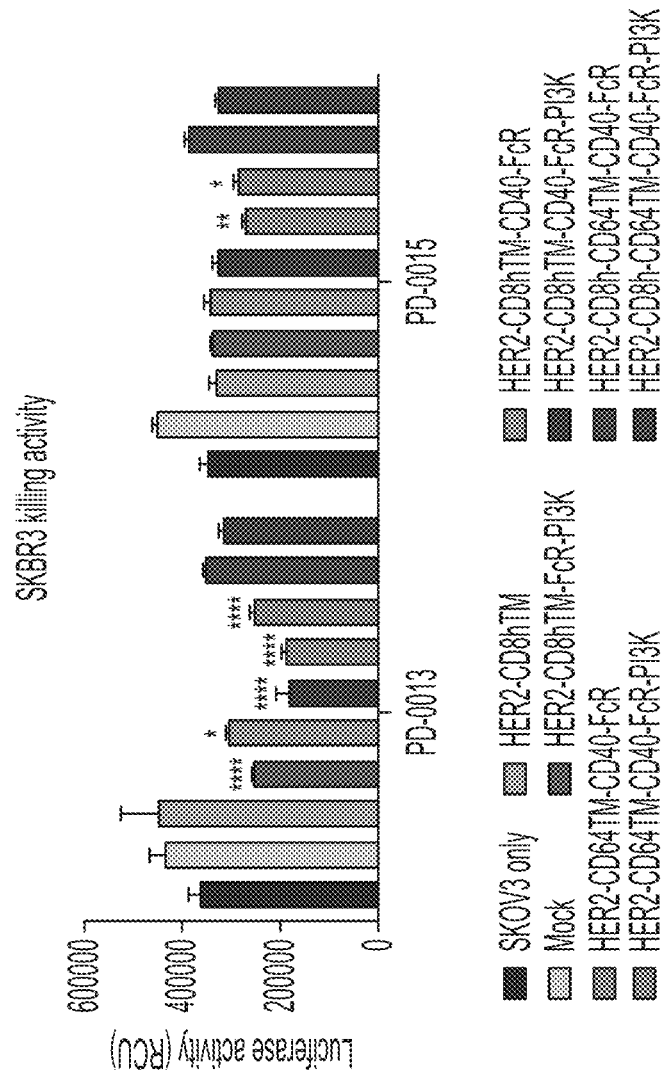
FIG. 9B shows a graph of SKBR3 killing activity by primary human monocytes from two different donors that were electroporated with the indicated HER2-CFP constructs. 100,000 primary human monocytes electroporated with the indicated HER2-CFP constructs were co-cultured with 20,000 SKBR3-Luciferase tumor cells. Luciferase activity of the tumor cells was detected after 72 hours of co-culture and killing was determined by a decrease in luciferase signal intensity.
Figure 9B:
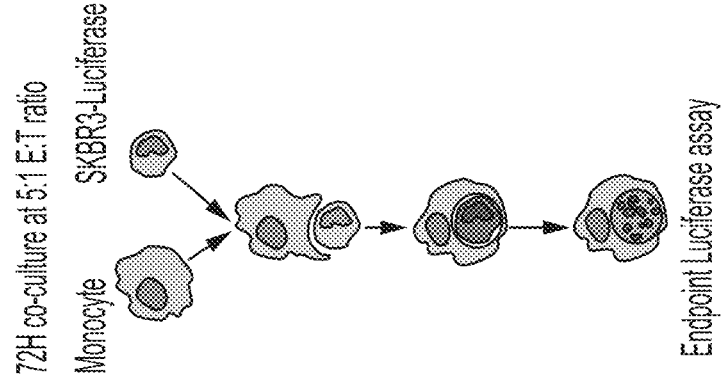

To test SKBR3 tumor killing activity of human primary monocytes expressing the constructs above, 100,000 primary human monocytes electroporated with the indicated HER2-CFP constructs were co-cultured with 20,000 SKBR3-Luciferase tumor cells. Luciferase activity of the tumor cells was detected after 72 hours of co-culture and killing was determined by a decrease in luciferase signal intensity. FIG. 9B shows a graph of SKBR3 killing activity by primary human monocytes from two different donors that were electroporated with the indicated HER2-CFP constructs.

Figure 10A:
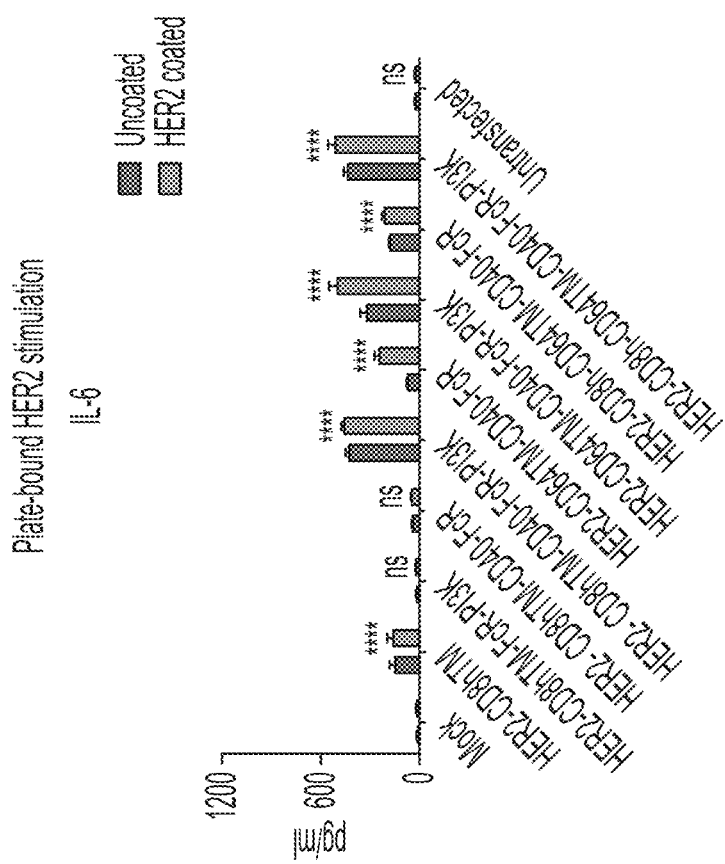
FIG. 10A shows graphs of pro-inflammatory cytokine IL-6 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). For antigen stimulated HER2-CFP primary monocyte samples, a 96-well plate coated with 2.5 μg/mL of HER2-his protein and 100,000 primary human monocytes electroporated with the indicated HER2-CFP constructs were added per well. Supernatant was collected after 48 hours of stimulation and secreted cytokine was analyzed by Luminex. For tumor cell stimulated HER2-CFP primary monocyte samples, 100,000 primary human monocytes electroporated with the indicated HER2-CFP constructs were co-cultured with 20,000 tumor cells (SKOV3-GFP-Luciferase cells or SKBR3-Luciferase cells). Supernatant was collected after 48 hours of stimulation and secreted cytokine was analyzed by Luminex Statistical significance was determined between HER2-CFP electroporated primary monocyte samples co-cultured with tumor cells and mock electroporated primary monocyte samples co-cultured with tumor cells.
Figure 10A:
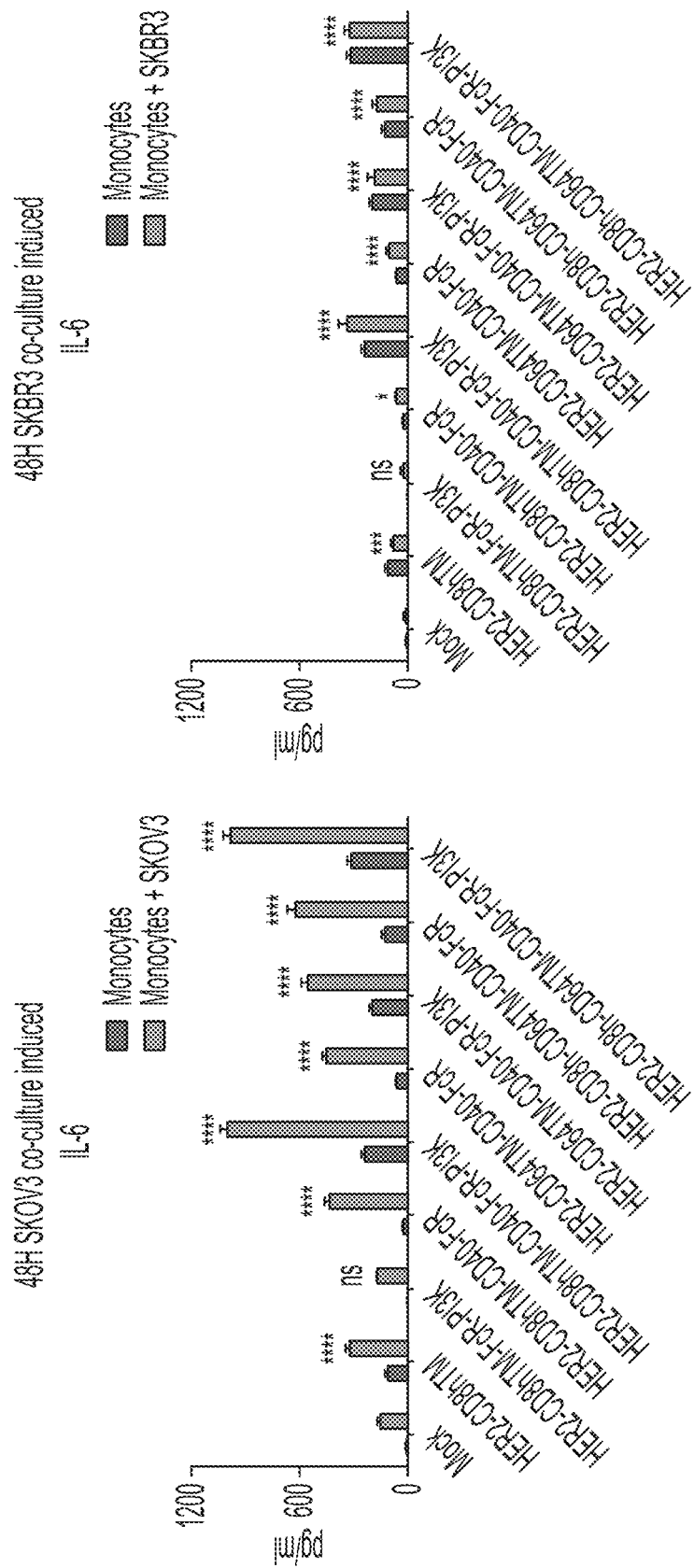
Figure 10B:
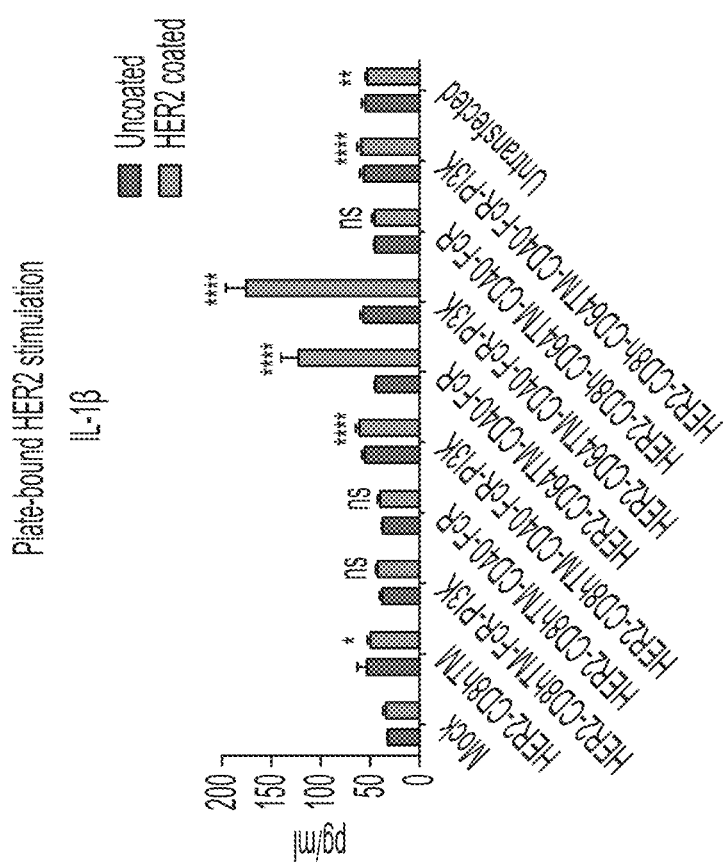
FIG. 10B shows graphs of pro-inflammatory cytokine IL-1β induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 10A.
Figure 10B:
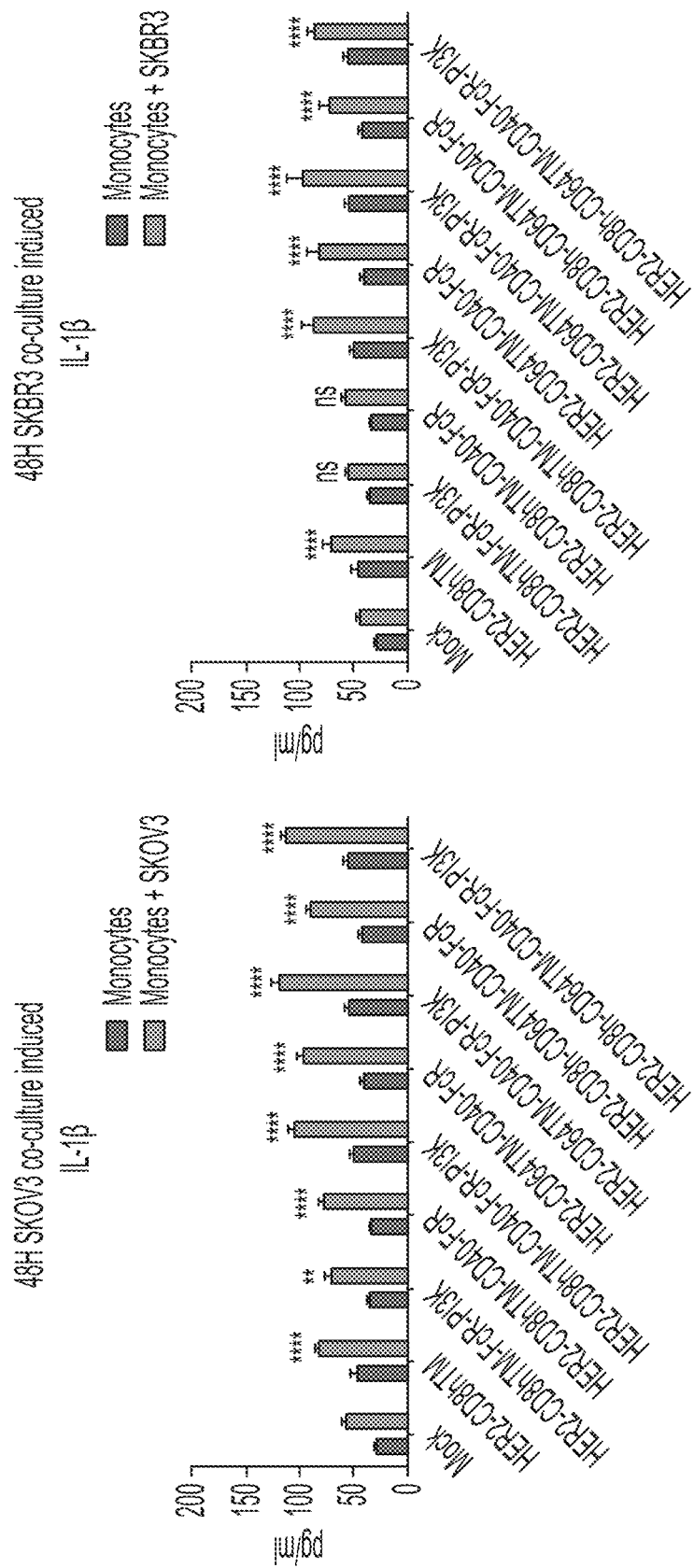
Figure 10C:
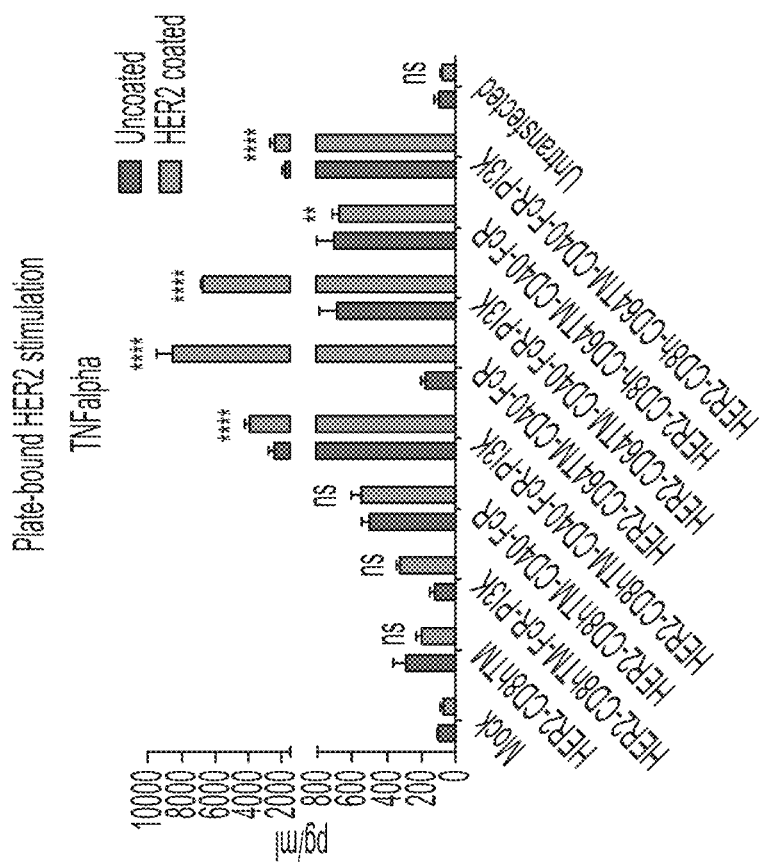
FIG. 10C shows graphs of TNF-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 10A.
Figure 10C:
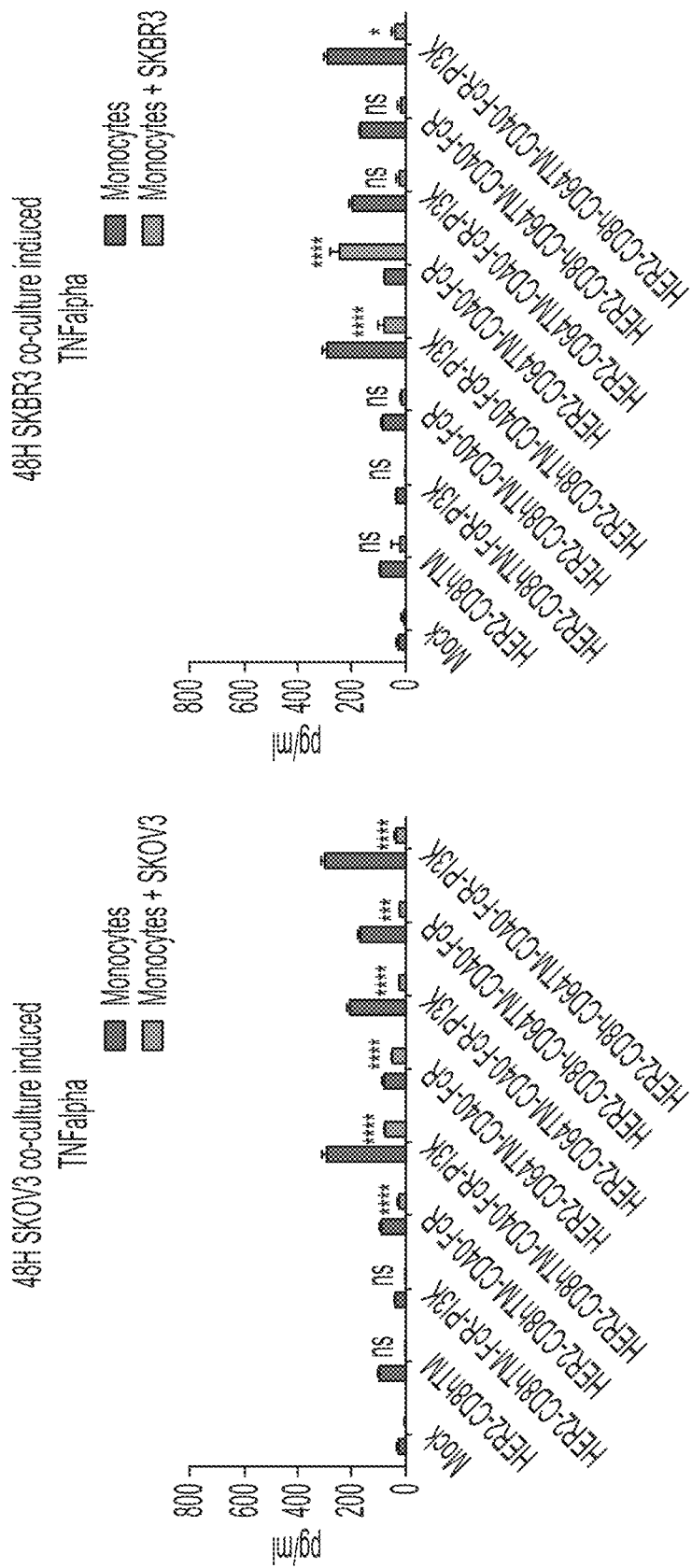
Figure 10D:
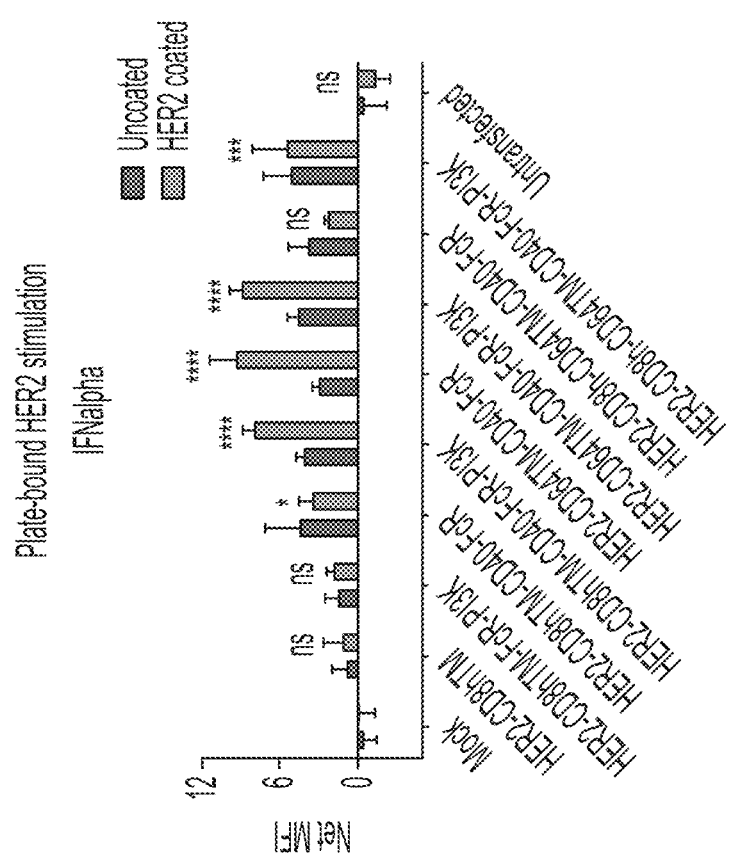
FIG. 10D shows graphs of IFN-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 10A.
Figure 10D:
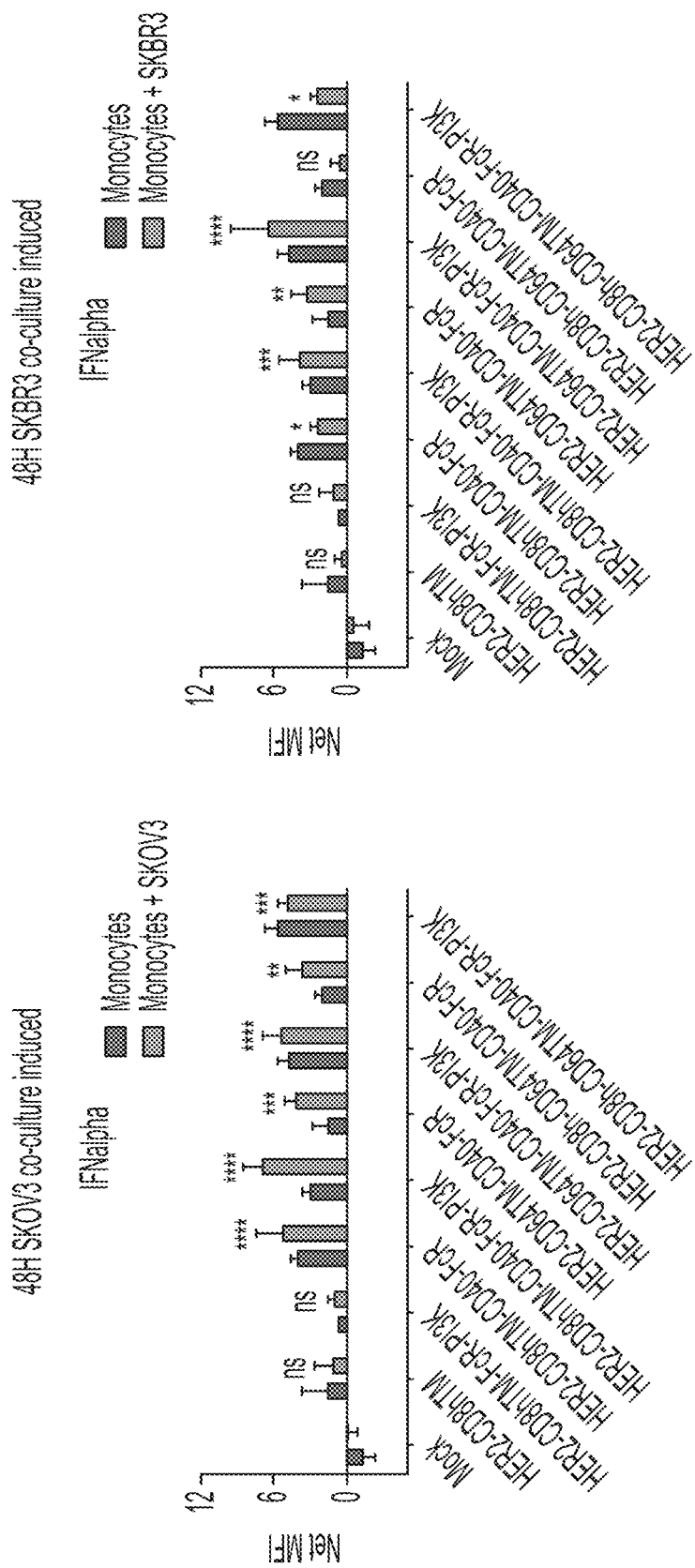
Figure 10E:
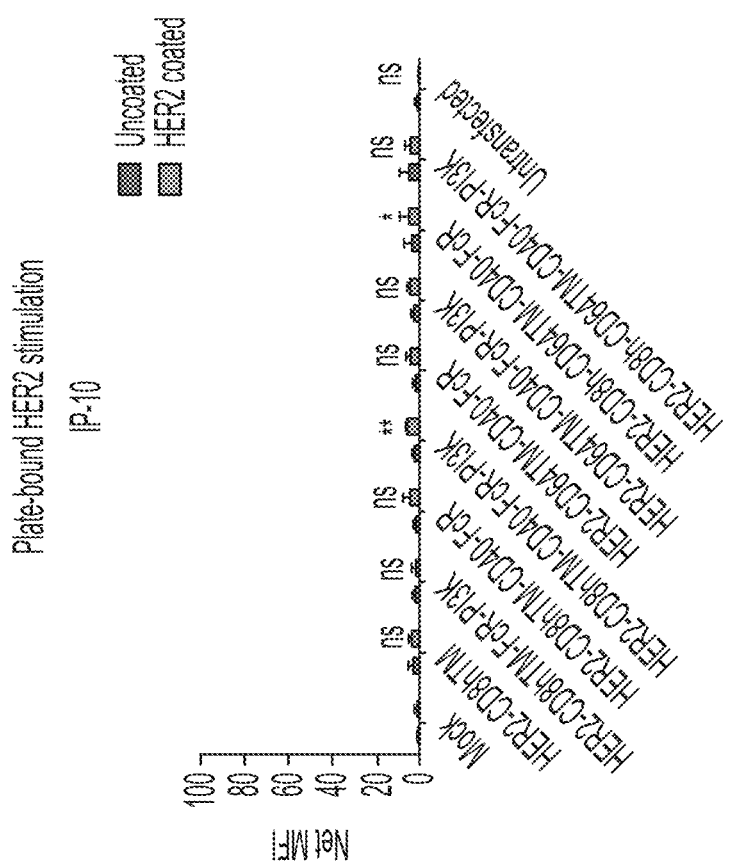
FIG. 10E shows graphs of IP10 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 10A.
Figure 10E:
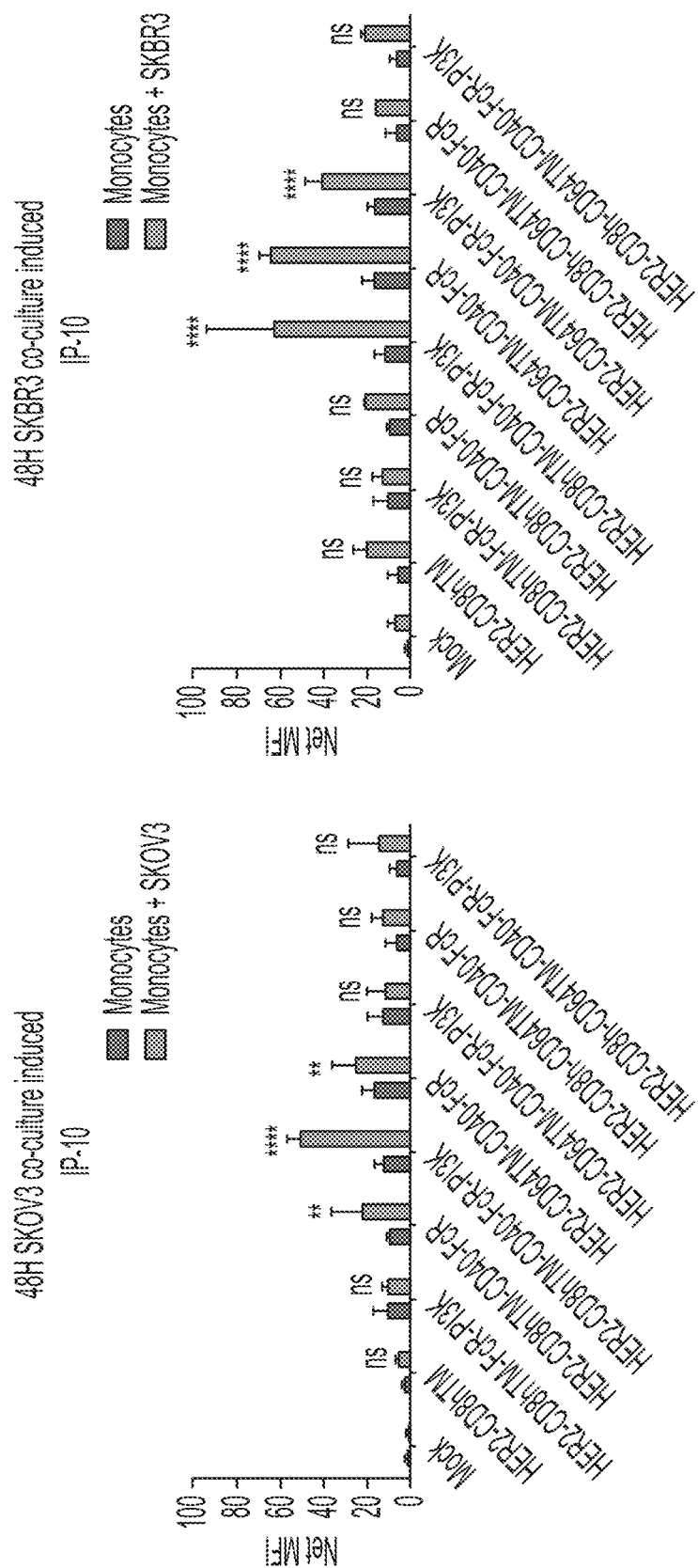
Figure 10F:
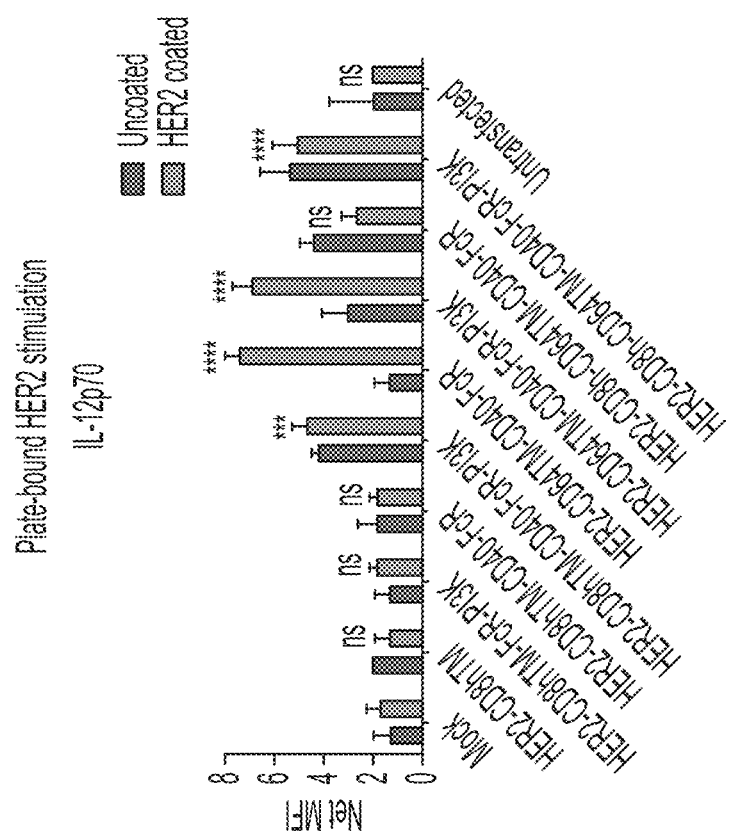
FIG. 10F shows graphs of IL-12 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). The experiments and analyses were performed as in FIG. 10A.
Figure 10F:
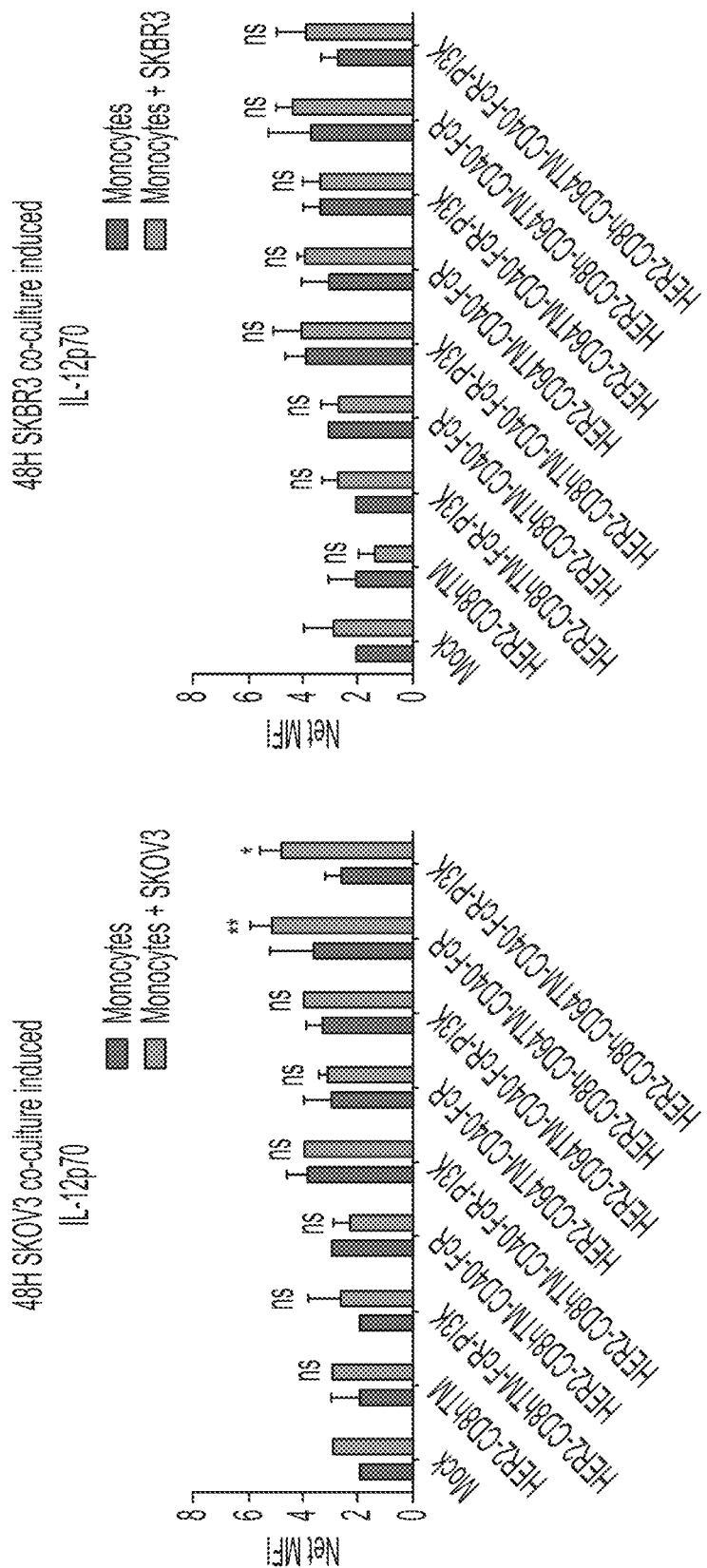

To test the cytokine/chemokine induction ability of human primary monocytes expressing the constructs above, antigen stimulated and tumor cell stimulated human primary monocytes expressing the constructs above were tested. For antigen stimulated HER2-CFP primary monocyte samples, a 96-well plate coated with 2.5 µg/mL of HER2-his protein and 100,000 primary human monocytes electroporated with the indicated HER2-CFP constructs were added per well. Supernatant was collected after 48 hours of stimulation and secreted cytokine was analyzed by Luminex. For tumor cell stimulated HER2-CFP primary monocyte samples, 100,000 primary human monocytes electroporated with the indicated HER2-CFP constructs were co-cultured with 20,000 tumor cells (SKOV3-GFP-Luciferase cells or SKBR3-Luciferase cells). Supernatant was collected after 48 hours of stimulation and secreted cytokine was analyzed by Luminex Statistical significance was determined between HER2-CFP electroporated primary monocyte samples co-cultured with tumor cells and mock electroporated primary monocyte samples co-cultured with tumor cells. FIG. 10A shows graphs of pro-inflammatory cytokine IL-6 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 10B shows graphs of pro-inflammatory cytokine IL-1β induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 10C shows graphs of TNF-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 10D shows graphs of IFN-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 10E shows graphs of IP10 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 10F shows graphs of IL-12 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). It was seen from the studies above that the constructs induced high cytokine and chemokine response (e.g., FIG. 10A, FIG.

10B; specifically, a combination of CD40, FcR and PI3K intracellular domains with the CD64TM domains induced high levels of cytokines, e.g., IL-1b and IL6). This indicates that the monocytes were highly activated upon engagement of these chimeric receptor to target antigen, and were capable of enhanced inflammatory response. In addition to phagocytosis of the target cell by the activated cells themselves, the activated CFP-mediated induction of NF-kappa B and IFN responsive genes, as well as release of inflammatory cytokines and chemokines by the myeloid cell are indications that these cells could potentially lead to an enhanced immune activation in vivo. To further characterize human primary monocytes expressing the constructs above, Nanostring gene expression analysis will be employed using the Human nCounter Myeloid Innate Immunity V2 Panel (770 genes).

Example 6. Testing of Primary Human Monocytes with Various HER2-TRIF CFP Constructs To test surface expression of HER2-TRIF CFP constructs in primary monocytes, primary monocytes were harvested from two healthy human donors and electroporated with the constructs in the table below (Table 10).

TABLE 10

List of HER2-TRIF CFP Constructs tested
HER2-TRIF CFP Constructs tested

Figure 11A:
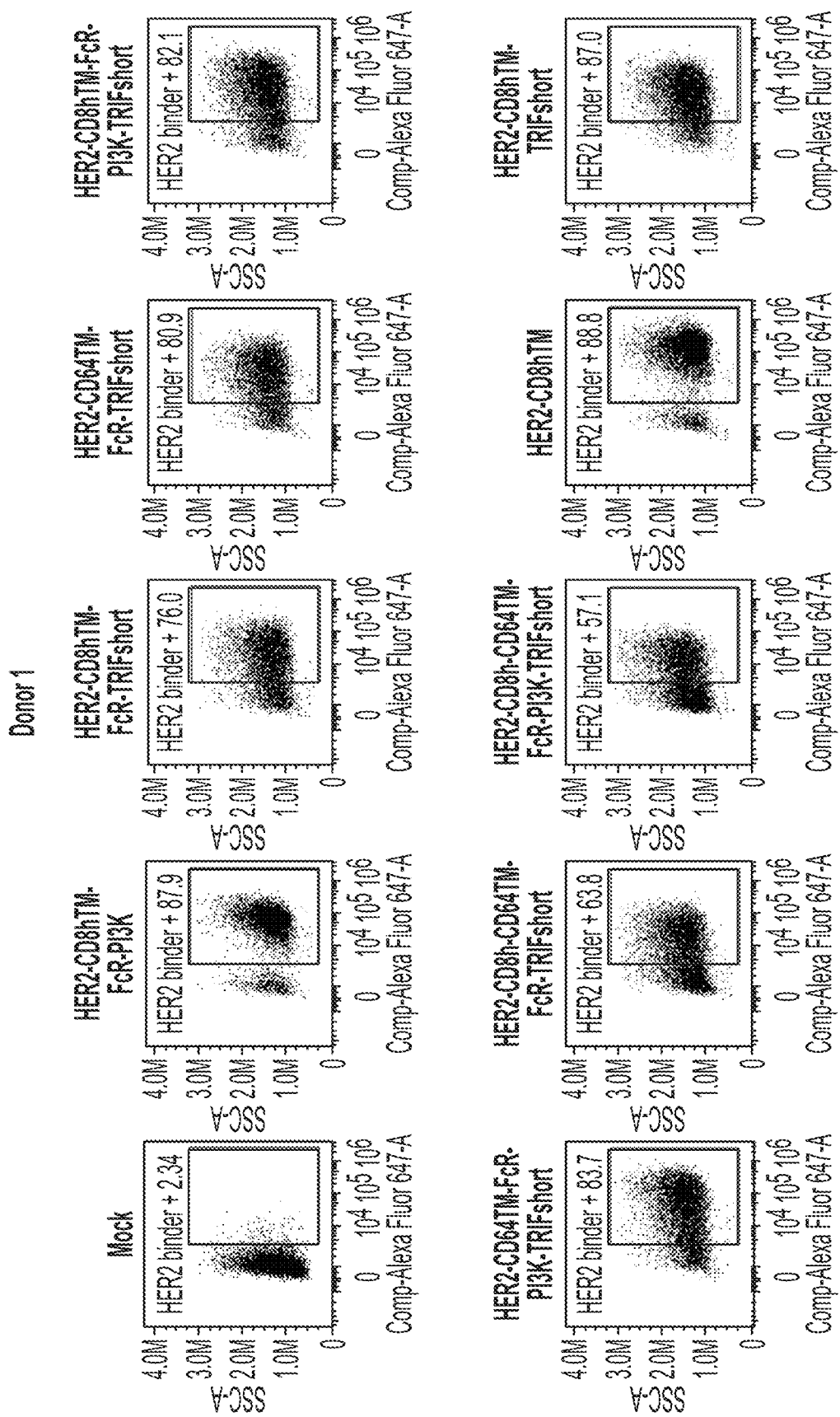
FIG. 11A shows flow cytometry data demonstrating expression of the indicated HER2-CFP constructs in primary human monocytes from a first donor after electroporation of the indicated HER2-CFP constructs.
Figure 11B:
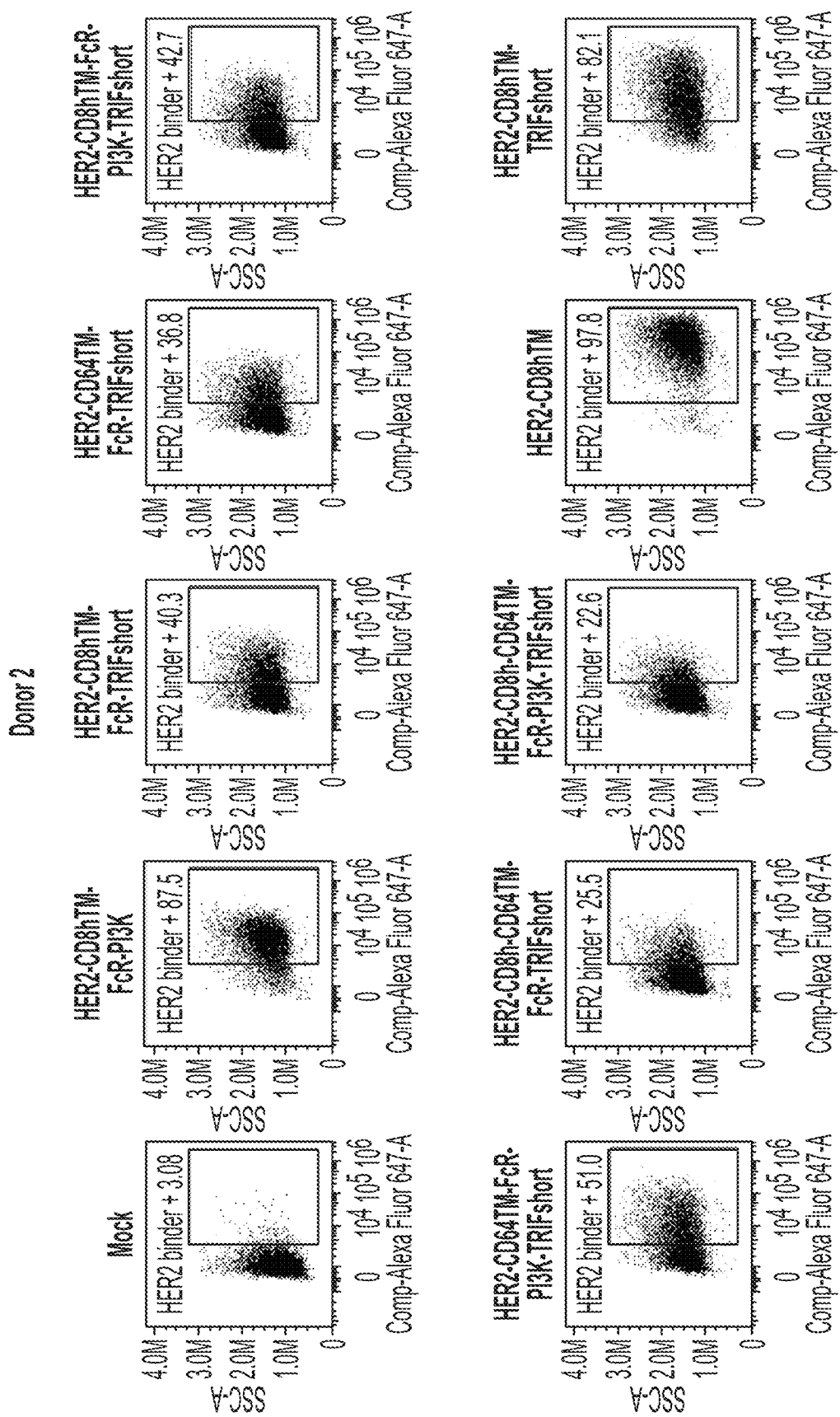
FIG. 11B shows flow cytometry data demonstrating expression of the indicated HER2-CFP constructs in primary human monocytes from a second donor after electroporation of the indicated HER2-CFP constructs.
Figure 11C:
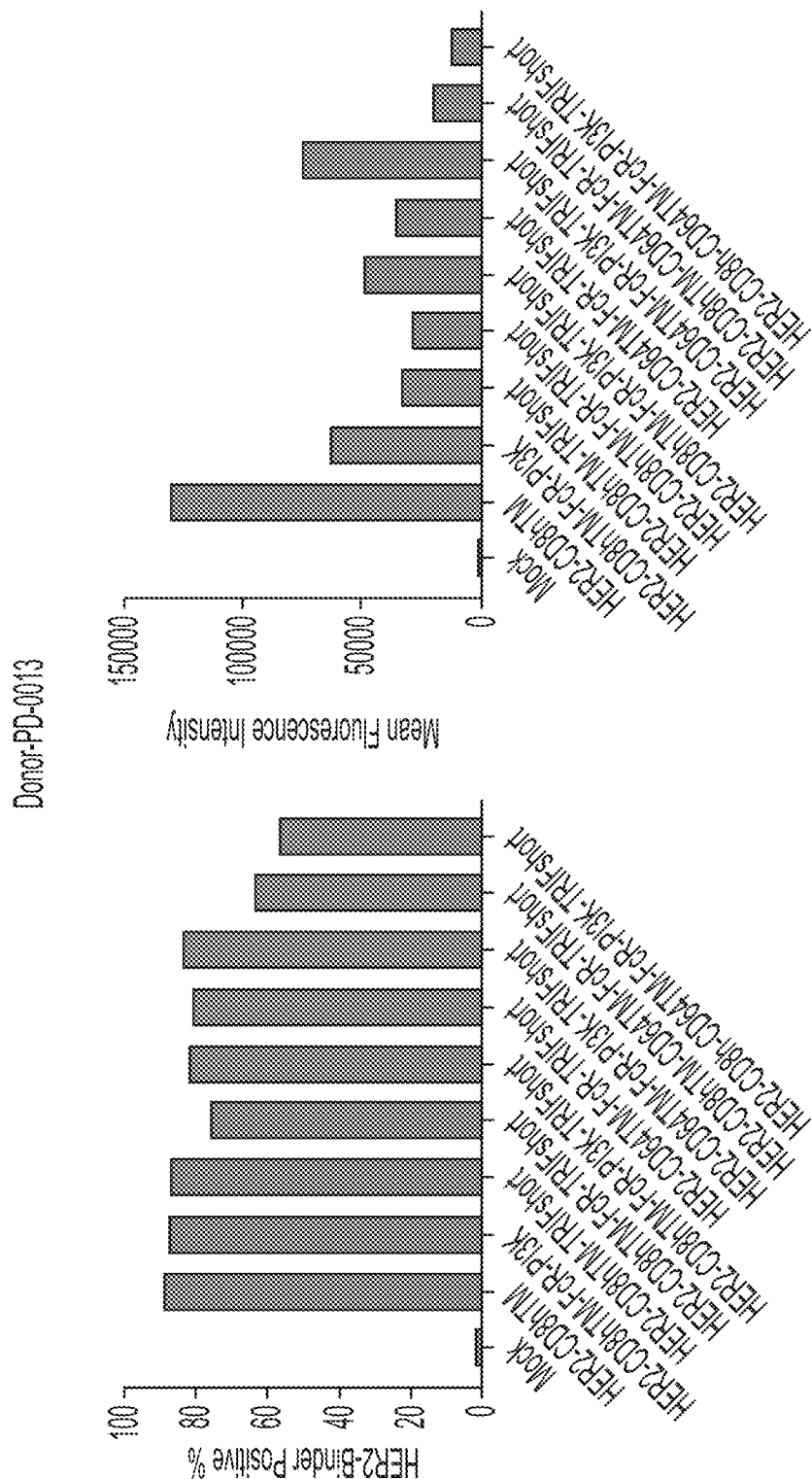
FIG. 11C shows graphs of the percentage of cells positive for the indicated HER2-CFP constructs and the mean fluorescence intensity using the data from FIG. 11A and FIG. 11B.
Figure 11C:
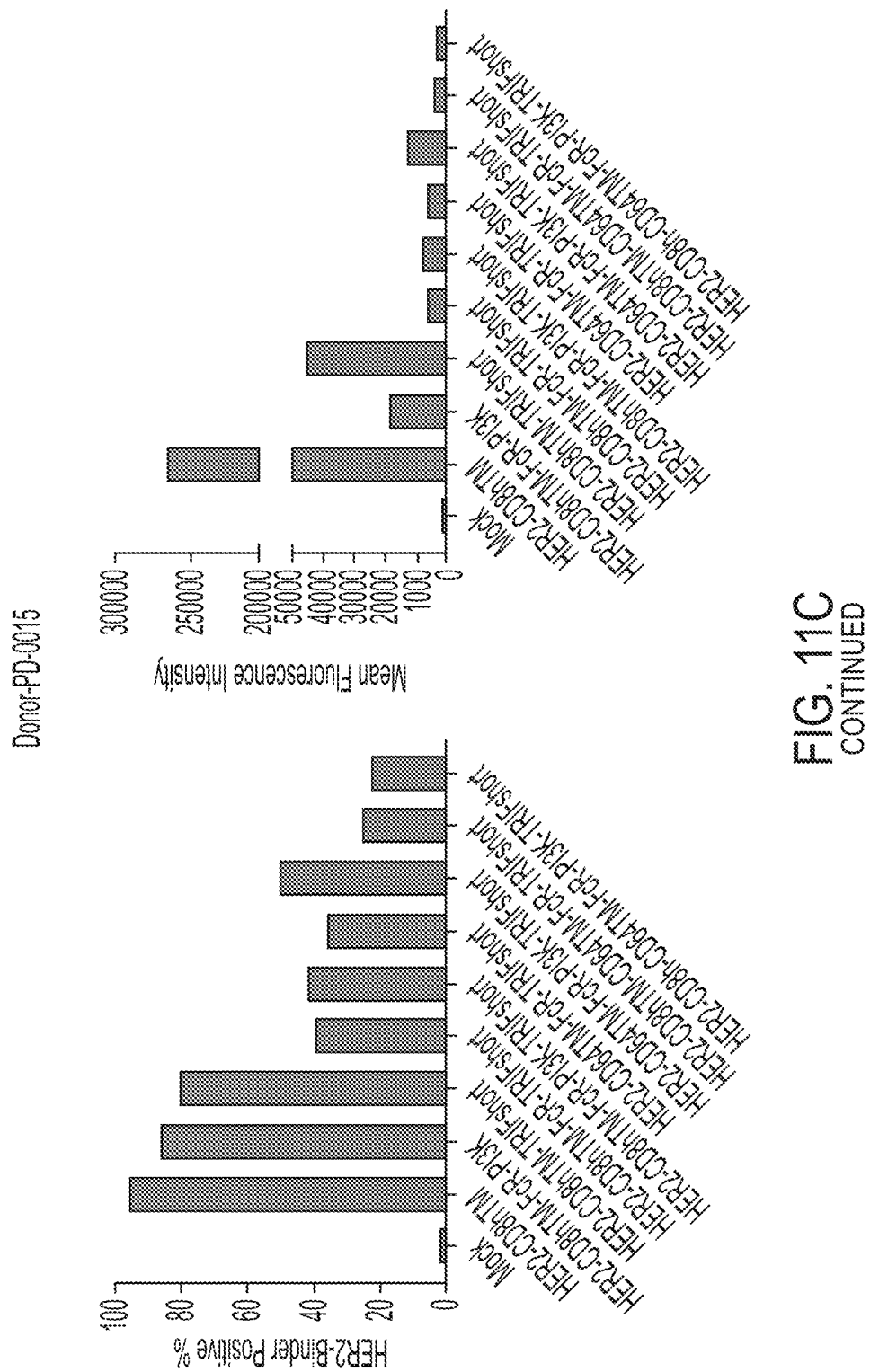

HER2-CD8h-CD8TM
HER2-CD8h-CD8TM-FcR-PI3K
HER2-CD8h-CD8TM-FcR-TRIFshort
HER2-CD8h-CD8TM-FcR-PI3K-TRIFshort
HER2-CD64TM-FcR-TRIFshort
HER2-CD64TM-FcR-PI3K-TRIFshort
HER2-CD8h-CD64TM-FcR-TRIFshort
HER2-CD8h-CD64TM-FcR-PI3K-TRIFshort FIG. 11A shows flow cytometry data demonstrating expression of the indicated HER2-CFP constructs in primary human monocytes from a first donor after electroporation of the indicated HER2-CFP constructs. FIG. 11B shows flow cytometry data demonstrating expression of the indicated HER2-CFP constructs in primary human monocytes from a second donor after electroporation of the indicated HER2-CFP constructs. FIG. 11C shows graphs of the percentage of cells positive for the indicated HER2-CFP constructs and the mean fluorescence intensity using the data from FIG. 11A and FIG. 11B.

Figure 12A:
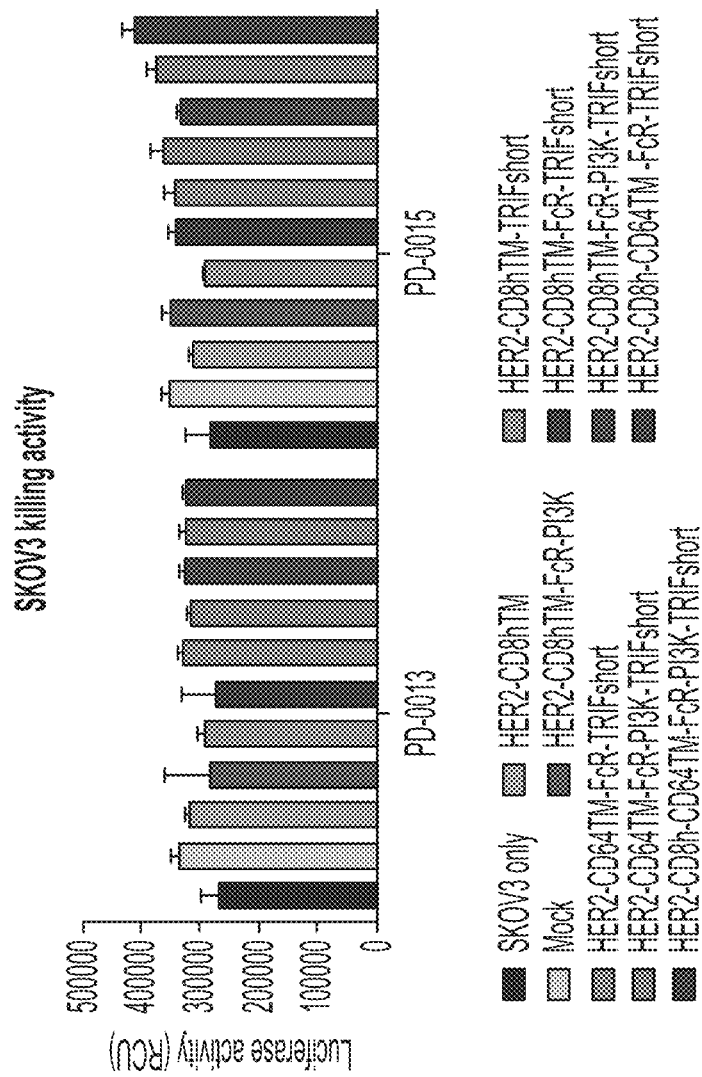
FIG. 12A shows a graph of SKOV3 killing activity by primary human monocytes from two different donors that were electroporated with the indicated HER2-CFP constructs. 100,000 primary human monocytes electroporated with the indicated HER2-CFP constructs were co-cultured with 20,000 SKOV3-GFP-Luciferase tumor cells. Luciferase activity of the tumor cells was detected after 72 hours of co-culture and killing was determined by a decrease in luciferase signal intensity.

To test SKOV3 tumor killing activity of human primary monocytes expressing the constructs above, 100,000 primary human monocytes electroporated with the indicated HER2-CFP constructs were co-cultured with 20,000 SKOV3-GFP-Luciferase tumor cells. Luciferase activity of the tumor cells was detected after 72 hours of co-culture and killing was determined by a decrease in luciferase signal intensity. FIG. 12A shows a graph of SKOV3 killing activity by primary human monocytes from two different donors that were electroporated with the indicated HER2-CFP constructs.

Figure 12B:
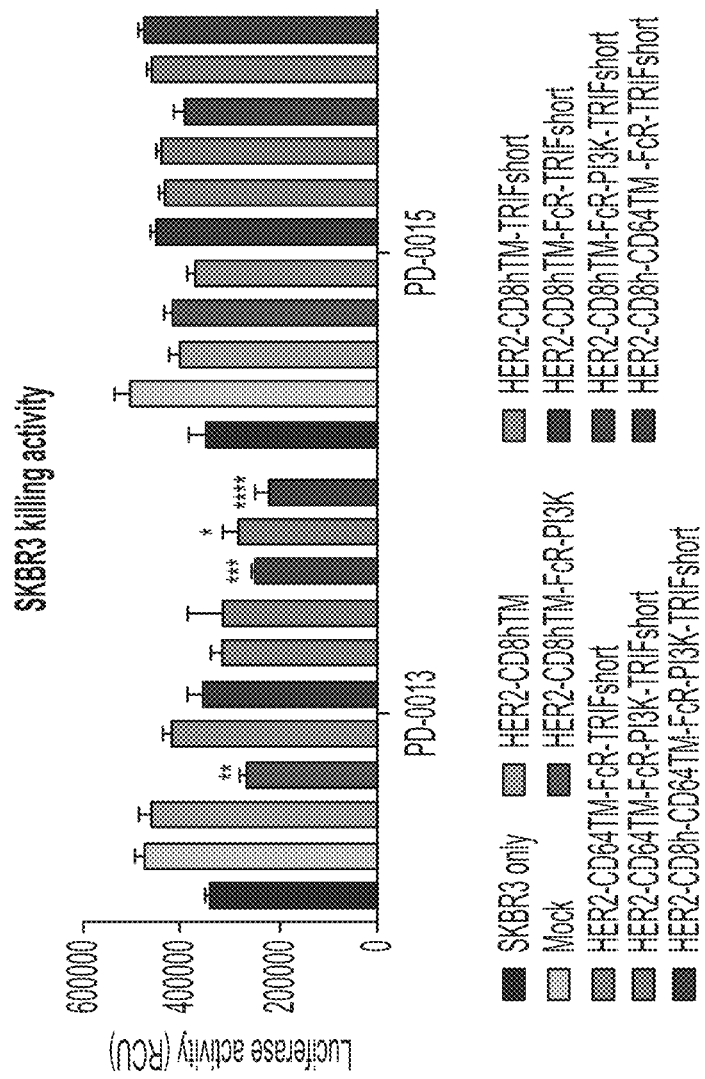
FIG. 12B shows a graph of SKBR3 killing activity by primary human monocytes from two different donors that were electroporated with the indicated HER2-CFP constructs. 100,000 primary human monocytes electroporated with the indicated HER2-CFP constructs were co-cultured with 20,000 SKBR3-Luciferase tumor cells. Luciferase activity of the tumor cells was detected after 72 hours of co-culture and killing was determined by a decrease in luciferase signal intensity.

To test SKBR3 tumor killing activity of human primary monocytes expressing the constructs above, 100,000 primary human monocytes electroporated with the indicated HER2-CFP constructs were co-cultured with 20,000 SKBR3-Luciferase tumor cells. Luciferase activity of the tumor cells was detected after 72 hours of co-culture and killing was determined by a decrease in luciferase signal intensity. FIG. 12B shows a graph of SKBR3 killing activity by primary human monocytes from two different donors that were electroporated with the indicated HER2-CFP constructs.

To test the cytokine/chemokine induction ability of human primary monocytes expressing the constructs above, antigen stimulated and tumor cell stimulated human primary monocytes expressing the constructs above were tested. For antigen stimulated HER2-CFP primary monocyte samples, a 96-well plate coated with 2.5 μg/mL of HER2-his protein and 100,000 primary human monocytes electroporated with the indicated HER2-CFP constructs were added per well. Supernatant was collected after 48 hours of stimulation and secreted cytokine was analyzed by Luminex. For tumor cell stimulated HER2-CFP primary monocyte samples, 100,000 primary human monocytes electroporated with the indicated HER2-CFP constructs were co-cultured with 20,000 tumor cells (SKOV3-GFP-Luciferase cells or SKBR3-Luciferase cells). Supernatant was collected after 48 hours of stimulation and secreted cytokine was analyzed by Luminex Statistical significance was determined between HER2-CFP electroporated primary monocyte samples co-cultured with tumor cells and mock electroporated primary monocyte samples co-cultured with tumor cells. FIG. 13A shows graphs of pro-inflammatory cytokine IL-6 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 13B shows graphs of pro-inflammatory cytokine IL-1β induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 13C shows graphs of TNF-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 13D shows graphs of IFN-α induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 13E shows graphs of IP10 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). FIG. 13F shows graphs of IL-12 induction by primary human monocytes from a human donor that were electroporated with the indicated HER2-CFP constructs and stimulated with HER-2 antigen (top) or co-cultured with SKOV3 tumor cells (bottom, left) or SKBR3 tumor cells (bottom, right). Nanostring gene expression analysis will be employed using the Human nCounter Myeloid Innate Immunity V2 Panel (770 genes).

Additionally, in a preliminary in vivo study, a CFP comprising TRIF and CD40 intracellular domains indicate that the ICDs were indeed conferring protective immunity, as shown in FIG. 14. Primary monocytes armed with TRIF or CD40 based ATAK receptors showed strong anti-tumor response in B16 melanoma tumor model (Left) Posttreatment melanoma tumor volume in mice treated with ATAK-monocytes. (Right) Survival of tumor-bearing mice treated with FcR-PI3K ATAK receptor or ATAK receptors with TRIF/CD40 domains.

What is claims is:

1. A method of treating a GPC3-expressing cancer in a subject in need thereof, comprising: administering to the subject a therapeutically effective amount of a composition comprising a recombinant polynucleic acid encapsulated by a nanoparticle delivery vehicle, wherein the recombinant polynucleic acid comprises a sequence encoding a chimeric fusion protein (CFP), the CFP comprising:
   (a) an extracellular domain comprising an anti-GPC3 binding domain, wherein the extracellular domain further comprises an extracellular domain or fragment thereof from CD16a, CD64, CD68 or CD89, and
   (b) a transmembrane domain operatively linked to the extracellular domain, wherein the transmembrane domain comprises a transmembrane domain from CD16a, CD64, CD68 or CD89;
   wherein the CFP is expressed on the surface of myeloid cells of the subject that express endogenous FcR-gamma receptors;
   wherein the anti-GPC3 binding domain comprises:
      (i) a heavy chain comprising a heavy chain variable domain, the heavy chain variable domain comprising a heavy chain complementarity determining region 1 (HC CDR1) sequence of DYEMH (amino acid residues 31-35 of SEQ ID NO: 97), a HC CDR2 sequence of ALDPKTGDTAYSQKFKG (amino acid residues 50-66 of SEQ ID NO: 97) and a HC CDR3 (HC CDR3) sequence of FYSYTY (amino acid residues 99-104 of SEQ ID NO: 97); and
      (ii) a light chain comprising a light chain variable domain comprising: a light chain complementarity determining region 1 (LC CDR1) sequence of RSSQSLVHSNRNTYLH (amino acid residues 24-39 of SEQ ID NO: 98), a LC CDR2 sequence of KVSNRFS (amino acid residues 55-61 of SEQ ID NO: 98) and a LC CDR3 sequence of SQNTHVPPT (amino acid residues 94-102 of SEQ ID NO: 98).

2. The method of claim 1, wherein the GPC3-expressing cancer is selected from the group consisting of ovarian cancer, renal cancer, breast cancer, prostate cancer, liver cancer, brain cancer, lymphoma, leukemia, skin cancer, pancreatic cancer, colorectal cancer, and lung cancer.

3. The method of claim 1, wherein the GPC3-expressing cancer is a liver cancer.

4. The method of claim 3 wherein the liver cancer is hepatocellular carcinoma.

5. The method of claim 1, wherein the anti-GPC3 binding domain comprises an scFv domain.

6. The method of claim 5, wherein the anti-GPC3 binding domain comprises a sequence with at least 80% sequence identity to SEQ ID NO: 106.

7. The method of claim 6, wherein the anti-GPC3 binding domain comprises a sequence with at least 90% sequence identity to SEQ ID NO: 106.

8. The method of claim 7, wherein the anti-GPC3 binding domain comprises a sequence with at least 95% sequence identity to SEQ ID NO: 106.

9. The method of claim 1, wherein the anti-GPC3 binding domain comprises a heavy chain variable domain having a sequence with at least 80% sequence identity to SEQ ID NO: 97.

10. The method of claim 9, wherein the anti-GPC3 binding domain comprises a heavy chain variable domain having a sequence with at least 90% sequence identity to SEQ ID NO: 97.

11. The method of claim 10, wherein the anti-GPC3 binding domain comprises a heavy chain variable domain having a sequence with at least 95% sequence identity to SEQ ID NO: 97.

12. The method of claim 1, wherein the anti-GPC3 binding domain comprises a light chain variable domain having a sequence with at least 80% sequence identity to SEQ ID NO: 98.

13. The method of claim 12, wherein the anti-GPC3 binding domain comprises a light chain variable domain having a sequence with at least 90% sequence identity to SEQ ID NO: 98.

14. The method of claim 13, wherein the anti-GPC3 binding domain comprises a light chain variable domain having a sequence according to SEQ ID NO: 98.

15. The method of claim 1, wherein the extracellular domain further comprises an extracellular domain that has an amino acid sequence of DSIHQDYTTQN (amino acid residues 267-277 of SEQ ID NO: 58).

16. The method of claim 1, wherein the extracellular domain further comprises an extracellular domain from CD89 or a fragment thereof.

17. The method of claim 1, wherein the transmembrane domain has an amino acid sequence of LIRMAVAGLVLVALLAILV (amino acid residues 278-296 of SEQ ID NO: 58).

18. The method of claim 1, wherein the transmembrane domain is a transmembrane domain from CD89.

19. The method of claim 1, wherein the CFP further comprises an intracellular domain comprising one or more intracellular signaling domains, wherein the one or more intracellular signaling domains comprises an intracellular signaling domain from CD16a, CD64, CD68, CD89, FCERIG, CD40 or CD3zeta.

20. The method of claim 19, wherein the one or more intracellular signaling domains comprises an intracellular signaling domain from CD89.

21. The method of claim 19, wherein the one or more intracellular signaling domains has an amino acid sequence of ENWHSHTALNKEASADVAEPSWSQQMCQPGLTFARTPSVCK (amino acid residues 297-337 of SEQ ID NO: 58).

22. The method of claim 1, wherein after administration of the composition to a human subject the CFP is preferentially or specifically expressed in myeloid cells, monocytes or macrophages of the human subject.

23. The method of claim 1, wherein after administration of the composition to a human subject the CFP is not substantially expressed on the surface of T cells of the subject.

24. The method of claim 1, wherein the nanoparticle delivery vehicle comprises a lipid nanoparticle.

25. The method of claim 24, wherein the lipid nanoparticle comprises a polar lipid and a non-polar lipid.

26. The method of claim 24, wherein the lipid nanoparticle comprises a cationic lipid, a non-cationic lipid, a neutral lipid, or a PEGylated lipid.

27. The method of claim 24, wherein the lipid nanoparticle is from 100 to 300 nm in diameter.

28. The method of claim 1, wherein the CFP further comprises a GMCSF signal peptide sequence.

29. The method of claim 28, wherein the GMCSF signal peptide sequence is MWLQSLLLLGTVACSIS (SEQ ID NO: 7).

30. The method of claim 1, wherein
the extracellular domain comprises an extracellular domain from CD89;
the transmembrane domain comprises a transmembrane domain from CD89; and
the CFP further comprises an intracellular domain comprising an intracellular domain from CD89.

* * * * *